US011345740B2

(12) United States Patent
Malik

(10) Patent No.: US 11,345,740 B2

(45) Date of Patent: May 31, 2022

(54) FETAL HEMOGLOBIN FOR GENETIC CORRECTION OF SICKLE CELL DISEASE

(71) Applicant: Children's Hospital Medical Center, Cincinnati, OH (US)

(72) Inventor: Punam Malik, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 1035 days.

(21) Appl. No.: 15/995,675

(22) Filed: Jun. 1, 2018

(65) Prior Publication Data

US 2018/0346552 A1 Dec. 6, 2018

Related U.S. Application Data

(63) Continuation of application No. 15/115,530, filed as application No. PCT/US2015/013960 on Jan. 30, 2015, now Pat. No. 10,072,067.

(60) Provisional application No. 61/933,788, filed on Jan. 30, 2014.

(51) Int. Cl.

*C07K 14/805* (2006.01)
*C12N 15/86* (2006.01)
*A61K 48/00* (2006.01)

(52) U.S. Cl.

CPC ............ *C07K 14/805* (2013.01); *C12N 15/86* (2013.01); *A61K 48/005* (2013.01); *C12N 2740/10043* (2013.01); *C12N 2740/16043* (2013.01); *C12N 2830/008* (2013.01); *C12N 2830/40* (2013.01); *C12N 2830/50* (2013.01)

(58) Field of Classification Search

None

See application file for complete search history.

(56) References Cited

U.S. PATENT DOCUMENTS

| | | | |
|---|---|---|---|
| 5,827,693 | A | 10/1998 | De Angelo et al. |
| 6,524,851 | B1 | 2/2003 | Ellis |
| 7,276,340 | B1 | 10/2007 | Ballantyne et al. |
| 8,318,690 | B2 | 11/2012 | Collard et al. |
| 9,551,010 | B2 | 1/2017 | Van Der Loo et al. |
| 10,072,067 | B2 | 9/2018 | Malik |
| 2005/0014166 | A1 | 1/2005 | Trono et al. |
| 2006/0292599 | A1 | 12/2006 | Ritz et al. |
| 2007/0066548 | A1 | 3/2007 | Nagel |
| 2009/0156534 | A1 | 6/2009 | Lisowski et al. |
| 2011/0294114 | A1 | 12/2011 | Van Der Loo et al. |
| 2013/0302898 | A1 | 11/2013 | Van Der Loo et al. |
| 2015/0315611 | A1 | 11/2015 | Malik |
| 2017/0145077 | A1 | 5/2017 | Malik |

OTHER PUBLICATIONS

[No Author Listed] Sickle-cell anaemia. World Health Organization Fifth-Ninth World Health Assembly Provisional Agenda Item 11.4. Apr. 2006;24:A59/9.

Aiuti et al., Correction of ADA-SCID by stem cell gene therapy combined with nonmyeloablative conditioning. Science. Jun. 28, 2002;296(5577):2410-3.

Aiuti et al., Gene therapy for immunodeficiency due to adenosine deaminase deficiency. N Engl J Med. Jan. 29, 2009;360(5):447-58. doi: 10.1056/NEJMoa0805817.

Aiuti et al., Immune reconstitution in ADA-SCID after PBL gene therapy and discontinuation of enzyme replacement. Nat Med. May 2002;8(5):423-5.

Aker et al., Extended core sequences from the cHS4 insulator are necessary for protecting retroviral vectors from silencing position effects. Hum Gene Ther. Apr. 2007;18(4):333-43.

Anson et al., Rational development of a HIV-1 gene therapy vector. J Gene Med. Oct. 2003;5(10):829-38.

Arumugam et al., Improved human beta-globin expression from self-inactivating lentiviral vectors carrying the chicken hypersensitive site-4 (cHS4) insulator element. Mol Ther. Oct. 2007;15(10):1863-71. Epub Jul. 10, 2007.

Arumugam et al., The 3' region of the chicken hypersensitive site-4 insulator has properties similar to its core and is required for full insulator activity. PLoS One. Sep. 10, 2009;4(9):e6995. doi: 10.1371/journal.pone.0006995.

Baskurt et al., Blood rheology and hemodynamics. Semin Thromb Hemost. Oct. 2003;29(5):435-50.

Baudin et al., Functional sites in the 5' region of human immunodeficiency virus type 1 RNA form defined structural domains. J Mol Biol. Jan. 20, 1993;229(2):382-97.

Baum et al., cis-Active elements of Friend spleen focus-forming virus: from disease induction to disease prevention. Acta Haematol. 1998;99(3):156-64.

Baum et al., Side effects of retroviral gene transfer into hematopoietic stem cells. Blood. Mar. 15, 2003;101(6):2099-114. Epub Jan. 2, 2003.

Bell et al., Stopped at the border: boundaries and insulators. Curr Opin Genet Dev. Apr. 1999;9(2):191-8.

Bell et al., Insulators and boundaries: versatile regulatory elements in the eukaryotic genome. Science. Jan. 19, 2001;291(5503):447-50.

Bell et al., The establishment of active chromatin domains. Cold Spring Harb Symp Quant Biol. 1998;63:509-14.

Bell et al., The protein CTCF is required for the enhancer blocking activity of vertebrate insulators. Cell. Aug. 6, 1999;98(3):387-96.

Bender et al., A majority of mice show long-term expression of a human beta-globin gene after retrovirus transfer into hematopoietic stem cells. Mol Cell Biol. Apr. 1989;9(4):1426-34.

Benhamida et al., Transduced CD34+ cells from adrenoleukodystrophy patients with HIV-derived vector mediate long-term engraftment of NOD/SCID mice. Mol Ther. Mar. 2003;7(3):317-24.

(Continued)

*Primary Examiner* — James D Schultz

(74) *Attorney, Agent, or Firm* — McDermott Will & Emery LLP

(57) ABSTRACT

Methods and compositions disclosed herein generally relates to methods of determining minimum hematopoietic stem cell (HSC) chimerism and gene dosage for correction of a hematopoietic disease; in particular, in in vivo models. The invention also relates to modified lentiviral expression vectors for increasing a viral titer and various methods for increasing such titers as well as expression vectors capable of enhancing such titers. The invention also relates to CHS4 chromatin insulator-derived functional insulator sequences. The invention also relates to methods for genetic correction of diseases or reducing symptoms thereof, such as sickle cell anemia or β-thalassemia.

24 Claims, 51 Drawing Sheets

Specification includes a Sequence Listing.

(56) References Cited

OTHER PUBLICATIONS

Berkhout et al., Structural features in the HIV-1 repeat region facilitate strand transfer during reverse transcription. RNA. Aug. 2001;7(8):1097-114.
Bernaudin et al., Long-term results of related myeloablative stem-cell transplantation to cure sickle cell disease. Blood. Oct. 1, 2007;110(7):2749-56. Epub Jul. 2, 2007.
Berthold et al., cis-acting elements in human immunodeficiency virus type 1 RNAs direct viral transcripts to distinct intranuclear locations. J Virol. Jul. 1996;70(7):4667-82.
Biffi et al., Gene therapy of metachromatic leukodystrophy reverses neurological damage and deficits in mice. J Clin Invest. Nov. 2006;116(11):3070-82.
Blouin et al., Genetic correction of sickle cell disease: insights using transgenic mouse models. Nat Med. Feb. 2000;6(2):177-82.
Brandt et al., Rev proteins of human and simian immunodeficiency virus enhance RNA encapsidation. PLoS Pathog. Apr. 2007;3(4):e54.
Brooks et al., Glycosidase active site mutations in human alpha-L-iduronidase. Glycobiology. Sep. 2001;11(9):741-50.
Brown et al., Correct integration of retroviral DNA in vitro. Cell. May 8, 1987;49(3):347-56.
Brule et al., In vitro evidence for the interaction of tRNA(3)(Lys) with U3 during the first strand transfer of HIV-1 reverse transcription. Nucleic Acids Res. Jan. 15, 2000;28(2):634-40.
Buchman et al., Comparison of intron-dependent and intron-independent gene expression. Mol Cell Biol. Oct. 1988;8(10):4395-405.
Buchschacher et al., Human immunodeficiency virus vectors for inducible expression of foreign genes. J Virol. May 1992;66(5):2731-9.
Bukrinsky et al., Active nuclear import of human immunodeficiency virus type 1 preintegration complexes. Proc Natl Acad Sci U S A. Jul. 15, 1992;89(14):6580-4.
Bushman, Retroviral integration and human gene therapy. J Clin Invest. Aug. 2007;117(8):2083-6.
Butler et al., A quantitative assay for HIV DNA integration in vivo. Nat Med. May 2001;7(5):631-4.
Carr et al., Effect of deletion and the site of insertion in double copy anti-tat retroviral vectors: viral titres and production of anti-tat mRNA. Arch Virol. 2001;146(11):2191-200.
Cavazzana-Calvo et al., Gene therapy of human severe combined immunodeficiency (SCID)-X1 disease. Science. Apr. 28, 2000;288(5466):669-72.
Cavazzana-Calvo et al., Hematopoietic stem cell gene therapy trial with lentiviral vector in X-linked adrenoleukodystrophy. Blood (ASH Annual Meeting Abstracts), 2008, (suppl)112, Abstract 821.
Challita et al., Lack of expression from a retroviral vector after transduction of murine hematopoietic stem cells is associated with methylation in vivo. Proc Natl Acad Sci U S A. Mar. 29, 1994;91(7):2567-71.
Chang et al., A 36-base-pair core sequence of locus control region enhances retrovirally transferred human beta-globin gene expression. Proc Natl Acad Sci U S A. Apr. 1, 1992;89(7):310710.
Chang et al., Messenger RNA transport and HIV rev regulation. Science. Aug. 10, 1990;249(4969):614-5.
Chang et al., Stem cell-derived erythroid cells mediate long-term systemic protein delivery. Nat Biotechnol. Aug. 2006;24(8):1017-21. Epub Jul. 16, 2006.
Chang et al., The genetic engineering of hematopoietic stem cells: the rise of lentiviral vectors, the conundrum of the ltr, and the promise of lineage-restricted vectors. Mol Ther. Mar. 2007;15(3):445-56.
Charache et al., Hydroxyurea-induced augmentation of fetal hemoglobin production in patients with sickle cell anemia. Blood. Jan. 1987;69(1):109-16.
Chasis et al., Erythroblastic islands: niches for erythropoiesis. Blood. Aug. 1, 2008;112(3):470-8. doi: 10.1182/bload-2008-03-077883.
Chung et al., Characterization of the chicken beta-globin insulator. Proc Natl Acad Sci U S A. Jan. 21, 1997;94(2):575-80.
Coffin, Retroviridae and their replication. Fields Virology (2nd Edition). New York, Raven Press. 1990. 1437-500.
Cone et al., Regulated expression of a complete human beta-globin gene encoded by a transmissible retrovirus vector. Mol Cell Biol. Feb. 1987;7(2):887-97.
Costa et al., Expansion of human embryonic stem cells in vitro. Curr Protoc Stem Cell Biol. May 2008;Chapter 1:Unit 1C.1.1-1C.1.7. doi: 10.1002/9780470151808.sc01c01s5.
Crusselle-Davis et al., Antagonistic regulation of beta-globin gene expression by helix-loop-helix proteins USF and TFII-I. Mol Cell Biol. Sep. 2006;26(18):6832-43.
Cuddapah et al., Global analysis of the insulator binding protein CTCF in chromatin barrier regions reveals demarcation of active and repressive domains. Genome Res. Jan. 2009;19(1):24-32. doi: 10.1101/gr.082800.108. Epub Dec. 3, 2008.
Cui et al., Contributions of viral splice sites and cis-regulatory elements to lentivirus vector function. J Virol. Jul. 1999;73(7):6171-6.
Darbari et al., Circumstances of death in adult sickle cell disease patients. Am J Hematol. Nov. 2006;81(11):858-63.
Davis et al., National trends in the mortality of children with sickle cell disease, 1968 through 1992. Am J Public Health. Aug. 1997;87(8):1317-22.
Di Domenico et al., Gene therapy for a mucopolysaccharidosis type I murine model with lentiviral-IDUA vector. Hum Gene Ther. Jan. 2005;16(1):81-90.
Dull et al., A third-generation lentivirus vector with a conditional packaging system. J Virol. Nov. 1998;72(11):8463-71.
Dzierzak et al., Lineage-specific expression of a human beta-globin gene in murine bone marrow transplant recipients reconstituted with retrovirus-transduced stem cells. Nature. Jan. 7, 1988;331(6151):35-41.
Ellis, Silencing and variegation of gammaretrovirus and lentivirus vectors. Hum Gene Ther. Nov. 2005;16(11):1241-6.
Elnitski et al., Conserved E boxes function as part of the enhancer in hypersensitive site 2 of the beta-globin locus control region. Role of basic helix-loop-helix proteins. J Biol Chem. Jan. 3, 1997;272(1):369-78.
Emery et al., Development of virus vectors for gene therapy of beta chain hemoglobinopathies: flanking with a chromatin insulator reduces gamma-globin gene silencing in vivo. Blood. Sep. 15, 2002;100(6):2012-9.
EP 15744021.5, mailed May 19, 2017, Extended European Search Report.
Evans-Galea et al., Suppression of clonal dominance in cultured human lymphoid cells by addition of the cHS4 insulator to a lentiviral vector. Mol Ther. 2000;15:801-9.
Fabry et al., Second generation knockout sickle mice: the effect of HbF. Blood. Jan. 15, 2001;97(2):410-8.
Favaro et al., Effect of Rev on the intranuclear localization of HIV-1 unspliced RNA. Virology. Sep. 30, 1998;249(2):286-96.
Felber et al., rev protein of human immunodeficiency virus type 1 affects the stability and transport of the viral mRNA. Proc Natl Acad Sci U S A. Mar. 1989;86(5):1495-9.
Felsenfeld et al., Chromatin boundaries and chromatin domains. Cold Spring Harb Symp Quant Biol. 2004;69:245-50.
Fischer et al., Evidence that HIV-1 Rev directly promotes the nuclear export of unspliced RNA. EMBO J. Sep. 1, 1994;13(17):4105-12.
Fischer et al., LMO2 and gene therapy for severe combined immunodeficiency. N Engl J Med. Jun. 10, 2004;350(24):2526-7; author reply 2526-7.
Fitzhugh et al., Late effects of myeloablative bone marrow transplantation (BMT) in sickle cell disease (SCD). Blood. Feb. 1, 2008;111(3):1742-3; author reply 1744. doi: 10.1182/blood-2007-10-118257.
Franco et al., Time-dependent changes in the density and hemoglobin F content of biotin-labeled sickle cells. J Clin Invest. Jun. 15, 1998;101(12):2730-40.

(56) References Cited

OTHER PUBLICATIONS

Gaspar et al., Successful reconstitution of immunity in ADA-SCID by stem cell gene therapy following cessation of PEG-ADA and use of mild preconditioning. Mol Ther. Oct. 2006;14(4):505-13. Epub Aug. 14, 2006.
Gelinas et al., The v-rel oncogene encodes a cell-specific transcriptional activator of certain promoters. Oncogene. Oct. 1988;3(4):349-55.
Geminard et al., Reticulocyte maturation: mitoptosis and exosome release. Biocell. Aug. 2002;26(2):205-15.
Gerasimova et al., A chromatin insulator determines the nuclear localization of DNA. Mol Cell. Nov. 2000;6(5):1025-35.
Giralt, Reduced-intensity conditioning regimens for hematologic malignancies: what have we learned over the last 10 years? Hematology Am Soc Hematol Educ Program. 2005:384-9.
Grande et al., Transcriptional targeting of retroviral vectors to the erythroblastic progeny of transduced hematopoietic stem cells. Blood. May 15, 1999;93(10):3276-85.
Grewal et al., Continued neurocognitive development and prevention of cardiopulmonary complications after successful BMT for I-cell disease: a long-term follow-up report. Bone Marrow Transplant. Nov. 2003;32(9):957-60.
Grubb et al., Chemically modified beta-glucuronidase crosses blood-brain barrier and clears neuronal storage in murine mucopolysaccharidosis VII. Proc Natl Acad Sci U S A. Feb. 19, 2008;105(7):2616-21. doi: 10.1073/pnas.0712147105. Epub Feb. 11, 2008.
Hacein-Bey-Abina et al., Insertional oncogenesis in 4 patients after retrovirus-mediated gene therapy of SCID-X1. J Clin Invest. Sep. 2008;118(9):3132-42. doi: 10.1172/JCI35700.
Hacein-Bey-Abina et al., LMO2-associated clonal T cell proliferation in two patients after gene therapy for SCID-X1. Science. Oct. 17, 2003;302(5644):415-9. Erratum in: Science. Oct. 24, 2003;302(5645):568.
Hacein-Bey-Abina et al., Sustained correction of X-linked severe combined immunodeficiency by ex vivo gene therapy. N Engl J Med. Apr. 18, 2002;346(16):1185-93.
Hanenberg et al., Phenotypic correction of primary Fanconi anemia T cells with retroviral vectors as a diagnostic tool. Exp Hematol. May 2002;30(5):410-20.
Hansen et al., Integration complexes derived from HIV vectors for rapid assays in vitro. Nat Biotechnol. Jun. 1999;17(6):578-82.
Hardeman et al., Clinical potential of in vitro measured red cell deformability, a myth? Clin Hemorheol Microcirc. 1999;21(3-4):277-84.
Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.
Heilman-Miller et al., Alteration of nucleic acid structure and stability modulates the efficiency of minus-strand transfer mediated by the HIV-1 nucleocapsid protein. J Biol Chem. Oct. 15, 2004;279(42):44154-65. Epub Jul. 22, 2004.
Herman et al., Efficient packaging of readthrough RNA in ALV: implications for oncogene transduction. Science. May 15, 1987;236(4803):845-8.
Higashimoto et al., The woodchuck hepatitis virus post-transcriptional regulatory element reduces readthrough transcription from retroviral vectors. Gene Ther. Sep. 2007;14(17):1298-304. Epub Jun. 28, 2007.
Hildinger et al., Design of 5' untranslated sequences in retroviral vectors developed for medical use. J Virol. May 1999;73(5):4083-9.
Hopwood et al., The mucopolysaccharidoses. Diagnosis, molecular genetics and treatment. Mol Biol Med. Oct. 1990;7(5):381-404.
Horan et al., Hematopoietic stem cell transplantation for multiply transfused patients with sickle cell disease and thalassemia after low-dose total body irradiation, fludarabine, and rabbit antithymocyte globulin. Bone Marrow Transplant. Jan. 2005;35(2):171-7.
Howe et al., Insertional mutagenesis combined with acquired somatic mutations causes leukemogenesis following gene therapy of SCID-X1 patients. J Clin Invest. Sep. 2008;118(9):3143-50. doi: 10.1172/JC135798.
Huang et al., Derepression of human embryonic zeta-globin promoter by a locus-control region sequence. Proc Natl Acad Sci U S A. Dec. 8, 1998;95(25):14669-74.
Huang et al., Intronless mRNA transport elements may affect multiple steps of pre-mRNA processing. EMBO J. Mar. 15, 1999;18(6):1642-52.
Huang et al., USF1 recruits histone modification complexes and is critical for maintenance of a chromatin barrier. Mol Cell Biol. Nov. 2007;27(22):7991-8002. Epub Sep. 10, 2007.
Iannone et al., Effects of mixed hematopoietic chimerism in a mouse model of bone marrow transplantation for sickle cell anemia. Blood. Jun. 15, 2001;97(12):3960-5.
Iannone et al., Results of minimally toxic nonmyeloablative transplantation in patients with sickle cell anemia and beta-thalassemia. Biol Blood Marrow Transplant. Aug. 2003;9(8):519-28.
Ilves et al., Retroviral vectors designed for targeted expression of RNA polymerase III-driven transcripts: a comparative study. Gene. Jun. 1, 1996;171(2):203-8.
Imren et al., Permanent and panerythroid correction of murine beta thalassemia by multiple lentiviral integration in hematopoietic stem cells. Proc Natl Acad Sci U S A. Oct. 29, 2002;99(22):14380-5. Epub Oct. 21, 2002.
Julias et al., Replication of phenotypically mixed human immunodeficiency virus type 1 virions containing catalytically active and catalytically inactive reverse transcriptase. J Virol. Jul. 2001;75(14):6537-46.
Junker et al., Antiviral potency of drug-gene therapy combinations against human immunodeficiency virus type 1. AIDS Res Hum Retroviruses. Nov. 1, 1997;13(16):1395-402.
Junker et al., Genetic instability of a MoMLV-based antisense double-copy retroviral vector designed for HIV-1 gene therapy. Gene Ther. Nov. 1995;2(9):639-46.
Kalberer et al., Preselection of retrovirally transduced bone marrow avoids subsequent stem cell gene silencing and age-dependent extinction of expression of human beta-globin in engrafted mice. Proc Natl Acad Sci U S A. May 9, 2000;97(10):5411-5.
Kalfa et al., Rac1 and Rac2 GTPases are necessary for early erythropoietic expansion in the bone marrow but not in the spleen. Haematologica. Jan. 2010;95(1):27-35. doi: 10.3324/haematol.2009.006239.
Karlsson et al., Expression of the human beta-globin gene following retroviral-mediated transfer into multipotential hematopoietic progenitors of mice. Proc Natl Acad Sci U S A. 1998;85:6062-6.
Kaye et al., cis-acting sequences involved in human immunodeficiency virus type 1 RNA packaging. J Virol. Oct. 1995;69(10):6588-92.
Kean et al., A cure for murine sickle cell disease through stable mixed chimerism and tolerance induction after nonmyeloablative conditioning and major histocompatibility complex-mismatched bone marrow transplantation. Blood. Mar. 1, 2002;99(5):1840-9.
Kean et al., Chimerism and cure: hematologic and pathologic correction of murine sickle cell disease. Blood. Dec. 15, 2003;102(13):4582-93. Epub Aug. 21, 2003.
Kelly et al., Stem cell collection and gene transfer in Fanconi anemia. Mol Ther. Jan. 2007;15(1):211-9.
Kennedy et al., Mature monocytic cells enter tissues and engraft. Proc Natl Acad Sci. 1998;USA 95:14944-9.
Kim et al., Analysis of the vertebrate insulator protein CTCF-binding sites in the human genome. Cell. Mar. 23, 2007;128(6):1231-45.
Kim et al., Distinctive signatures of histone methylation in transcribed coding and noncoding human beta-globin sequences. Mol Cell Biol. Feb. 2007;27(4):1271-9. Epub Dec. 11, 2006.
Kohn et al., Occurrence of leukaemia following gene therapy of X-linked SCID. Nat Rev Cancer. Jul. 2003;3(7):477-88. Erratum in: Nat Rev Cancer. Nov. 2003;3(11):883.

(56) References Cited

OTHER PUBLICATIONS

Kohn et al., T lymphocytes with a normal ADA gene accumulate after transplantation of transduced autologous umbilical cord blood CD34+ cells in ADA-deficient SCID neonates. Nat Med. Jul. 1998;4(7):775-80.
Kohn, Lentiviral vectors ready for prime-time. Nat Biotechnol. Jan. 2007;25(1):65-6.
Koshy et al., 2-deoxy 5-azacytidine and fetal hemoglobin induction in sickle cell anemia. Blood. Oct. 1, 2000;96(7):2379-84.
Kraunus et al., Murine leukemia virus regulates alternative splicing through sequences upstream of the 5' splice site. J Biol Chem. Dec. 8, 2006;281(49):37381-90. Epub Oct. 11, 2006.
Kraunus et al., Self-inactivating retroviral vectors with improved RNA processing. Gene Ther. Nov. 2004;11(21):1568-78.
Krishnamurti et al., Bone marrow transplantation without myeloablation for sickle cell disease. N Engl J Med. Jan. 4, 2001;344(1):68.
Krishnamurti et al., Stable long-term donor engraftment following reduced-intensity hematopoietic cell transplantation for sickle cell disease. Biol Blood Marrow Transplant. Nov. 2008;14(11):1270-8. doi: 10.1016/j.bbmt.2008.08.016.
Kumar et al., Systematic determination of the packaging limit of lentiviral vectors. Hum Gene Ther. Oct. 10, 2001;12(15):1893-905.
Kurukuti et al., CTCF binding at the H19 imprinting control region mediates maternally inherited higher-order chromatin conformation to restrict enhancer access to Igf2. Proc Natl Acad Sci U S A. Jul. 11, 2006; 103(28): 10684-9. Epub Jun. 30, 2006.
Lavenu-Bombled et al., Glycoprotein Ibalpha promoter drives megakaryocytic lineage-restricted expression after hematopoietic stem cell transduction using a self-inactivating lentiviral vector. Stem Cells. Jun. 2007;25(6):1571-7. Epub Mar. 22, 2007.
Leboulch et al., Mutagenesis of retroviral vectors transducing human beta-globin gene and beta-globin locus control region derivatives results in stable transmission of an active transcriptional structure. EMBO J. Jul. 1, 1994;13(13):3065-76.
Levasseur et al., Correction of a mouse model of sickle cell disease: lentiviral/antisickling beta-globin gene transduction of unmobilized, purified hematopoietic stem cells. Blood. Dec. 15, 2003;102(13):4312-9. Epub Aug. 21, 2003.
Li et al., The cHS4 chromatin insulator reduces gammaretroviral vector silencing by epigenetic modifications of integrated provirus. Gene Ther. Jan. 2008;15(1):49-53. Epub Nov. 8, 2007.
Litt et al., Transitions in histone acetylation reveal boundaries of three separately regulated neighboring loci. EMBO J. May 1, 2001;20(9):2224-35.
Litt et al., Correlation between histone lysine methylation and developmental changes at the chicken beta-globin locus. Science. Sep. 28, 2001;293(5539):2453-5. Epub Aug. 9, 2001.
Luban et al., Binding of human immunodeficiency virus type 1 (HIV-1) RNA to recombinant HIV-1 gag polyprotein. J Virol. 1991;65:3203-12.
Maier-Redelsperger et al., Fetal hemoglobin and F-cell responses to long-term hydroxyurea treatment in young sickle cell patients. The French Study Group on Sickle Cell Disease. Blood. Jun. 15, 1998;91(12):4472-9.
Maier-Redelsperger et al., Variation in fetal hemoglobin parameters and predicted hemoglobin S polymerization in sickle cell children in the first two years of life: Parisian Prospective Study on Sickle Cell Disease. Blood. Nov. 1, 1994;84(9):3182-8.
Malim et al., The HIV-1 rev trans-activator acts through a structured target sequence to activate nuclear export of unspliced viral mRNA. Nature. Mar. 16, 1989;338(6212):254-7.
Manci et al., Pathology of Berkeley sickle cell mice: similarities and differences with human sickle cell disease. Blood. Feb. 15, 2006;107(4):1651-8. Epub Sep. 15, 2005.
Marcus et al., Physiologic decline in fetal hemoglobin parameters in infants with sickle cell disease: implications for pharmacological intervention. J Pediatr Hematol Oncol. Sep.-Oct. 1999;21(5):407-11.
May et al., Therapeutic haemoglobin synthesis in beta-thalassaemic mice expressing lentivirus-encoded human beta-globin. Nature. Jul. 6, 2000;406(6791):82-6.
McGrath et al., Multispectral imaging of hematopoietic cells: where flow meets morphology. J Immunol Methods. Jul. 31, 2008;336(2):91-7. doi: 10.1016/j.jim.2008.04.012. Epub May 15, 2008.
Metais et al., The MDS1-EVI1 gene complex as a retrovirus integration site: impact on behavior of hematopoietic cells and implications for gene therapy. Mol Ther. Mar. 2008;16(3):439-49. doi: 10.1038/sj.mt.6300372. Epub Jan. 29, 2008.
Miller et al., Human immunodeficiency virus type 1 preintegration complexes: studies of organization and composition. J Virol. Jul. 1997;71(7):5382-90.
Miyoshi et al., Development of a self-inactivating lentivirus vector. J Virol. Oct. 1998;72(10):8150-7.
Modlich et al., Cell-culture assays reveal the importance of retroviral vector design far insertional genotoxicity. Blood. Oct. 15, 2006;108(8):2545-53. Epub Jul. 6, 2006.
Mohamedali et al., Self-inactivating lentiviral vectors resist proviral methylation but do not confer position-independent expression in hematopoietic stem cells. Mol Ther. Aug. 2004;10(2):249-59.
Montini et al., Hematopoietic stem cell gene transfer in a tumor-prone mouse model uncovers law genotoxicity of lentiviral vector integration. Nat Biotechnol. Jun. 2006;24(6):687-96. Epub May 28, 2006.
Moreau-Gaudry et al., High-level erythroid-specific gene expression in primary human and murine hematopoietic cells with self-inactivating lentiviral vectors. Blood. Nov. 1, 2001;98(9):266472.
Mutskov et al., The barrier function of an insulator couples high histone acetylation levels with specific protection of promoter DNA from methylation. Genes Dev. Jun. 15, 2002;16(12):1540-54.
Neff et al., Stem cell gene therapy, position effects and chromatin insulators. Stem Cells. 1997;15 Suppl 1:265-71.
Negroni et al., Copy-choice recombination by reverse transcriptases: reshuffling of genetic markers mediated by RNA chaperones. Proc Natl Acad Sci U S A. Jun. 6, 2000;97(12):6385-90.
Ney et al., Gene expression during terminal erythroid differentiation. Curr Opin Hematol. Jul. 2006;13(4):203-8.
Noronha et al., Hemoglobin-specific antibody in a multiply transfused patient with sickle cell disease. Blood. Mar. 15, 1997;89(6):2155-8.
Novak et al., High-level beta-globin expression after retroviral transfer of locus activation region-containing human beta-globin gene derivatives into murine erythroleukemia cells. Proc Natl Acad Sci U S A. May 1990;87(9):3386-90.
Ohi et al., Sequences in the 5' and 3' R elements of human immunodeficiency virus type 1 critical for efficient reverse transcription. J Virol. Sep. 2000;74(18):8324-34.
Ohmi et al., Activated microglia in cortex of mouse models of mucopolysaccharidoses I and IIIB. Proc Natl Acad Sci U S A. Feb. 18, 2003;100(4):1902-7. Epub Feb. 7, 2003.
Ono et al., Nucleotide sequence of human endogenous retrovirus genome related to the mouse mammary tumor virus genome. J Virol. Nov. 1986;60(2):589-98.
Osborne et al., Amelioration of retroviral vector silencing in locus control region beta-globin-transgenic mice and transduced F9 embryonic cells. J Virol. Jul. 1999;73(7):5490-6.
Ott et al., Correction of X-linked chronic granulomatous disease by gene therapy, augmented by insertional activation of MDS1-EVI1, PRDM16 or SETBP1. Nat Med. Apr. 2006; 12(4):401-9. Epub Apr. 2, 2006.
Pan et al., Biodistribution and toxicity studies of VSVG-pseudotyped lentiviral vector after intravenous administration in mice with the observation of in vivo transduction of bone marrow. Mol Ther. Jul. 2002;6(1):19-29.
Pan et al., Improved gene transfer and normalized enzyme levels in primitive hematopoietic progenitors from patients with mucopolysaccharidosis type I using a bioreactor. J Gene Med. Dec. 2004;6(12):1293-303.
Pan et al., Progression of multiple behavioral deficits with various ages of onset in a murine model of Hurler syndrome. Brain Res. Jan. 10, 2008;1188:241-53. Epub Oct. 23, 2007.

(56) References Cited

OTHER PUBLICATIONS

Pan et al., Retroviral vector design studies toward hematopoietic stem cell gene therapy for mucopolysaccharidosis type I. Gene Ther. Nov. 2000;7(21):1875-83.
Pannell et al., Retrovirus vector silencing is de novo methylase independent and marked by a repressive histone code. EMBO J. Nov. 1, 2000;19(21):5884-94.
Pant et al., Mutation of a single CTCF target site within the H19 imprinting control region leads to loss of Igf2 imprinting and complex patterns of de novo methylation upon maternal inheritance. Mol Cell Biol. Apr. 2004;24(8):3497-504.
Parelho et al., Cohesins functionally associate with CTCF on mammalian chromosome arms. Cell. Feb. 8, 2008;132(3):422-33. doi: 10.1016/j.cell.2008.01.011. Epub Jan. 31, 2008.
Parolin et al., Analysis in human immunodeficiency virus type 1 vectors of cis-acting sequences that affect gene transfer into human lymphocytes. J Virol. Jun. 1994;68(6):3888-95.
Paszty et al., Transgenic knockout mice with exclusively human sickle hemoglobin and sickle cell disease. Science. Oct. 31, 1997;278(5339):876-8.
Pathak et al., Broad spectrum of in vivo forward mutations, hypermutations, and mutational hotspots in a retroviral shuttle vector after a single replication cycle: deletions and deletions with insertions. Proc Natl Acad Sci U S A. Aug. 1990;87(16):6024-8.
Pawliuk et al., Correction of sickle cell disease in transgenic mouse models by gene therapy. Science. Dec. 14, 2001;294(5550):2368-71.
PCT/US2015/013960, mailed Aug. 11, 2016, International Preliminary Report on Patentability.
PCT/US2015/013960, mailed May 15, 2015, International Search Report and Written Opinion.
Persons et al., The degree of phenotypic correction of murine beta-thalassemia intermedia following lentiviral-mediated transfer of a human gamma-globin gene is influenced by chromosomal position effects and vector copy number. Blood. Mar. 15, 2003;101(6):2175-83. Epub Oct. 31, 2002.
Perumbeti et al., A novel human gamma-globin gene vector for genetic correction of sickle cell anemia in a humanized sickle mouse model: critical determinants for successful correction. Blood. Aug. 6, 2009;114(6):1174-85. doi:10.1182/blood-2009-01-201863. Epub May 27, 2009.
Pestina et al., Correction of murine sickle cell disease using gamma-globin lentiviral vectors to mediate high-level expression of fetal hemoglobin. Mol Ther. Feb. 2009;17(2):245-52. doi: 10.1038/mt.2008.259. Epub Dec. 2, 2008.
Peters et al., Outcome of unrelated donor bone marrow transplantation in 40 children with Hurler syndrome. Blood. Jun. 1, 1996;87(11):4894-902.
Pfarr et al., Differential effects of polyadenylation regions on gene expression in mammalian cells. DNA. Apr. 1986;5(2):115-22.
Pikaart et al., Loss of transcriptional activity of a transgene is accompanied by DNA methylation and histone deacetylation and is prevented by insulators. Genes Dev. Sep. 15, 1998;12(18):2852-62.
Platt et al., Mortality in sickle cell disease. Life expectancy and risk factors for early death. N Engl J Med. Jun. 9, 1994;330(23):1639-44.
Plavec et al., A human beta-globin gene fused to the human beta-globin locus control region is expressed at high levels in erythroid cells of mice engrafted with retrovirus-transduced hematopoietic stem cells. Blood. Mar. 1, 1993;81(5):1384-92.
Prandini et al., Characterization of a specific erythromegakaryocytic enhancer within the glycoprotein IIb promoter. J Biol Chem. May 25, 1992;267(15):10370-4.
Puthenveetil et al., Gene therapy for hemoglobinopathies: are we there yet? Curr Hematol Rep. Jul. 2004;3(4):298-305.
Puthenveetil et al., Successful correction of the human beta-thalassemia major phenotype using a lentiviral vector. Blood. Dec. 1, 2004;104(12):3445-53. Epub Aug. 3, 2004.
Ramezani et al., Performance- and safety-enhanced lentiviral vectors containing the human interferon-beta scaffold attachment region and the chicken beta-globin insulator. Blood. Jun. 15, 2003;101(12):4717-24. Epub Feb. 13, 2003.
Recillas-Targa et al., Position-effect protection and enhancer blocking by the chicken beta-globin insulator are separable activities. Proc Natl Acad Sci U S A. May 14, 2002;99(10):6883-8.
Recillas-Targa et al., Positional enhancer-blocking activity of the chicken beta-globin insulator in transiently transfected cells. Proc Natl Acad Sci U S A. Dec. 7, 1999;96(25):14354-9.
Richardson et al., Packaging of human immunodeficiency virus type 1 RNA requires cis-acting sequences outside the 5' leader region. J Virol. Jul. 1993;67(7):3997-4005.
Rivella et al., A novel murine model of Cooley anemia and its rescue by lentiviral-mediated human beta-globin gene transfer. Blood. Apr. 15, 2003;101(8):2932-9. Epub Dec. 12, 2002.
Rivella et al., The cHS4 insulator increases the probability of retroviral expression at random chromosomal integration sites. J Virol. May 2000;74(10):4679-87.
Roces et al., Efficacy of enzyme replacement therapy in alpha-mannosidosis mice: a preclinical animal study. Hum Mol Genet. Sep. 15, 2004;13(18):1979-88. Epub Jul. 21, 2004.
Rubin et al., Locus control region activity by 5'HS3 requires a functional interaction with beta-globin gene regulatory elements: expression of novel beta/gamma-globin hybrid transgenes. Blood. May 15, 2000;95(10):3242-9.
Ryu et al., A chromatin insulator blocks interactions between globin regulatory elements and cellular promoters in erythroid cells. Blood Cells Mol Dis. Nov.-Dec. 2007;39(3):221-8. Epub Jun. 29, 2007.
Ryu et al., An experimental system for the evaluation of retroviral vector design to diminish the risk for proto-oncogene activation. Blood. Feb. 15, 2008; 111(4):1866-75. Epub Nov. 8, 2007.
Sabatino et al., A minimal ankyrin promoter linked to a human gamma-globin gene demonstrates erythroid specific copy No. dependent expression with minimal position or enhancer dependence in transgenic mice. J Biol Chem. Sep. 15, 2000;275(37):28549-54.
Sabatino et al., Long-term expression of gamma-globin mRNA in mouse erythrocytes from retrovirus vectors containing the human gamma-globin gene fused to the ankyrin-1 promoter. Proc Natl Acad Sci U S A. Nov. 21, 2000;97(24):13294-9.
Sadelain et al., Generation of a high-titer retroviral vector capable of expressing high levels of the human beta-globin gene. Proc Natl Acad Sci U S A. Jul. 18, 1995;92(15):6728-32.
Saitoh et al., Structural and functional conservation at the boundaries of the chicken beta-globin domain. EMBO J. May 15, 2000;19(10):2315-22.
Samakoglu et al., A genetic strategy to treat sickle cell anemia by coregulating globin transgene expression and RNA interference. Nat Biotechnol. Jan. 2006;24(1):89-94. Epub Dec. 25, 2005.
Schambach et al., Improving transcriptional termination of self-inactivating gamma-retroviral and lentiviral vectors. Mol Ther. Jun. 2007;15(6):1167-73. Epub Apr. 3, 2007.
Schambach et al., Overcoming promoter competition in packaging cells improves production of self-inactivating retroviral vectors. Gene Ther. Nov. 2006;13(21):1524-33. Epub Jun. 8, 2006.
Schwartz et al., Mutational inactivation of an inhibitory sequence in human immunodeficiency virus type 1 results in Rev-independent gag expression. J Virol. Dec. 1992;66(12):7176-82.
Scott et al., Human alpha-L-iduronidase: cDNA isolation and expression. Proc Natl Acad Sci USA. Nov. 1, 1991;88(21):9695-9.
Shang et al., Cofactor dynamics and sufficiency in estrogen receptor-regulated transcription. Cell. Dec. 8, 2000;103(6):843-52.
Shin et al., Replication of lengthened Moloney murine leukemia virus genomes is impaired at multiple stages. J Virol. Mar. 2000;74(6):2694-702.
Sly et al., Enzyme therapy in mannose receptor-null mucopolysaccharidosis VII mice defines roles for the mannose 6-phosphate and mannose receptors. Proc Natl Acad Sci USA. Oct. 10, 2006;103(41):15172-7. Epub Oct. 2, 2006.
Smith et al., Genome wide ChIP-chip analyses reveal important roles for CTCF in *Drosophila* genome organization. Dev Biol. Apr. 15, 2009;328(2):518-28. doi: 10.1016/j.ydbio.2008.12.039. Epub Jan. 8, 2009.

(56) References Cited

OTHER PUBLICATIONS

Socolovsky et al., Ineffective erythropoiesis in Stat5a(-/-)5b(-/-) mice due to decreased survival of early erythroblasts. Blood. Dec. 1, 2001;98(12):3261-73.
Souillet et al., Outcome of 27 patients with Hurler's syndrome transplanted from either related or unrelated haematopoietic stem cell sources. Bone Marrow Transplant. Jun. 2003;31(12):1105-17.
Splinter et al., CTCF mediates long-range chromatin looping and local histone modification in the beta-globin locus. Genes Dev. Sep. 1, 2006;20(17):2349-54.
Staba et al., Cord-blood transplants from unrelated donors in patients with Hurler's syndrome. N Engl J Med. May 6, 2004;350(19):1960-9.
Steinberg et al., Effect of hydroxyurea on mortality and morbidity in adult sickle cell anemia: risks and benefits up to 9 years of treatment. JAMA. Apr. 2, 2003;289(13):1645-51. Erratum in: JAMA. Aug. 13, 2003;290(6):756.
Stumph et al., Genomic structure and possible retroviral origin of the chicken CR1 repetitive DNA sequence family. Proc Natl Acad Sci USA. Nov. 1984;81(21):6667-71.
Sundquist et al., Evidence for interstrand quadruplex formation in the dimerization of human immunodeficiency virus 1 genomic RNA. Proc Natl Acad Sci U S A. Apr. 15, 1993;90(8):3393-7.
Surinya et al., Identification and characterization of a conserved erythroid-specific enhancer located in intron 8 of the human 5-aminolevulinate synthase 2 gene. J Biol Chem. Jul. 3, 1998;273(27):16798-809.
Swanson et al., Doms RW, Malim MH. Retroviral mRNA nuclear export elements regulate protein function and virion assembly. EMBO J. Jul. 7, 2004;23(13):2632-40. Epub Jun. 17, 2004.
Thrasher et al., Gene therapy. X-SCID transgene leukaemogenicity. Nature. Sep. 21, 2006;443(7109):E5-6; discussion E6-7.
Topping et al., Cis-acting elements required for strong stop acceptor template selection during Moloney murine leukemia virus reverse transcription. J Mol Biol. Aug. 7, 1998;281(1):1-15.
Trudel et al., Sickle cell disease of transgenic SAD mice. Blood. Nov. 1, 1994;84(9):3189-97.
Urbinati et al., Mechanism of reduction in titers from lentivirus vectors carrying large inserts in the 3'LTR. Mol Ther. Sep. 2009;17(9):1527-36. doi: 10.1038/mt.2009.89. Epub Apr. 21, 2009.
Vogler et al., Overcoming the blood-brain barrier with high-dose enzyme replacement therapy in murine mucopolysaccharidosis VII. Proc Natl Acad Sci U S A. Oct. 11, 2005;102(41):14777-82. Epub Sep. 14, 2005.
Von Kalle et al., Lenti in red: progress in gene therapy for human hemoglobinopathies. J Clin Invest. Oct. 2004;114(7):889-91.
Wallace et al., We gather together: insulators and genome organization. Curr Opin Genet Dev. Oct. 2007;17(5):400-7. Epub Oct. 24, 2007.
Walters et al., Barriers to bone marrow transplantation for sickle cell anemia. Biol Blood Marrow Transplant. May 1996;2(2):100-4.
Walters et al., Stable mixed hematopoietic chimerism after bone marrow transplantation for sickle cell anemia. Biol Blood Marrow Transplant. 2001;7(12):665-73.
Wang et al., Reprogramming erythroid cells for lysosomal enzyme production leads to visceral and CNS cross-correction in mice with Hurler syndrome. Proc Natl Acad Sci USA. Nov. 24, 2009;106(47):19958-63. doi: 10.1073/pnas.0908528106. Epub Nov. 10, 2009.
Wendt et al., Cohesin mediates transcriptional insulation by CCCTC-binding factor. Nature. Feb. 14, 2008;451(7180):796-801. doi: 10.1038/nature06634. Epub Jan. 30, 2008.
West et al., Recruitment of histone modifications by USF proteins at a vertebrate barrier element. Mol Cell. Nov. 5, 2004;16(3):453-63.
Williams et al., The role of CTCF in regulating nuclear organization. J Exp Med. Apr. 14, 2008;205(4):747-50. doi: 10.1084/jem.20080066. Epub Mar. 17, 2008.
Wiznerowicz et al., Development of a double-copy bicistronic retroviral vector for human gene therapy. Adv Exp Med Biol. 1998;451:441-7.
Wiznerowicz et al., Double-copy bicistronic retroviral vector platform for gene therapy and tissue engineering: application to melanoma vaccine development. Gene Ther. Oct. 1997;4(10):1061-8.
Worsham et al., In vivo gene transfer into adult stem cells in unconditioned mice by in situ delivery of a lentiviral vector. Mol Ther. Oct. 2006;14(4):514-24. Epub Aug. 7, 2006.
Wu et al., Effects of nucleic acid local structure and magnesium ions on minus-strand transfer mediated by the nucleic acid chaperone activity of HIV-1 nucleocapsid protein. Nucleic Acids Res. 2007;35(12):3974-87. Epub Jun. 6, 2007.
Xie et al., Systematic discovery of regulatory motifs in conserved regions of the human genome, including thousands of CTCF insulator sites. Proc Natl Acad Sci U S A. Apr. 24, 2007;104(17):7145-50. Epub Apr. 18, 2007.
Yanez-Munoz et al., Effective gene therapy with nonintegrating lentiviral vectors. Nat Med. Mar. 2006;12(3):348-53. Epub Feb. 19, 2006.
Yannaki et al., Topological constraints governing the use of the chicken HS4 chromatin insulator in oncoretrovirus vectors. Mol Ther. May 2002;5(5 Pt 1):589-98.
Yao et al., Retrovirus silencer blocking by the cHS4 insulator is CTCF independent. Nucleic Acids Res. Sep. 15, 2003;31(18):5317-23.
Yu et al., Construction of a retroviral vector production system with the minimum possibility of a homologous recombination. Gene Ther. Apr. 2003;10(8):706-11.
Yusufzai et al., CTCF tethers an insulator to subnuclear sites, suggesting shared insulator mechanisms across species. Mol Cell. Jan. 30, 2004;13(2):291-8.
Yusufzai et al., The 5'-HS4 chicken beta-globin insulator is a CTCF-dependent nuclear matrix-associated element. Proc Natl Acad Sci U S A. Jun. 8, 2004;101(23):8620-4. Epub May 28, 2004.
Zaiss et al., RNA 3' readthrough of oncoretrovirus and lentivirus: implications for vector safety and efficacy. J Virol. Jul. 2002;76(14):7209-19.
Zennou et al., HIV-1 genome nuclear import is mediated by a central DNA flap. Cell. Apr. 14, 2000;101(2):173-85.
Zhao et al., Carbohydrate structures of recombinant human alpha-L-iduronidase secreted by Chinese hamster ovary cells. J Biol Chem. Sep. 5, 1997;272(36):22758-65.
Zhuang et al., Human immunodeficiency virus type 1 recombination: rate, fidelity, and putative hot spots. J Virol. Nov. 2002;76(22):11273-82.
Zufferey et al., Self-inactivating lentivirus vector for safe and efficient in vivo gene delivery. J Virol. Dec. 1998;72(12):9873-80.
Zychlinski et al., Physiological promoters reduce the genotoxic risk of integrating gene vectors. Mol Ther. Apr. 2008;16(4):718-25. doi: 10.1038/mt.2008.5.
U.S. Appl. No. 12/928,302 Final Office action dated Jan. 12, 2015, 18 pages.
U.S. Appl. No. 12/928,302 non-final Office action dated Apr. 27, 2012, 7 pages.
U.S. Appl. No. 12/928,302 Restriction Requirement dated Mar. 1, 2012, 7 pages.
U.S. Appl. No. 13/946,746 Final Office action dated May 12, 2016, 8 pages.
U.S. Appl. No. 13/946,746 nonfinal Office action dated Nov. 3, 2015, 6 pages.
U.S. Appl. No. 13/946,746 Restriction Requirement dated Jul. 15, 2015, 6 pages.
U.S. Appl. No. 14/707,557 Advisory Action dated Sep. 19, 2016, 7 pages.
U.S. Appl. No. 14/707,557 Final Office action dated Dec. 29, 2017, 18 pages.
U.S. Appl. No. 14/707,557 Final Office action dated May 31, 2016, 18 pages.
U.S. Appl. No. 14/707,557 non-final Office action dated Jun. 14, 2017, 23 pages.
U.S. Appl. No. 14/707,557 non-final Office action dated Nov. 5, 2015, 6 pages.

| Vector | RRE | NB-1 | NB-2 |
|---|---|---|---|
| SBG-1[i] | - | 1.00 | 1.00 |
| SBG-2[i] | + | 1.82 | 2.40 |
| SBG-3 | + | 1.91 | 3.34 |
| SBG-4 | + | 5.01 | 5.14 |
| SBG-5 | + | 3.35 | 2.76 |
| SBG-6 | + | 3.45 | 2.42 |
| SBG-7[ii] | + | 4.13 | 2.33 |
| SBG-8[iii] | + | 2.18 | 1.70 |
| SBG-9[ii] | - | 6.35 | NA |
| SBG-10[iii] | - | 5.34 | 5.75 |

Figure 6E

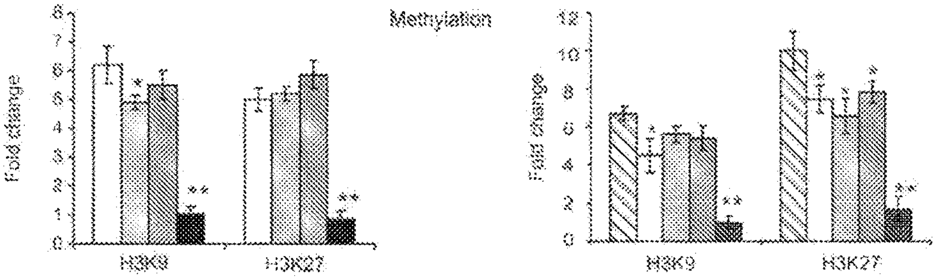

Figure 10F

RBC parameters, reticulocytes and vector copies in mice 24 weeks following transplant

| | Mock | sBG | sBG$^{C}$ | sBG$^{400}$ | sBG$^{2C}$ | sBG-I |
|---|---|---|---|---|---|---|
| Hb (g/dl) | 8 ± 0.2 | 10 ± 0.7 | 10 ± 0.5 | 10 ± 0.5 | 10 ± 0.3 | 11 ± 0.2 |
| Hematocrit (%) | 24 ± 1.5 | 32 ± 2.8 | 36 ± 1.2 | 38 ± 1.4 | 35 ± 1.6 | 38 ± 1.3 |
| Reticulocyte count | 30 ± 2 | 11 ± 4 | 10 ± 2 | 12 ± 7 | 11 ± 0 | 8 ± 1* |
| RBC (M/μl) | 6.8 ± 0.4 | 8.6 ± 0.6 | 8.5 ± 0.3 | 7.9 ± 0.2 | 7.5 ± 0.2 | 8.8 ± 0.2 |
| MCV (fL) | 45 ± 1.8 | 44 ± 1.6 | 40 ± 1.4 | 45 ± 1.6 | 43 ± 2.2 | 49 ± 1.3* |
| MCHC (g/dL) | 24 ± 1.1 | 28 ± 1.4 | 28 ± 1.6 | 29 ± 1.7 | 27 ± 1.6 | 33 ± 0.9* |
| Vector copy | N/A | 1.2 ± 0.2 | 1 ± 0.1 | 1 ± 0.1 | 1.2 ± 0.3 | 0.6 ± 0.1 |

Values represent means ± SEM. Hb=hemoglobin. MCV=mean corpuscular volume, MCHC=mean corpuscular hemoglobin concentration. vector copy=average number of vector copies in leukocytes by qPCR

Figure 11A

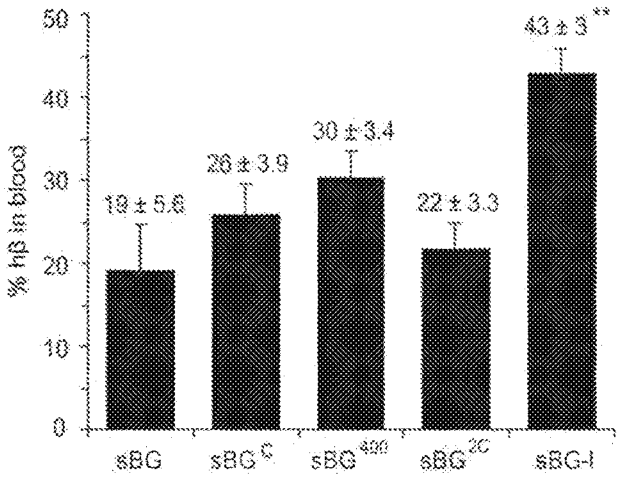

Figure 11B

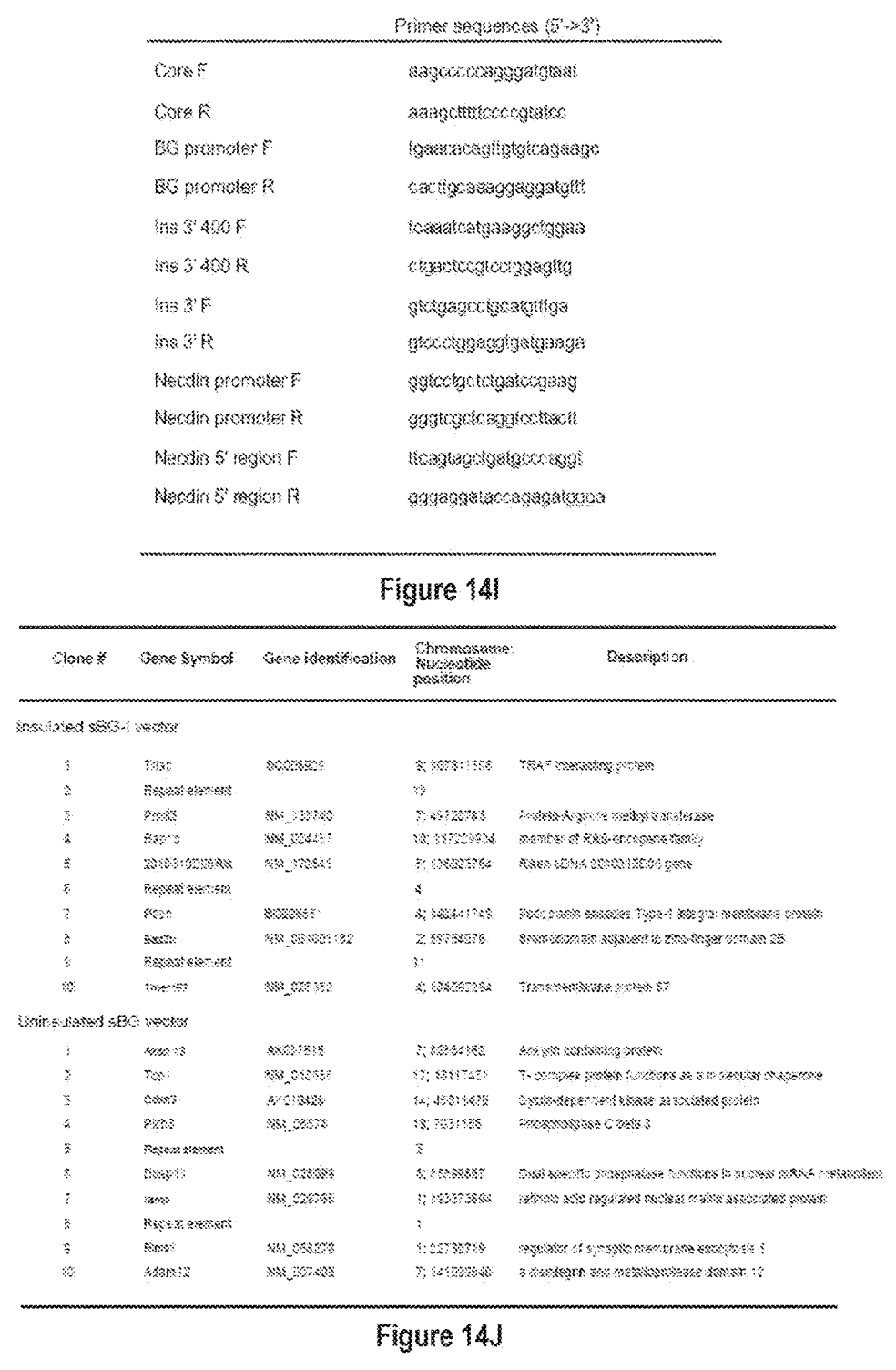

| | Primer sequences (5'->3') |
|---|---|
| Core F | aagcccccagggatgtaat |
| Core R | aaagcttttccccgtatcc |
| BG promoter F | tgaacacagttgtgtcagaagc |
| BG promoter R | cacttgcaaaggaggatgttt |
| Ins 3' 400 F | tcaaatcatgaaggctggaa |
| Ins 3' 400 R | ctgactccgtccrggagttg |
| Ins 3' F | gtctgagcctgcatgtttga |
| Ins 3' R | gtccctggaggtgatgaaga |
| Necdin promoter F | ggtcctgctctgatccgaag |
| Necdin promoter R | gggtcgctcaggtccttactt |
| Necdin 5' region F | ttcagtagctgatgcccaggt |
| Necdin 5' region R | gggaggataccagagatggga |

Figure 14I

| Clone # | Gene Symbol | Gene Identification | Chromosome: Nucleotide position | Description |
|---|---|---|---|---|
| Insulated sBG-I vector | | | | |
| 1 | Traip | [illegible] | 9; [illegible] | TRAF interacting protein |
| 2 | Repeat element | | 10 | |
| 3 | Prmt3 | NM_133740 | 7; 49120783 | Protein-Arginine methyl transferase |
| 4 | [illegible] | NM_[illegible] | 10; [illegible] | member of RAS-oncogene family |
| 5 | 2010310D06Rik | NM_[illegible] | [illegible] | Riken cDNA 2010310D06 gene |
| 6 | Repeat element | | 4 | |
| 7 | Pdpn | [illegible] | 4; [illegible] | Podoplanin encodes Type-1 integral membrane protein |
| 8 | Baz2b | NM_001001182 | 2; [illegible] | Bromodomain adjacent to zinc-finger domain 2B |
| 9 | Repeat element | | 11 | |
| 10 | Tmem57 | NM_[illegible] | 4; [illegible] | Transmembrane protein 57 |
| Uninsulated sBG vector | | | | |
| 1 | [illegible] | [illegible] | 7; [illegible] | Ank-rpt containing protein |
| 2 | Tcp1 | NM_013686 | 17; [illegible] | T- complex protein functions as a molecular chaperone |
| 3 | Cdkn3 | [illegible] | 14; [illegible] | Cyclin-dependent kinase associated protein |
| 4 | Plcb3 | NM_[illegible] | 19; [illegible] | Phospholipase C beta 3 |
| 5 | Repeat element | | 3 | |
| 6 | Dusp11 | NM_[illegible] | 6; [illegible] | Dual specific phosphatase functions in nuclear mRNA metabolism |
| 7 | Ramp | NM_[illegible] | 1; [illegible] | retinoic acid regulated nuclear matrix associated protein |
| 8 | Repeat element | | 1 | |
| 9 | Rims1 | NM_[illegible] | 1; [illegible] | regulator of synaptic membrane exocytosis 1 |
| 10 | Adam12 | NM_[illegible] | 7; [illegible] | a disintegrin and metalloprotease domain 12 |

Figure 14J

| Vector | Single Copy clones | Insulator core PCR+ | 1.2Kb cHS4 PCR+ |
|---|---|---|---|
| $sBG^{IC}$ | 14 | 14/14 | NA |
| $sBG^{2C}$ | 24 | 18/24 | NA |
| $sBG^{400}$ | 35 | 35/35 | NA |
| $sBG^{800}$ | 12 | 12/12 | NA |
| sBG-I | 18 | 18/18 | 18 |
| $sBG^{400S}$ | 18 | 18/18 | NA |
| $sBG^{800S}$ | 12 | 12/12 | NA |
| $sBG^{1200S}$ | 6 | 6/6 | NA |

| | |
|---|---|
| InsF | aatgatatctctagagggacagccccccc |
| Ins400R | aatgatatccctgcaggcattcaaggccag |
| Ins800R | aatgatatcaccatcaaacatgcaggctca |
| Core1F | cgggatcccgagctcacggggacagcccccc |
| Core1R | ggaattccgatatcaagcttttccccgtatccc |
| Core2F | ggaattccgatatcgagctcacggggacagcccccc |
| Core2R | cggggtaccccgaagctttttccccgtatccccc |
| 3' 400 F | actggatatcatgtgtctgagcctgcatgttt |
| 3' 400 R | tgactccggaagccccatcctcactgactccgtcc |
| SpacerF1 | ggaattccgcttgccaacgacat |
| SpacerR1 | ccatcgatcacaccctgtttctcc |
| SpacerR2 | ccatcgatcgctggcgttctcgc |
| SpacerR3 | ccatcgatttcgcactcaatccgcc |

Figure 20E

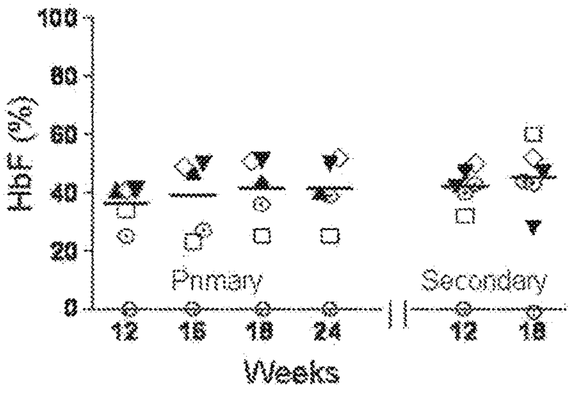
Figure 21A
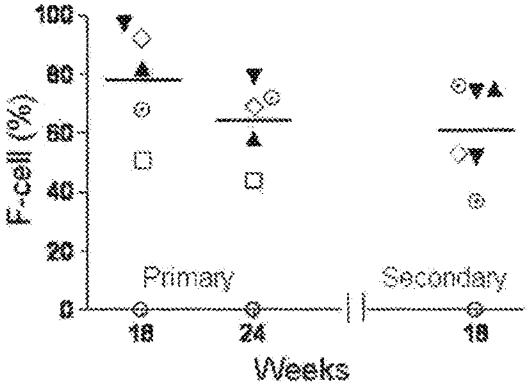
Figure 21B
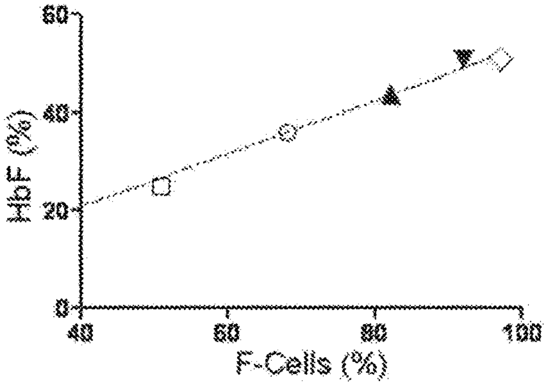
Figure 21C
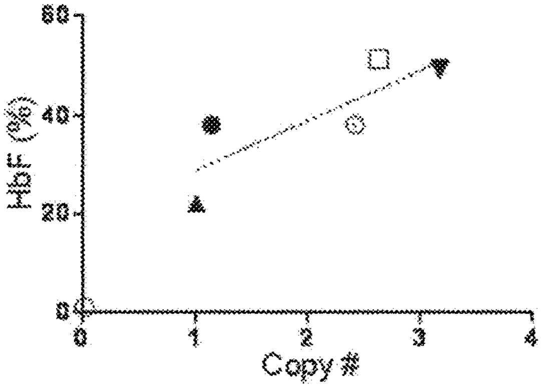
Figure 21D
| Mouse type | No. | WBC, $10^3/\mu L$ | RBC, $10^6/\mu L$ | Hb, g/dL | MCV, fL | MCH, pg | RDW, % | Plt, $10^3/\mu L$ | Reticulocytes, % |
|---|---|---|---|---|---|---|---|---|---|
| BERK | 5 | 52.8 ± 5.4 | 5.3 ± 0.4 | 5.8 ± 0.5 | 48.2 ± 1.05 | 10.7 ± 0.5 | 35.3 ± 1.6 | 733 ± 80 | 60.8 ± 5.0 |
| $G^{\gamma}G$ pri | 5 | 10.6 ± 3.1 | 9.4 ± 0.8 | 10.0 ± 0.8 | 40.7 ± 1.3 | 10.4 ± 0.6 | 27.6 ± 1.1 | 733 ± 82 | 15.8 ± 3.2 |
| Mock pri | 10 | 29.7 ± 1.4 | 5.8 ± 0.4 | 7.8 ± 0.7 | 48.5 ± 1.8 | 10.7 ± 0.2 | 32.0 ± 0.9 | 921 ± 50 | 40.0 ± 3.0 |
| P* | | .001 | .007 | .03 | .001 | .9 | .009 | .06 | .006 |
| $G^{\gamma}G$ sec | 6 | 6.8 ± 1.4 | 9.9 ± 0.4 | 10.1 ± 0.5 | 40.5 ± 1.6 | 11.4 ± 0.5 | 28.3 ± 1.4 | 858 ± 33 | 13.8 ± 2.9 |
| Mock sec | 1 | 31.7 | 5.2 | 6.4 | 47.5 | 12.2 | 32.1 | 923 | 49 |
Figure 21E

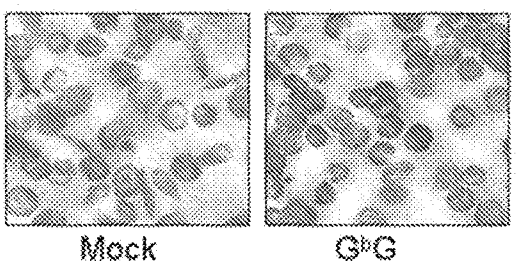
Figure 23A
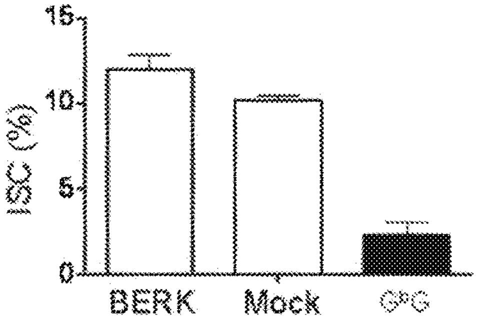
Figure 23B
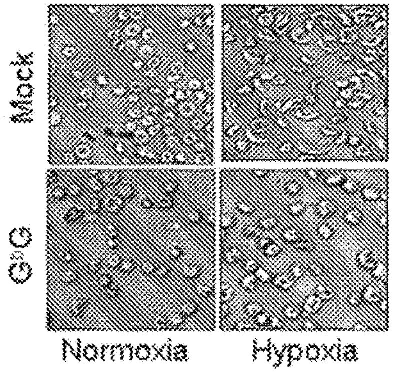
Figure 23C
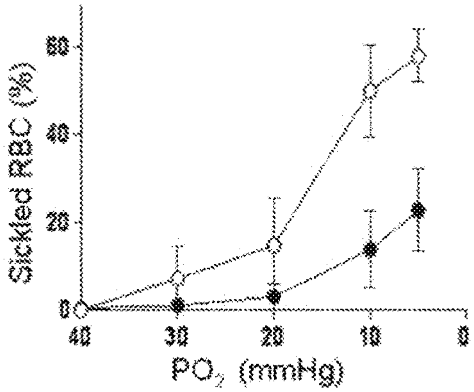
Figure 23D
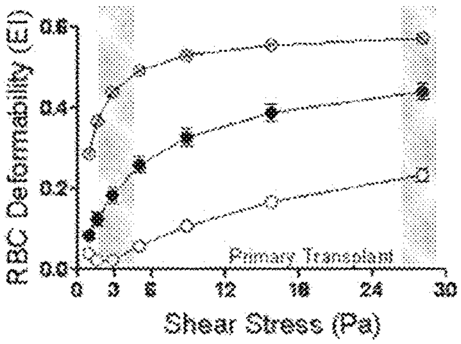
Figure 23E
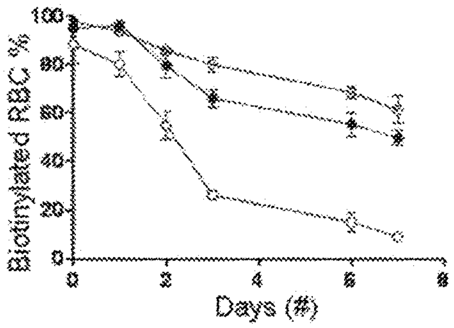
Figure 23F
| | Kidney | Liver | Spleen | Bone marrow |
|---|---|---|---|---|
| Mock mice, n = 5 | Focal tubular atrophy (1/5), mild congestion (3/5) | 2+ liver infarction (1/5), 3+ liver infarction (1/5), E-M hematopoiesis (2/5) | Weight 506 ± 60 mg, severe erythroid hyperplasia (5/5) | Severe erythroid hyperplasia (5/5) |
| GβG mice, n = 5 | Normal kidney (5/5) | Normal liver (5/5) | Weight 256 ± 51 mg, mild erythroid hyperplasia (5/5), mild congestion (5/5) | Mild erythroid hyperplasia (5/5) |
Figure 23G

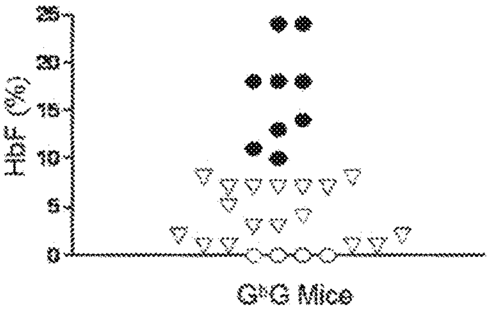
Figure 24A
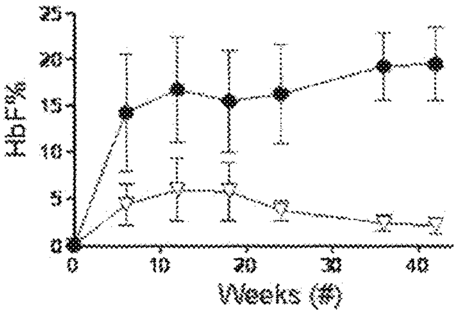
Figure 24B
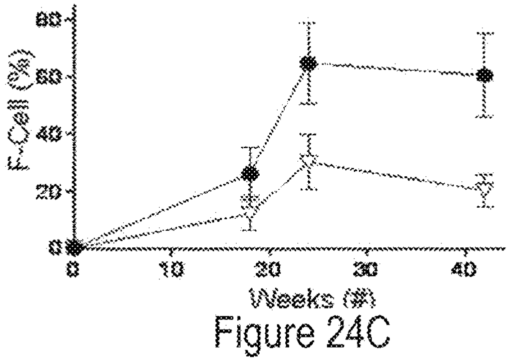
Figure 24C
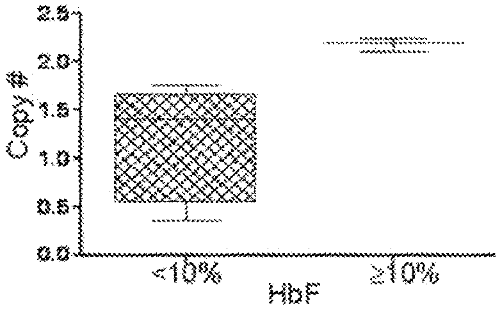
Figure 24D
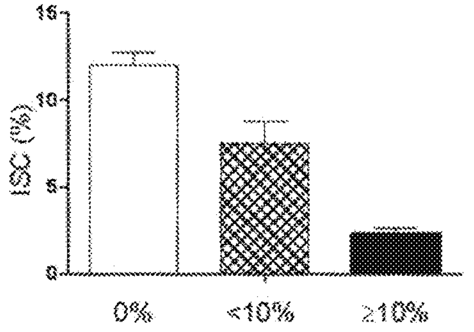
Figure 24E
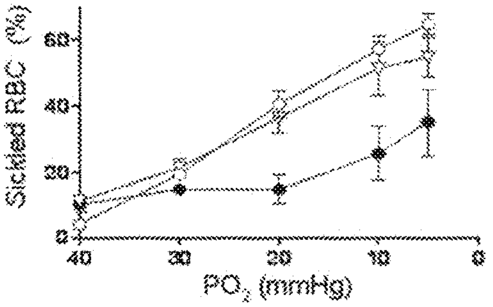
Figure 24F
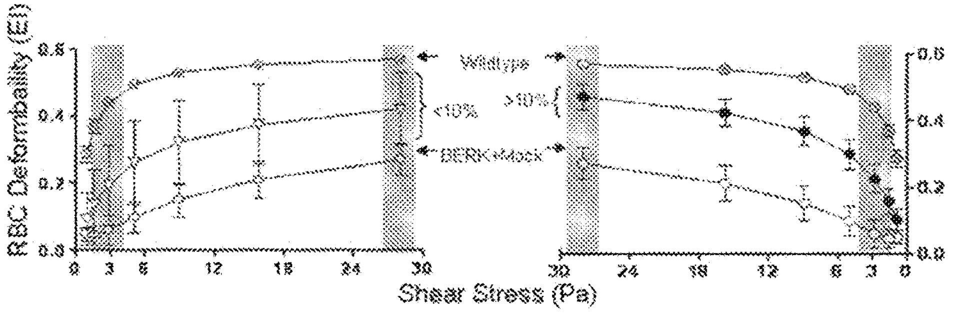
Figure 24G
Figure 24H

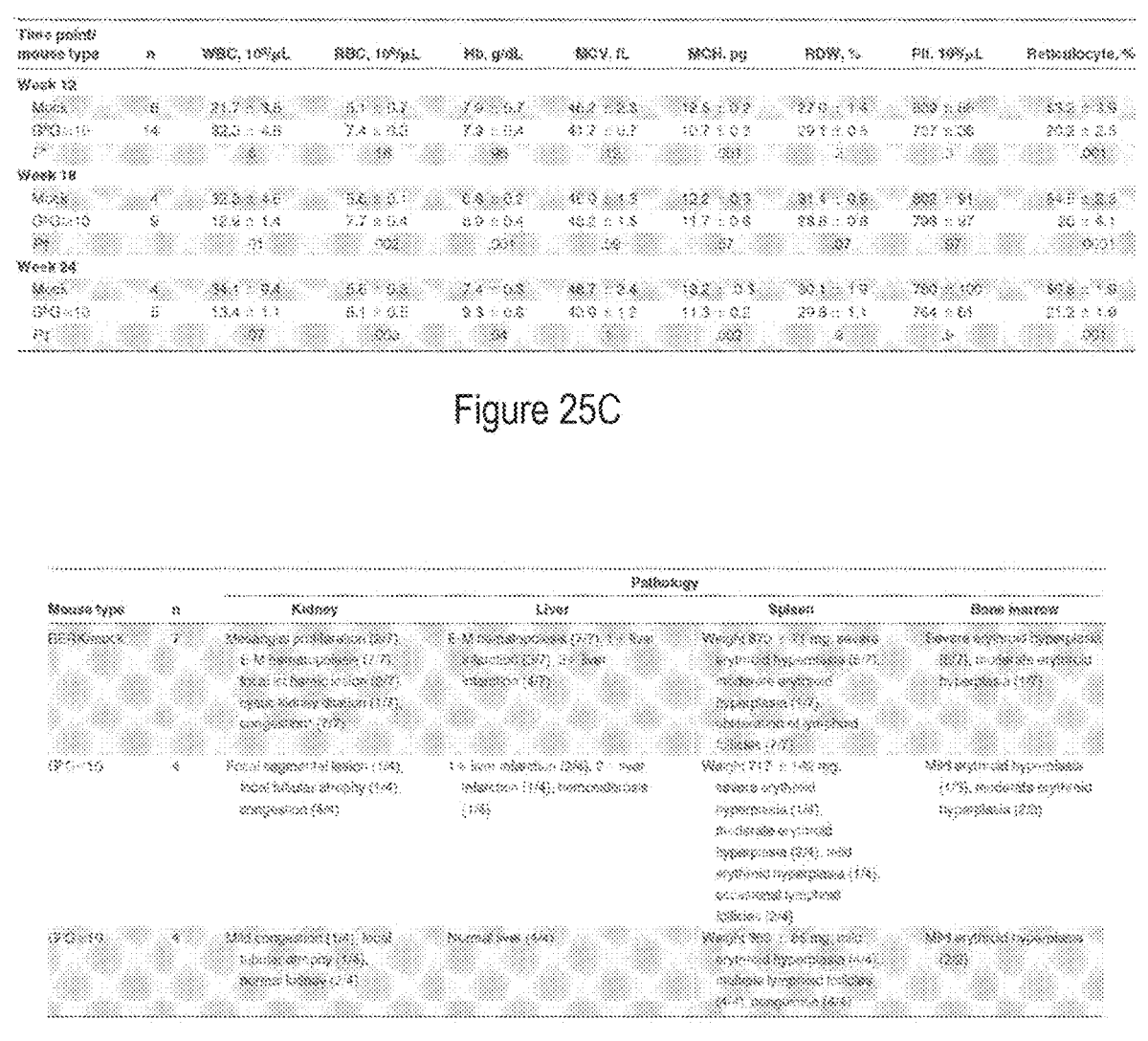

| Time point/ mouse type | n | WBC, $10^3$/μL | RBC, $10^6$/μL | Hb, g/dL | MCV, fL | MCH, pg | RDW, % | Plt, $10^3$/μL | Reticulocyte, % |
|---|---|---|---|---|---|---|---|---|---|
| Week 12 | | | | | | | | | |
| Mock | 6 | 21.7 ± 3.6 | [illegible] | [illegible] | [illegible] | [illegible] | [illegible] | [illegible] | [illegible] |
| GPG=10 | 14 | 32.3 ± 4.8 | 7.4 ± 0.3 | 7.9 ± 0.4 | 40.7 ± 0.7 | 10.7 ± 0.3 | 29.1 ± 0.5 | 737 ± 36 | 20.3 ± 2.5 |
| P | | .6 | .18 | .36 | [illegible] | .001 | .4 | .3 | .001 |
| Week 18 | | | | | | | | | |
| Mock | 4 | [illegible] | [illegible] | [illegible] | [illegible] | [illegible] | [illegible] | [illegible] | [illegible] |
| GPG=10 | 5 | 12.8 ± 1.4 | 7.7 ± 0.4 | 8.9 ± 0.4 | 40.2 ± 1.5 | 11.7 ± 0.6 | 28.8 ± 0.8 | 798 ± 87 | 30 ± 4.1 |
| P | | .11 | .002 | [illegible] | [illegible] | .07 | .007 | [illegible] | .0001 |
| Week 24 | | | | | | | | | |
| Mock | 4 | [illegible] | [illegible] | [illegible] | [illegible] | [illegible] | [illegible] | [illegible] | [illegible] |
| GPG=10 | 5 | 13.4 ± 1.1 | 8.1 ± 0.8 | 9.3 ± 0.8 | 40.9 ± 1.2 | 11.3 ± 0.2 | 29.8 ± 1.1 | 764 ± 61 | 21.2 ± 1.9 |
| P | | [illegible] | [illegible] | [illegible] | [illegible] | [illegible] | [illegible] | [illegible] | .001 |

Figure 25C

| | | Pathology | | | |
|---|---|---|---|---|---|
| Mouse type | n | Kidney | Liver | Spleen | Bone marrow |
| BERK mock | 7 | Mesangial proliferation (6/7), E-M hematopoiesis (7/7), focal ischemic lesion (6/7), cystic kidney dilation (1/7), congestion (7/7) | E-M hematopoiesis (7/7), 1+ liver infarction (3/7), 2+ liver infarction (4/7) | Weight [illegible] mg, severe erythroid hyperplasia (6/7), moderate erythroid hyperplasia (1/7), obliteration of lymphoid follicles (7/7) | Severe erythroid hyperplasia (6/7), moderate erythroid hyperplasia (1/7) |
| GPG=10 | 4 | Focal segmental lesion (1/4), focal tubular atrophy (1/4), congestion (4/4) | 1+ liver infarction (2/4), 2+ liver infarction (1/4), hemosiderosis (1/4) | Weight 717 ± 145 mg, severe erythroid hyperplasia (1/4), moderate erythroid hyperplasia (2/4), mild erythroid hyperplasia (1/4), occasional lymphoid follicles (2/4) | Mild erythroid hyperplasia (1/3), moderate erythroid hyperplasia (2/3) |
| GPG=10 | 4 | Mild congestion (1/4), focal tubular atrophy (1/4), normal kidney (2/4) | Normal liver (4/4) | Weight [illegible] mg, mild erythroid hyperplasia (4/4), multiple lymphoid follicles (4/4), congestion (4/4) | Mild erythroid hyperplasia (3/3) |

Figure 25D

Molecule: Gamma Globin M, 11868 bps DNA Circular

| Start | End | Name |
|---|---|---|
| 132 | 989 | Amp |
| 2360 | 2876 | CMV |
| 2892 | 2988 | U5 |
| 2989 | 3071 | R |
| 3273 | 3591 | Gag |
| 3747 | 3978 | RRE |
| 3979 | 4446 | Env |
| 4491 | 4608 | cPPT |

| Start | End | Name |
|---|---|---|
| 6513 | 4638 | gamma globin M |
| 6830 | 6514 | Beta Promoter |
| 7561 | 6839 | HS2 |
| 8508 | 7562 | HS3 |
| 8510 | 9908 | HS4 |
| 9910 | 10310 | 3' LTR |
| 10323 | 10812 | Poly A |
| 11411 | 11868 | ori |

Figure 31A

```
13 Sep 2013                              Sequence Data

Molecule:        sGbGM,  11868 bps DNA Circular
File Name:       sGbGM-edited.cm5,  dated 12 Sep 2013
Description:
Printed:         1 to 11868 bps (Full)

   1  caggtggcac ttttcgggga aatgtgcgcg gaacccctat ttgtttattt ttctaaatac
      gtccaccgtg aaaagcccct ttacacgcgc cttggggata aacaaataaa aagatttatg

  61  attcaaatat gtatccgctc atgagacaat aaccctgata aatgcttcaa taatattgaa
      taagtttata cataggcgag tactctgtta ttgggactat ttacgaagtt attataactt

 121  aaaggaagag tatgagtatt caacatttcc gtgtcgccct tattcccttt tttgcggcat
      tttccttctc atactcataa gttgtaaagg cacagcggga ataagggaaa aaacgccgta
                 >>.....................Amp.......................>

 181  tttgccttcc tgtttttgct cacccagaaa cgctggtgaa agtaaaagat gctgaagatc
      aaacggaagg acaaaaacga gtgggtcttt gcgaccactt tcattttcta cgacttctag
      >...........................Amp............................>

 241  agttgggtgc acgagtgggt tacatcgaac tggatctcaa cagcggtaag atccttgaga
      tcaacccacg tgctcaccca atgtagcttg acctagagtt gtcgccattc taggaactct
      >...........................Amp............................>

 301  gttttcgccc cgaagaacgt tttccaatga tgagcacttt taaagttctg ctatgtggcg
      caaaagcggg gcttcttgca aaaggttact actcgtgaaa atttcaagac gatacaccgc
      >...........................Amp............................>

 361  cggtattatc ccgtattgac gccgggcaag agcaactcgg tcgccgcata cactattctc
      gccataatag ggcataactg cggcccgttc tcgttgagcc agcggcgtat gtgataagag
      >...........................Amp............................>

 421  agaatgactt ggttgagtac tcaccagtca cagaaaagca tcttacggat ggcatgacag
      tcttactgaa ccaactcatg agtggtcagt gtcttttcgt agaatgccta ccgtactgtc
      >...........................Amp............................>

 481  taagagaatt atgcagtgct gccataacca tgagtgataa cactgcggcc aacttacttc
      attctcttaa tacgtcacga cggtattggt actcactatt gtgacgccgg ttgaatgaag
      >...........................Amp............................>

 541  tgacaacgat cggaggaccg aaggagctaa ccgctttttt gcacaacatg ggggatcatg
      actgttgcta gcctcctggc ttcctcgatt ggcgaaaaaa cgtgttgtac cccctagtac
      >...........................Amp............................>

 601  taactcgcct tgatcgttgg gaaccggagc tgaatgaagc cataccaaac gacgagcgtg
      attgagcgga actagcaacc cttggcctcg acttacttcg gtatggtttg ctgctcgcac
      >...........................Amp............................>

 661  acaccacgat gcctgtagca atggcaacaa cgttgcgcaa actattaact ggcgaactac
      tgtggtgcta cggacatcgt taccgttgtt gcaacgcgtt tgataattga ccgcttgatg
      >...........................Amp............................>

 721  ttactctagc ttcccggcaa caattaatag actggatgga ggcggataaa gttgcaggac
      aatgagatcg aagggccgtt gttaattatc tgacctacct ccgcctattt caacgtcctg
      >...........................Amp............................>

 781  cacttctgcg ctcggccctt ccggctggct ggtttattgc tgataaatct ggagccggtg
      gtgaagacgc gagccgggaa ggccgaccga ccaaataacg actatttaga cctcggccac
      >...........................Amp............................>

 841  agcgtgggtc tcgcggtatc attgcagcac tggggccaga tggtaagccc tcccgtatcg
      tcgcacccag agcgccatag taacgtcgtg accccggtct accattcggg agggcatagc
      >...........................Amp............................>
```

sGbGM

Figure 31B

```
 901  tagttatcta cacgacgggg agtcaggcaa ctatggatga acgaaataga cagatcgctg
      atcaatagat gtgctgcccc tcagtccgtt gatacctact tgctttatct gtctagcgac
      >............................Amp...............................>

 961  agataggtgc ctcactgatt aagcattggt aactgtcaga ccaagtttac tcatatatac
      tctatccacg gagtgactaa ttcgtaacca ttgacagtct ggttcaaatg agtatatatg
      >............Amp............>>

1021  tttagattga tttaaaactt catttttaat ttaaaaggat ctaggtgaag atcctttttg
      aaatctaact aaattttgaa gtaaaaatta aattttccta gatccacttc taggaaaaac

1081  ataatctcat gaccaaaatc ccttaacgtg agttttcgtt ccactgagcg tcagaccccg
      tattagagta ctggttttag ggaattgcac tcaaaagcaa ggtgactcgc agtctggggc

1141  tagaaaagat caaaggatct tcttgagatc ctttttttct gcgcgtaatc tgctgcttgc
      atcttttcta gtttcctaga agaactctag gaaaaaaaga cgcgcattag acgacgaacg

1201  aaacaaaaaa accaccgcta ccagcggtgg tttgtttgcc ggatcaagag ctaccaactc
      tttgtttttt tggtggcgat ggtcgccacc aaacaaacgg cctagttctc gatggttgag

1261  tttttccgaa ggtaactggc ttcagcagag cgcagatacc aaatactgtc cttctagtgt
      aaaaaggctt ccattgaccg aagtcgtctc gcgtctatgg tttatgacag gaagatcaca

1321  agccgtagtt aggccaccac ttcaagaact ctgtagcacc gcctacatac ctcgctctgc
      tcggcatcaa tccggtggtg aagttcttga gacatcgtgg cggatgtatg gagcgagacg

1381  taatcctgtt accagtggct gctgccagtg gcgataagtc gtgtcttacc gggttggact
      attaggacaa tggtcaccga cgacggtcac cgctattcag cacagaatgg cccaacctga

1441  caagacgata gttaccggat aaggcgcagc ggtcgggctg aacggggggt tcgtgcacac
      gttctgctat caatggccta ttccgcgtcg ccagcccgac ttgcccccca agcacgtgtg

1501  agcccagctt ggagcgaacg acctacaccg aactgagata cctacagcgt gagctatgag
      tcgggtcgaa cctcgcttgc tggatgtggc ttgactctat ggatgtcgca ctcgatactc

1561  aaagcgccac gcttcccgaa gggagaaagg cggacaggta tccggtaagc ggcagggtcg
      tttcgcggtg cgaagggctt ccctctttcc gcctgtccat aggccattcg ccgtcccagc

1621  gaacaggaga gcgcacgagg gagcttccag ggggaaacgc ctggtatctt tatagtcctg
      cttgtcctct cgcgtgctcc ctcgaaggtc cccctttgcg gaccatagaa atatcaggac

1681  tcgggtttcg ccacctctga cttgagcgtc gatttttgtg atgctcgtca ggggggcgga
      agcccaaagc ggtggagact gaactcgcag ctaaaaacac tacgagcagt ccccccgcct

1741  gcctatggaa aaacgccagc aacgcggcct ttttacggtt cctggccttt tgctggcctt
      cggatacctt tttgcggtcg ttgcgccgga aaaatgccaa ggaccggaaa acgaccggaa

1801  ttgctcacat gttctttcct gcgttatccc ctgattctgt ggataaccgt attaccgcct
      aacgagtgta caagaaagga cgcaataggg gactaagaca cctattggca taatggcgga

1861  ttgagtgagc tgataccgct cgccgcagcc gaacgaccga gcgcagcgag tcagtgagcg
      aactcactcg actatggcga gcggcgtcgg cttgctggct cgcgtcgctc agtcactcgc

1921  aggaagcgga agagcgccca atacgcaaac cgcctctccc cgcgcgttgg ccgattcatt
      tccttcgcct tctcgcgggt tatgcgtttg gcggagaggg gcgcgcaacc ggctaagtaa

1981  aatgcagctg gcacgacagg tttcccgact ggaaagcggg cagtgagcgc aacgcaatta
      ttacgtcgac cgtgctgtcc aaagggctga cctttcgccc gtcactcgcg ttgcgttaat

2041  atgtgagtta gctcactcat taggcacccc aggctttaca ctttatgctt ccggctcgta
      tacactcaat cgagtgagta atccgtgggg tccgaaatgt gaaatacgaa ggccgagcat
```

sGbGM

Figure 31C

```
2101  tgttgtgtgg aattgtgagc ggataacaat ttcacacagg aaacagctat gaccatgatt
      acaacacacc ttaacactcg cctattgtta aagtgtgtcc tttgtcgata ctggtactaa

2161  acgccaagcg cgcaattaac cctcactaaa gggaacaaaa gctggagctg caagcttggc
      tgcggttcgc gcgttaattg ggagtgattt cccttgtttt cgacctcgac gttcgaaccg

2221  cattgcatac gttgtatcca tatcataata tgtacattta tattggctca tgtccaacat
      gtaacgtatg caacataggt atagtattat acatgtaaat ataaccgagt acaggttgta

2281  taccgccatg ttgacattga ttattgacta gttattaata gtaatcaatt acggggtcat
      atggcggtac aactgtaact aataactgat caataattat cattagttaa tgccccagta

2341  tagttcatag cccatatatg gagttccgcg ttacataact tacggtaaat ggcccgcctg
      atcaagtatc gggtatatac ctcaaggcgc aatgtattga atgccattta ccgggcggac
                                  >>...................CMV....................>

2401  gctgaccgcc caacgacccc cgcccattga cgtcaataat gacgtatgtt cccatagtaa
      cgactggcgg gttgctgggg gcgggtaact gcagttatta ctgcatacaa gggtatcatt
      >..............................CMV..............................>

2461  cgccaatagg gactttccat tgacgtcaat gggtggagta tttacggtaa actgcccact
      gcggttatcc ctgaaaggta actgcagtta cccacctcat aaatgccatt tgacgggtga
      >..............................CMV..............................>

                            NdeI
2521  tggcagtaca tcaagtgtat catatgccaa gtacgccccc tattgacgtc aatgacggta
      accgtcatgt agttcacata gtatacggtt catgcggggg ataactgcag ttactgccat
      >..............................CMV..............................>

2581  aatggcccgc ctggcattat gcccagtaca tgaccttatg ggactttcct acttggcagt
      ttaccgggcg gaccgtaata cgggtcatgt actggaatac cctgaaagga tgaaccgtca
      >..............................CMV..............................>

2641  acatctacgt attagtcatc gctattacca tggtgatgcg gttttggcag tacatcaatg
      tgtagatgca taatcagtag cgataatggt accactacgc caaaaccgtc atgtagttac
      >..............................CMV..............................>

2701  ggcgtggata gcggtttgac tcacggggat ttccaagtct ccaccccatt gacgtcaatg
      ccgcacctat cgccaaactg agtgccccta aaggttcaga ggtggggtaa ctgcagttac
      >..............................CMV..............................>

2761  ggagtttgtt ttggcaccaa aatcaacggg actttccaaa atgtcgtaac aactccgccc
      cctcaaacaa aaccgtggtt ttagttgccc tgaaaggttt tacagcattg ttgaggcggg
      >..............................CMV..............................>

2821  cattgacgca aatgggcggt aggcgtgtac ggtgggaggt ctatataagc agagctcgtt
      gtaactgcgt ttacccgcca tccgcacatg ccaccctcca gatatattcg tctcgagcaa
      >............................CMV............................>>

2881  tagtgaaccg gggtctctct ggttagacca gatctgagcc tgggagctct ctggctaact
      atcacttggc cccagagaga ccaatctggt ctagactcgg accctcgaga gaccgattga
                  >>.....................US.........................>

2941  agggaaccca ctgcttaagc ctcaataaag cttgccttga gtgcttcaag tagtgtgtgc
      tcccttgggt gacgaattcg gagttatttc gaacggaact cacgaagttc atcacacacg
      >.........................US.........................>>
                                                              >>....R.....>

3001  ccgtctgttg tgtgactctg gtaactagag atccctcaga cccttttagt cagtgtggaa
      ggcagacaac acactgagac cattgatctc tagggagtct gggaaaatca gtcacacctt
      >...............................P...............................>
```

sGbGM

Figure 31D

```
                  SfoI
                  NarI
                  KasI
3061  aatctctagc agtggcgccc gaacagggac ttgaaagcga aagggaaacc agaggagctc
      ttagagatcg tcaccgcggg cttgtccctg aactttcgct ttccctttgg tctcctcgag
      >.....R.....>>

3121  tctcgacgca ggactcggct tgctgaagcg cgcacggcaa gaggcgaggg gcggcgactg
      agagctgcgt cctgagccga acgacttcgc gcgtgccgtt ctccgctccc cgccgctgac

3181  gtgagtacgc caaaaatttt gactagcgga ggctagaagg agagagatgg gtgcgagagc
      cactcatgcg gtttttaaaa ctgatcgcct ccgatcttcc tctctctacc cacgctctcg

3241  gtcagtatta agcgggggag aattagatcg cgatgggaaa aaattcggtt aaggccaggg
      cagtcataat tcgccccctc ttaatctagc gctacccttt ttttaagccaa ttccggtccc
                                          >>............Gag.............>

3301  ggaaagaaaa aatataaatt aaaacatata gtatgggcaa gcagggagct agaacgattc
      cctttctttt ttatatttaa ttttgtatat catacccgtt cgtccctcga tcttgctaag
      >...............................Gag...............................>

3361  gcagttaatc ctggcctgtt agaaacatca gaaggctgta gacaaatact gggacagcta
      cgtcaattag gaccggacaa tctttgtagt cttccgacat ctgtttatga ccctgtcgat
      >...............................Gag...............................>

3421  caaccatccc ttcagacagg atcagaagaa cttagatcat tatataatac agtagcaacc
      gttggtaggg aagtctgtcc tagtcttctt gaatctagta atatattatg tcatcgttgg
      >...............................Gag...............................>

3481  ctctattgtg tgcatcaaag gatagagata aaagacacca aggaagcttt agacaagata
      gagataacac acgtagtttc ctatctctat tttctgtggt tccttcgaaa tctgttctat
      >...............................Gag...............................>

                                                 NotI
3541  gaggaagagc aaaacaaaag taagaccacc gcacagcaag cggccgctga tcttcagacc
      ctccttctcg ttttgttttc attctggtgg cgtgtcgttc gccggcgact agaagtctgg
      >.........................Gag..........................>>

3601  tggaggagga gatatgaggg acaattggag aagtgaatta tataaatata aagtagtaaa
      acctcctcct ctatactccc tgttaacctc ttcacttaat atatttatat ttcatcattt

3661  aattgaacca ttaggagtag cacccaccaa ggcaaagaga agagtggtgc agagagaaaa
      ttaacttggt aatcctcatc gtgggtggtt ccgtttctct tctcaccacg tctctctttt

3721  aagagcagtg ggaataggag ctttgttcct tgggttcttg ggagcagcag gaagcactat
      ttctcgtcac ccttatcctc gaaacaagga acccaagaac cctcgtcgtc cttcgtgata
                                 >>.................RRE.................>

3781  gggcgcagcg tcaatgacgc tgacggtaca ggccagacaa ttattgtctg gtatagtgca
      cccgcgtcgc agttactgcg actgccatgt ccggtctgtt aataacagac catatcacgt
      >...............................RRE...............................>

3841  gcagcagaac aatttgctga gggctattga ggcgcaacag catctgttgc aactcacagt
      cgtcgtcttg ttaaacgact cccgataact ccgcgttgtc gtagacaacg ttgagtgtca
      >...............................RRE...............................>

3901  ctggggcatc aagcagctcc aggcaagaat cctggctgtg gaaagatacc taaaggatca
      gaccccgtag ttcgtcgagg tccgttctta ggaccgacac ctttctatgg atttcctagt
      >...............................RRE...............................>
```

sGbGM

Figure 31E

```
3961  acagctcctg gggatttggg gttgctctgg aaaactcatt tgcaccactg ctgtgccttg
      tgtcgaggac ccctaaaccc caacgagacc ttttgagtaa acgtggtgac gacacggaac
      >........RRE.......>>
                                >>....................Env.......................>

4021  gaatgctagt tggagtaata aatctctgga acagatttgg aatcacacga cctggatgga
      cttacgatca acctcattat ttagagacct tgtctaaacc ttagtgtgct ggacctacct
      >...............................Env...................................>

4081  gtgggacaga gaaattaaca attacacaag cttaatacac tccttaattg aagaatcgca
      caccctgtct ctttaattgt taatgtgttc gaattatgtg aggaattaac ttcttagcgt
      >...............................Env...................................>

4141  aaaccagcaa gaaaagaatg aacaagaatt attggaatta gataaatggg caagtttgtg
      tttggtcgtt cttttcttac ttgttcttaa taaccttaat ctatttaccc gttcaaacac
      >...............................Env...................................>

4201  gaattggttt aacataacaa attggctgtg gtatataaaa ttattcataa tgatagtagg
      cttaaccaaa ttgtattgtt taaccgacac catatatttt aataagtatt actatcatcc
      >...............................Env...................................>

4261  aggcttggta ggtttaagaa tagtttttgc tgtactttct atagtgaata gagttaggca
      tccgaaccat ccaaattctt atcaaaaacg acatgaaaga tatcacttat ctcaatccgt
      >...............................Env...................................>

4321  gggatattca ccattatcgt ttcagaccca cctcccaacc ccgaggggac ccgacaggcc
      ccctataagt ggtaatagca aagtctgggt ggagggttgg ggctcccctg ggctgtccgg
      >...............................Env...................................>

4381  cgaaggaata gaagaagaag gtggagagag agacagagac agatccattc gattagtgaa
      gcttccttat cttcttcttc cacctctctc tctgtctctg tctaggtaag ctaatcactt
      >...............................Env...................................>

4441  cggatctcga cggtatcgat agcgggacaa atggcagtat tcatccacaa ttttaaaaga
      gcctagagct gccatagcta tcgccctgtt taccgtcata agtaggtgtt aaaattttct
      >...>> Env
                                                                >>.cPPT..>

4501  aaagggggga ttggggggta cagtgcaggg gaaagaatag tagacataat agcaacagac
      tttcccccct aaccccccat gtcacgtccc ctttcttatc atctgtatta tcgttgtctg
      >.............................cPPT....................................>

4561  atacaaacta aagaattaca aaaacaaatt acaaaaattc aaaattttcg ggtttattac
      tatgtttgat ttcttaatgt ttttgtttaa tgtttttaag ttttaaaagc ccaaataatg
      >........................cPPT.........................>>

4621  agggacagca gagatccagt ttggatcgtc gacatcgccg gtgaattcac tagtggatcg
      tccctgtcgt ctctaggtca aacctagcag ctgtagcggc cacttaagtg atcacctagc
                               <<...............gamma Globin M..................<

        XhoI
4681  ctctcgaggg gatcctctag agtcgagctc gcgaggatca tcaccggtgc tagccggagc
      gagagctccc ctaggagatc tcagctcgag cgctcctagt agtggccacg atcggcctcg
      <.........................gamma Globio M.............................<

4741  cagaagcacc ataagggaca tgataaggga gccagcagac ctctgatctc ttcctgaatg
      gtcttcgtgg tattccctgt actattccct cggtcgtctg gagactagag aaggacttac
      <.........................gamma Globin M.............................<

4801  ctaatcttaa acatcctgag gaagaatggg acttccattt ggggtgggcc tatgataggg
      gattagaatt tgtaggactc cttcttaccc tgaaggtaaa ccccacccgg atactatccc
      <.........................gamma Globin M.............................<
```

sGbGM

Figure 31F

```
4861  taataagaca gtagtgaata tcaagctaca aaaagccccc tttcaaattc ttctcagtcc
      attattctgt catcacttat agttcgatgt ttttcggggg aaagtttaag aagagtcagg
      <........................gamma Globin M........................<

                                                             PfoI
4921  taacttttca tactaagccc agtccttcca aagcagactg tgaaagagtg atagttccgg
      attgaaaagt atgattcggg tcaggaaggt ttcgtctgac actttctcac tatcaaggcc
      <........................gamma Globin M........................<

4981  gagactagca ccggctagcc gagcttggaa cactttccct tcattaagaa ccatccttgc
      ctctgatcgt ggccgatcgg ctcgaacctt gtgaaaggga agtaattctt ggtaggaacg
      <........................gamma Globin M........................<

5041  tactcagctg caatcaatcc agccccccagg tcttcactga accttttccc atctcttcca
      atgagtcgac gttagttagg tcggggtcc agaagtgact tggaaaaggg tagagaaggt
      <........................gamma Globin M........................<

5101  aaacatctgt ttctgagaag tcctgtccta tagaggtctt tcttcccacc ggatttctcc
      tttgtagaca aagactcttc aggacaggat atctccagaa agaagggtgg cctaaagagg
      <........................gamma Globin M........................<

5161  tacaccattt actcccactt gcagaactcc cgtgtacaag tgtctttact gcttttattt
      atgtggtaaa tgagggtgaa cgtcttgagg gcacatgttc acagaaatga cgaaaataaa
      <........................gamma Globin M........................<

5221  gctcaacaaa atgcacatct catataaaaa taaatgagga gcatgcacac accacaaaca
      cgagttgttt tacgtgtaga gtatattttt atttactcct cgtacgtgtg tggtgtttgt
      <........................gamma Globin M........................<

5281  caaacaggca tgcagaaata cacatacaca cttccctcaa tataaaccct ttgtggctca
      gtttgtccgt acgtctttat gtgtatgtgt gaagggagtt atatttggga aacaccgagt
      <........................gamma Globin M........................<

5341  tatatttaaa aagatgtaaa aaaaagagct gaagaaaatc atgtgtgatc tctcagcaga
      atataaattt ttctacattt tttttctcga cttcttttag tacacactag agagtcgtct
      <........................gamma Globin M........................<

5401  atagatttat tatttgtatt gcttgcagaa taaagcctat ccttgaaagc tctgaatcat
      tatctaaata ataaacataa cgaacgtctt atttcggata ggaactttcg agacttagta
      <........................gamma Globin M........................<

5461  gggcaagagg ctcagtggta tctggaggac agggcactgg ccactgcagt caccatcttc
      cccgttctcc gagtcaccat agacctcctg tcccgtgacc ggtgacgtca gtggtagaag
      <........................gamma Globin M........................<

5521  tgccaggaag cctgcacctc aggggtgaat tctttgccaa agtgaatggc cagcacggtg
      acggtccttc ggacgtggag tccccactta agaaacggtt tcacttaccg gtcgtgccac
      <........................gamma Globin M........................<

5581  accagcacgt tgcccaggag ctgtgggagg aagataagag gtatgaacat gattagcaaa
      tggtcgtgca acgggtcctc gacaccctcc ttctattctc catacttgta ctaatcgttt
      <........................gamma Globin M........................<

5641  agggcctagc ttggactcag aataatccag ccttatccca accataaaat aaaagcagaa
      tcccggatcg aacctgagtc ttattaggtc ggaatagggt tggtatttta ttttcgtctt
      <........................gamma Globin M........................<

5701  tggtagctgg attgtagctg ctattagcaa tatgaaacct cttacatcag ttacaattta
      accatcgacc taacatcgac gataatcgtt atactttgga gaatgtagtc aatgttaaat
      <........................gamma Globin M........................<
```

sGbGM

Figure 31G

```
5761  tatgcagaaa tatttatatg cagaaatatt gctattgcct taacccagaa attatcactg
      atacgtcttt ataaatatac gtctttataa cgataacgga attgggtctt taatagtgac
      <......................gamma Globin M.........................<

5821  ttattcttta gaatggtgca aagaggcatg atacattgta tcattattgc cctgaaagaa
      aataagaaat cttaccacgt ttctccgtac tatgtaacat agtaataacg ggactttctt
      <......................gamma Globin M.........................<

5881  agagattagg gaaagtatta gaaataagat aaacaaaaaa gtatattaaa agaagaaagc
      tctctaatcc ctttcataat ctttattcta tttgtttttt catataattt tcttctttcg
      <......................gamma Globin M.........................<

5941  attttttaaa attacaaatg caaaattacc ctgatttggt caatatgtgt accctgttac
      taaaaaattt taatgtttac gttttaatgg gactaaacca gttatacaca tgggacaatg
      <......................gamma Globin M.........................<

6001  ttctcccctt cctatgacat gaacttaacc atagaaaaga aggggaaaga aaacatcaag
      aagaggggaa ggatactgta cttgaattgg tatcttttct tcccctttct tttgtagttc
      <......................gamma Globin M.........................<

6061  ggtcccatag actcaccttg aagttctcag gatccacatg cagcttgtca cagtgcagtt
      ccagggtatc tgagtggaac ttcaagagtc ctaggtgtac gtcgaacagt gtcacgtcaa
      <......................gamma Globin M.........................<

                                                Xcmi
6121  cactcagctg ggcaaaggtg cccttgagat catccaggtg ctttatggca tctcccaagg
      gtgagtcgac ccgtttccac gggaactcta gtaggtccac gaaataccgt agagggttcc
      <......................gamma Globin M.........................<

6181  aagtcagcac cttcttgcca tgtgccttga ctttggggtt gcccatgatg gcagaggcag
      ttcagtcgtg gaagaacggt acacggaact gaaaccccaa cgggtactac cgtctccgtc
      <......................gamma Globin M.........................<

6241  aggacaggtt gccaaagctg tcaaagaacc tctgggtcca tgggtagaca accaggagcc
      tcctgtccaa cggtttcgac agtttcttgg agacccaggt acccatctgt tggtcctcgg
      <......................gamma Globin M.........................<

6301  tgtgagattg acaagaacag tttgacagtc agaaggtgcc acaaatcctg agaagcaacc
      acactctaac tgttcttgtc aaactgtcag tcttccacgg tgtttaggac tcttcgttgg
      <......................gamma Globin M.........................<

6361  tggacttttg ccaggcacag ggtccttcct tccctccctt gtcctggtca ccagagccta
      acctgaaaac ggtccgtgtc ccaggaagga agggagggaa caggaccagt ggtctcggat
      <......................gamma Globin M.........................<

6421  ccttcccagg gtttctcctc cagcatcttc cacattcacc ttgtcccaca ggcttgtgat
      ggaagggtcc caaagaggag gtcgtagaag gtgtaagtgg aacagggtgt ccgaacacta
      <......................gamma Globin M.........................<

6481  agtagccttg tcctcctctg tgaaatgacc catggtgtct gtttgaggtt gctagtgaac
      tcatcggaac aggaggagac actttactgg gtaccacaga caaactccaa cgatcacttg
      <..........gamma Globin M..........<<
                                           <<..........Beta Pr..........<

6541  acagttgtgt cagaagcaaa tgtaagcaat agatggctct gccctgactt ttatgcccag
      tgtcaacaca gtcttcgttt acattcgtta tctaccgaga cgggactgaa aatacgggtc
      <..........................Beta Pr...........................<

6601  ccctggctcc tgccctccct gctcctggga gtagattggc caaccctagg gtgtggctcc
      gggaccgagg acgggaggga cgaggaccct catctaaccg gttgggatcc cacaccgagg
      <..........................Beta Pr...........................<
```

sGbGM

Figure 31H

```
6661  acagggtgag gtctaagtga tgacagccgt acctgtcctt ggctcttctg gcactggctt
      tgtcccactc cagattcact actgtcggca tggacaggaa ccgagaagac cgtgaccgaa
      <............................Beta Pr............................<

6721  aggagttgga cttcaaaccc tcagccctcc ctctaagata tatctcttgg ccccatacca
      tcctcaacct gaagtttggg agtcgggagg gagattctat atagagaacc ggggtatggt
      <............................Beta Pr............................<

6781  tcagtacaaa ttgctactaa aaacatcctc ctttgcaagt gtatttacga cggtatcgat
      agtcatgttt aacgatgatt tttgtaggag gaaacgttca cataaatgct gccatagcta
      <......................Beta Pr.......................<<
                                                                 HS2 <<

6841  gtatgtgagc atgtgtcctc taacagcaca ggccttttgc cacctagctg tccaggggtg
      catacactcg tacacaggag attgtcgtgt ccggaaaacg gtggatcgac aggtccccac
      <............................HS2............................<

6901  ccttaaaatg gcaaacaagg tttgttttct tttcctgttt tcatgccttc ctcttccata
      ggaattttac cgtttgttcc aaacaaaaga aaaggacaaa agtacggaag gagaaggtat
      <............................HS2............................<

6961  tccttgtttc atattaatac atgtgtatag atcctaaaaa tctatacaca tgtattaata
      aggaacaaag tataattatg tacacatatc taggattttt agatatgtgt acataattat
      <............................HS2............................<

                                          AarI
                                       ..........
7021  aagcctgatt ctgccgcttc taggtataga ggccacctgc aagataaata tttgattcac
      ttcggactaa gacggcgaag atccatatct ccggtggacg ttctatttat aaactaagtg
      <............................HS2............................<

7081  aataactaat cattctatgg caattgataa caacaaatat atatatatat atatatatac
      ttattgatta gtaagatacc gttaactatt gttgtttata tatatatata tatatatatg
      <............................HS2............................<

7141  gtatatgtgt atatatatat atatatatat atattcagga aataatatat tctagaatat
      catatacaca tatatatata tatatatata tataagtcct ttattatata agatcttata
      <............................HS2............................<

7201  gtcacattct gtctcaggca tccattttct ttatgatgcc gtttgaggtg gagttttagt
      cagtgtaaga cagagtccgt aggtaaaaga aatactacgg caaactccac ctcaaaatca
      <............................HS2............................<

7261  caggtggtca gcttctcctt tttttgcca tctgccctgt aagcatcctg ctggggaccc
      gtccaccagt cgaagaggaa aaaaaacggt agacgggaca ttcgtaggac gacccctggg
      <............................HS2............................<

7321  agataggagt catcactcta ggctgagaac atctgggcac acaccctaag cctcagcatg
      tctatcctca gtagtgagat ccgactcttg tagacccgtg tgtgggattc ggagtcgtac
      <............................HS2............................<

7381  actcatcatg actcagcatt gctgtgcttg agccagaagg tttgcttaga aggttacaca
      tgagtagtac tgagtcgtaa cgacacgaac tcggtcttcc aaacgaatct tccaatgtgt
      <............................HS2............................<

7441  gaaccagaag gcgggggtgg ggcactgacc ccgacagggg cctggccaga actgctcatg
      cttggtcttc cgcccccacc ccgtgactgg ggctgtcccc ggaccggtct tgacgagtac
      <............................HS2............................<

7501  cttggactat gggaggtcac taatggagac acacagaaat gtaacaggaa ctaagggaat
      gaacctgata ccctccagtg attacctctg tgtgtcttta cattgtcctt gattccctta
      <............................HS2............................<
```

sGbGM

Figure 31 I

```
                                                             BlpI
7561  tccggtgccc tgcttaggag cttaatcttt aatgaaagct aagctttcat taaaaaaagt
      aggccacggg acgaatcctc gaattagaaa ttactttcga ttcgaaagta atttttttca
      < RS2
       <<............................HS3............................<

7621  ctaaccagct gcattcgact ttgactgcag cagctggtta gaaggttcta ctggaggagg
      gattggtcga cgtaagctga aactgacgtc gtcgaccaat cttccaagat gacctcctcc
      <.............................HS3.............................<

7681  gtcccagccc attgctaaat taacatcagg ctctgagact ggcagtatat ctctaacagt
      cagggtcggg taacgattta attgtagtcc gagactctga ccgtcatata gagattgtca
      <.............................HS3.............................<

7741  ggttgatgct atcttctgga acttgcctgc tacattgaga ccactgaccc atacatagga
      ccaactacga tagaagacct tgaacggacg atgtaactct ggtgactggg tatgtatcct
      <.............................HS3.............................<

7801  agcccatagc tctgtcctga actgttaggc cactggtcca gagagtgtgc atctcctttg
      tcgggtatcg agacaggact tgacaatccg gtgaccaggt ctctcacacg tagaggaaac
      <.............................HS3.............................<

                                                                 BsaBI
7861  atcctcataa taaccctatg agatagacac aattattact cttactttat agatgatgat
      taggagtatt attgggatac tctatctgtg ttaataatga gaatgaaata tctactacta
      <.............................HS3.............................<

7921  cctgaaaaca taggagtcaa ggcacttgcc cctagctggg ggtatagggg agcagtccca
      ggacttttgt atcctcagtt ccgtgaacgg ggatcgaccc ccatatcccc tcgtcagggt
      <.............................HS3.............................<

7981  tgtagtagta gaatgaaaaa tgctgctatg ctgtgcctcc cccacctttc ccatgtctgc
      acatcatcat cttacttttt acgacgatac gacacggagg gggtggaaag ggtacagacg
      <.............................HS3.............................<

8041  cctctactca tggtctatct ctcctggctc ctgggagtca tggactccac ccagcaccac
      ggagatgagt accagataga gaggaccgag gaccctcagt acctgaggtg ggtcgtggtg
      <.............................HS3.............................<

8101  caacctgacc taaccaccta tctgagcctg ccagcctata acccatctgg gccctgatag
      gttggactgg attggtggat agactcggac ggtcggatat tgggtagacc cgggactatc
      <.............................HS3.............................<

8161  ctggtggcca gccctgaccc caccccaccc tccctggaac ctctgataga cacatctggc
      gaccaccggt cgggactggg gtggggtggg agggaccttg gagactatct gtgtagaccg
      <.............................HS3.............................<

8221  acaccagctc gcaaagtcac cgtgagggtc ttgtgtttgc tgagtcaaaa ttccttgaaa
      tgtggtcgag cgtttcagtg gcactcccag aacacaaacg actcagtttt aaggaacttt
      <.............................HS3.............................<

8281  tccaagtcct tagagactcc tgctcccaaa tttacagtca tagacttctt catggctgtc
      aggttcagga atctctgagg acgagggttt aaatgtcagt atctgaagaa gtaccgacag
      <.............................HS3.............................<

8341  tcctttatcc acagaatgat tcctttgctt cattgcccca tccatctgat cctcctcatc
      aggaaatagg tgtcttacta aggaaacgaa gtaacggggt aggtagacta ggaggagtag
      <.............................HS3.............................<

8401  agtgcagcac agggcccatg agcagtagct gcagagtctc acataggtct ggcactgcct
      tcacgtcgtg tcccgggtac tcgtcatcga cgtctcagag tgtatccaga ccgtgacgga
      <.............................HS3.............................<
```

sGbGM

Figure 31J

```
8461  ctgacatgtc cgaccttagg caaatgcttg actcttctga gctcggatcc cttgagctca
      gactgtacag gctggaatcc gtttacgaac tgagaagact cgagcctagg gaactcgagt
      <.......................HS3.......................<<
                                                            >>..HS4....>

8521  ggaggtcaag gctgcagtga gacatgatct tgccactgca ctccagcctg gacagcagag
      cctccagttc cgacgtcact ctgtactaga acggtgacgt gaggtcggac ctgtcgtctc
      >............................HS4............................>

8581  tgaaaccttg cctcacgaaa cagaatacaa aaacaaacaa acaaaaaact gctccgcaat
      actttggaac ggagtgcttt gtcttatgtt tttgtttgtt tgttttttga cgaggcgtta
      >............................HS4............................>

8641  gcgcttcctt gatgctctac cacataggtc tgggtacttt gtacacatta tctcattgct
      cgcgaaggaa ctacgagatg gtgtatccag acccatgaaa catgtgtaat agagtaacga
      >............................HS4............................>

8701  gttcataatt gttagattaa ttttgtaata ttgatattat tcctagaaag ctgaggcctc
      caagtattaa caatctaatt aaaacattat aactataata aggatctttc gactccggag
      >............................HS4............................>

8761  aagatgataa cttttatttt ctggacttgt aatagctttc tcttgtattc accatgttgt
      ttctactatt gaaaataaaa gacctgaaca ttatcgaaag agaacataag tggtacaaca
      >............................HS4............................>

8821  aactttctta gagtagtaac aatataaagt tattgtgagt tttgcaaac acagcaaaca
      ttgaaagaat ctcatcattg ttatatttca ataacactca aaaacgtttg tgtcgtttgt
      >............................HS4............................>

8881  caacgaccca tatagacatt gatgtgaaat tgtctattgt caatttatgg gaaaacaagt
      gttgctgggt atatctgtaa ctacacttta acagataaca gttaaatacc cttttgttca
      >............................HS4............................>

8941  atgtactttt tctactaagc cattgaaaca ggaataacag aacaagattg aaagaataca
      tacatgaaaa agatgattcg gtaactttgt ccttattgtc ttgttctaac tttcttatgt
      >............................HS4............................>

                                               PmlI
9001  ttttccgaaa ttacttgagt attatacaaa gacaagcacg tggacctggg aggagggtta
      aaaaggcttt aatgaactca taatatgttt ctgttcgtgc acctggaccc tcctcccaat
      >............................HS4............................>

9061  ttgtccatga ctggtgtgtg gagacaaatg caggtttata atagatggga tggcatctag
      aacaggtact gaccacacac ctctgtttac gtccaaatat tatctaccct accgtagatc
      >............................HS4............................>

9121  cgcaatgact ttgccatcac ttttagagag ctcttggggg ccccagtaca caagagggga
      gcgttactga aacggtagtg aaaatctctc gagaaccccc ggggtcatgt gttctcccct
      >............................HS4............................>

9181  cgcagggtat atgtagacat ctcattcttt ttcttagtgt gagaataaga atagccatga
      gcgtcccata tacatctgta gagtaagaaa aagaatcaca ctcttattct tatcggtact
      >............................HS4............................>

9241  cctgagttta tagacaatga gcccttttct ctctcccact cagcagctat gagatggctt
      ggactcaaat atctgttact cgggaaaaga gagagggtga gtcgtcgata ctctaccgaa
      >............................HS4............................>

9301  gccctgcctc tctactaggc tgactcactc caaggcccag caatgggcag ggctctgtca
      cgggacggag agatgatccg actgagtgag gttccgggtc gttacccgtc ccgagacagt
      >............................HS4............................>
```

sGbGM

Figure 31K

```
 9361  gggctttgat agcactatct gcagagccag ggccgagaag ggtggactc cagagactct
       cccgaaacta tcgtgataga cgtctcggtc ccggctcttc cccacctgag gtctctgaga
       >.............................HS4..............................>

                                                  SwaI
 9421  ccctcccatt cccgagcagg gtttgcttat ttatgcattt aaatgatata tttattttaa
       gggagggtaa gggctcgtcc caaacgaata aatacgtaaa tttactatat aaataaaatt
       >.............................HS4..............................>

 9481  aagaaataac aggagactgc ccagccctgg ctgtgacatg gaaactatgt agaatatttt
       ttctttattg tcctctgacg ggtcgggacc gacactgtac ctttgataca tcttataaaa
       >.............................HS4..............................>

 9541  gggttccatt ttttttcct tctttcagtt agaggaaaag ggctcactg cacatacact
       cccaaggtaa aaaaaaagga agaaagtcaa tctccttttc cccgagtgac gtgtatgtga
       >.............................HS4..............................>

                                             BclI
 9601  agacagaaag tcaggagctt tgaatccaag cctgatcatt tccatgtcat actgagaaag
       tctgtctttc agtcctcgaa acttaggttc ggactagtaa aggtacagta tgactctttc
       >.............................HS4..............................>

 9661  tccccaccct tctctgagcc tcagtttctc tttttataag taggagtctg gagtaaatga
       aggggtggga agagactcgg agtcaaagag aaaaatattc atcctcagac ctcatttact
       >.............................HS4..............................>

 9721  tttccaatgg ctctcatttc aatacaaaat ttccgtttat taaatgcatg agcttctgtt
       aaaggttacc gagagtaaag ttatgtttta aaggcaaata atttacgtac tcgaagacaa
       >.............................HS4..............................>

 9781  actccaagac tgagaaggaa attgaacctg agactcattg actggcaaga tgtccccaga
       tgaggttctg actcttcctt taacttggac tctgagtaac tgaccgttct acaggggtct
       >.............................HS4..............................>

 9841  ggctctcatt cagcaataaa attctcacct tcacccaggc ccactgagtg tcagatttgc
       ccgagagtaa gtcgttattt taagagtgga agtgggtccg ggtgactcac agtctaaacg
       >.............................HS4..............................>

 9901  atgcggatcc actagttcta gagcggccgg ggtcgacgaa ttcgagctcg gtacctttaa
       tacgcctagg tgatcaagat ctcgccggcc ccagctgctt aagctcgagc catggaaatt
       >.HS4.>>
                 >>......................3' LTR.......................>

 9961  gaccaatgac ttacaaggca gctgtagatc ttagccactt tttaaaagaa aaggggggac
       ctggttactg aatgttccgt cgacatctag aatcggtgaa aaattttctt ttcccccctg
       >...........................3' LTR.............................>

                                                            BspEI
                                                    EcoRV
10021  tggaagggct aattcactcc caacgaagac aagatcgcta gcgatatctc cggatttatt
       accttcccga ttaagtgagg gttgcttctg ttctagcgat cgctatagag gcctaaataa
       >...........................3' LTR.............................>

10081  tgtgaaattt gtgatgctat tgctttattt gaccggtctg ctttttgctt gtactgggtc
       acactttaaa cactacgata acgaaataaa ctggccagac gaaaaacgaa catgacccag
       >...........................3' LTR.............................>

10141  tctctggtta gaccagatct gagcctggga gctctctggc taactaggga acccactgct
       agagaccaat ctggtctaga ctcggaccct cgagagaccg attgatccct tgggtgacga
       >...........................3' LTR.............................>
```

sGbGM

Figure 31L

```
10201  taagcctcaa taaagcttgc cttgagtgct tcaagtagtg tgtgcccgtc tgttgtgtga
       attcggagtt atttcgaacg gaactcacga agttcatcac acacgggcag acaacacact
       >..........................3' LTR............................>

                                                               MluI
10261  ctctggtaac tagagatccc tcagaccctt ttagtcagtg tggaaaatct ctagcaacgc
       gagaccattg atctctaggg agtctgggaa aatcagtcac accttttaga gatcgttgcg
       >.......................3' LTR.......................>>

10321  gtccatctgt tgtttgcccc tcccccgtgc cttccttgac cctggaaggt gccactccca
       caggtagaca acaaacgggg agggggcacg gaaggaactg ggaccttcca cggtgagggt
         >>..........................PolyA............................>

10381  ctgtcctttc ctaataaaat gaggaaattg catcgcattg tctgagtagg tgtcattcta
       gacaggaaag gattatttta ctcctttaac gtagcgtaac agactcatcc acagtaagat
       >............................PolyA............................>

10441  ttctgggggg tggggtgggg cagcacagca agggggagga ttgggaagac aatagcaggc
       aagacccccc accccacccc gtcgtgtcgt tccccctcct aacccttctg ttatcgtccg
       >............................PolyA............................>

10501  atgctgggga tgcggtgggc tctatgggta cccaggtgct gaagaattga cccggttcct
       tacgacccct acgccacccg agatacccat gggtccacga cttcttaact gggccaagga
       >............................PolyA............................>

                                                               BstXI
10561  cctgggccag aaagaagcag gcacatcccc ttctctgtga cacaccctgt ccacgcccct
       ggacccggtc tttcttcgtc cgtgtagggg aagagacact gtgtgggaca ggtgcgggga
       >............................PolyA............................>

10621  ggttcttagt tccagcccca ctcataggac actcatagct caggagggct ccgccttcaa
       ccaagaatca aggtcggggt gagtatcctg tgagtatcga gtcctcccga ggcggaagtt
       >............................PolyA............................>

10681  tcccacccgc taaagtactt ggagcggtct ctccctccct catcagccca ccaaaccaaa
       agggtgggcg atttcatgaa cctcgccaga gagggaggga gtagtcgggt ggtttggttt
       >............................PolyA............................>

10741  cctagcctcc aagagtggga agaaattaaa gcaagatagg ctattaagtg cagagggaga
       ggatcggagg ttctcaccct tctttaattt cgttctatcc gataattcac gtctccctct
       >............................PolyA............................>

                  SacII
10801  gaaaatgcct ccnnnnccgc gggtagtagt tcatgtcatc ttattattca gtatttataa
       cttttacgga ggnnnnggcg cccatcatca agtacagtag aataataagt cataaatatt
       >...PolyA..>>

10861  cttgcaaaga aatgaatatc agagagtgag aggaacttgt ttattgcagc ttataatggt
       gaacgtttct ttacttatag tctctcactc tccttgaaca aataacgtcg aatattacca

10921  tacaaataaa gcaatagcat cacaaatttc acaaataaag cattttttc actgcattct
       atgtttattt cgttatcgta gtgtttaaag tgtttatttc gtaaaaaaag tgacgtaaga

10981  agttgtggtt tgtccaaact catcaatgta tcttatcatg tctggctcta gctatcccgc
       tcaacaccaa acaggtttga gtagttacat agaatagtac agaccgagat cgatagggcg

11041  ccctaactcc gcccatcccg cccctaactc cgcccagttc cgcccattct ccgccccatg
       gggattgagg cgggtagggc ggggattgag gcgggtcaag gcgggtaaga ggcggggtac

                                                  SfiI
11101  gctgactaat tttttttatt tatgcagagg ccgaggccgc ctcggcctct gagctattcc
       cgactgatta aaaaaaataa atacgtctcc ggctccggcg gagccggaga ctcgataagg
```

sGbGM

Figure 31M

```
                                                                   BsmBI
11161  agaagtagtg aggaggcttt tttggaggcc taggcttttg cgtcgagacg tacccaattc
       tcttcatcac tcctccgaaa aaacctccgg atccgaaaac gcagctctgc atgggttaag

11221  gccctatagt gagtcgtatt acgcgcgctc actggccgtc gttttacaac gtcgtgactg
       cgggatatca ctcagcataa tgcgcgcgag tgaccggcag caaaatgttg cagcactgac

11281  ggaaaaccct ggcgttaccc aacttaatcg ccttgcagca catccccctt tcgccagctg
       ccttttggga ccgcaatggg ttgaattagc ggaacgtcgt gtagggggaa agcggtcgac

11341  gcgtaatagc gaagaggccc gcaccgatcg cccttcccaa cagttgcgca gcctgaatgg
       cgcattatcg cttctccggg cgtggctagc gggaagggtt gtcaacgcgt cggacttacc

11401  cgaatggcgc gacgcgccct gtagcggcgc attaagcgcg gcgggtgtgg tggttacgcg
       gcttaccgcg ctgcgcggga catcgccgcg taattcgcgc cgcccacacc accaatgcgc
                  >>......................ori........................>

11461  cagcgtgacc gctacacttg ccagcgccct agcgcccgct cctttcgctt tcttcccttc
       gtcgcactgg cgatgtgaac ggtcgcggga tcgcgggcga ggaaagcgaa agaagggaag
       >.............................ori..............................>

                   NaeI
                   NgoMIV
11521  ctttctcgcc acgttcgccg gctttccccg tcaagctcta aatcgggggc tccctttagg
       gaaagagcgg tgcaagcggc cgaaaggggc agttcgagat ttagcccccg agggaaatcc
       >.............................ori..............................>

11581  gttccgattt agtgctttac ggcacctcga ccccaaaaaa cttgattagg gtgatggttc
       caaggctaaa tcacgaaatg ccgtggagct ggggtttttt gaactaatcc cactaccaag
       >.............................ori..............................>

11641  acgtagtggg ccatcgccct gatagacggt ttttcgccct ttgacgttgg agtccacgtt
       tgcatcaccc ggtagcggga ctatctgcca aaaagcggga aactgcaacc tcaggtgcaa
       >.............................ori..............................>

11701  ctttaatagt ggactcttgt tccaaactgg aacaacactc aaccctatct cggtctattc
       gaaattatca cctgagaaca aggtttgacc ttgttgtgag ttgggataga gccagataag
       >.............................ori..............................>

11761  ttttgattta taagggattt tgccgatttc ggcctattgg ttaaaaaatg agctgattta
       aaaactaaat attccctaaa acggctaaag ccggataacc aatttttttac tcgactaaat
       >.............................ori..............................>

11821  acaaaaattt aacgcgaatt ttaacaaaat attaacgttt acaatttc
       tgtttttaaa ttgcgcttaa aattgtttta taattgcaaa tgttaaag
       >.......................ori......................>>
```

FETAL HEMOGLOBIN FOR GENETIC CORRECTION OF SICKLE CELL DISEASE

CROSS-REFERENCE TO RELATED APPLICATIONS

This application is a continuation of U.S. application Ser. No. 15/115,530, filed Jul. 29, 2016, which is a national stage filing under U.S.C. § 371 of PCT International Application No. PCT/US2015/013960, with an international filing date of Jan. 30, 2015, which The present application claims the benefit of priority under 35 U.S.C. § 119(e) to U.S. Provisional Application No. 61/933,788, filed on Jan. 30, 2014, the contents of each of which are is hereby incorporated herein by reference in their entirety.

GOVERNMENT RIGHTS

This invention was made with government support under HL070871, HL070135, HL073104, and HL006008 awarded by the National Institutes of Health. The government has certain rights in the invention.

FIELD OF THE INVENTION

The invention disclosed herein generally relates to methods of determining minimum hematopoietic stem cell (HSC) chimerism and gene dosage for correction of a hematopoietic disease; in particular, in an in vivo model. The invention also relates to modified SIN lentiviral expression vectors for increasing a viral titer and various methods for increasing such titers as well as expression vectors capable of enhancing such titers. The invention also relates to CHS4 chromatin insulator-derived functional insulator sequences to help increase the safety of integrating vectors and to increase expression. The invention also relates to methods for genetic correction of diseases or reducing symptoms thereof, such as sickle cell anemia and β-thalassemia. The invention further relates to various expression vectors capable of genetically correcting sickle cell anemia or 3-thalassemia, or reducing symptoms thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Genetic Correction and Vector Design

Successful genetic correction of diseases, mediated by hematopoietic stem cells (HSCs), depends upon stable, safe, targeted gene expression of therapeutic quantities. Expression vectors are central to the process of genetic correction and consequently the subject of considerable research. Although significant advances in vector design have improved the efficacy of gene therapy, certain key obstacles have emerged as barriers to successful clinical application. Among those obstacles, vector genotoxicity is among the most formidable, as evidenced by the occurrence of gene therapy related leukemia in patients in X-SCID trials, as disclosed herein. As a result, gamma-retroviral vectors and lentiviral vectors have been modified to a self-inactivating (SIN) design to delete ubiquitously active enhancers in the U3 region of the long terminal repeats (LTR) (as disclosed herein). SIN design has been improved upon to increase vector titers. Several methods of improving transgene expression have been subsequently employed.

As an added measure of stabilizing expression, many vectors are now designed with chromatin insulating elements that reduce chromatin position effects. While these insulators can improve the safety and expression profiles of certain vectors, in some cases an undesirable side effect is decreased titers compared to non-insulated versions. Custom insulators have been designed that provide optimal insulation without lowering titers.

Thus, there is a need in the art for improved expression vector design, aimed at safely stabilizing the expression of transgenes, while maintaining clinically relevant viral titers.

Determining Critical Parameters of Correction in Sickle Cell Anemia

Expressing a tremendous amount of fetal/antisickling hemoglobin will undoubtedly correct disease, as has been demonstrated, but is not practically possible in a clinical setting. As an example, an initial gene therapy for adenosine deaminase (ADA) deficiency was performed using no conditioning, and was not therapeutic, even though few gene-marked stem cells engrafted, and a selective advantage to gene-corrected lymphocytes was evident upon withdrawal of ADA (as disclosed herein). In a subsequent trial, 4 mg/kg busulfan was used before transplantation, as conditioning, resulting in adequate gene-corrected stem cell dose and gene-modified T cells (as disclosed herein). Thus, there is a need in the art to establish methods of determining thresholds for genetic correction before embarking on clinical studies.

SUMMARY OF THE INVENTION

Methods and composition described herein are provided by way of example and should not in any way limit the scope of the invention.

Embodiments of the invention encompass mutated human gamma-globin genes. In some embodiments, the mutated human gamma-globin gene can encode a protein including SEQ ID NO: 1. In some embodiments, the mutated human gamma-globin gene can have a sequence identity of 70% or greater to SEQ ID NO: 2.

Embodiments of the invention also encompass methods of using a mutated human gamma-globin gene encoding a protein including SEQ ID NO:1 to genetically correct sickle cell anemia or β-thalassemia or reduce symptoms thereof, the method including identifying a subject in need of treatment for sickle cell anemia or β-thalassemia; transfecting autologous hematopoietic stem cells (HSCs) with a modified lentivirus including the mutated human gamma-globin gene encoding a protein including SEQ ID NO:1; and transplanting the transfected HSCs into the subject.

In some embodiments, the subject is a human subject. In some embodiments, the subject is treated with reduced intensity conditioning prior to transplantation.

In some embodiments, the modified lentivirus further includes a heterologous polyA signal sequence downstream from a viral 3' LTR sequence in a standard SIN lentiviral vector backbone; and one or more USE sequences derived from an SV40 late polyA signal in a U3 deletion region of a standard SIN lentiviral vector backbone. In some embodiments, the modified lentivirus further includes one or more flanking CHS4-derived reduced-length functional insulator sequences. In some embodiments, the modified lentivirus further includes a beta-globin locus control region. In some embodiments, the modified lentivirus further includes an erythroid lineage specific enhancer element.

In some embodiments, post-transplantation fetal hemoglobin exceeds at least 20%; F cells can be at least ⅔ of the circulating red blood cells; fetal hemoglobin per F cells can be for at least ⅓ of total hemoglobin in sickle red blood cells; and at least 20% gene-modified HSCs can re-populate bone marrow of the subject.

Embodiments of the invention also encompass lentiviral expression vectors capable of genetically correcting sickle cell anemia or β-thalassemia or reducing symptoms thereof, includes a mutated human gamma-globin gene encoding a protein in SEQ ID NO: 1. In some embodiments, the lentiviral expression vector, further includes a heterologous polyA signal sequence downstream from a viral 3' LTR sequence in a standard SIN lentiviral vector backbone; and one or more USE sequences derived from an SV40 late polyA signal in a U3 deletion region of a standard SIN lentiviral vector backbone. In some embodiments, the lentiviral expression vector further includes one or more flanking CHS4-derived reduced-length functional insulator sequences. In some embodiments, the lentiviral expression vector further includes one or more elements of a beta-globin locus control region cloned in reverse orientation to a viral transcriptional unit. In some embodiments, the lentiviral expression vector further includes an erythroid lineage specific enhancer element.

BRIEF DESCRIPTION OF THE FIGURES

Those of skill in the art will understand that the drawings, described below, are for illustrative purposes only. The drawings are not intended to limit the scope of the present teachings in any way.

FIG. 1A: A schematic representation of SIN lentiproviruses. sSIN-GFP, sBG-6 and sFIG are SIN-LV carrying GFP, the β-globin gene (BG) or the Fanconi Anemia A cDNA, -IRES-GFP respectively. dsSIN-GFP, sBG-1 and ds-FIG are their gutted counterparts. SD=splice donor. SA=splice acceptor. ψ packaging sequence. cPPT: central poly purine tract. The gag (360 bp) and the env fragment containing the RRE (~850 bp) are indicated. FIG. 1B: The viral obtained after infection of MEL cells and analysis for GFP and hβ-globin expressing cells with different iterations of the "SIN" design. Titers are expressed as IU/mL of concentrated supernatant (n=3).

FIG. 3A: Viral supernatants of sBG-1 to sBG-10 SIN lentiviral vectors were concentrated 1400-fold and titered on MEL cells by monitoring for β-globin positive cells by flow cytometry (n=4). FIG. 3B: Fold increase in titers with inclusion of cis-elements. The titers were normalized to that of the completely gutted vector (sBG-1), which was considered 1. The sBG-6 design showed a marked increase in titers.

FIG. 4A: Proviral integrity: Southern blot analysis of MEL cells transduced with sBG-127 to sBG-10, restricted with AflII that cuts in the viral LTRs, and probed with a hβ-globin fragment. All SIN vectors are transmitted stably. FIG. 4B: Expression of hβ-globin in MEL cells: dot plot analysis of sBG-1 to sBG-10 transduced MEL cells from one representative experiment; MFI are indicated in the upper right corner of the dot-plot.

FIG. 5B: Cytoplasmic RNA for vectors with and without RRE from the same experiment shown in panel A, showing the efficiency of vRNA export into the cytoplasm. The phosphoimager quantified ratios cytoplasmic/total are shown in FIG. 6E.

FIGS. 6A-6E depict packaging of vRNA into virons. FIG. 6A: A representative dot blot analysis on vRNA extracted from sBG series of virus supernatants showing that the amount of vRNA is proportional to infectious titers. Virus was made from all ten vectors and concentrated identically as described and the dot-blot was probed with a β-globin fragment. NC=negative control. Four different dilutions for each vector were loaded in duplicate in the representative experiment shown. A total of three experiments were performed. FIG. 6B: Phosphoimager counts obtained on the 28 dot blot shown in FIG. 6A. FIG. 6C: Relative quantification of vRNA from all three experiments. FIG. 6D: p24 activity in concentrated virus from all vectors (n=2). FIG. 6E: Ratio of Cytoplasmic/Total RNA from 2 Northern Blot Analysis (NB) in Packaging Cells (The ratio cytoplasmic/total RNA was normalized to the value for the completely gutted vector lacking the RRE (SBG-1) and to 18S RNA (for loading) in two independent experiments. Analogous vectors with and without RRE are marked as I, II and III to allow ready comparisons).

FIG. 7A: Self-inactivating (SIN) lentiviral vector carrying the hβ-globin gene and the HS2, HS3 and HS4 of the locus control region is shown as sBG. Using this backbone, a series of vectors were generated to incorporate either the cHS4 59 250 bp core, 2 tandem repeats of the core, 5' 400 bp or 59 800 bp of cHS4, and the full-length 1.2 Kb cHS4 insulator. Vectors sBG400S and sBG800S carry in addition to the core inert DNA spacers from 1 bacteriophage. FIG. 7B: Schema of In vitro and in vivo analyses: MEL cells were transduced with various vectors to derive single copy MEL clones and hβ-globin expression and ChIP analysis was performed in differentiated clones. In vivo analysis was done using vector transduced $Hbb^{th3/+}$ donor LSK cells transplanted into lethally irradiated $Hbb^{th3/+}$ recipients and analyzed at 6 months post-transplant. Secondary transplants were performed for CFU-S analysis. FIG. 7C: Representative FACS plot showing hβ-globin-expressing cells (% hβ+)

for uninsulated (sBG, green) and insulated (sBG-I, Pink) single copy MEL clone with coefficient of variation (CV) of expression shown by arrows.

Figure 8A:
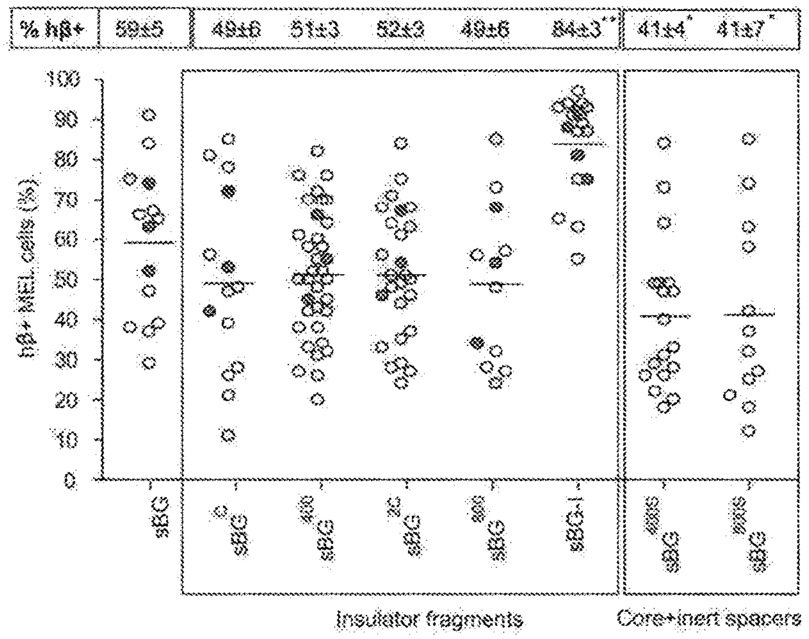
Figure 8B:
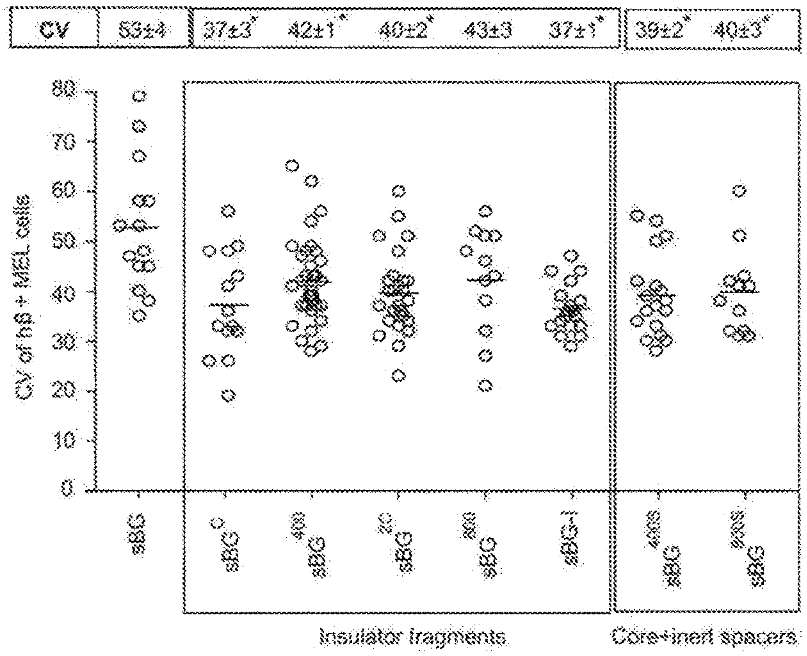

FIGS. 8A-8B depict human β-globin expressing cells in MEL clones. FIG. 8A: Proportion of hβ-globin-expressing cells (% hβ+) in MEL clones. Each circle represents an individual single copy MEL clone. FIG. 8B: CV values of hβ-globin expression of each clone. The means are represented with a horizontal line and the mean 6 SEM of % hβ+ MEL cells and CV of hβ-globin expression for each vector are indicated in the box above. Filled circles represent representative clones picked for ChIP analysis. *P<0.05 by ANOVA, as compared to sBG.

Figure 9A:
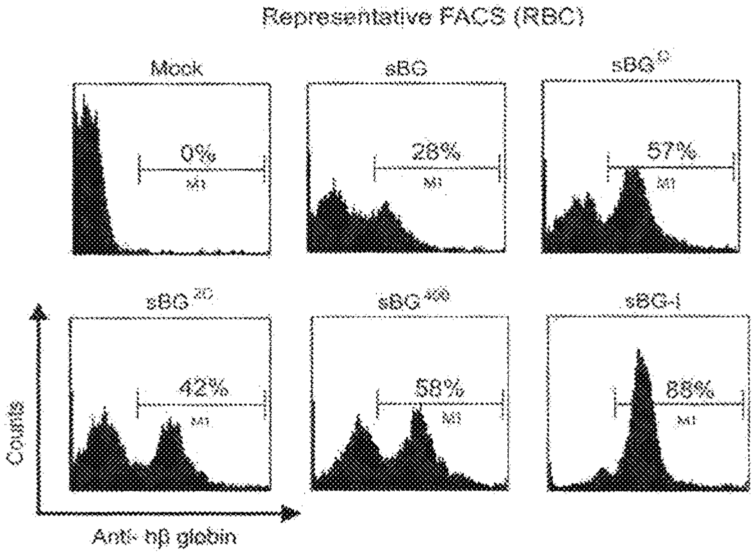
Figure 9B:
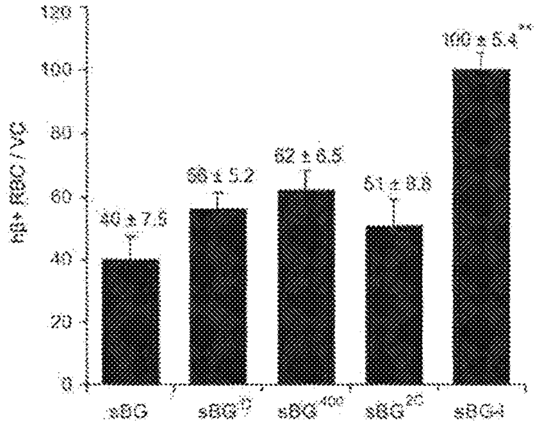
Figure 9C:
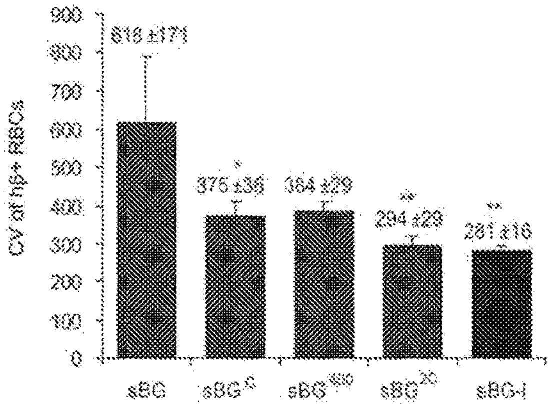
Figure 9D:
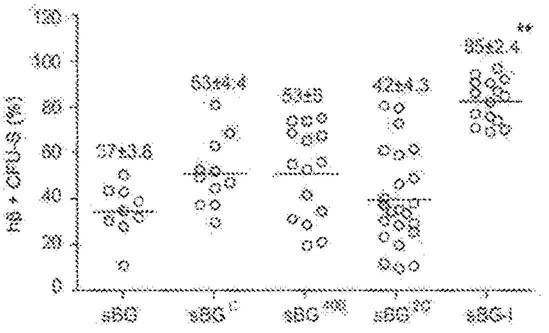
Figure 9E:
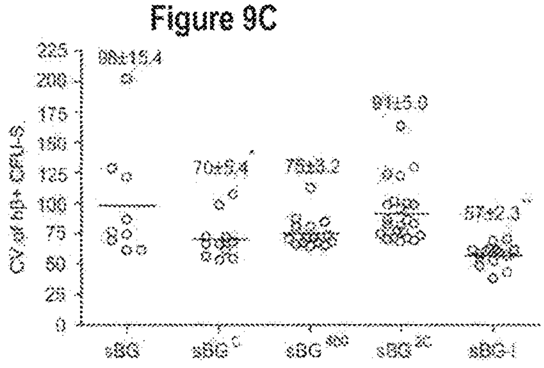

FIGS. 9A-9E depict human β-globin expression in RBCs and single copy secondary CFU-S. FIG. 9A: Representative FACS histograms showing (% hβ+ RBC are indicated within the histogram). FIG. 9B: Cumulative data on the percentage of hβ+ RBCs normalized to vector copy. FIG. 9C: The coefficient of variation (CV) of hβ expression in RBCs. FIG. 9D: Cumulative data on % hβ+ cells/CFU-S. Each circle represents an individual single integrant CFU-S. FIG. 9E: The CV of hβ expression in the individual CFU-S. Numbers above bar diagrams represent mean 6 SEM and values significantly different from controls by ANOVA are marked by an asterisk. *P<0.05; **P<0.01.

Figure 10A:
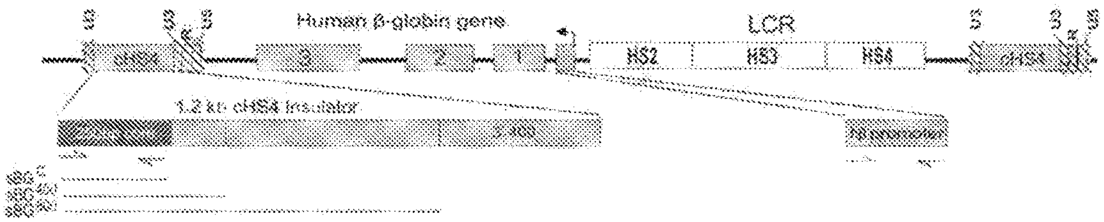
Figure 10B:
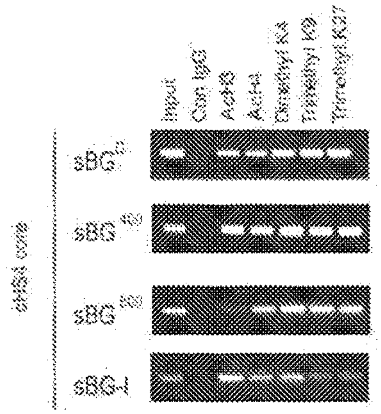
Figure 10C:
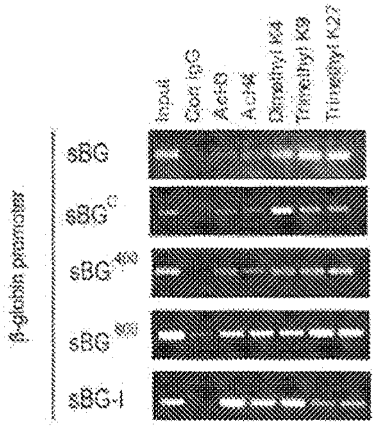
Figure 10D:
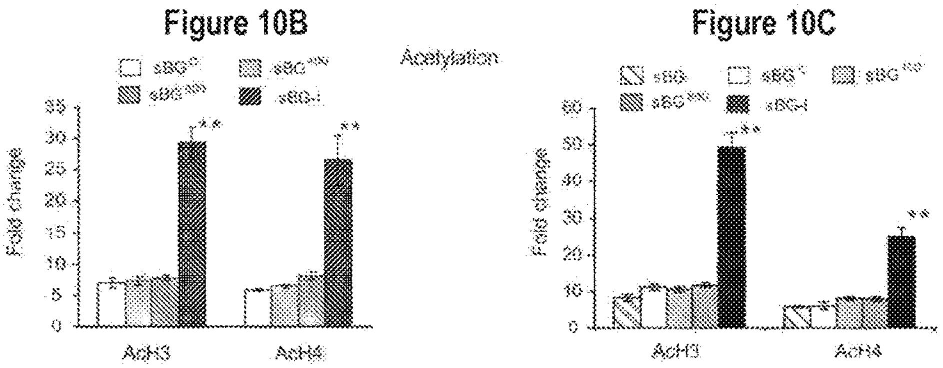
Figure 10E:
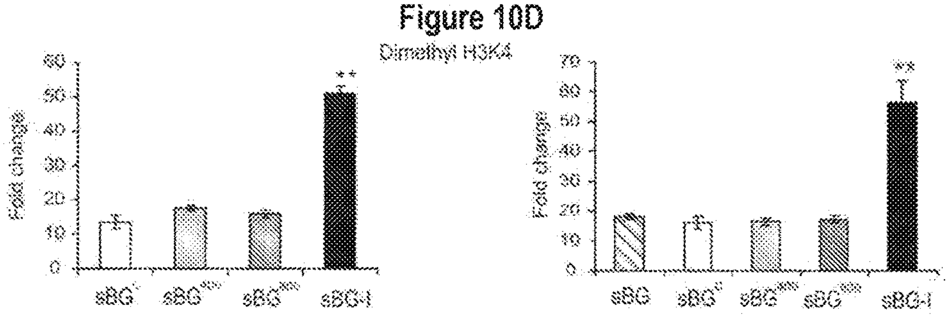

FIGS. 10A-10F depict chIP analysis showing the active and repressive histone marks on the 5' 250 bp cHS4 core and the hβ promoter in MEL cell clones. FIG. 10A: Map of the proviral form of the vector. Arrows show the position of the primer pairs used for PCR and qPCR; and the lines represent insulator fragments. FIGS. 10B-10C: ChIP with antibodies against control IgG, acH3, acH4, H3K4-me2, H3K9-me3 and H3K27-me3 and semiquantitative PCR primers to the β-globin promoter region D-F ChIP with antibodies to AcH3 and AcH4 (FIG. 10D), H3K4-me2 (FIG. 10E); H3K9-me3 and H3K27-me3 (FIG. 10F) followed by qPCR using primers amplifying cHS4 core (left panels) and hβ-globin promoter (right panel) on pooled clones (shown in FIG. 2A). *P<0.05; **P<0.01.

FIGS. 11A-11B depict human β-globin expression in mice. FIG. 11A: RBC parameters, reticulocytes and vector copies. Values represent means±SEM. Hb=hemoglobin, MCV=mean corpuscular volume, MCHC=mean corpuscular hemoglobin concentration, vector copy=vector copies in leukocytes by qPCR. FIG. 11B: HPLC analysis of human β-globin protein in blood lysates as a percentage of total hemoglobin [hβ-mα/(hβ-mα+mβ-mα)]. Data is normalized to vector copy/cell in leukocytes. *P<0.05; **P<0.01.

Figure 12A:
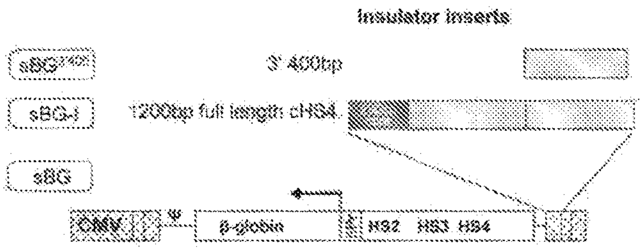
Figure 12B:
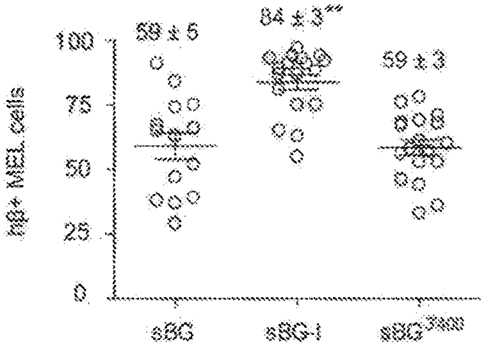
Figure 12C:
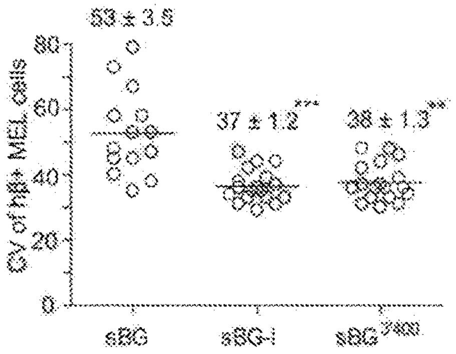
Figure 12D:
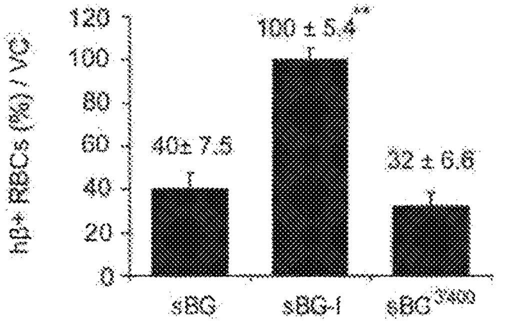
Figure 12E:
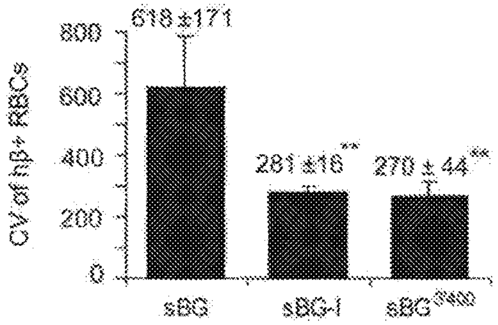
Figure 12F:
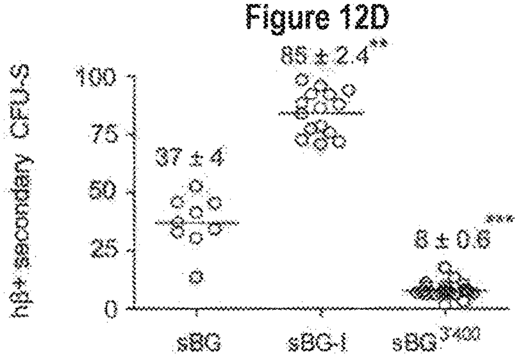
Figure 12G:
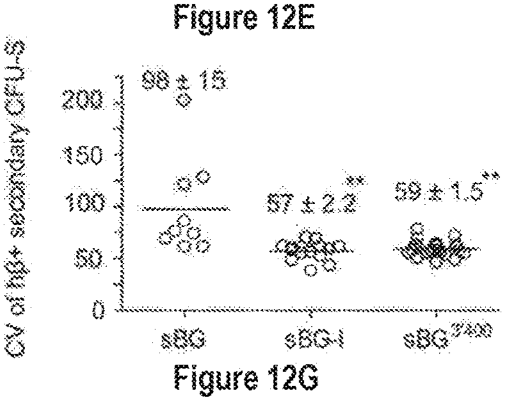

FIGS. 12A-12G depict effect of 3'400 bp region of the cHS4 insulator. FIG. 12A: Vector design of $sBG^{3'400}$ vector. The full length cHS4 is shown for comparison. FIGS. 12B-12C: Proportion of hβ+ cells (FIG. 12B) and the coefficient of variation of hβ expression of $sBG^{3'400}$ (FIG. 12C) in MEL clones. Each circle represents a single integrant MEL clone. The means are represented with a horizontal line and the mean±SEM are represented in the figure. FIGS. 12D-12E: The percentage of hβ-globin+ RBC (FIG. 12D), and the CV of hβ expression (FIG. 12E) in mice. FIGS. 12F-12G: hβ-globin-expressing cells (FIG. 12F) and the CV of hb expression (FIG. 12G) in single copy CFU-S following secondary transplant. Each circle represents individual CFU-S. Mean±SEM and P-values are shown. *P<0.05; P<0.01; *P<0.001.

Figure 13A:
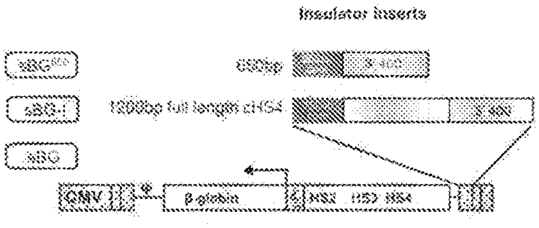
Figure 13B:
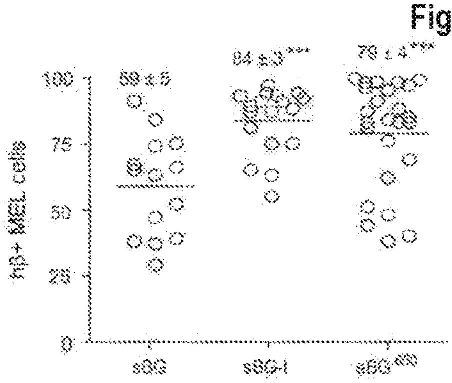
Figure 13C:
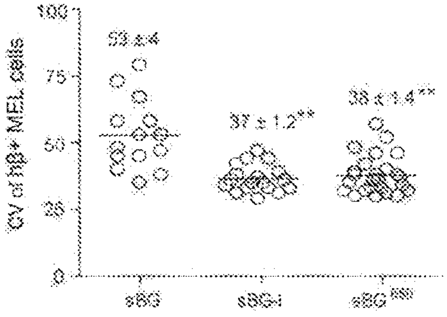
Figure 13D:
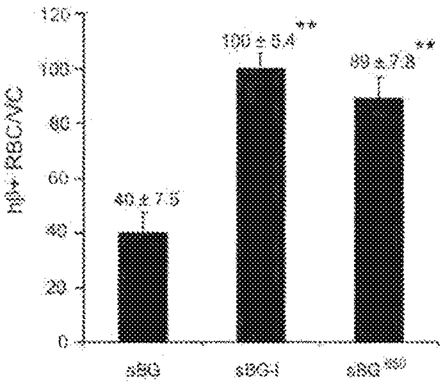
Figure 13E:
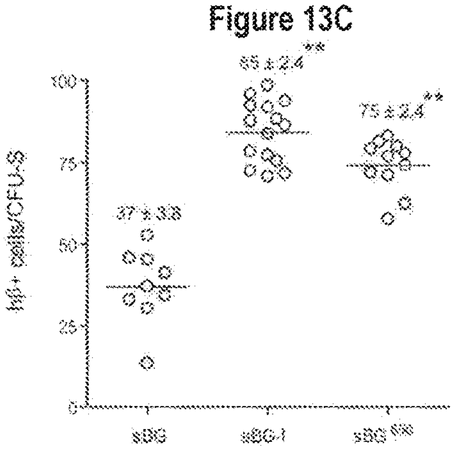
Figure 13F:
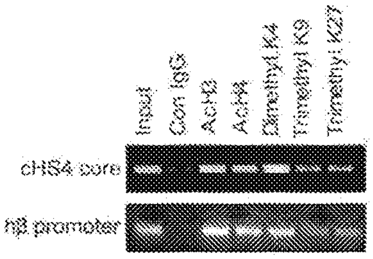
Figure 13G:
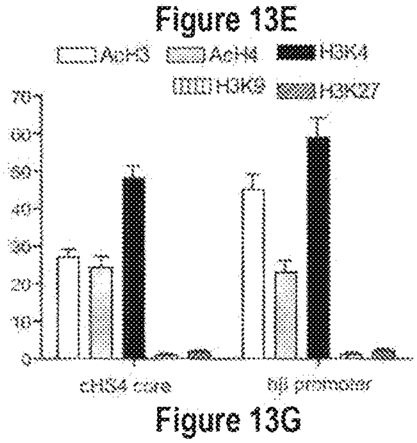

FIGS. 13A-13G depict effect of the combination of the 5' core with the 3' 400 bp regions of the cHS4 insulator. FIG. 13A: Vector design of $sBG^{650}$. The full length cHS4 is shown for comparison. FIG. 13B: Proportion of hβ+ cells and FIG. 13C: CV of hb-globin expression in $sBG^{650}$ MEL clones. Each circle represents a single copy MEL clone. The means are represented with a horizontal line and the mean±SEM is indicated above each group. FIG. 13D: Percentage of hbglobin expressing RBC in transplanted mice. FIG. 13E: Percentage hβ-globin expressing cells in single copy CFU-S from secondary mice. FIGS. 13F-13G: ChIP active and repressive chromatin followed by semiquantitative PCR (FIG. 13F) or qPCR (FIG. 13G) of the cHS4 core region or the hβ-globin promoter region.

Figure 14A:
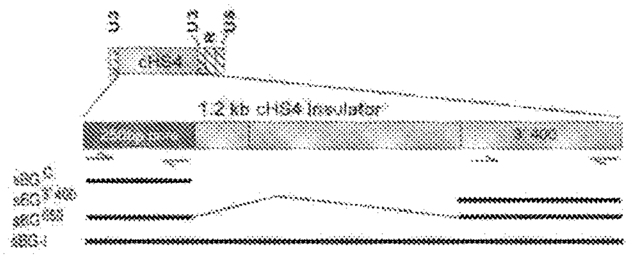
Figure 14B:
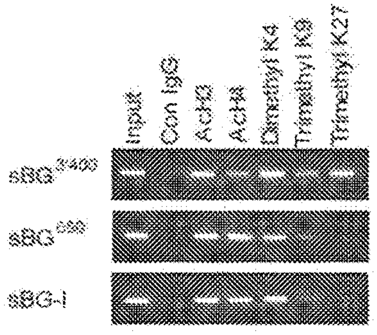
Figure 14C:
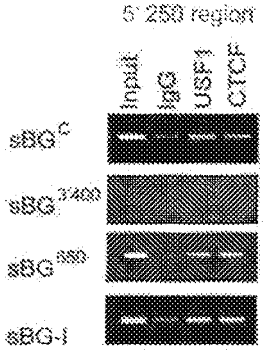
Figure 14D:
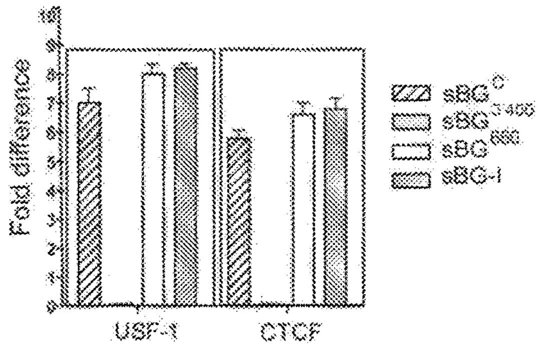
Figure 14E:
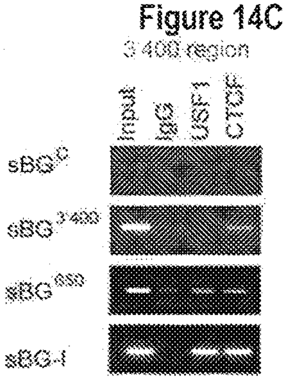
Figure 14F:
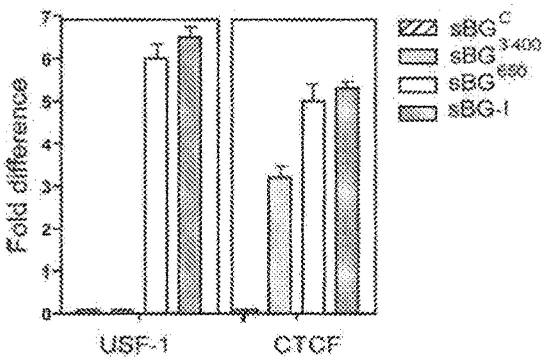
Figure 14G:
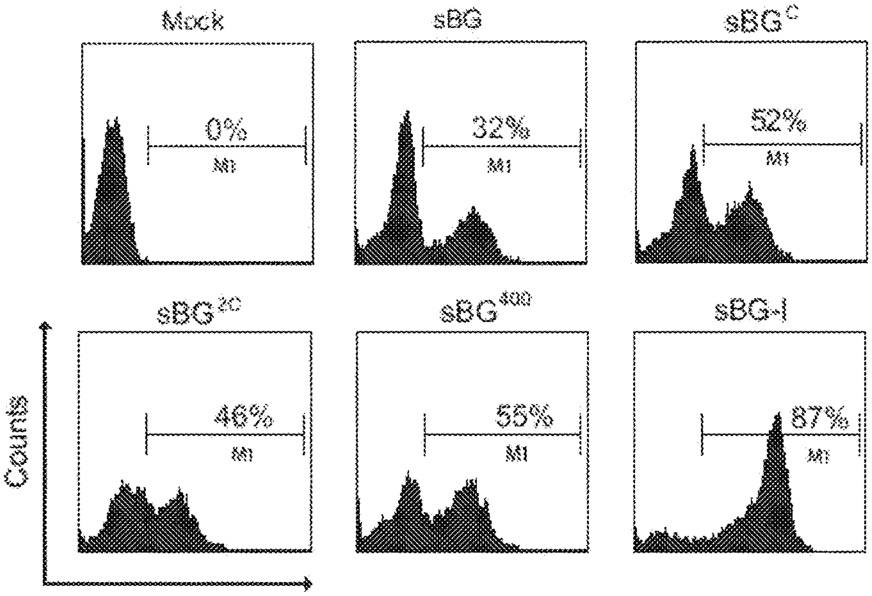
Figure 14H:
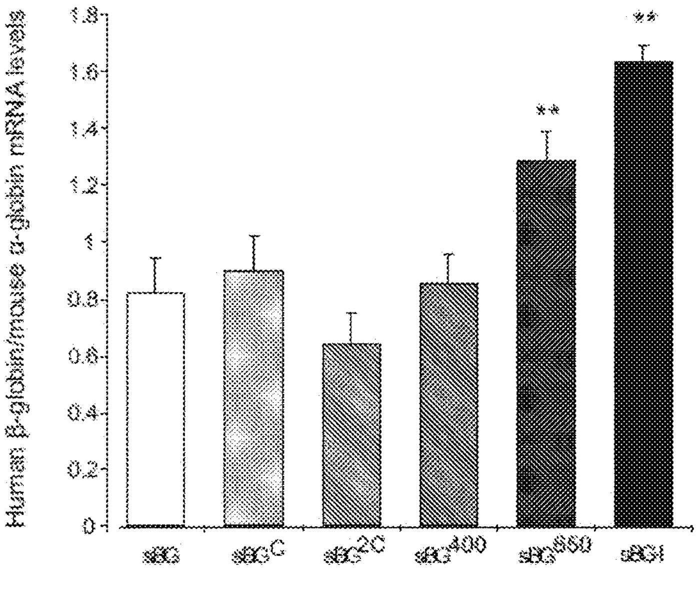

FIGS. 14A-14J depict chromatin patterns over the 3'400 bp and its interaction with the 5' core region. FIG. 14A: A map of 3'LTR showing location of full length 1.2 kb insulator and the position of primers used in ChIP analysis. Vectors tested with the indicated regions of the cores are depicted beneath map. FIG. 14B: ChIP with antibodies to AcH3 and AcH4, H3K4-me2 and H3K9-me3 and H3K27-me3 followed by a semiquantitative PCR of the 3'400 region in $sBG^{3'400}$, $sBG^{650}$, sBG-I provirus. FIG. 14C-14D: ChIP with antibodies to USF-1 and CTCF followed by semi-quantitative PCR (FIG. 14C) or qPCR (FIG. 14D) for the core region. FIGS. 14E-14F: ChIP with antibodies to USF-1 and CTCF followed by semi-quantitative PCR (FIG. 14C) or qPCR (FIG. 14D) for the 3/400 bp region of the sBGC, $sBG^{3'400}$, $sBG^{650}$ and sBG-I provirus in pools of three single copy MEL clones. FIG. 14G: Representative histograms (FACS) showing hb expressing cells in mock, sBG, sBGC, sBG2C, sBG400 and sBGI sBGI single copy CFU-S. The % of hβ+ cells are indicated within the histogram. FIG. 14H: Human β-globin messenger RNA (mRNA) expression in single copy secondary CFU-S of sBG, sBGC, sBG2C, sBG400 and sBG-I by qPCR. Murine α-globin expression served as the internal control against which hβ-globin expression was normalized. P values are shown in the figure.  indicates P<0.01. FIG. 14I: The primers and probes used in chromatin immunoprecipitation (ChIP) is shown. 'F' represents forward primer and 'R' represents reverse primer. FIG. 14**J: Insertional site analysis on single copy MEL clones from uninsulated sBG and insulated sBG-I vector with gene hits according to genome.ucsc.edu.

Figure 15A:
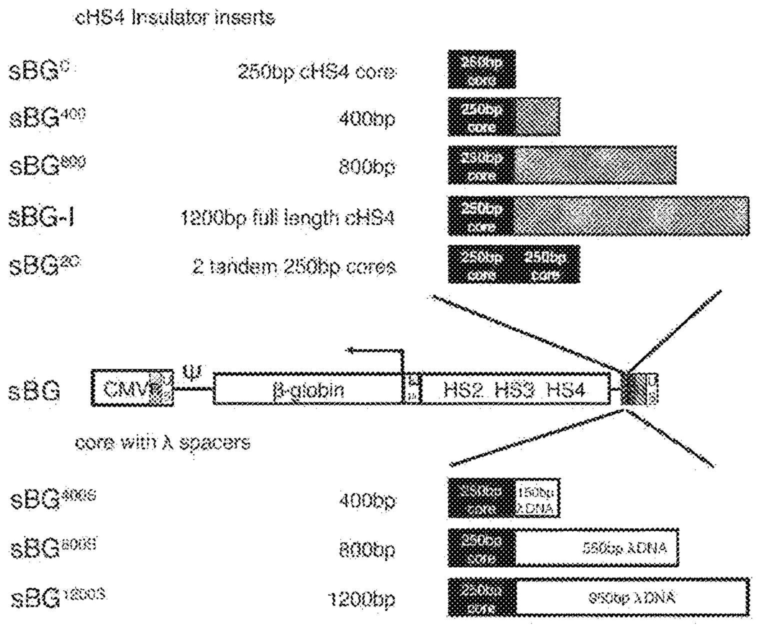
Figure 15B:
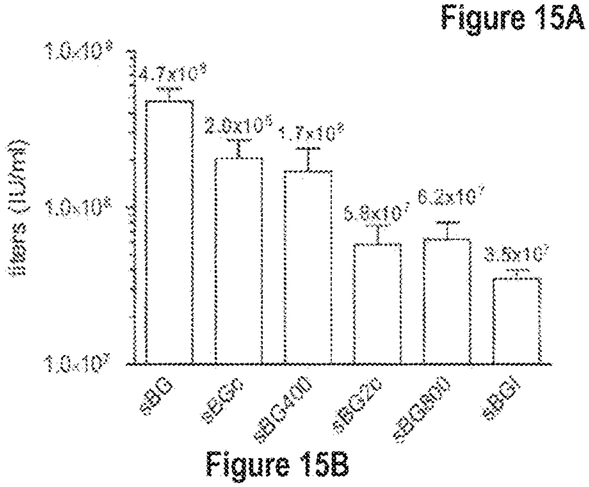
Figure 15C:
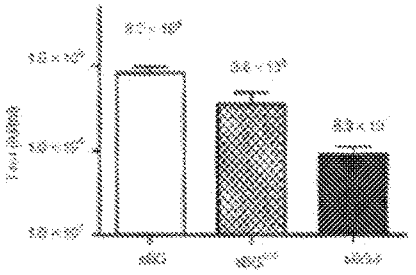
Figure 15D:
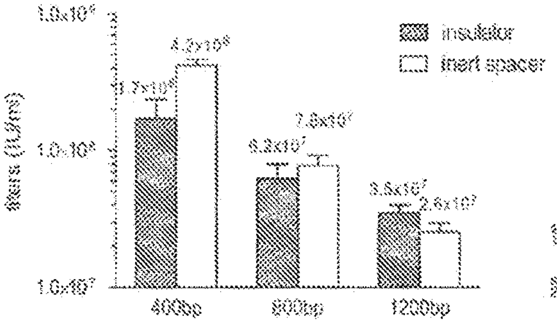
Figure 15E:
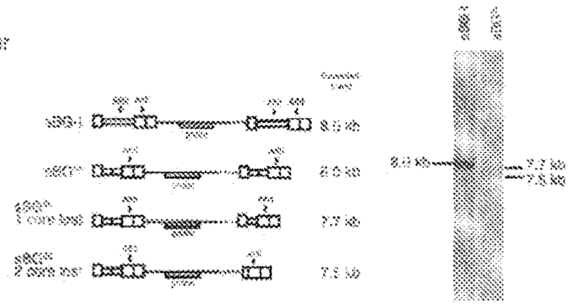

FIGS. 15A-15E depict viral titers of lentiviral vectors with inserts into the 3'LTR were inversely proportional to the length of the LTR insert. FIG. 15A: Schematic representation of the lentiviral vectors. All vectors were based on sBG, a SIN lentiviral vector carrying the β-globin gene, β-globin promoter and the locus control region elements HS2, HS3 and HS4. Different fragments of the cHS4 site were inserted in the U3 region of the sBG 3'LTR (shown above the sBG vector). Similar sized inserts were made by replacing the region downstream of cHS4 core with inert DNA spacers from the lambda phage DNA (shown below the sBG vector). FIG. 15B: Viral titers of insulated vectors decreased as the length of the insulator insert increased. Titers reflect concentrated virus made concurrently for all vectors in each experiment (n=4). All titers were significantly lower than the titers of the control vector sBG (p<0.01; 1-way ANOVA). FIG. 15C: Titers fell with insertion of increasing length of an inert DNA spacer downstream of the core. Titers of insulated lentivirus vectors (hatched bars) are similar to those containing inert DNA spacers in the LTR (open bar) in four independent experiments. The titers of sBG with a 400 bp spacer were slightly higher (*p<0.05). FIG. 15D: The $sBG^{2C}$ vector, carrying tandem repeats of the cHS4 core recombined with high frequency. FIG. 15E: A schematic representation of the vectors sBG-I and $sBG^{2C}$ proviruses, when intact, or when the core elements recombine with loss of one or two cores with the region probed and restriction site of the enzyme used (AflII) is shown. The size of the expected band is shown adjacent to each vector cartoon. The right panel is the Southern blot analysis showing a single 8 Kb expected band for sBG-I transduced MEL cell population, and two bands in the $sBG^{2C}$ transduced MEL cell population, representing $sBG^{2C}$ with either loss of one or both cores.

Figure 16:
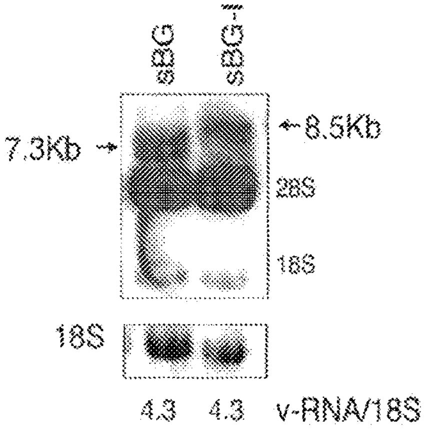

FIG. 16 depicts similar amounts of viral RNA were produced from the insulated and uninsulated vectors in packaging cells. Northern blot analysis on the 293T packaging cells after transfection with sBG and sBG-I vectors showed the expected length viral RNA. The membrane was hybridized with a $^{32}P$ labeled p-globin probe (top panel) and 18S (bottom panel) as a loading control. An expected 7.3 Kb and 8.5 Kb band corresponds to sBG and sBG-I viral RNA were detected. The 18S and 28S rRNA was non-specifically probed with this probe. No extraneous recombined bands were detected with either vector. The phosphoimager quantified ratios of viral RNA and 18S rRNA of both vectors are listed below the lanes and show no difference in the amount of v-RNA between the two vectors.

Figure 17A:
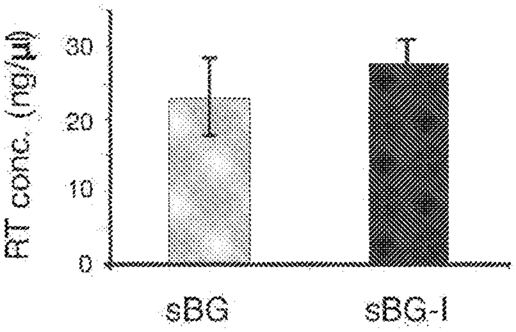
Figure 17B:
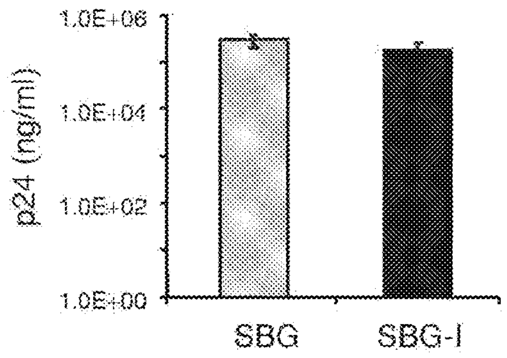
Figure 17C:
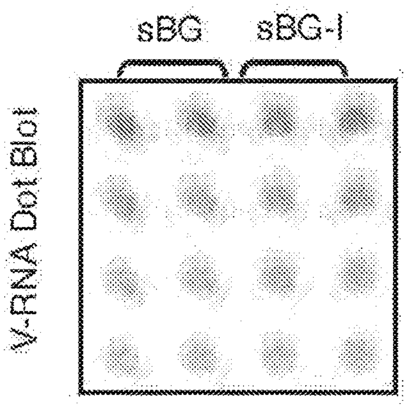
Figure 17D:
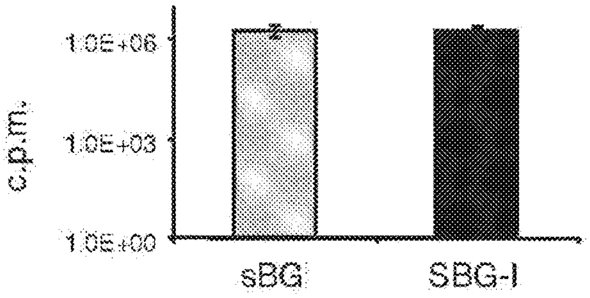

FIGS. 17A-17D depict virus production was not impaired by insertion of cHS4 in the 3'LTR. FIG. 17A: Reverse transcriptase activity in sBG and sBG-I viral supernatants is similar (23±5 vs. 27-3; n=3, p>0.5). FIG. 17B: p24 levels detected in the concentrated viral preparation is the same with sBG and sBG-I. ($2.9\pm0.5\times10^5$ versus $1.7\pm0.5\times10^5$; n=3, p>0.1) FIG. 17C: Dot-Blot analysis of viral RNA extracted from sBG and sBG-I viral supernatant shows similar amounts of viral RNA packaged into virions in both vectors. Note that 4 different dilutions of viral RNA were loaded in duplicate for the two vectors. The membrane was hybridized with a $^{32}P$ labeled p-globin probe. Only one of two representative experiments is shown. FIG. 17D: Phosphoimager quantification of two independent experiments was plotted and showed similar amounts of viral RNA in sBG and sBG-I virions ($1.9\pm0.7\times10^6$ vs. $1.9\pm0.6\times10^6$n=2, p>0.5).

Figure 18A:
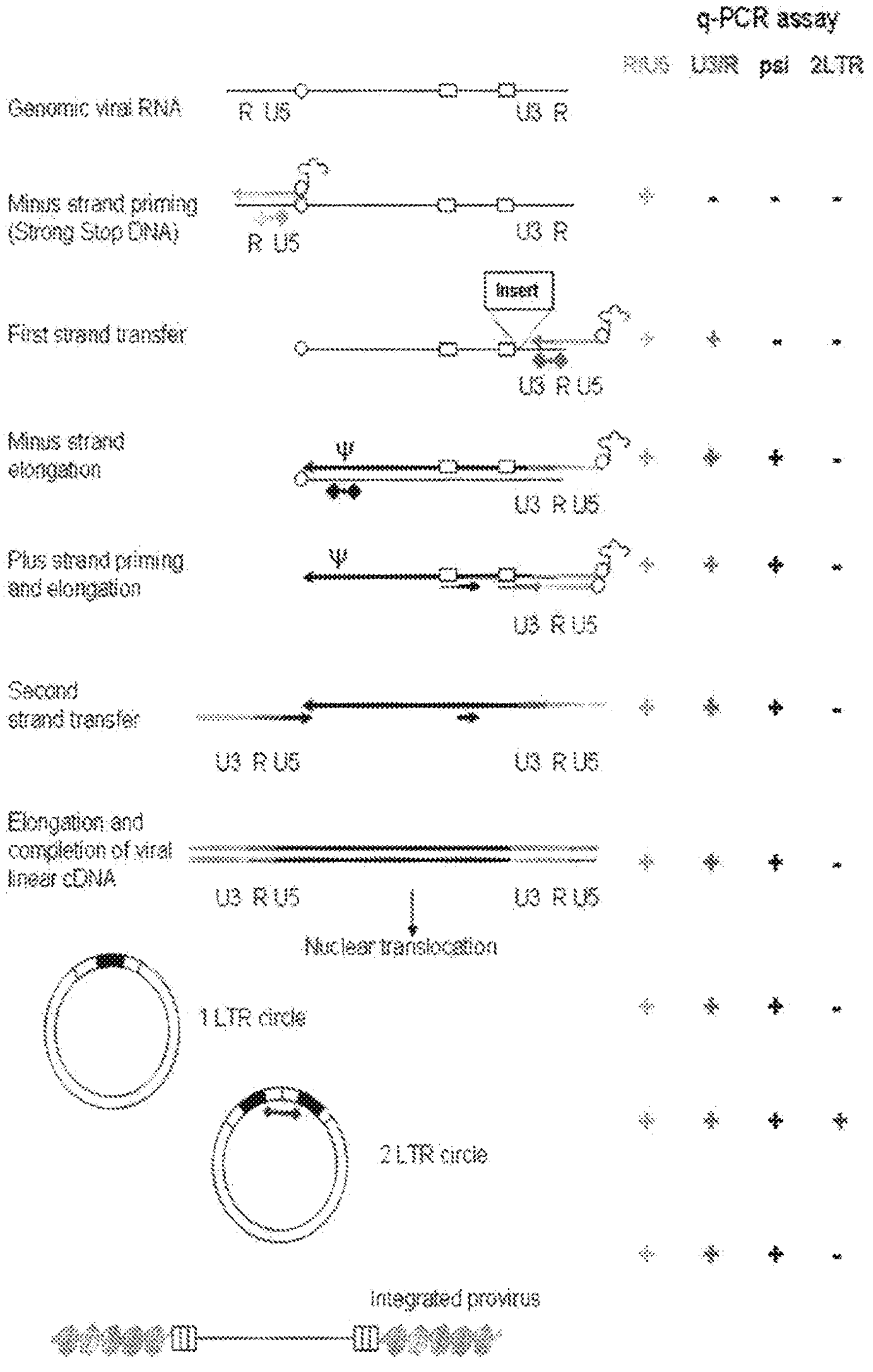
Figure 18B:
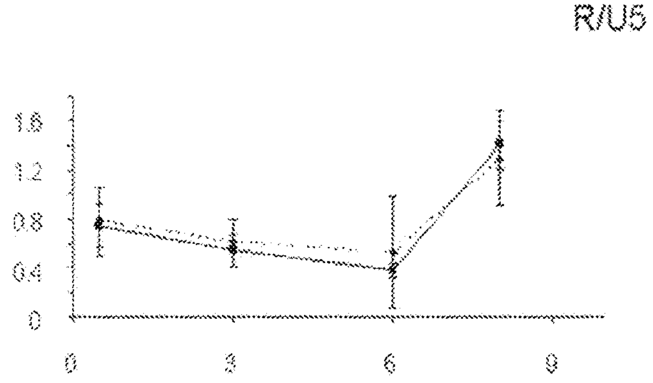
Figure 18C:
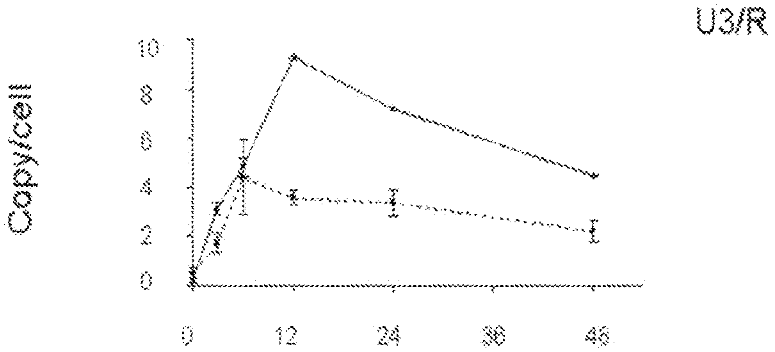
Figure 18D:
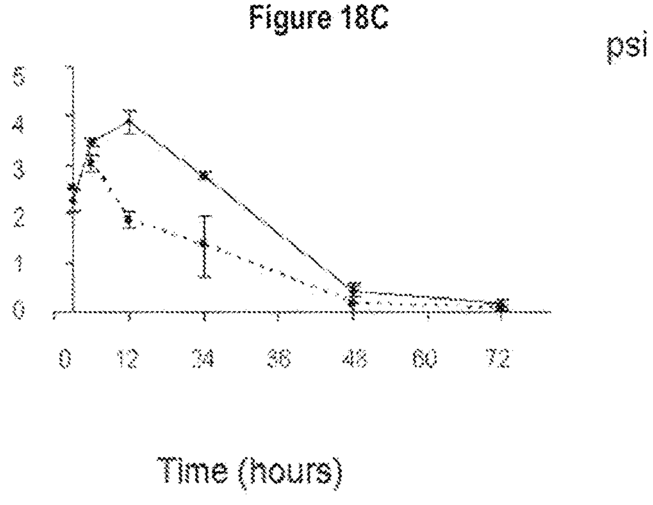

FIGS. 18A-18D depict kinetic of reverse transcription and nuclear translocation in lentivirus vector carrying insulator element in the LTR. In FIG. 18A a schema of the lentivirus reverse transcription and nuclear translocation process is illustrated. On the right a summary of q-PCR assays performed to analyze several steps of the process. Thin line: RNA; thick line: DNA. Open boxes: polypurine tract (PPT). Open circle: priming binding site (PBS). The 3' LTR DNA insert is illustrated in the first strand transfer diagram. The positions of the q-PCR assays are shown. DNA from MEL cells after infection with sBG and sBG-I virus was collected at different time points after infection and analyzed by qPCR. Solid line: sBG. Dashed line: sBGI. FIG. 18B: Kinetic of reverse transcription before the first strand transfer (R/U5) shows no difference between the two viruses. FIGS. 18C-18D: After the first strand transfer (U3/R and Psi) there is a decrease in reverse transcription efficiency in presence of the insulator. (n=3).

Figure 19A:
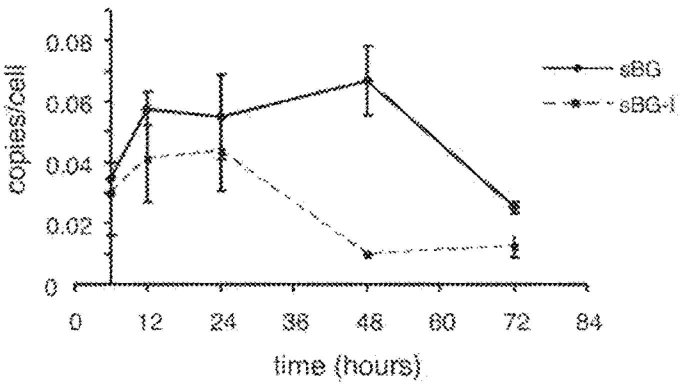
Figure 19B:
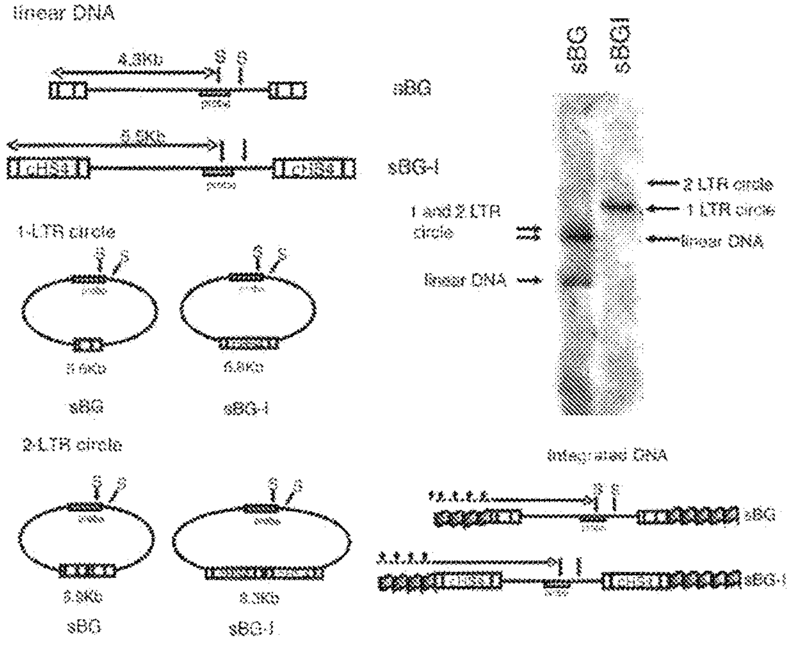
Figure 19C:
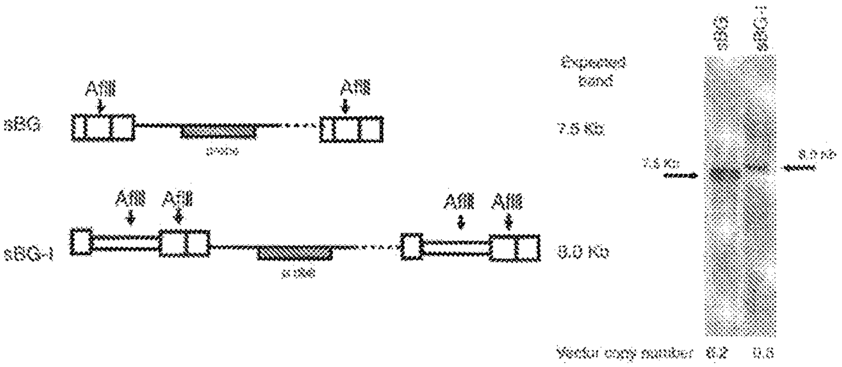

FIGS. 19A-19C depict insertion of cHS4 in the LTR affected viral integration. Linear viral cDNA circularizes and is the form that integrates; 1-LTR and 2-LTR circles represent abortive integration products from homologous recombination and non-homologous end joining, respectively. The 1- and 2-LTR circles are therefore used as markers of nuclear translocation. FIG. 19A: There are reduced 2-LTR circles, analyzed by qPCR on DNA extracted from MEL cells infected at different times after infection with virus suggesting reduced nuclear translocation or non-homologous end-joining. FIG. 19B: Southern blot analysis of MEL cells 72 h after infection with same amount of sBG and sBG-I virus. StuI digestion of genomic DNA allows identification of 1-LTR circles, 2-LTR circles, linear DNA and integrated DNA (a smear) for sBG and sBG-I. Expected band sizes are shown for both vectors. While linear, 1- and 2-LTR circles are seen in the sBG lane, no linear DNA or 2-LTR circles are detected in the sBG-I lane. However, 1-LTR circles are almost as prominent as in the sBG lane. The relative ratios of linear, 1- and 2-LTR circles suggest increased recombined abortive integration products with the sBG-I vector, and hence result in inefficient integration. FIG. 19C: sBG and sBGI transduced MEL cells show intact proviral integrants (7.5 Kb and 8.0 Kb respectively). There was an 8-fold difference in phosphoimager counts of the two bands. Vector copy number per cell was also quantified by qPCR and is depicted below the lanes.

Figure 20A:
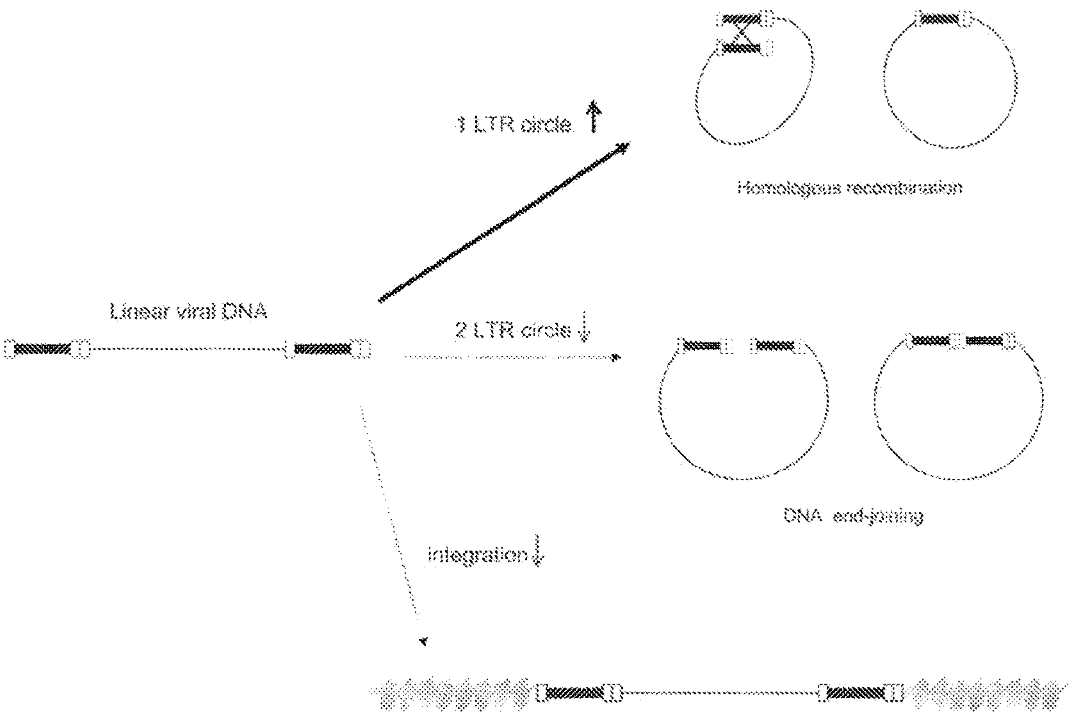
Figure 20B:
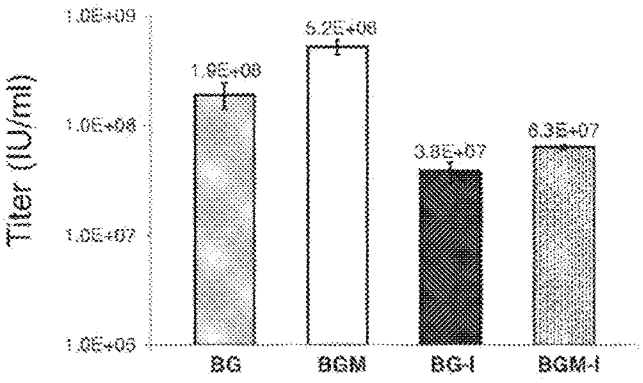
Figures 20C, 20D:
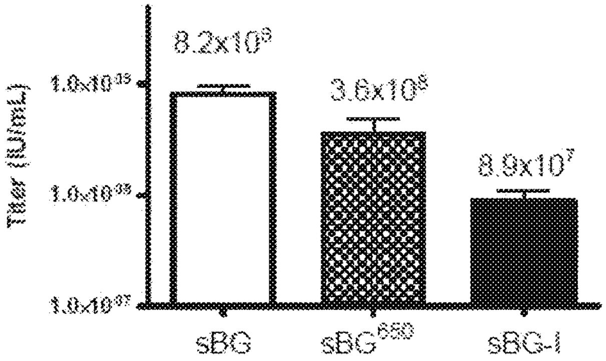

FIGS. 20A-20E depict hypothesis of mechanism by which insulator sequence decrease viral titer. FIG. 20A: In wild type HIV, linear cDNA molecules translocate to the nucleus where a small percentage undergoes recombination and end-joining ligation to form 1- and 2-LTR circles, respectively. Only the linear form is the immediate precursor to the integrated provirus. In the case of insulated LV vectors, it is shown an increase in 1LTR circle formation, due to the presence of a larger U3 sequence that could facilitate an increase in homologous recombination. This process depletes the amount of viral DNA available for integration as well as the amount of 2-LTR circle formation, as shown herein. The decreased amount of DNA available for integration could explain the loss in titers for lentivirus vector carrying large inserts in the LTR. FIG. 20B: A further addition of a 1.2 Kb PGK-MGMT internal cassette to the BG-I vector, termed BGM-I, did not reduce the titers any further. FIG. 20C: An optimized vector design results in reasonable virus titers without loss of insulator activity. A 650 bp sequence of cHS4, optimized for insulator activity through a structure function analysis. A vector containing this 650 bp fragment (sBG650), was found to have ~2-fold lower titers than the uninsulated vector sBG (n=3). FIG. 20D: PCR for Presence of 3'LTR Inserts in Proviruses Derived from Single Copy MEL Clones Shows Stable Transmission of all Inserts Except those Present as Tandem Repeats MEL cells were cloned from pools with ≤5% gene transfer. Single copy clones were detected using β-globin primers and confirmed by a qPCR using primers spanning the ψ region. PCR with primers spanning the 250 bp core was performed in the single copy clones, as these core sequences were common to all vectors. The 1.2 Kb cHS4 insert in the sBG-I vector was further confirmed by PCR primers spanning the 5' core and the 3' end of cHS4. FIG. 20E: PCR primers.

FIGS. 21A-21E depict $sG^bG$ mice that underwent transplantation after myeloablative conditioning have high HbF production that is stable and sustained in primary and secondary mice. $sG^bG$ mice that were fully chimeric for donor RBCs were analyzed at different time points. The proportion of IHbF (FIG. 21A) and F cells (FIG. 21B) in blood of individual mice, as determined by ion-exchange HPLC and FACS analysis, respectively, is shown at different time points after primary and secondary transplantations. FIG. 21C: The amount of HbF in blood directly correlated with the proportion of F cells. FIG. 21D: The amount of HbF produced was directly in proportion to the vector copy number in bone marrow. Each symbol represents one mouse (and consistently depicts the same particular mouse in all the panels). FIG. 21E: Hematologic parameters of $sG^bG$ mice that underwent transplantation after myeloablative conditioning. Hb indicates hemoglobin; MCV, mean corpuscular volume; MCH, mean corpuscular hemoglobin; RDW, red cell distribution width; Plt, platelets; pri, primary mice; and sec, secondary mice. *P values represent comparison of primary mock mice with the $sG^bG$ group. Statistical comparisons of secondary mice were not made as only one secondary mock mouse was alive at the time of analysis.

Figure 22A:
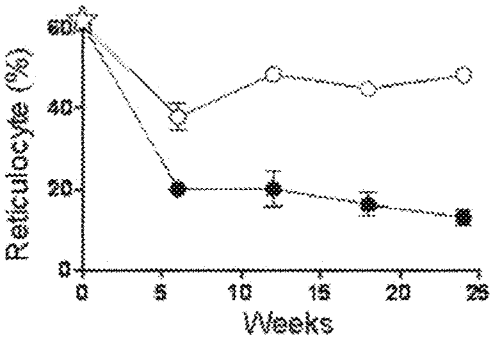
Figure 22B:
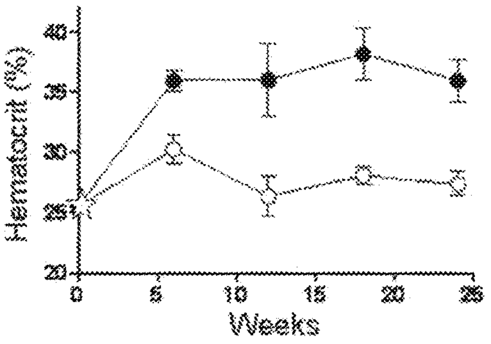
Figure 22C:
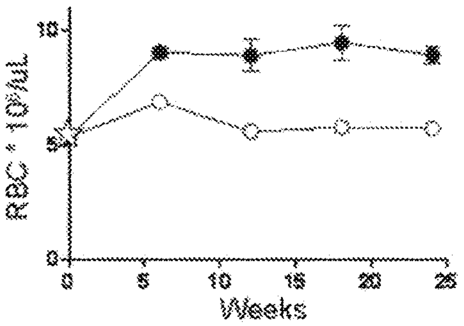
Figure 22D:
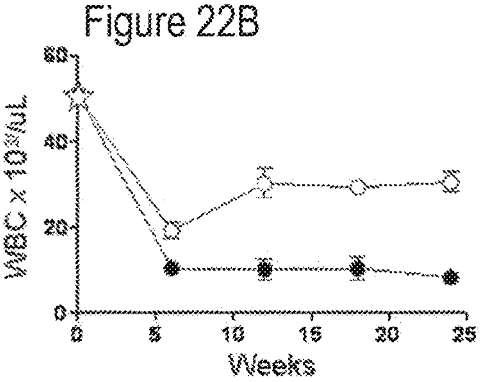
Figure 22E:
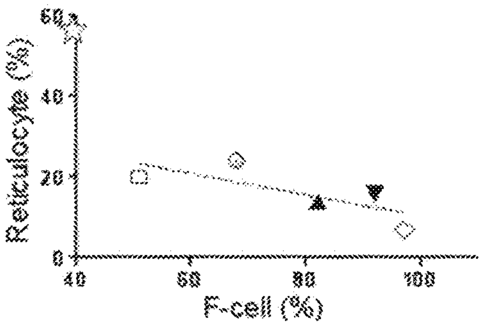
Figure 22F:
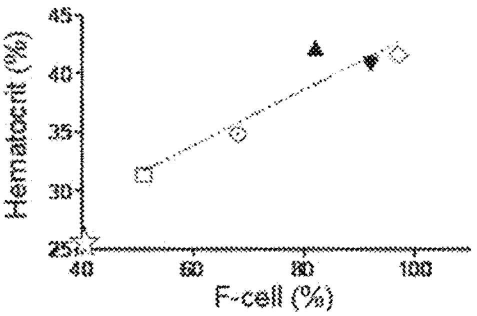
Figure 22G:
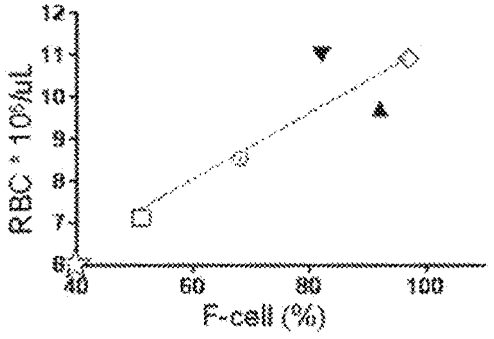
Figure 22H:
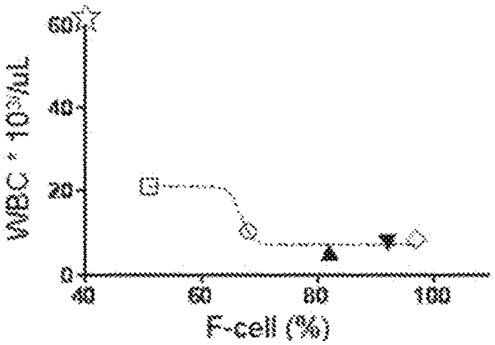

FIGS. 22A-22H depict $sG^bG$ mice that underwent transplantation after myeloablative conditioning, which resulted in correction of hematologic parameters that correlated with the HbF expression. There was sustained reduction in reticulocytes (FIG. 22A), and increase in hematocrit (FIG. 22B) and RBC numbers (FIG. 22C) over time. FIG. 22D: Leukocytosis decreased with normalization of WBC counts. Data shown represent mean (±SEM) values of $sG^bG$ mice (n=5; •) and mice that underwent mock transplantation (n=10; O). A star represents mean values in BERK mice that were HSC donors for the $sG^bG$ and mock transplantations. FIGS. 22E-22G: Decrease in reticulocytes, and increased hematocrit and RBC numbers correlated with the proportion of F cells in individual mice. FIG. 22H: WBC counts decreased but normalized when the F cells exceeded 60%. WBC counts, counted on an automated analyzer, were representative of circulating leukocytes, since only occasional nucleated RBCs were seen in peripheral smears. Each data point/symbol in panels E-H represents one $sG^bG$ mouse and symbols for individual mice have been kept consistent, to trace individual mice. A star represents mean values in BERK mice that were HSC donors for the $sG^bG$ and mock transplantations.

FIGS. 23A-23G depict $sG^bG$ mice that underwent transplantation after myeloablative conditioning, which resulted in correction of functional RBC parameters in primary and secondary mice. FIG. 23A: Peripheral blood smears showing numerous irreversibly sickled cells (ISCs) in a mouse that underwent mock transplantation and a paucity of ISCs in a $sG^bG$ mouse. FIG. 23B: Quantification of ISCs in peripheral blood smears of BERK mice that did not undergo transplantation (n=5), mock mice (n=3), and $sG^bG$ mice (n=5). (*P<0.05; **P<0.01). FIG. 23C: Deoxygenation of blood induces sick-ling of RBCs in a mock mouse; sickling is largely absent in a $sG^bG$ mouse. FIG. 23D: Quantification of sickle RBCs upon graded hypoxia (by tonometry) in the $sG^bG$ mice (•), compared with mock mice (0). FIG. 23E: RBC deformability by LORCA analysis in $sG^bG$, mock, and normal mice (C57, circle with x in center) analyzed at 18 weeks in primary transplant recipients. Similar data were seen in secondary recipients. Flow at low (3 Pa) and high (28 Pa) shear stress is represented by shaded areas. FIG. 23F: RBC half-life (determined by in vivo biotin labeling) in the $sG^bG$ mice, mock/BERK mice, and normal mice after primary transplantations. Similar results were seen in secondary recipients. FIG. 23G: Correction of organ pathology in $sG^bG$ mice that underwent transplantation with myeloablative conditioning. 2+ liver infarction indicates 2 to 3 infarctions/section; 3+ liver infarction, more than 3 infarctions/section; and E-M, extramedullary. Mild congestion of the spleen vessels with sickle RBCs is seen when splenic architecture is restored. This is not noted when the splenic architecture is effaced by extramedullary erythropoiesis. Splenic erythroid hyperplasia: severe is complete obliteration of splenic follicles; moderate, more than 1 follicle present/section; and mild, preservation of follicles with evidence of erythroid islands. Bone marrow: normal erythropoiesis indicates M/E=5:2; mild erythroid hyperplasia, M/E=2:1; moderate erythroid hyperplasia, M/E=1:1; and severe erythroid hyperplasia, M/E=1:3. Bone marrow erythropoiesis expressed as myeloid-erythroid ratio (M/E). Numbers in parentheses indicate the histologic feature seen in the number of mice/total number of mice analyzed in that group.

FIGS. 24A-24H depict HbF expression and functional correction in $sG^bG$ mice that underwent transplantation after reduced-intensity conditioning, separated into 2 groups: mice with HbF of 10% or more ($sG^bG$>10) and mice with HbF of less than 10% ($sG^bG$<10). FIG. 24A: HbF in individual BERK mice 18 weeks after transplantation of $sG^bG$-transduced BERK HSCs, after reduced-intensity conditioning. FIGS. 24B-24C: Stable and high HbF expression and F-cell repopulation in long-term survivors analyzed at 11 months. FIG. 24D: Box and whisker plot showing vector copy numbers in $sG^bG$<10 and $sG^bG$>10 mice, with mean vector copy number denoted by the line. Symbols in panels A through C represent mouse groups: O=mock (HbF 0%), ▼=$sG^bG$<10 (HbF<10%), and ●=$sG^bG$>10 (HbF>10%). FIG. 24E: The proportion of ISCs was reduced (P<0.04) in $sG^bG$<10 mice, but was markedly reduced in $sG^bG$>10 mice (P<0.001), compared with mock mice. FIG. 24F: Graded deoxygenation via tonometry demonstrates significant reduction in sickling at physiologically relevant partial oxygen pressures (PO2) in $sG^bG$>10 mice, whereas $sG^bG$<10 mice RBC sickled similar to controls. FIGS. 24G-24H: RBC deformability showed highly variable improvement in deformability in $sG^bG$<10 mice. In contrast, RBC deformability in $sG^bG$>10 mice was highly significantly improved at low and high shear stress (P<0.001). Symbols represent mouse groups: O, mock; ▼, sGG<10; ●, $sG^bG$>10; and (circle with x in center), wild-type mice (C57BL/6). Gray shaded rectangles are representative of low and high shear stress through microvessels and large vessels, respectively. Error bars indicate SEM.

Figure 25A:
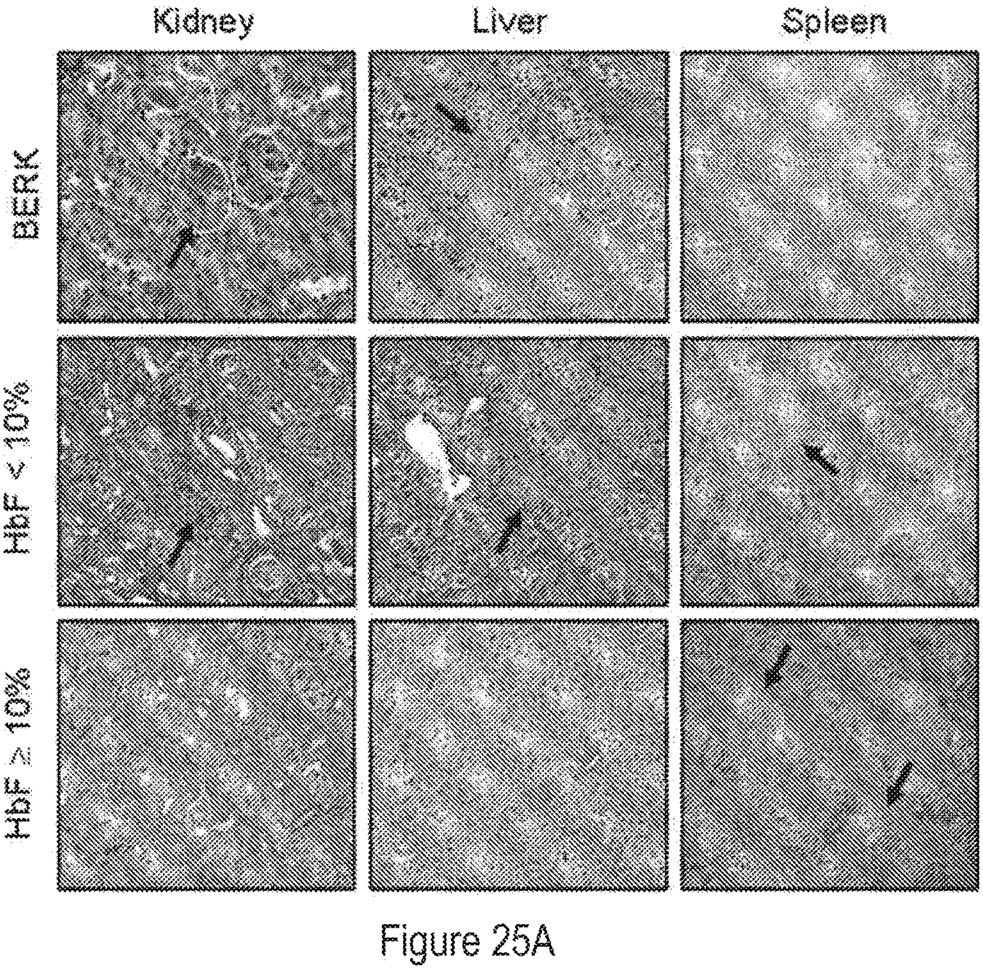
Figure 25B:
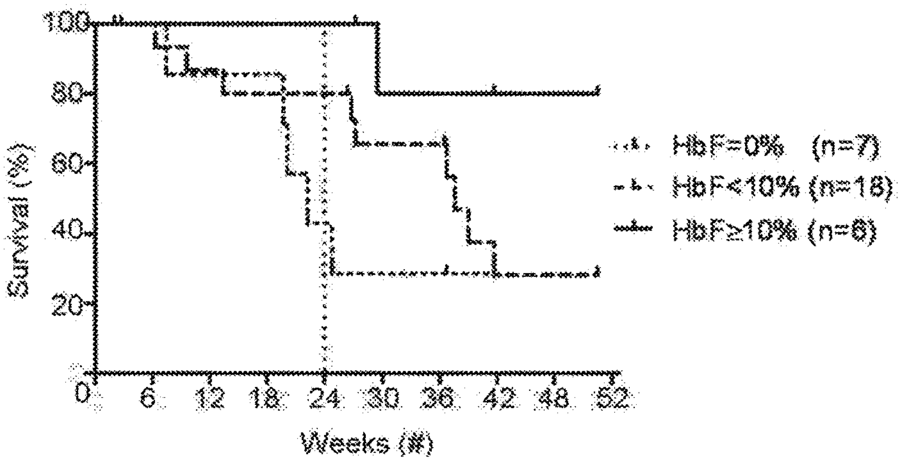

FIGS. 25A-25D depict correction of organ pathology in $sG^bG$^10 mice that underwent transplantation after reduced-intensity conditioning and improved overall survival. FIG. 25A: Representative hematoxylin-eosin-stained sections of a kidney, liver, and spleen of $sG^bG$>10 and $sG^bG$<10 mice 48 to 50 weeks after reduced-intensity conditioning transplantation and a 3-month-old BERK control. Image acquisition information is available in supplemental data. FIG. 25B: Kaplan-Meier survival curve showed significantly improved survival of the $sG^bG$>10 mice compared with mock/$sG^bG$<10 mice at 50 weeks. Survival at 24 weeks is denoted by a dashed vertical line to compare with survival of the $sG^bG$ mice in the myeloablative transplantation model. FIG. 25C: Hematologic parameters of $sG^bG$ mice that underwent transplantation following reduced-intensity conditioning. Hematologic parameters and abbreviations as stated in the figure. P values represent comparisons of mock mice with $sG^bG$≥10 at 12(*), 18 (†), and 24(‡). FIG. 25D: Organ pathology in $sG^bG$ mice that underwent transplantation after reduced-intensity transplantation. E-M indicates extramedullary; and 1+ liver infarction. 1 infarction/section. *Congestion of vessels and presence of sickle RBC in vessels. Notably, congested vessels were visible in spleens only when erythroid hyperplasia effecting splenic architecture was reduced. The terminology used to quantify organ pathology is the same as documented in the figure.

Figure 26A:
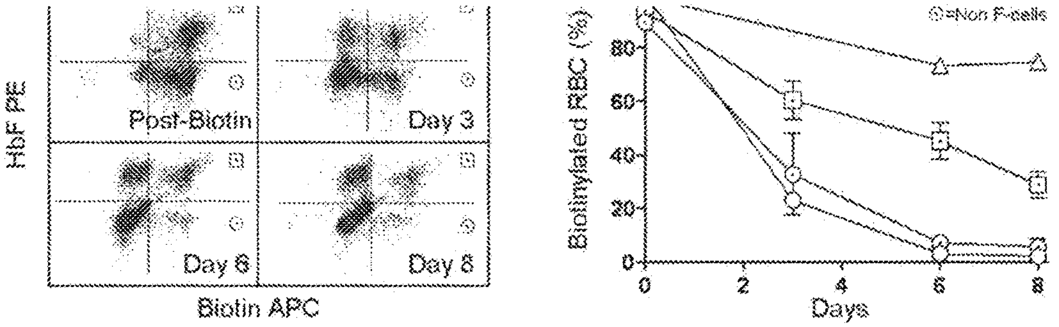
Figure 26B:
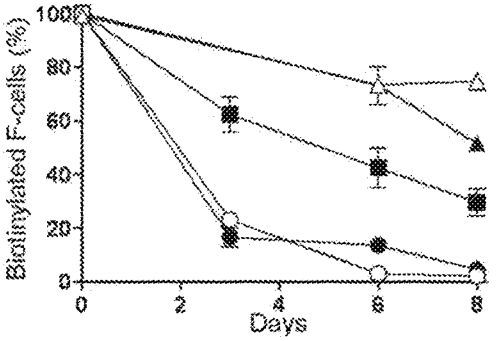
Figure 26C:
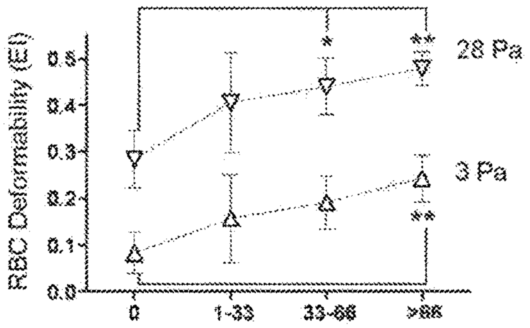

FIGS. 26A-26C depict effect of HbF, F cells, and percentage HbF/F cell required for functional improvement in RBC survival and deformability. FIG. 26A: RBC half-life. Left panel shows a representative $sG^bG$ mouse injected with biotin with biotin-labeled F cells (upper right quadrants) and non-F cells (lower right quadrants) determined by FACS. Right panel shows survival of F cells (hollow square with solid circle in center), compared with the non-F cells (Hollow circle with solid circle in center) in $sG^bG$ mice (n=4);

wild-type mice (A); and Berkeley mice (0). FIG. 26B: A cohort of $sG^bG$ mice analyzed for RBC survival in vivo, based upon the percentage of HbF/F cell. Each symbol represents a mouse group with HbF percentage and number of mice listed in the adjacent table legend. FIG. 26C: All $sG^bG$ and mock mice (n=34) that were analyzed for RBC deformability were divided into groups based on proportion of F cells 0%, 1% to 33%, 33% to 66%, and more than 66%, and deformability of total RBC in these mice was plotted at low (3 Pa. A) and high (28 Pa, upside down hollow triangle) shear stress. Significantly improved deformability over mock controls is denoted by *(P<0.05) and **(P<0.01). Error bars indicate SEM.

Figure 27A:
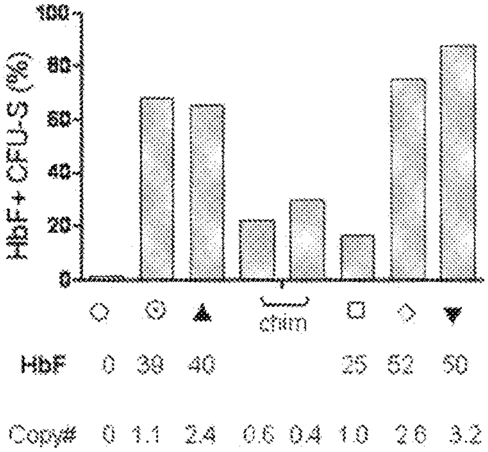
Figure 27B:
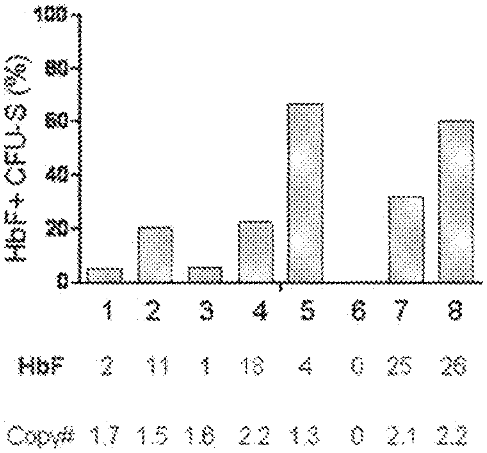

FIGS. 27A-27B depict proportion of transduced HSCs in $sG^bG$ mice. Proportions in the myeloablative (FIG. 27A) and reduced-intensity (FIG. 27B) transplantation models are shown. The proportion of $sG^bG$-transduced HSCs was determined by spleen colonies (30-36 colonies/mouse) by intracellular staining with HbF and HbS. Each bar represents an individual mouse. FIG. 27A: In the myeloablative transplantation model, symbols beneath each bar (representing one mouse) are consistent with the symbols in mice labeled. FIG. 27B: In the reduced-intensity group, bone marrow was successfully aspirated from 8 mice at 24 weeks and mice were followed for an additional 24 weeks. The HbF expression in peripheral blood by HPLC and bone marrow copy number of the respective mice at 24 weeks are labeled under each bar.

Figure 28:
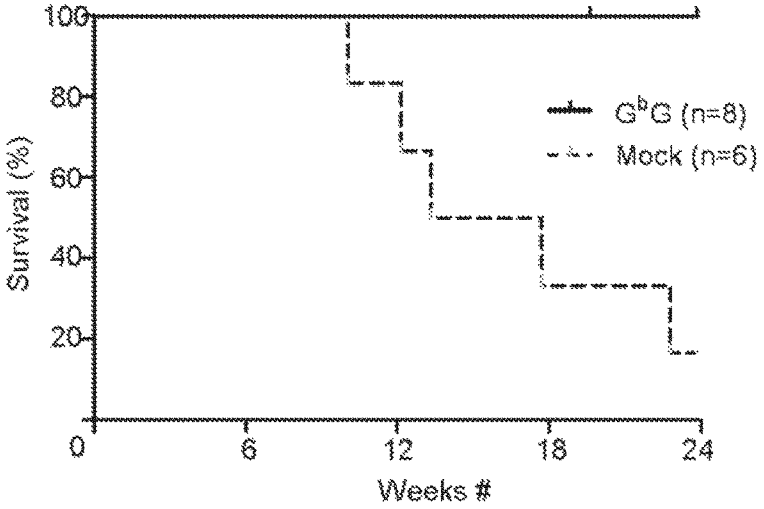

FIG. 28 shows the improvement in survival of mice following successful gene therapy.

Figure 29A:
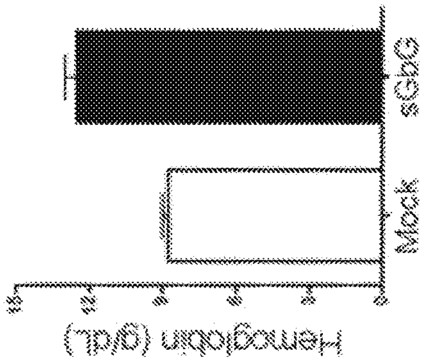
Figure 29B:
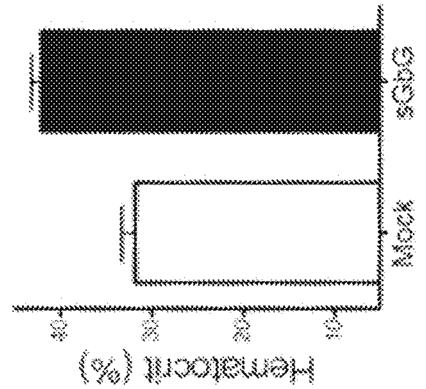
Figure 29C:
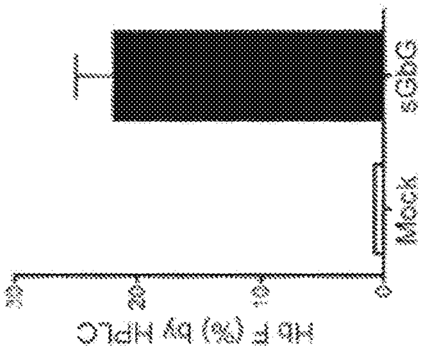

FIGS. 29A-29D depict correction of thalassemia in $Hbb^{th3/+}$ mice with the $sG^bG$ vector. Hemoglobin (FIG. 29A) and hematocrit (FIG. 29B) were corrected to normal levels with approximately 20% HbF expression (FIG. 29C). Reticulocyte counts (FIG. 29D) were also significantly lowered, showing reduced erythroid cell turnover.

Figure 30:
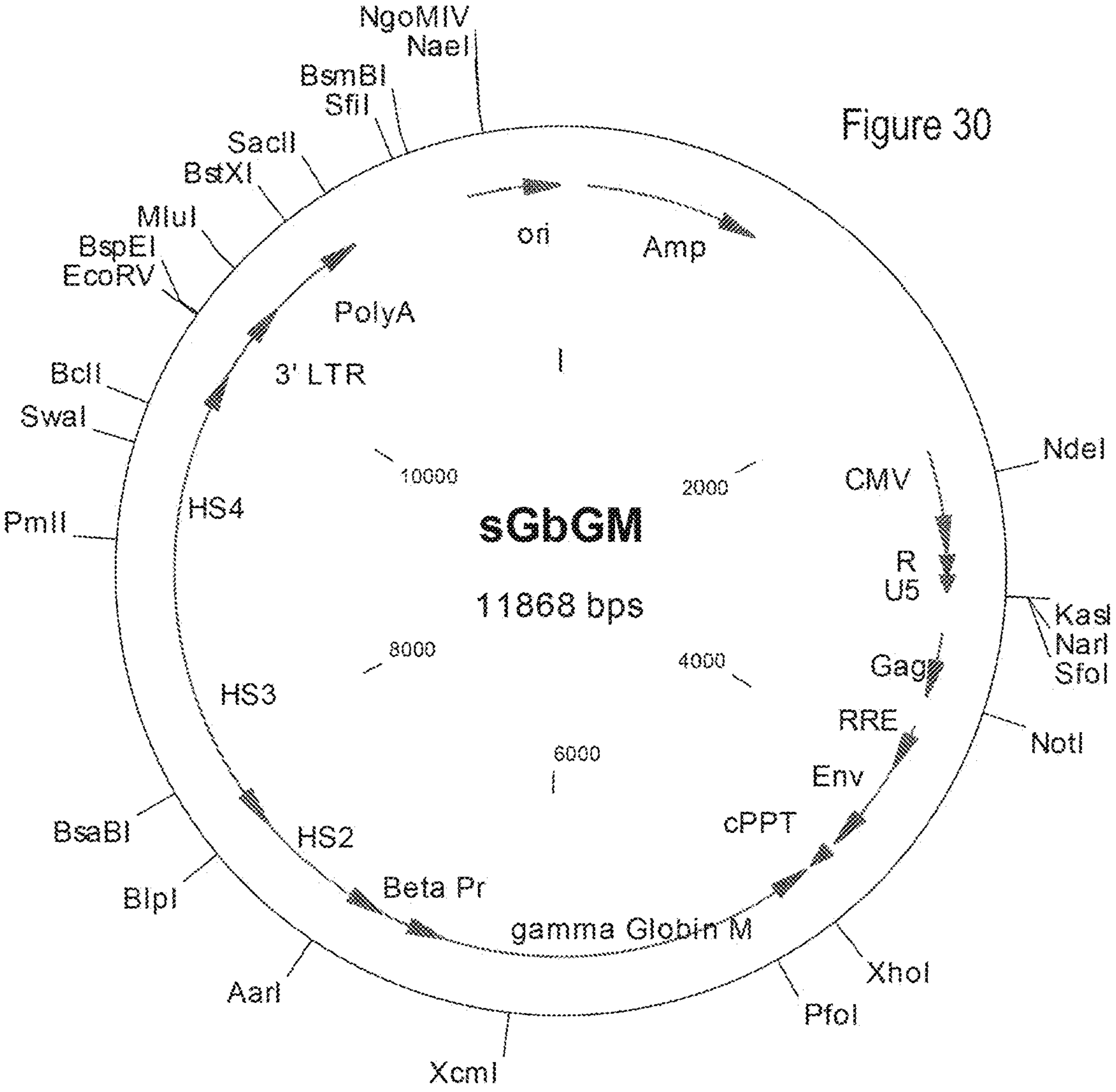

FIG. 30 depicts the annotated vector map for the $sG^bG^M$ vector.

FIGS. 31A-31M together depict the $sG^bG^M$ vector sequence, along with the various regions of the sequence.

Figure 32A:
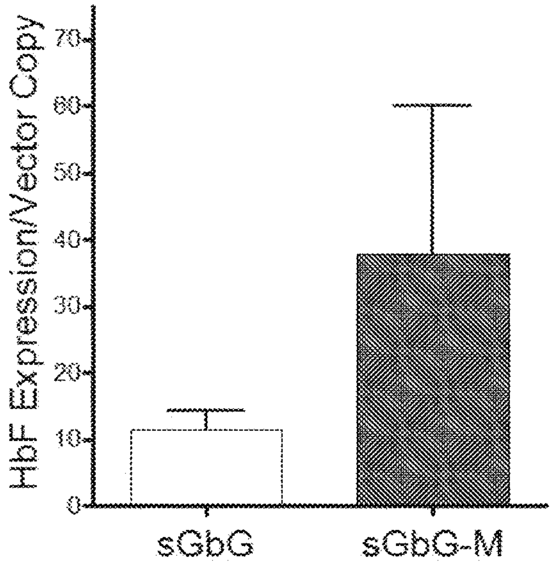
Figure 32B:
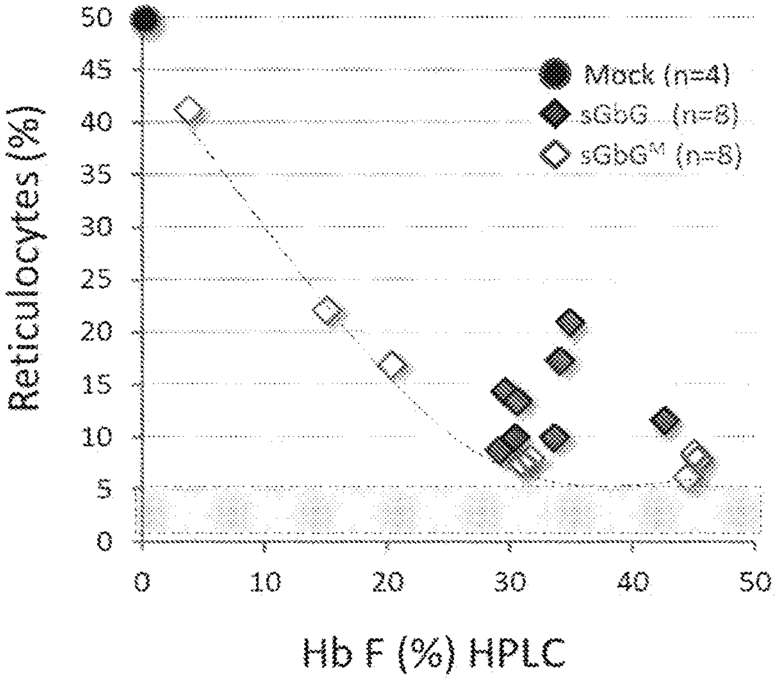

FIGS. 32A-32B depict superior HbF expression from the $sG^bG^M$ vector. HbF expression from the $sG^bG^M$ vector in Berkeley sickle mice shows superior HbF expression per vector copy, when compared to the $sG^bG$ vector (FIG. 32A). Sickle mice transplanted with $sG^bG^M$ transduced hematopoietic stem cells show a reduction in reticulocyte count that is proportional to HbF production (FIG. 32B). Mice with 30% or more HbF produced from the $sG^bG^M$ vector have nearly normal reticulocyte counts. Normal reticulocyte values are depicted via the shaded rectangle.

FIGS. 33A-33F depict HbF expression from the $sG^bG^M$ vector as compared to the $sG^bG$ vector in sickle mice. HbF expression from the $sG^bG^M$ vector in Berkeley sickle mice (FIG. 33A) and knock-in UAB sickle mice (FIG. 33B) shows superior HbF expression per vector copy, as compared to the $sG^bG$ vector. Sickle mice transplanted with $sG^bG^M$ transduced hematopoietic stem cells show superior correction of anemia (FIGS. 33C-33D) and reduction in reticulocytosis (FIGS. 33E-33F) that is proportional to HbF production. Mice with 30% or more HbF produced from the $sG^bG^M$ vector have nearly normal reticulocyte counts and correction of the sickle phenotype.

DESCRIPTION OF THE INVENTION

All references cited herein are incorporated by reference in their entirety as though fully set forth. Also incorporated herein by reference in their entirety include: U.S. Non-Provisional application Ser. No. 12/928,302, filed on Dec. 6, 2010, and U.S. Provisional Application No. 61/267,008, filed on Dec. 4, 2009. Also incorporated herein by reference in their entirety is a novel human gamma-globin gene vector for genetic correction of sickle cell anemia in a humanized mouse model and critical determinants for successful correction thereof as described in, "A novel human gamma-globin gene vector for genetic correction of sickle cell anemia in a humanized mouse model: critical determinants for successful correction". *Blood* (2009) 114: 1174-1185 Perumbeti A, Higashimoto T, Urbinati F, Franco R, Meiselman H et al.

Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the term "SIN" is an abbreviation of self-inactivating.

As used herein, the term "HIV" is an abbreviation of human immunodeficiency virus.

As used herein, the term "GFP" is an abbreviation of green fluorescent protein.

As used herein, the term "cDNA" is an abbreviation of complimentary DNA.

As used herein, the term "LTR" is an abbreviation of long terminal repeat.

As used herein, the term "USE sequence" refers to an upstream sequence element.

As used herein, the term "polyA" is an abbreviation of polyadenylation.

As used herein, the term "cHS4" is an abbreviation of chicken hypersensitive site-4 element.

As used herein, the term "HSC" is an abbreviation of hematopoietic stem cells.

As used herein, the term "GOI" is an abbreviation of gene of interest.

As used herein, the term "HbF" is an abbreviation of fetal hemoglobin.

As used herein, the term "RBC" is an abbreviation of red blood cell. As used herein, the term "IDUA" is an abbreviation of alpha-L-iduronidase.

As used herein, the term "LCR" is an abbreviation of locus control region.

As used herein, the term "subject" refers to any member of the animal kingdom. In some embodiments, a subject is a human patient.

As used herein, the terms "treatment," "treating," "treat," "correct," and the like, with respect to a specific condition, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition. The term "treatment" is used in some embodiments to refer to administration of a compound of the present invention to mitigate a disease or a disorder in a host, preferably in a mammalian subject, more preferably in humans. Thus, the term "treatment" can include includes: preventing a disorder from occurring in a host, particularly when the host is predisposed to acquiring the disease, but has not yet been diagnosed with the disease; inhibiting the disorder; and/or alleviating or reversing the disorder. Insofar as the methods of the present invention are directed to preventing disorders, it is understood that the term "prevent" does not require that the disease state be completely thwarted (see Webster's Ninth Collegiate Dictionary). Rather, as used herein, the term preventing refers to the ability of the skilled artisan to identify a population that is susceptible to disorders, such that administration of the compounds of the present invention can occur prior to onset of a disease. The term does not mean that the disease state must be completely avoided.

As used herein, the terms "mutated," "mutation," "mutant," and the like, refer to a change in a sequence, such as a nucleotide or amino acid sequence, from a native, wild-type, standard, or reference version of the respective sequence, i.e. the non-mutated sequence. These terms can refer to one or more mutated genes, such as deoxyribonucleic acids, ribonucleic acids, and the like, or one or more mutated gene products, such as proteins. A mutated gene can result in a mutated gene product. A mutated gene product will differ from the non-mutated gene product by one or more amino acid residues.

In some embodiments, a mutated gene which results in a mutated gene product can have a sequence identity of 70%, 75%, 80%, 85%, 90%, 95%, or greater to the corresponding non-mutated nucleotide sequence. In some embodiments, a mutated gene which results in a mutated gene product can have a sequence identity of 96%, 97%, 98%, 99%, or greater to the corresponding non-mutated nucleotide sequence. In some embodiments of the invention, the mutated gene is a mutated human gamma-globin gene. In some embodiments, the mutated human gamma-globin gene encodes a protein comprising SEQ ID NO:1.

In some embodiments, the mutated human gamma-globin gene is used to genetically correct sickle cell anemia or β-thalassemia or reduce symptoms thereof, including the steps of identifying a subject in need of treatment for sickle cell anemia or β-thalassemia; transfecting autologous hematopoietic stem cells (HSCs) with a modified lentivirus comprising the mutated human gamma-globin gene; and transplanting the transfected HSCs into the subject.

In some embodiments, post-transplantation fetal hemoglobin exceeds at least 20%; F cells constitute at least ⅔ of the circulating red blood cells; fetal hemoglobin per F cells account for at least ⅓ of total hemoglobin in sickle red blood cells; and at least 20% gene-modified HSCs re-populate bone marrow of the subject. In some embodiments, post-transplantation fetal hemoglobin exceeds 25%, 30%, 35%, 40%, 45%, 50%, or greater. In some embodiments, post-transplantation fetal hemoglobin exceeds 55%, 60%, 65%, 70%, 75%, 80%, 85%, 90%, 95%, or greater. In some embodiments, F cells constitute at least 70%, 75%, 80%, 85%, 90%, 95%, or greater of the circulating red blood cells. In some embodiments, fetal hemoglobin per F cells account for at least ⅓ of total hemoglobin in sickle red blood cells. In some embodiments, fetal hemoglobin per F cells account for at least 40%, 45%, 50%, 55%, 60%, 65%, 70%, 75%, 80%, 85%, 90%, 95% or greater of total hemoglobin in sickle red blood cells. In some embodiments, 20%, 25%, 30%, 35%, 40%, 45%, 50%, 55%, 60%, 65%, 70%, 75%, 80%, 85%, 90%, 95%, or greater gene-modified HSCs re-populate bone marrow of the subject.

Essential Cis Elements and the Optimization of Vector Design

As described herein, experimentation was conducted to determine whether lentivirus non-coding cis-sequences played a specific role in the RNA export, packaging or expression of β-globin. The vector life-cycle was studied in self-inactivating (SIN)-lentiviruses, carrying the β-globin gene and locus control region (BG), or GFP cDNA. Systematic analysis started with a completely 'gutted' minimal SIN-lentivirus carrying only the packaging region; and SIN-lentiviruses containing increasing HIV cis-elements, along with a SIN-gamma-retrovirus in order to identify optimal cis-elements to include in the SIN-LV backbone. To clone the sSIN-GFP vector, the 3'LTR of a standard SIN-LV backbone previously used, as described herein, was modified to improve transcript termination. Specifically, β-growth hormone polyadenylation signal was added downstream of the 3'LTR and a USE sequence derived from SV40 late polyadenylation signal was added in the U3 deletion.

As further described herein, SIN-gamma-retrovirus or a gutted/minimal SIN-lentivirus encoding GFP generated high titers and mediated high GFP expression. However, SIN-gamma-retrovirus or the gutted SIN-lentivirus encoding either BG or a similar sized large transgene had barely detectable titers compared to the SIN-lentivirus carrying cis-elements. Systematic addition of cis-elements demonstrated that Rev/RRE was most essential, followed by gag and env splice acceptor sequences, for efficient assembly/packaging of lentivirus particles, not mRNA export. However, these HIV cis-sequences were dispensable for smaller transgenes. These studies identify key lentivirus cis-elements and the role they play in vectors carrying large inserts, and have important implications for gene therapy.

In one embodiment, the present invention provides a method of increasing titer of a modified SIN lentiviral expression vector compared to a standard SIN lentiviral expression vector. In another embodiment, the SIN lentiviral expression vector is modified by inserting a heterologous polyadenylation (polyA) signal sequence downstream from a viral 3' long terminal repeat sequence in a standard SIN lentiviral vector backbone. In another embodiment, the polyA signal is the bovine growth hormone polyA signal sequence. In another embodiment, the SIN lentiviral vector is modified by inserting one or more of an upstream polyA-enhancer sequence (USE sequence) into a 3'LTR of a standard SIN lentiviral vector backbone. In another embodiment, the USE sequence is derived from the SV40 late polyA signal. In another embodiment, 2-3 copies of the USE sequence are inserted into a 3'LTR of a standard SIN lentiviral vector backbone. In another embodiment, 2-10 copies of the USE sequence are inserted into a 3'LTR of a standard SIN lentiviral vector backbone. In another embodiment, 3-5 copies of the USE sequence are inserted into a 3'LTR of a standard SIN lentiviral vector backbone. In another embodiment, one or more copies of the USE sequence is inserted into the U3 region. In another embodiment, the 3-growth hormone polyA signal and one or more copies of the USE sequence derived from the SV40 late polyA signal are both incorporated into the expression vector. In another embodiment, the expression vector contains a gene of interest (GOI). In another embodiment, the gene is operably linked to a promoter. In another embodiment, the promoter is a lineage-specific promoter. In another embodiment, the promoter is an erythroid specific promoter. In another embodiment, of the GOI is β-globin. In another embodiment, the GOI is gamma-globin. In another embodiment of the invention the gamma-globin gene is under the control of β-globin regulatory elements. In another embodiment, the vector is used to treat sickle cell anemia via gene therapy. In another embodiment, the vector is used in conjunction with reduced intensity conditioning to treat sickle cell anemia. In another embodiment, the SIN lentivirus comprises a bovine, equine, feline, ovine/caprine or primate derived variety of lentivirus. In another embodiment, the SIN lentivirus is an HIV derived SIN lentivirus. In another embodiment the modified SIN lentiviral vector is introduced into a eukaryotic cell by transfection.

In one embodiment, the present invention provides a method of designing a gutted/minimal, and thus less recombinigenic and safer SIN lentiviral vector for the expression of small therapeutic transgenes that do not require extensive Cis elements for efficiency. In another embodiment the small therapeutic transgenes are equal in size or smaller than green fluorescent protein (GFP). In another embodiment the small therapeutic transgenes are smaller than human β-globin.

Chromatin Insulator Elements

As described herein, chromatin insulator elements prevent the spread of heterochromatin and silencing of genes, reduce chromatin position effects and have enhancer blocking activity. These properties are desirable for consistent predictable expression and safe transgene delivery with randomly integrating vectors. Overcoming chromatin position effects can reduce the number of copies required for a therapeutic effect and reduce the risk of genotoxicity of vectors. Vector genotoxicity has become an area of intense study since the occurrence of gene therapy related leukemia in patients in the X-SCID trials. Gamma-retroviral vectors and lentiviral vectors have been modified to a self-inactivating (SIN) design to delete ubiquitously active enhancers in the U3 region of the long terminal repeats (LTR). A 1.2 Kb DNAse hypersensitive site-4 (cHS4) from the chicken p-globin locus has been inserted in the 3'LTR to allow its duplication into the 5'LTR in gamma-retrovirus and lentivirus vectors. Insulated vectors have reduced chromatin position effects and, provide consistent, and therefore improved overall expression. A side-by-side comparison of cHS4 insulated and uninsulated lentivirus vectors carrying hβ-globin and the locus control region was performed, and resulted in the discovery that insulated vectors showed consistent, predictable expression, regardless of integration site in the differentiated progeny of hematopoietic stem cells, resulting in a 2-4 fold higher overall expression. Recent evidence also suggests that cHS4 insulated lentivirus vectors may reduce the risk of insertional activation of cellular oncogenes. Despite the beneficial effects of insulated vectors, they also lead to a significant reduction in titers with insertion of the full-length 1.2 Kb cHS4 insulator element in the 3'LTR of lentivirus vectors. There are similar reports of lowering of viral titers or unstable transmission with gamma-retrovirus vectors containing insertions in the 3' LTR. This reduction in titers becomes practically limiting for scale up of vector production for clinical trials, especially with vectors carrying relatively large expression cassettes, such as the human β-globin gene (hβ) and locus control region (LCR), that have moderate titers even without insulator elements.

The effects of insertions of exogenous fragments into the LTR on viral life cycle have not been addressed. The mechanism by which insertion of cHS4, or other inserts in the viral 3'LTR lower titers of lentiviral vectors was therefore studied. Large LTR inserts lower titers via a post-entry restriction in reverse transcription, and increased homologous recombination in the LTRs of viral cDNA, thus reducing the amount of virus DNA available for integration. These results have important implications for vector design for clinical gene therapy. Studies on the chicken hypersensitive site-4 (cHS4) element, a prototypic insulator, have identified CTCF and USF-1/2 motifs in the proximal 250 bp of cHS4, termed the “core”, which provide enhancer blocking activity and reduce position effects. However, the core alone does not insulate viral vectors effectively. While the full-length cHS4 has excellent insulating properties, its large size severely compromises vector titers. A structure-function analysis of cHS4 flanking lentivirus-vectors was performed and transgene expression in the clonal progeny of hematopoietic stem cells and epigenetic changes in cHS4 and the transgene promoter were analyzed.

As further described herein, the core only reduced the clonal variegation in expression. Unique insulator activity resided in the distal 400 bp cHS4 sequences, which when combined with the core, restored full insulator activity and open chromatin marks over the transgene promoter and the insulator. These data consolidate the known insulating activity of the canonical 5' core with a novel 3' 400 bp element with properties similar to the core. Together, they have excellent insulating properties and viral titers. This data has important implications with respect to understanding the molecular basis of insulator function and design of gene therapy vectors.

In one embodiment, the present invention provides a method of increasing the titer of lentiviral vectors by incorporating one or more reduced-length chromatin insulators containing functional portions of a full-length chromatin insulator. In another embodiment, the functional portions are derived from a single type of full length chromatin insulator. In another embodiment, the reduced-length functional insulator comprises functional portions of two or more separate varieties of chromatin insulators. In another embodiment, the functional reduced-length chromatin insulator is derived from a chicken hypersensitive site-4 (cHS4) element. In another embodiment, the functional reduced-length insulator is a cHS4-derived insulator of 650 base pairs or less. In another embodiment, one or more reduced-length cHS4-derived insulators is combined with other modifications to a SIN lentivirus expression vector in order to increase titer and improve stability of transgene expression. In another embodiment, one or more reduced-length cHS4-derived insulators is added to a vector containing a heterologous polyadenylation (polyA) signal sequence downstream from a viral 3'LTR and a USE sequence in the U3 deletion.

Sickle Cell Disease

Sickle cell disease (SCD) affects the β-globin gene and is one of the most common genetic defects, resulting in the production of a defective sickle globin (HbS, comprised of two normal a globin and two $\beta^{sickle}$ globin molecules, denoted as $\alpha_2\beta^S{}_2$). HbS polymerizes upon deoxygenation and changes the shape of discoid red blood cells (RBCs) to bizarre sickle/hook shapes. Sickled RBCs clog the microvasculature, causing painful acute organ ischemic events and chronic organ damage that foreshortens the life span of SCD patients to 45 years. This disease affects over 110,000 Americans, with 1000 newborns with SCD born every year and nearly 1000 babies born with this disease annually in Africa.

Therapeutic options for SCD are extremely limited and involve a bone marrow hematopoietic stem cell transplant (HCT). HCT is available only to 10-15% of patients with matched normal sibling donors and is often associated with serious immune side effects. Fetal hemoglobin (HbF, comprised of $\alpha$ and $\gamma$ globins, $\alpha_2\gamma_2$) is produced during the fetal life and the first 6-9 months of age and has strong anti-sickling properties and protects the infant from sickling in the first year of life. Indeed, individuals with hereditary persistence of HbF that have SCD are asymptomatic. Hydroxyurea, a chemotherapeutic drug that increases HbF, is FDA-approved for ameliorating symptoms of SCD. However, hydroxyurea does not work for all patients, and due to daily life-long intake, is associated with poor compliance. Hence, better therapeutic options are needed for SCD.

Genetic correction of autologous bone marrow stem cells (hematopoietic stem cells) with a lentivirus vector encoding the γ-globin gene would be able to permanently result in production of the anti-sickling HbF, thereby preventing RBC sickling. This method has advantages over currently available therapies, including its availability to all patients, particularly those who do not have a matched sibling donor, and the fact that it would be a one-time treatment, resulting in lifelong correction and devoid of any immune side effects. An effective gene therapy approach will revolutionize the way SCD is treated and improve the outcomes of patients with this devastating disorder.

Determining Critical Parameters of Disease Correction—Sickle Cell Anemia

As disclosed herein, lentiviral delivery of human γ-globin under β-globin regulatory control elements in HSCs results in sufficient postnatal HbF expression to correct SCA in mice. The amount of HbF and transduced HSCs was then de-scaled, using reduced-intensity conditioning and varying multiplicity of infection (MOI), to assess critical parameters needed for correction. A systematic quantification of functional and hematologic RBC indices, organ pathology, and life span were critical to determine the minimal amount of HbF, F cells, HbF/F cell, and gene-modified HSCs required for reversing the sickle phenotype.

As further disclosed herein, amelioration of disease occurred when HbF exceeded 10%, F cells constituted two-thirds of the circulating RBCs, and HbF/F cell was one-third of the total hemoglobin in RBCs; and when approximately 20% $sG^bG$ modified HSCs repopulated the marrow. Genetic correction was sustained in primary or secondary transplant recipients followed long-term. The present study describes a method of determining minimum HSC chimerism for correction of a hematopoietic disease in an in vivo model, which would contribute to design of cell dose and conditioning regimens to achieve equivalent genetically corrected HSCs in human clinical trials. Moreover, this study addresses the gene dosage and the gene-modified hematopoietic stem cell dosage required for correction of a genetic defect.

In one embodiment, the present invention provides a method of determining minimum HSC chimerism for correction of a hematopoeitic disease in an in vivo model. In another embodiment, reduced intensity conditioning prior to transplantation is used as a method of varying HSC chimerism. In another embodiment, the proportion of transduced HSCs and vector copy/cell is varied by transducing the cells at a range of MOI (30-100). In another embodiment, the MOI is 20-120. In another embodiment, the minimum determined chimerism and gene dosage can be used to design cell dose and conditioning regimens to achieve equivalent genetically corrected HSCs in human clinical trials. In another embodiment, reduced intensity conditioning is used prior to transplantation in a clinical setting to reduce transplantation-related morbidity. In another embodiment, the hematopoeitic disease is sickle cell anemia. In another embodiment, the hematopoeitic disease is β-thalassemia.

Gene Therapy for Sickle Cell Disease Via Mutant Gamma Globin

As disclosed herein, an improved mutant γ-globin gene has been engineered from a lentivirus vector, $sG^bG^M$. This vector has a higher tendency to form HbF and improved anti-sickling properties, resulting in superior correction of SCD in stringent homozygous SCD mouse models. The engineered γ-globin gene has an increased affinity to bind α-globin without altering its function, thereby greatly improving the efficiency of HbF formation in RBCs and resulting in a far more efficient anti-sickling effect that will correct the SCD phenotype.

As further disclosed herein, the engineered $sG^bG^M$ vector has a two-fold higher tendency to form HbF than the native γ-globin gene (encoding a native human gamma-globin protein set forth in SEQ ID NO: 49) from the $sG^bG$ vector and readily corrects the UAB sickle mice efficiently. Both vectors correct SCD in Berkeley sickle mice. Thus, the $sG^bG^M$ vector provides twice the amount of HbF per vector copy in sickle mice as compared to the $sG^bG$ vector. In addition to providing an increased amount of HbF, the mutant HbF produced from the $sG^bG^M$ vector also confers sickle RBCs with much longer lifespans as compared to natural HbF, due to reduced sickling. Accordingly, this vector can efficiently correct SCD in human patients.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Lentivirus Cis Elements Required for Efficient Packaging of Large Transgenes Cassettes Like β-Globin This study investigated whether lentivirus non-coding cis-sequences played a specific role in the RNA export, packaging or expression of β-globin. The vector life-cycle was studied in self-inactivating (SIN)-lentiviruses, carrying the β-globin gene and locus control region (BG), or GFP cDNA. Systematic analysis started with a completely 'gutted' minimal SIN-lentivirus carrying only the packaging region; and SIN-lentiviruses containing increasing HIV cis-elements, along with a SIN-gamma-retrovirus. It was discovered that (i) SIN-gamma-retrovirus or a gutted/minimal SIN-lentivirus encoding GFP generated high titers and mediated high GFP expression. (ii) However, SIN-gamma-retrovirus or the gutted SIN-lentivirus encoding either BG or a similar sized large transgene had barely detectable titers compared to the SIN-lentivirus carrying cis-elements. (iii) Systematic addition of cis-elements demonstrated that Rev/RRE was most essential, followed by gag and env splice acceptor sequences, for efficient assembly/packaging of lentivirus particles, not mRNA export. However, these HIV cis-sequences were dispensable for smaller transgenes. These studies identify key lentivirus cis-elements and the role they play in vectors carrying large inserts, and have important implications for gene therapy.

Example 2

BG Expression from Gutted SIN-γRV

It has been postulated that γRV are unable to successfully express hβ-globin due to transcriptional interference between the strong γRV LTR promoter/enhancer elements and the internal LCR enhancer. SRS 11.SF is a SIN-γRV that encodes the GFP cDNA under control of an internal Spleen Focus-Forming Virus (SFFV) promoter/enhancer. The SFFV-GFP in SRS 11.SF was replaced with BG, an expression cassette that was successfully utilized in a standard SIN-LV to achieve therapeutic human β-globin expression in thalassemia, to generate SRS 11.BG. The rationale for using SRS.11, despite the notoriety of β-globin γRV was: (i) it contains the minimal packaging region (W), lacks gag sequences and can carry a larger vector payload, yet retains extremely high titers; (ii) it carries a large 400 bp U3 deletion of the 3'LTR, comparable to the deletion in SIN-LV. (iii) Large LCR elements have never been tested in γRV due to restrictions on vector payload.

Infectious titers and expression of SRS 11.BG and SRS 11.SF γRV vectors were compared on the murine erythroleukemia (MEL) cell line. Human p-globin protein expression was almost undetectable from SRS 11.BG-transduced MEL cells, in contrast to the high expression of GFP in cells transduced with SRS.11 SF. The unconcentrated viral titers of SRS 11 BG versus SRS 11.SF vector were $6.8\pm5\times10^3$ IU/mL versus $4\pm0.2\times10^6$ IU/mL. Viral RNA (vRNA) transcripts were barely detectable in 293T cells with the SRS 11.BG via northern blot analysis (data not shown). Therefore, production of BG vRNA and viral particles from γRV, even those optimized for a SIN design and high vector payload was severely impaired.

Example 3

Expression of Large/Small Transgenes from Standard or Gutted/Minimal LV

In contrast to the SIN-γRV used herein, the "standard" SIN-LV commonly used retains relatively large portions of viral sequences amounting to about 20-25% of the HIV genome. These cis elements are: the LTR (634 bp for wt HIV LTR or 235 bp for SIN-LV LTR), the packaging signal ψ (150 bp), 5' portion of the gag gene (300 or 600 bp), env sequences including the rev response element (RRE, 840 bp) and the central flap/polypurine tract (cPPT) from the pol gene (120 bp).

Figure 1A:
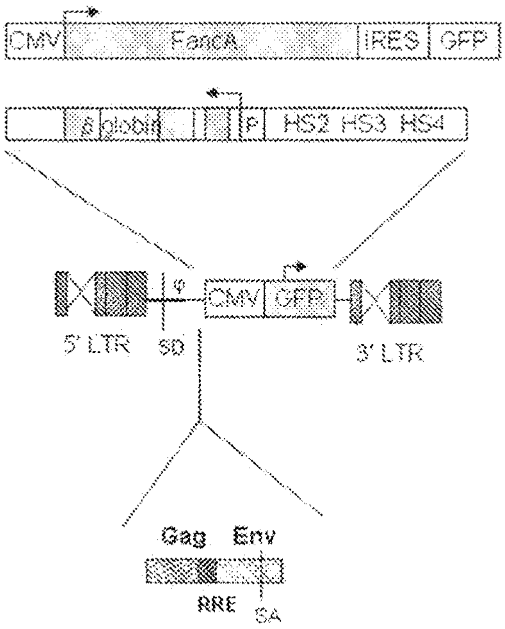
FIGS. 1A-1B depict titers from the standard and gutted SIN-LV.
Figure 1B:
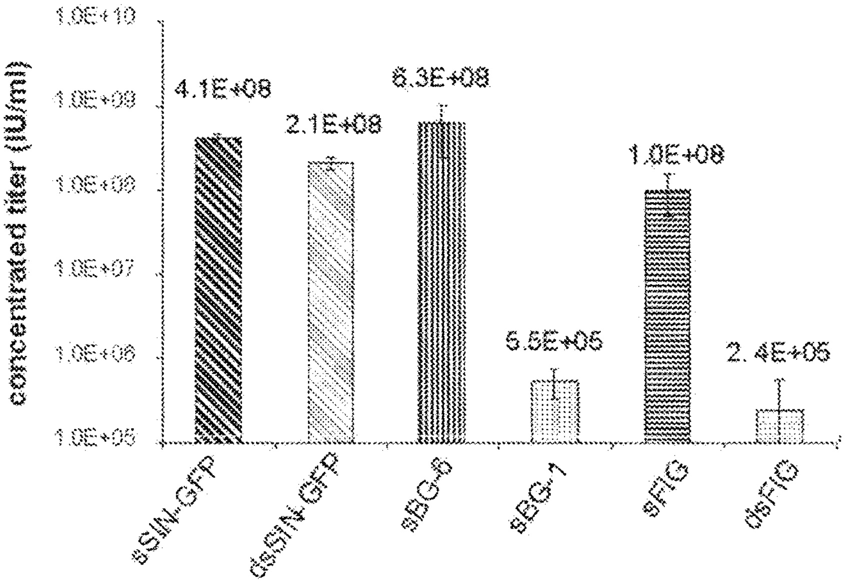

To examine the requirement of cis-sequences for GFP versus BG, the CMV-GFP cassette was cloned in a) the "standard" SIN-LV containing cis sequences listed above (sSIN-GFP), and b) a 'gutted' minimal SIN-LV where the gag, RRE and the rest of the env sequences were deleted and only the ψ region was retained (dsSIN-GFP; FIG. 1A). The titers of the minimal dsSIN-GFP LV were only 2-times lower than the titers of the "standard" LV sSIN-GFP FIG. 1B; $p<0.01$; n=3. In sharp contrast to the GFP vectors, the difference in titers of the analogous standard and gutted BG SIN-LV, sBG-6 and sBG-1 vectors was 1100-fold $p<0.01$; n=4; (FIG. 1B). Clearly, the LV non-coding sequences are necessary either for production of LV particles and/or for β-globin expression; and these sequences have a pronounced effect on infectious titers of LV encoding the β-globin gene, but not those encoding GFP. Next, vectors were constructed with a similar size transgene cassette, CMV-FANCA-IRES-GFP (FIG) as sBG (FIG. 1A) in the "standard" (sFIG) or the gutted (dsFIG) SIN LV. The same dependence of FIG on LV cis sequences: titers of dsFIG vector were three orders of magnitude lower than those of sFIG were observed (FIG. 1B). Therefore LV cis elements are dispensable for small inserts, but necessary for high titers of large inserts.

Example 4

LV Constructs Designed to Study the Role of Cis-Sequences

Figure 2:
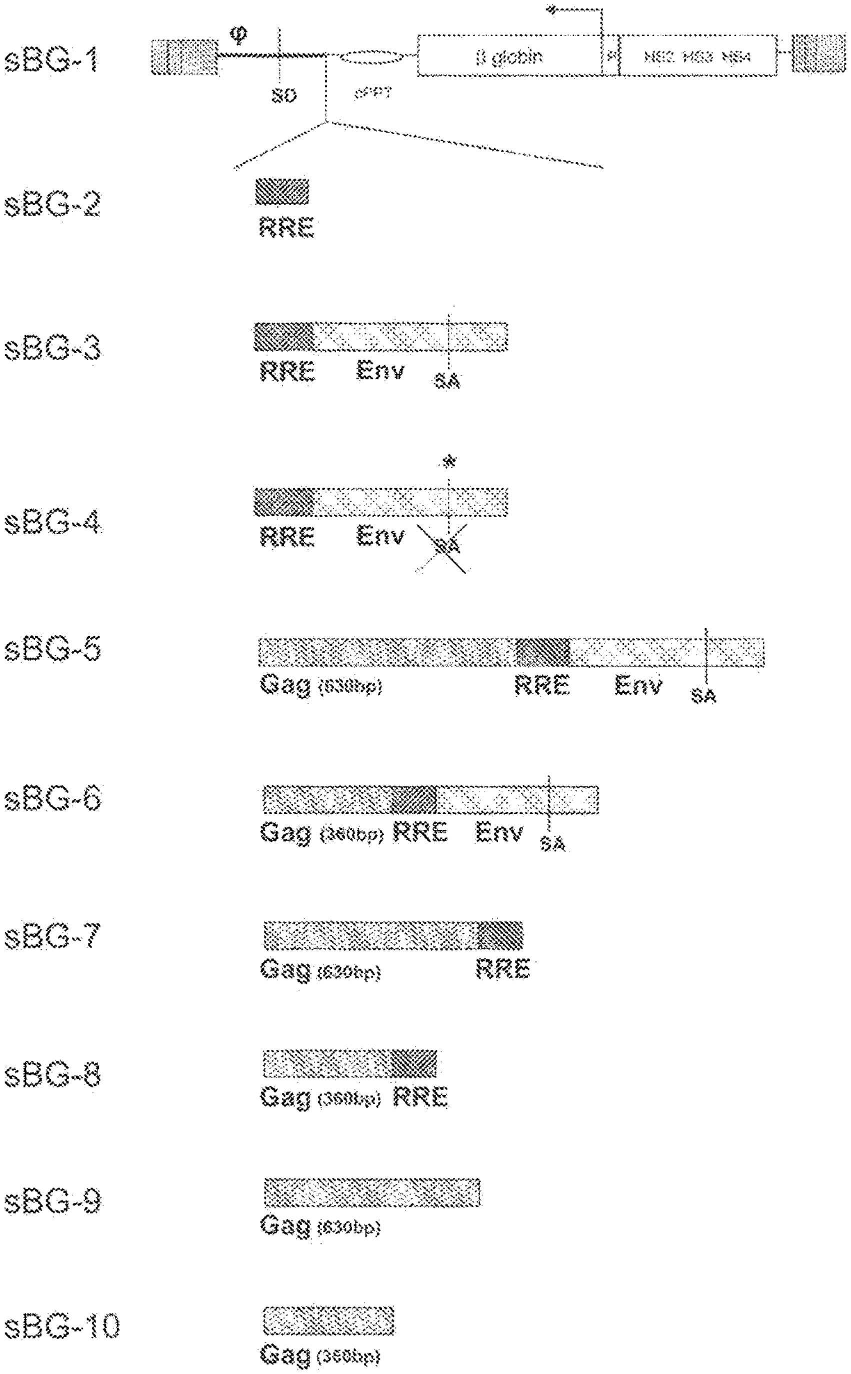
FIG. 2 depicts BG SIN-LV constructs. A schematic representation of 10 SIN-lentiviral proviral forms (sBG-1 to sBG-10). All the vectors contain BG (HS2, 3, and 4 elements of the LCR, the (β-promoter and gene) and cPPT. Gag (630 bp or 360 bp), RRE, env fragments are shown. * indicates a point mutation that disrupts the SA.

To study which particular LV cis sequences were important for this effect, and what step of the vector life cycle they affected, a series of ten SIN-LV vectors were cloned; all of them carrying the BG cassette but carrying different lentiviral non-coding cis elements (FIG. 2). The rationale for studying specific env (RRE and SA) and gag sequences in the context of BG was: (i) The RRE element in the env fragment in a "standard" LV facilitate transport of unspliced/singly spliced transcripts from the nucleus following binding with the Rev protein. (ii) The env splice sites play a fundamental role in the stability of vRNA and its availability for packaging, and absence of known downstream splice acceptor (SA) sequences results in cis-acting repressor sequence (CRS) activity, which hinders cytoplasmic accumulation of HIV-1 RNA. (iii) A portion of the gag gene is retained in vectors to help vRNA packaging. Gag sequences promote folding of the RNA secondary structure of the packaging signal, facilitate the interaction of vRNA with Gag proteins during particle formation, and are important for the dimerization of the vRNA. Sequences mapped to the 5' splice donor site and the first 360 bp of the gag gene direct unspliced and singly spliced viral mRNA to specific subnuclear compartments from where it is exported with the help of Rev/RRE.

The first vector (sBG-1) maintained only the packaging signal (containing the 5' splicing donor site) and the cPPT/flap (FIG. 2). Starting from this vector, the RRE, the rest of the env fragment containing the SA, and two different size gag fragments (360 bp and 630 bp) were sequentially cloned into sBG-2, sBG-3, sBG-5 and sBG-6. To verify the activity of the splicing acceptor (SA) the sequence in the env fragment was mutated by PCR site-specific mutagenesis (sBG-4). In the last four vectors, the entire env fragment including the RRE was first removed, leaving only the long and short version of the gag fragments (sBG-9, sBG-10); or additionally added RRE (sBG-7, sBG-8) downstream of the long and short gag fragments.

Example 5

Viral Titers with Inclusion of Different HIV Cis Sequences

Figure 3A:
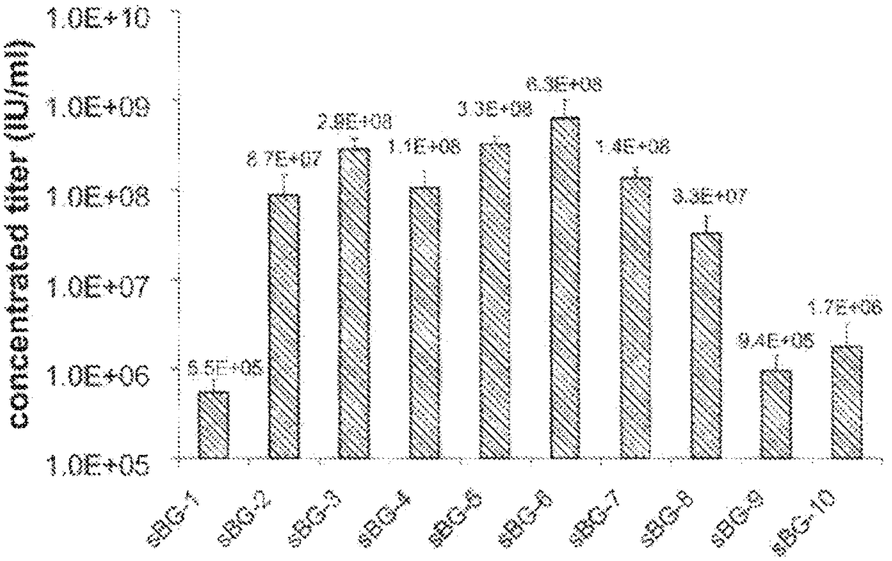
FIGS. 3A-3B depict viral titers of BG SIN-LV.
Figure 3B:
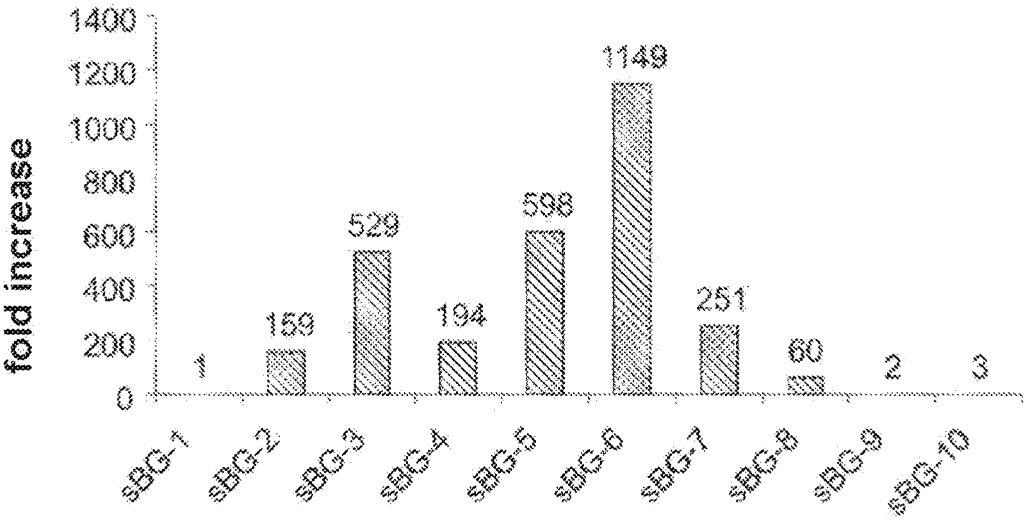

The vectors without the RRE element (sBG-1, sBG-9 and sBG-10) had a concentrated titer ranging from $5.5\pm2.1\times10^5$ IU/mL to $1.7\pm1.4\times10^6$ IU/mL, which was 2-3 orders of magnitude lower than vectors that carry the RRE sequence (sBG-2 to sBG-8; $p<0.01$). Indeed when only the RRE sequence was added to sBG-1 to generate sBG-2, the titer increased by more than a 100-fold ($5.5\pm2.1\times10^5$ IU/mL versus $8.7\pm6.5\times10^7$ IU/mL; $p<0.01$; FIGS. 3A-3B).

Addition of the env fragment containing the SA site increased vector titers 3-5 fold: $2.9\pm0.9\times10^8$ IU/mL for sBG-3 versus $8.7\pm0.7\times10^7$ IU/mL for sBG-2 ($p<0.01$). This effect was specific to the SA, since titers of sBG-4 vector, which contains the env sequence with a mutated SA were $1.1\pm0.61\times10^8$ IU/mL, and were similar to that of sBG-2 carrying only the RRE (sBG4 vs. sBG-3 $p<0.01$). The addition of a long and short fragment of gag to env (RRE and SA) containing vectors sBG-5 and sBG-6, respectively, showed a further increase in titers by ~4-5 fold, with titers from sBG-6 reaching $6.3\times10^8$ IU/mL (sBG-4 vs. sBG-5 and sBG-6 $p<0.01$). The data suggested that the longer portion of gag was not necessary for high BG titers. However, titers of vectors carrying only the short/long gag fragments, without the RRE and env SA were low (sBG-9 and sBG-10), as compared to those containing the RRE as well (sBG-7 and sBG-8; $p<0.01$). Titers of sBG-7, 8, 9, and 10 ranged from $9.4\pm4.7\times10^5$ IU/mL to $1.4\pm0.4\times10^8$ IU/mL. Titers improved further by 3-5 fold with the inclusion of env SA. Thus, the gag fragment alone, or the combination gag/RRE was not sufficient to confer optimal titers to BG vectors, suggesting HIV-1 cis sequences acted cooperatively.

To study whether the strong effect of the RRE on viral titers was Rev-dependent, the sBG-6 vector was packaged with and without Rev. In these experiments, the packaging system was changed from 3-plasmid to a 4-plasmid system, wherein Rev and Gag-Pol were provided from different plasmids. The titers of sBG-6 were approximately 400-fold higher with Rev ($3.8\pm0.3\times10^7$ IU/mL) than without the Rev protein ($9.4x\pm5.8\times10^4$ IU/ml; $p<0.01$), showing that interaction of Rev with RRE was necessary for high titers.

Taken together, these data indicate that HIV-1 Rev/RRE, gag and env SA were critical for high titers of LV carrying a large cargo such as BG or FIG, although they are dispensable for small GFP based cassettes.

Example 6

Role of LV Cis-Elements in the Vector Life Cycle

In order to assess the role of LV cis-elements in proviral stability and expression a genomic Southern blot analysis on transduced MEL cells was performed.

Figure 4A:
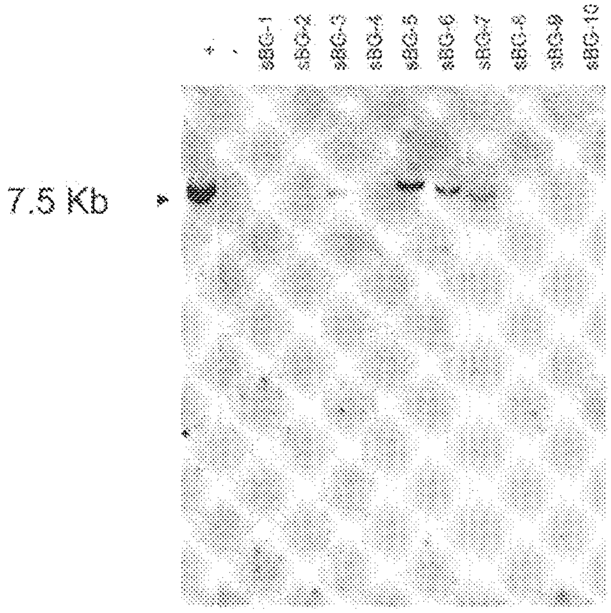
FIGS. 4A-4B depict effect of LV cis-elements on the provirus stability and expression.

Surprisingly, given previous difficulties with genomic rearrangements of hβ-globin-containing γRV, only one proviral band of the expected size was detected in most of the LV FIG. 4A. Some low titer vectors were undetectable at the level of sensitivity of a Southern blot. Subsequent northern blot analysis in packaging cells confirmed that the expected full-length vRNA transcripts were generated from all LV (FIG. 5A), confirming that LV carrying the large BG cassette do not require cis-sequences for stable transmission.

Figure 4B:
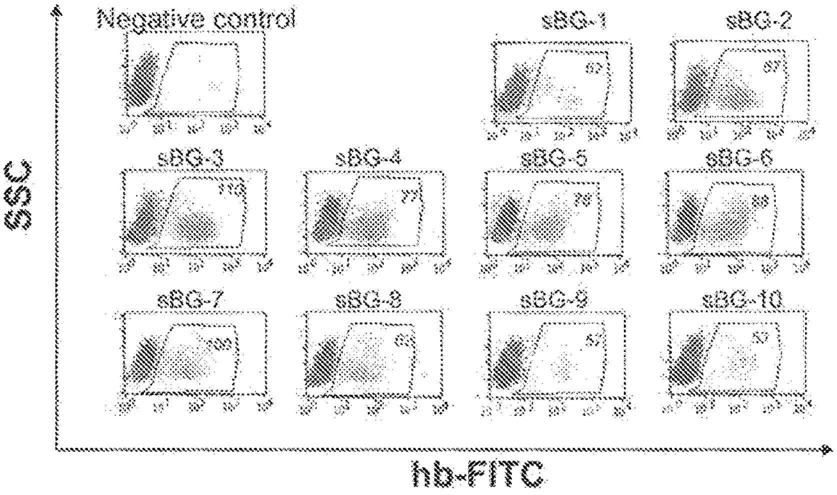

In order to determine whether LV cis-sequences affected the level of expression of integrated BG proviruses, MEL cells were transduced with vectors sBG-1 through sBG-10 at a range of multiplicity of infection. Mean fluorescence intensity (MFI) was compared in MEL cell pools with a similar percentage of hβ-globin expressing cells (15-20%), except in vectors with low titers, where only a small percentage of gene transfer could be achieved. The MFI of the transduced MEL cell population was comparable among all the vectors (ranging from 62 to 110 arbitrary units), including that of the low titer vectors (FIG. 4B). Thus, LV cis-elements did not play a major role in regulating the expression of BG.

In order to determine the role of RRE, gag and env SA in vRNA production and cytoplasmic export the steps of vector life cycle that could impair generation of full-length vRNA in the packaging cells, its subsequent cytoplasmic export, assembly and packaging into vector particles was studied.

Figure 5A:
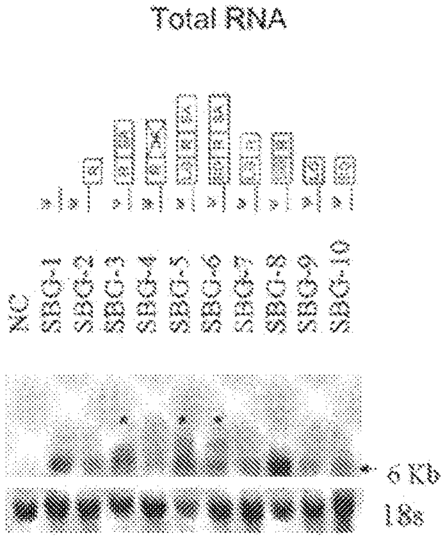
FIGS. 5A-5B depict vRNA transcripts in packaging cells. Northern blot analysis of (FIG. 5A) total RNA from 293T packaging cells transfected with SIN LV plasmids and probed with a $^{32}P$ labeled hβ-globin fragment. Lower panel shows the same blot hybridized with an 18S probe as loading control. A full length band of the expected size is visible for all the vectors. * indicate vectors in which SA is present and both full length and spliced bands are visible. A small schematic of the vector cis-sequences are shown above the vector lanes to depict the Ψ packaging sequence; R: RRE; SA: Splice Acceptor in the env fragment; SG: short gag fragment (360 bp); LG: long gag fragment (630 bp) in vectors.

Total, cytoplasmic and nuclear RNA was fractionated from 293T packaging cells transfected with sBG-1 through sBG-10. FIG. 5A shows a northern blot analysis on total RNA probed with hβ-globin probe. Correctly size bands of intact vRNA from all the vectors, including the vectors without the RRE were determined (sBG-1, sBG-9 and SBG-10). The spliced and unspliced vRNA transcripts were only present for the vectors sBG-3, sBG-5 and sBG-6, since these vectors carry the env SA site. Thus, no appreciable aberrant splicing occurred in any of the LV backbones, confirming lack of recombination of the hβ-globin gene and LCR elements, and contrasting results reported with γRV.

Significantly, all vectors with very low titers, including sBG-1, sBG-9 and sBG-10 that do not contain RRE, produced vRNA in quantities that were comparable to, or higher than the highest titer vectors (sBG-5 and sBG-6). Since this finding was unexpected, the northern blot was repeated in a separate experiment, with fractionation of total and cytoplasmic RNA, with identical results.

Figure 5B:
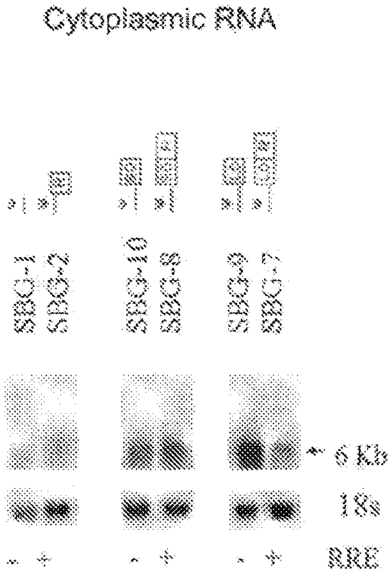

Rev/RRE has been best characterized for export of full-length vRNA to the cytoplasm. Therefore, the next step was to determine if RRE contributed to high titers via vRNA export. Northern blot analysis showed similar amounts of vRNA in the cytoplasm of analogous vectors without or with RRE (sBG-1 versus sBG-2, sBG10 versus sBG-8, and sBG-9 versus sBG-7; FIG. 5B). The ratio of cytoplasmic RNA to total RNA in northern blots from two separate experiments is shown in 6E. The cytoplasmic vRNA transcripts were only 2-fold higher in sBG-2, when compared to sBG-1. The converse was seen with sBG-10 and sBG-9 vectors, where cytoplasmic vRNA transcripts were ~2-fold higher than analogous vectors sBG-8 and sBG-7, which contained the RRE. Since the difference in titers between vectors with and without the RRE was 2-3 orders of magnitude, RRE likely played a minimal role in increasing nuclear export of vRNA transcripts via these vectors.

Example 7

LV Cis-Elements, Including RRE Improve Packaging

Figure 6A:
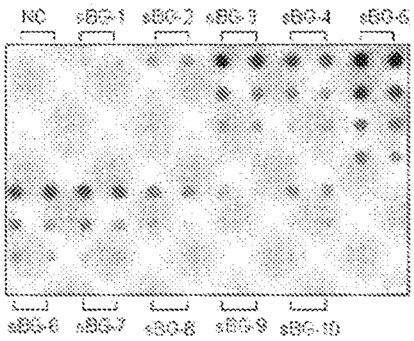
Figure 6B:
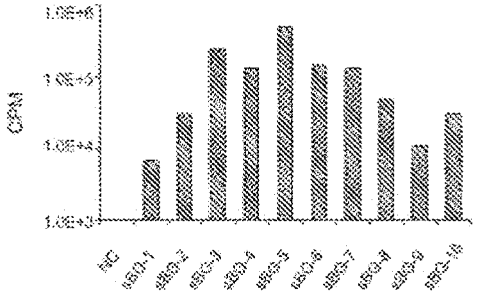
Figure 6C:
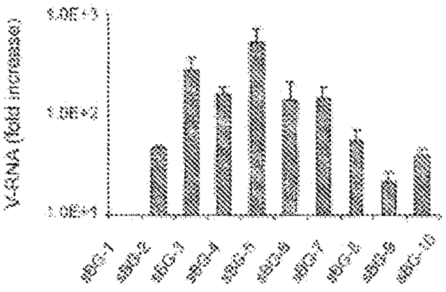

The effect of cis sequences on the packaging efficiency was next determined by analyzing vRNA, p24 levels and viral associated reverse transcriptase (RT) in purified virus particles from all ten vectors processed identically. FIG. 6A shows a representative dot blot analysis of sBG1 through sBG-10 LV. The amount of vRNA detected is proportional to the vector titer for most of the vectors, as determined by phospho-imager analysis, indicating a block in packaging efficiency in vectors lacking cis-sequences (FIGS. 6B-6C).

There were some exceptions that suggested cis-sequences may have some effect on steps following target cell entry: RNA in 293T cells and the infectious titers of sBG-2 and sBG-4 were comparable, although sBG-4 vRNA was 4-times higher. It seems that sBG-4 vRNA, even when packaged more efficiently, may not be stable post-target cell entry due to the absence of env SA, which is known to stabilize RNA. sBG-6 and sBG-7 had the same amount of vRNA but the titer of sBG-7 was 4-5 times lower; here again sBG-7 did not have the env SA. sBG-5, containing the inhibitory region of gag, had higher vRNA, but lower titers.

Figure 6D:
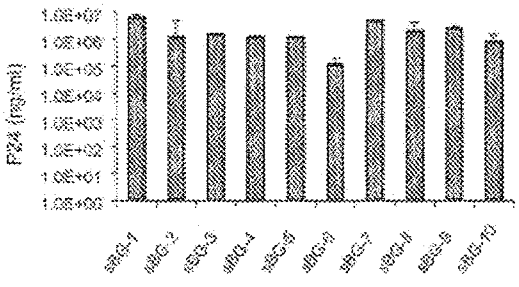

Overall, the amount of BG vRNA packaged in viral particles correlated with the transduction/infectious titers in target cells, despite high levels of mRNA produced in packaging cells with all 10 vectors. The p24 activity was similar in all the concentrated virus preparations (FIG. 6D), suggesting that viral like particles (containing no vRNA) were formed efficiently with all vectors.

Example 8

γRV and LV Size, Payload and Titer

Titers of the standard LV carrying BG are low to begin with, and require extensive concentration. However, the titers fall precipitously (by three orders of magnitude) with the removal of LV cis-elements. Perhaps these LV sequences protect large vRNA from degradation in packaging cells while promoting assembly, while the short GFP vRNA gets efficiently packaged without such requirements. The low titer of the 'gutted' BG LV are not from anti-sense RNA arising from the β-globin gene promoter inserted in the reverse orientation with respect to the 5'LTR vRNA transcript in 293T cells. There was no antisense transcript in the northern blot with any of the vectors. Besides, β-globin transcripts are erythroid-specific, and are not produced in 293T cells. Furthermore, the FIG cassette that was similar in size to BG, but in sense orientation also had the same effect on titers as BG.

Example 9

Cis Elements and Vector Life-Cycle

Several unique, rather unexpected results emerged from this study: (i) in packaging cells, large amounts of transcripts were produced with all BG LV in contrast to barely detectable RNA with BG γRV. One possibility is that LV minimal sequences (R, U5 and Ψ regions) confer stability to BG vRNA in specific sub-cellular compartments. Therefore, high amounts of vRNA are seen in 293T cells even from the gutted LV, an essential difference from the BG γRV. (ii) BG vRNA was of the expected size and efficiently exported into the cytoplasm even in the absence of Rev/RRE, contradicting the belief that the success of 'globin genes' in LV is secondary to the archetypal functions of RRE of preventing splicing and vRNA export. (iv) vRNA was efficiently packaged into virions when the gutted LV encoded a small transgene such as GFP. This data confirms LV cis-sequences, other than the minimal packaging sequence, are dispensable for small transgenes.

Example 10

Role of RRE in Packaging

Rev/RRE interaction was most critical for packaging and high titer virus production, while the well-established function of Rev/RRE in the export of the genomic vRNA and suppression of spliced message was not prominent in BG LV. In wild type HIV virus, the presence of Rev/RRE is required along the entire mRNA transport and utilization pathway for the stabilization, correct subcellular localization, and efficient translation of RRE-containing mRNA. The data presented here confirms and extends a recent study that shows that RRE had a minor effect on cytoplasmic vRNA levels, but reduced viral titers approximately 100-fold. It further shows that Rev/RRE requirement is specific for large transgenes, but dispensable for small expression cassettes. Unlike a previous report in the literature, the present research did not see a role of RRE in vRNA stabilization, since equal or higher amounts of vRNA was seen with vectors without RRE. The likely mechanism is the capacity of RRE to be involved in viral assembly and packaging.

Example 11

Role of Env SA and Gag Sequences

Presence of the env SA has been shown to stabilize the viral genome, resulting in a higher virus production. Presence of SA may also stabilize the vRNA at a post-entry level, since some vectors without the env SA, when compared to analogous vectors with the env SA had the same v-RNA but had lower transduction/titer in target cells. The gag sequence, with a start codon mutation to prevent the translation of the gag protein, helps the production of LV during viral packaging. In this study it was determined that this requirement was specific to large transgene cassettes. It was also demonstrated that removal of an inhibitory sequence present between 414 bp and 631 bp of the gag gene that has been previously shown to decrease the stability of gag-containing RNAs, increased titers by 3.5-fold.

In conclusion, this research describes the steps in the viral life-cycle affected by the non-coding cis-sequences when LV encodes large transgene cassettes; and their dispensability for smaller transgenes such as GFP. These results provide new insight in the design of LV vectors. Gutted/minimal LV could be designed for small therapeutic transgenes, which would be less recombinogenic and safer in gene therapy applications.

Example 12

Viral Vector Design

LV: To clone the sSIN-GFP vector, the 3'LTR of a standard SIN-LV backbone previously used was modified to improve transcript termination: β-growth hormone polyadenylation signal was added downstream the 3'LTR and a USE sequence derived from SV40 late polyadenylation signal was added in the U3 deletion. The dsSIN-GFP was obtained by removing the ClaI-NruI fragment from the sSIN-GFP plasmid. A multi-cloning site (MCS-ClaI-Eco47III, XhoI, SmaI, SalI, EcoRI: CCATCGATAGCGCTCTCGAGCCCGGGGTCGACGAATTCC) was cloned in the ClaI and EcoRI sites of sSIN. The β-globin-LCR (BG) cassette was cloned in reverse orientation into the XhoI and SmaI sites and this parent construct was termed sSIN-BG. sBG-0 was obtained removing the region between Eco47III and NruI, leaving behind only HIV-1 packaging sequence (ψ) following the 5'LTR from sSIN-BG. cPPT was cloned into sBG-0 ClaI site (sBG-1). PCR fragments for RRE, RRE-env, short gag (360 bp), long gag (630 bp) were cloned in XhoI blunted site, and these vectors were termed sBG-2, sBG-3, sBG-10, sBG-9, respectively. Primers sequences, where F denotes forward primers and R denotes reverse primers:

```
RRE_F:
ATAAACCCGGGAGCAGTGGGAATA;

RRE_R:
ACATGATATCGCAAATGAGTTTTCC;

ENV_R:
ACATGATATCATACCGTCGAGATCC;

GAG_F:
ACTGCTCTCGAGCAATGGGAAAAAATTCGGT;

GAG_1R:
ACTGCTCTCGAGGCAGCTTCCTCATTGATG;

GAG_2R:
ACTGCTCTCGAGATCAGCGGCCGCTTGCTGT.
```

A frame-shift mutation was inserted in the 5' sequence of gag in the start codon to disable the gag start site, using the primer Gag F that inserts the dinucleotide CA in the gag ATG. Vectors sBG-7 and sBG-8 were obtained cloning long gag and short gag PCR fragments into XhoI site of sBG-2. A point mutation to disrupt the SA site in the env sequence was performed using MutSA_F (TATCGTTTCGAACCCACCTCC) and MutSA_R (GGAGGTGGGTTCGAAACGATA) primers to generate sBG-4 (the wt SA sequence CAG inside the Env fragment was mutated into CGA). sBG-5 was obtained cloning the long gag PCR fragment into the XhoI site of sBG-3. γRV: SRS 11.SF γRV plasmid was kindly provided by Drs. Axel Schambach and Christopher Baum, (Hannover, Germany). In SRS 11.BG vector, the human β-globin-LCR (BG), was cloned in reverse orientation into the PstI site of SRS 11.SF retroviral vector plasmid. All vector cartoons are depicted in FIG. 2.

Example 13

Virus Production

LV was produced by transient co-transfection of 293T cells, as previously described using the vector plasmids, the packaging (Δ8.9) and the envelope (VSV-G) plasmids; virus-containing supernatant was collected at 60 hours after transfection and concentrated by ultracentrifugation. All vectors in an experiment were packaged simultaneously and the virus was concentrated 1400-fold from all viral supernatants by ultracentrifugation at 25,000 rpm. Viral titers were determined by infecting mouse erythroleukemia (MEL) cells or HT1080 cells with serial dilution of concentrated virus, differentiating them, and analyzing them for HbA or GFP expression by fluorescence-activated cell-sorter (FACS) as previously described. γRV were produced similarly but not concentrated. All transfections and subsequent titration were performed in triplicate. Packaging of vectors, with and without Rev, was performed following a similar method, except that the packaging plasmid Δ8.9 was replaced with pMDLg/pRRE and pRSV-Rev. The ratio of vector plasmid:pMDLg/pRRE:pRSV-Rev:VSV-G was 4:4:3:1.

Example 14

Cell Lines

Murine erythroleukemia cell (MEL) line and 293T cells were maintained in Dulbecco modified Eagle Medium (DMEM, Mediatech, Inc., Herndon, Va.) supplemented with 10% heat inactivated fetal bovine serum (FBS) (U.S. Biotechnologies, Inc, Parker Ford, Pa.). MEL cells were induced to differentiate in DMEM containing 20% FBS and 5 mM N,N'-hexamethylene bisacetamide (Sigma), as previously described in the art.

Example 15

HbA Staining and FACS Analysis

The methodology used to label human β-globin using the anti-human HbA antibody was as previously described. Briefly, cells were fixed in 4% paraformaldehyde for 60 minutes at room temperature, washed once with phosphate-buffered saline (PBS), and the pellet resuspended in 100% methanol for 5 minutes. The fixed cells were then washed with PBS, and nonspecific antibody (Ab) binding was blocked using 5% nonfat dry milk for 10 minutes at room temperature. Subsequently, cells were washed in PBS, pelleted, and permeabilized. The cells were divided into 2 tubes and stained with either anti-zeta globin-fluorescein isothiocyanate (FITC) Ab (1 µg/$10^6$ cells) as a negative control or anti-HbA-FITC Ab (0.1 µg/$10^6$ cells) (Perkin Elmer, Waltham, Mass.) for 30 minutes at room temperature in the dark. Unbound Ab was removed by a final wash with PBS before they were analyzed on FACS Calibur (Becton Dickinson, Franklin Lakes, N.J.).

Example 16

Total and Cytoplasmic RNA Northern Blot 293T cells were harvested and washed in PBS 72 hours after transfection. Isolation of nuclear and cytoplasmic RNA is obtained with a 7 minutes incubation on ice with NEB buffer (10 Mm Tris-HCl pH 7.4; 10 mM NaCl, 3 mM MgCl2; 5% IGEPAL). After centrifugation RNA-STAT (Tel-Test, INC, Texas) was added to the supernatant that contains cytoplasmic RNA, and proceeded with RNA extraction following manufacturer's instructions. Total RNA was extracted from 293T cells using RNA-STAT. Northern Blot was then performed according to standard protocol. The blot was hybridized with a $^{32}$P labeled β-globin probe. To normalize the loading of the RNA, membranes were then stripped and re-probed with a $^{32}$P labeled 18S probe. To test the purity of cytoplasmic RNA membranes were stripped and re-probed with a $^{32}$P labeled probe specific for GAPDH intron probe that detected no intronic transcript in the cytoplasmic preparation.

Example 17

Genomic Southern Blot

Genomic DNA was performed on DNA isolated from transduced MEL cells and 10 µg of genomic DNA was digested with AflII enzyme and Southern Blot performed according to standard protocol. The blot was hybridized with a HS2 fragment of the β-globin LCR probe. RNA dot blot vRNA was extracted from same volumes of concentrated viruses using the QIAamp vRNA Mini Kit (Qiagen) following the manufacturer's instructions. Briefly the virus was lysed under highly denaturing conditions and then bound to a silica-gel-based membrane. Two washing steps efficiently washed away contaminants and vRNA was eluted in 30 μl of DEPC-water. After elution vRNA was treated for 20 min at room temperature with DNAse I, amplification grade DNase I (Invitrogen, Carlsbad, Calif.) was inactivated by incubating the sample at 650. vRNA was then denatured in 3 vol of denaturation buffer (65% formamide, 8% formaldehyde, MOPS IX) for 15 min at 650. After denaturation 2 vol. of ice-cold 20×SSC were added and the RNA was bound to a nylon membrane by aspiration through a dot-blot apparatus. The blot was hybridized with a $^{32}$P labeled β-globin specific probe and an X-ray film was exposed overnight.

Example 18

Chromatin Insulators—Generally

Chromatin insulators separate active transcriptional domains and block the spread of heterochromatin in the genome. Studies on the chicken hypersensitive site-4 (cHS4) element, a prototypic insulator, have identified CTCF and USF-1/2 motifs in the proximal 250 bp of cHS4, termed the "core", which provide enhancer blocking activity and reduce position effects. However, the core alone does not insulate viral vectors effectively. The full-length cHS4 has excellent insulating properties, but its large size severely compromises vector titers. A structure-function analysis of cHS4 flanking lentivirus-vectors was performed and transgene expression in the clonal progeny of hematopoietic stem cells and epigenetic changes in cHS4 and the transgene promoter were analyzed. The core only reduced the clonal variegation in expression. Unique insulator activity resided in the distal 400 bp cHS4 sequences, which when combined with the core, restored full insulator activity and open chromatin marks over the transgene promoter and the insulator. These data consolidate the known insulating activity of the canonical 5' core with a novel 3' 400 bp element with properties similar to the core. Together, they have excellent insulating properties and viral titers. This data has important implications with respect to understanding the molecular basis of insulator function and design of gene therapy vectors.

Example 19

Vector Constructs and Experimental Design

Figure 7A:
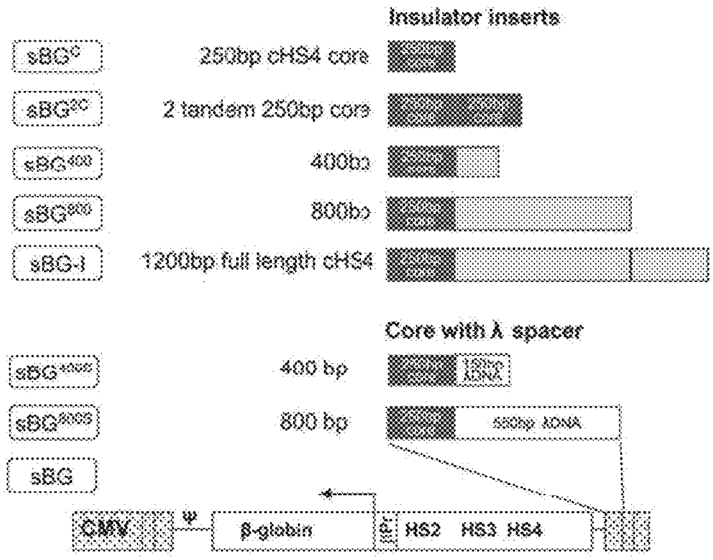
FIGS. 7A-7C depict vector constructs and experimental design.

Self-inactivating lentivirus vectors were designed to incorporate either the 5' 250 bp "core" (sBGC), two tandem repeats of the core (sBG2C), 5' 400 bp (sBG400), 5' 800 bp (sBG800) or the full-length 1.2 Kb cHS4 insulator (sBG-I). All vectors carried the human (h) β-globin gene and promoter and the locus control region enhancer. The different insulator fragments were cloned in the forward orientation into the U3 region of 3' LTR, so that upon reverse transcription, integrated provirus in target cells has the insulated 3' LTR copied to the 5'LTR, and flanks the hβ-globin expression cassette at both ends. To assess whether elements outside the 5' 250 bp core merely provided a spatial scaffold, vectors with inert DNA spacers downstream of the core, sBG400S and sBG800S, were also tested. All vectors were compared to the uninsulated control, sBG (FIG. 7A).

Figure 7B:
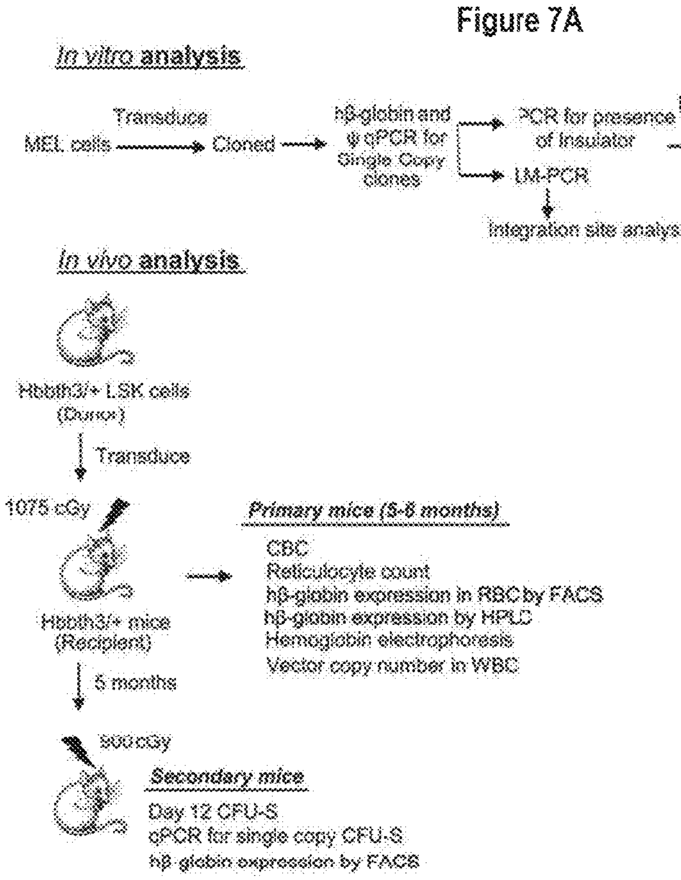
Figure 7C:
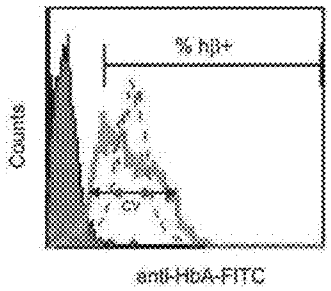

First, MEL cells were infected with each of the lentivirus vectors and single integrant MEL clones were identified (FIG. 7B). All analysis was performed only on single-copy MEL clones that carried hβ-globin and verified to have intact insulator sequences by PCR, and subjected to qPCR for vector copy number; hβ-globin expression was analyzed by FACS: 1) the percentage of hβ-globin expressing cells (% hβ+ cells) was used to determine chromosomal position effects, and 2) the variation of expression of hβ-globin expression in cells within a clone, as determined by the coefficient of variation (CV), was used to determine the clonal variegation in expression (FIG. 7C). ChIP analysis was performed on the histones over the insulator regions and hβ-globin gene promoter in the different proviruses to study epigenetic modifications. Chromatin position effects of these vectors were confirmed in vivo, in RBC of Hbbth3/+ thalassemia mice transplanted with vector-transduced HSCs 24 weeks after transplant. Secondary transplants were then performed and single-integrant CFU-S following transplants were analyzed for hβ-globin protein and mRNA. In mice, hematological analysis, and HPLC for hβ-globin protein were additionally performed to quantify expression.

Example 20

Regions of cHS4 Necessary to Protect from Chromatin Position Effects

Consistent with previous results, a very high % of hβ+ cells were present in the sBG-I single-integrant clones compared to control sBG clones ($P<0.01$); the % of hβ+ cells in sBGC, sBG2C, sBG400 and sBG800 clones were not significantly different from the sBG control clones (FIG. 8A) In order to ensure that the presence of cHS4 in the LTR did not bias integration, and that the analysis was performed on distinct clones, by LM PCR and integration site sequencing on ten randomly selected sBG or sBG-I MEL clones. Insertions occurred near/in distinct genes between uninsulated and insulated clones, with no apparent bias. The presence of the cHS4 core (sBGC), or extended sequences of the insulator downstream to the core, up to 800 bp, did not increase the % hβ+ cells further; neither did tandem repeats of the core sequence, even though the latter has been shown to confer enhancer blocking effect in plasmid-based systems.

Another phenomenon seen with transgene expression is clonal variegation, defined as varying levels of expression in daughter cells with the same integration site. A quantitative way to determine clonal variegation is by FACS analysis of transduced clones and calculation of the coefficient of variation (CV) of expression of the transgene around the average expression of the transgene in the clone. The CV is a unit-less measure of variability calculated as ratio between sample standard deviation (SD) and the sample average. A high CV was observed in the uninsulated sBG clones (FIG. 2B). The CV was significantly reduced in all vectors that contained the 5' 250 bp core. These results were confirmed in clones derived from vectors that carried inert DNA spacers downstream of the core: sBG400S and sBG800S, showing that the reduction in CV was specific to the insulator core, and in contrast to the data on % of hβ+ cells, which required the full-length insulator to be present.

It was notable that PCR for insulator sequences showed absence of the insulator sequences only in sBG2C proviruses, with 6 of 24 clones (25%) MEL clones having both copies of the core deleted from both LTRs. There was no observed deletion of the insulator sequences in clones from all other vectors. Southern blot analysis of sBG2C MEL pools confirmed deletion of one/both copies of the core in the majority of cells. Reverse transcription of repeat sequences, known to result in recombination events in retroviral vectors likely caused unstable transmission of the vector with repeat core sequences. This effect of the core versus the full-length cHS4 was confirmed in vivo, in thalassemia mice. Peripheral blood RBC were analyzed for hβ-globin expression 6 months following transplant. FACS analysis in RBC from sBG, sBGC, sBG2C, sBG400 and sBG-I groups of mice (representative plots shown in FIG. 9A) shows that the % hβ+ RBC were significantly higher only in the sBG-I group of mice, compared to sBG group of mice, like the data in MEL cells; and the CV was significantly lower in all vectors that carried the core ($P<0.01$; FIGS. 9B-9C). Taken together, this data indicates that the full-length cHS4 is required to shield against chromosomal position effects.

Example 21

Chromatin Position Effects in the Clonal Progeny of Murine HSC Following Secondary Transplants The chromatin position effects were next confirmed in single copy secondary CFU-S. The secondary colony forming units-spleen (CFU-S) assay is considered the most stringent assay that is a 'gold-standard' for studying epigenetic effects of chromatin insulator elements in cells derived from hematopoietic stem cells. Notably, no transduced CFU-S that was positive by PCR for vector-specific sequences that did not express hβ-globin by FACS were observed, consistent with results reported on lack of transgene silencing with erythroid-specific SIN lentivirus vectors. FACS analysis for (1) % hβ+ cells and (2) TER-119 positive erythroblasts showed no difference in the percentage of TER-119+ cells between different vector groups (not shown). However, significantly higher % of hβ+ cells were only present in secondary CFU-S with the sBG-I vector. Again, the CV was significantly lower in CFU-S transduced with all the vectors carrying the core, compared to uninsulated sBG transduced CFU-S (FIGS. 3D-3E). Real-time RT-PCR analysis on six randomly selected CFU-S from each group of mice showed that compared to the sBG vector, mRNA expression from the sBG-I CFU-S was approximately 2-fold higher. However, expression from sBGC, sBG2C and sBG400 transduced CFU-S was not significantly different from that of sBG CFU-S. Taken together, these data indicate that the 5' 250 bp core sequences in sBGC, sBG400, sBG400S, sBG800 and sBG800S specifically reduced the clonal variegation of hβ-globin expression. However, the full-length cHS4 element was required for improved probability of expression from different integration events.

Example 22

Patterns of Histone Acetylation and Methylation in the Core Region and the β-Globin Promoter Region in Insulated Vectors Next the epigenetic modifications that accompany the specific effects seen with the various insulator regions were determined by comparing the relative levels of active histone marks acH3, acH4 and H3K4me2 and repressive histone marksH3K9me3 and H3K27me3 between different proviruses in MEL clones. ChIP analysis was performed on the cHS4 core in three representative clones that were pooled together for each vector (clones chosen are shown as filled circles in FIG. 8A) by semi-quantitative PCR (FIGS. 10B-10C) and real-time PCR) (FIGS. 10D-10F). Clones carrying the sBG-I vector integrants showed approximately 6-fold enrichment of the active chromatin marks and decreased repressive chromatin marks over the cHS4 "core" fragment, compared to sBGC, sBG400 and sBG800, three vectors that carried the "core".

Histone modifications were analyzed over the hβ-globin promoter in the uninsulated vector (sBG) and all other vectors, which carried the "core", to assess whether differences in histone patterns over the transgene promoter in vectors may have contributed to the reduced clonal variegation. There was a small but significant reduction in repressive chromatin patterns H3K27me3 with sBGC, sBG400 and sBG800 proviruses, compared to the uninsulated sBG provirus (FIG. 10F, right panel). However, with the sBG-I provirus, where maximal insulator activity was present, the hβ-globin promoter region had markedly reduced repressive chromatin patterns.

These data show that the "core" sequences and extension of the core up to the 5' 800 bp of cHS4 reduced activation marks over the transgene promoter to a small extent. However, a major reduction in repressed histone modifications over cHS4 and the transgene promoter region only occurred when the distal 3' 400 bp sequences of cHS4 were present in addition.

Example 23

Hematological Parameters in Thalassemia Mice Transplanted with HSCs Transduced with Uninsulated and Insulated Vectors The anemia, reticulocytosis and other RBC indices were improved even with the sBG vector (FIG. 11A), consistent with published reports with uninsulated hβ-globin lentivirus vectors. Hemoglobin of mock-transplanted mice was 7.7±0.2 gm/dL and the sBG group of mice was 10.4±0.7, with 1.2 vector copy per cell. It was noteworthy that the sBG-I group of mice had higher hemoglobin and the lowest reticulocyte count, despite having half the vector copies per cell compared to the sBG group of mice (hemoglobin 11±0.2 gm/dL; 0.6 vector copies per cell). When normalized for transduction efficiency, this amounts to a 5.2 gm increase in hemoglobin per vector copy in sBG-I mice over mock mice, in contrast to a 2.3 gm increase in hemoglobin per vector copy in the sBG mice. RBC parameters from the experimental mice showed significant improvement (FIG. 11A; note that these data are not normalized for number of vector copies). Improvement in these indices was highest with the sBG-I mice, albeit not significantly different unless normalized for vector copy.

HPLC analysis for hβ-globin protein in blood confirmed significantly higher hβ-globin expression only in the sBG-I mice: 43±3% of the total hemoglobin in RBC was derived from hβ-globin (hβ2mα2) in sBG-I mice as compared to 19±6% in the sBG mice, while that in sBGC, sBG400 and sBG2C group of mice was not significantly different from control (FIG. 11B). Human hβ-globin expression and hematological parameters in the sBG2C group of mice were similar those seen in the uninsulated control group.

Example 24

Insulator Activity in the 3'400 cHS4 Region

Since the 5' 800 bp of cHS4 only reduced the CV, while full insulator activity was restored with the full-length 1.2 Kb insulator. A vector was generated carrying only the distal/3' 400 bp region of the cHS4 (sBG3'400) derived MEL clones and mice were transplanted with sBG3'400-transduced LSK cells. Note that unlike vectors described earlier, this vector does not contain the 5'250 bp "core" sequences (FIG. 12A). The sBG3'400 vector had no effect on % of hβ+ cells in MEL clones or the % hβ+ RBC in mice (FIGS. 6B, 6D), an effect comparable to sBG clones, or those carrying the 5' 250 bp "core" (sBGC). However, like all vectors carrying the 5' core, sBG3'400 significantly reduced the CV of hβ-globin expression in MEL clones and in RBC (FIGS. 12C, 12E).

The amount of hβ-globin protein in the sBG3'400 mice, determined by HPLC analysis, was not significantly different from sBG (17.5±3% versus 19.5±5.6%), but was at least 2-fold lower than that seen in the sBG-I mice (43±3%; P<0.01) (FIG. 12F). Overall, the 3' 400 bp of cHS4 had activity that was very similar to the 5' 250 bp core (FIGS. 9A-9E): it reduced clonal variegation, reflected in a reduced CV of hβ-globin expression in MEL clones and in RBC, but had no effect on the proportion of hβ-globin expressing red cells. "Core-like" effects of the 3' 400 bp in individual single copy secondary CFU-S (FIGS. 12G-12H), were confirmed, with results similar to those with the sBGC vector (FIGS. 9D-9E). The 3' 400 region has no known consensus sequences for CTCF or USF-1, and this region has not been previously analyzed. It was noteworthy that neither the 5' core, nor the 3' 400 bp, when present alone, were able to improve the probability of expression of integrants/protect from position effects.

Example 25

Insulator Activity of the 5' "Core" Combined with the 3'400 bp

When the 5' 250 bp core and the 3' 400 bp sequences of cHS4 insulator (sBG650 vector; FIG. 13A) were combined, this vector performed similarly to the sBG-I vector—in MEL clones, in RBCs of transplanted mice and in secondary CFU-S. The proportion of hβ-globin expressing cells in sBG650 MEL clones and RBC (FIGS. 13B-13D) was significantly higher compared to sBG clones (P<0.001), and was similar to sBG-I clones. Likewise, the CV of the sBG650 clones was comparable to sBG-I clones (FIG. 13C). The hβ-globin expression in the RBC of primary mice was comparable to sBG-I mice (FIG. 13D). The amount of hβ-globin protein in the sBG650 mice, determined by HPLC analysis, was not significantly different from sBG-I mice (41±2.6% versus 43±3%, respectively), but was at least 2-fold higher than that seen in the sBG mice (19±6%; P<0.01). Five months after transplant, secondary transplants were performed to generate CFU-S, which confirmed that the sBG650 vector restored insulator activity similar to that seen with sBG-I vector (FIG. 13E). The chromatin configuration over the core in sBG650 proviruses (FIG. 13F) showed restoration of open chromatin patterns both over the insulator core and the β-globin promoter, identical to those seen in the sBG-I proviruses (FIGS. 10A-10F).

Example 26

Epigenetic Modifications in the 3'400 bp Region of cHS4 and its Interaction with the Core The chromatin configuration of the distal 3' 400 bp portion of cHS4 have not been previously studied. The histone patterns were first analyzed over the 3' 400 bp region (sBG3'400) when present alone (sBG3'400), or when in combination with the 5' core (in sBG650 and sBG-I) (FIGS. 14A-14J). The acetylation and methylation patterns of the histones in the 3'400 region of sBG3'400 provirus (FIG. 14B) were similar to those seen in the 250 bp core region in the sBGC provirus (FIGS. 10A-10F). However, in sBG650 and sBG-I proviruses, the 3' 400 bp sequences had increased acetylation marks and reduced repressive, showing once again, that the combination of the proximal and distal ends of cHS4 is necessary for open chromatin patterns. This effect was reminiscent of the ChIP analysis over the 5' core region or the β-globin promoter region in sBG-I (FIGS. 10D and 10F) or sBG650 (FIGS. 13F and 13G). Taken together, the genetic and epigenetic analysis indicated that the 5' and 3' ends of the insulator were functioning as two cores, which interacted for epigenetic modifications of chromatin on the insulator and promoter, to impart adequate insulator activity.

The 3' 400 bp region, however, has no known CTCF or USF-1 motifs, that have been shown to impart enhancer blocking and barrier activity, respectively, to cHS4. It is conceivable; however that CTCF and/or USF-1 may perhaps be recruited to the 3'400 region. Using antibodies to USF-1 and CTCF, chromatin was immunoprecipitated from sBGC, sBG3'400, sBG650 and sBG-I proviruses from MEL clones. ChIP analysis was performed using semi-quantitative PCR and qPCR. When primers to the core region were used to amplify ChIP products, CTCF and USF-1 recruitment to the 5' core region was evident (FIGS. 14C-14D), as anticipated and shown previously. Interestingly, when 3'400 region primers were used to amplify the ChIP products, the sBG3'400 provirus showed enrichment for CTCF, albeit at somewhat lower levels than that seen over the core region. More notably, however, the sBG650 and sBG-I proviruses showed enrichment both USF-1 at the 3' 400 bp region, an effect seen when both the proximal core and the distal 400 bp sequences were present. The 3' 400 bp region, when present alone in sBG3'400, did not bind USF-1 (FIGS. 14E-14F). These data indicate that the 3' 400 bp region interacts with CTCF despite lack of the CCCTC consensus, which may explain the "core-like" activity in this region and the interaction between the 5' core region and the 3' 400 region of the cHS4 insulator (in sBG-I or sBG650) likely occurs via USF-1.

Example 27

Vector Titers with the 650 bp cHS4 Insulator

The 1.2 Kb cHS4 remarkably lowers titers of SIN-lentivirus vectors, limiting large-scale virus production for human trials. It has been recently shown that the mechanism of reduction in titers is specifically due to the length of the insert in the 3'LTR. Compared to sBG, sBG650 had very reasonable titers that were only 2.5±0.9 fold lower than sBG, in contrast to 10.4±2 fold lower titers of sBG-I (n=3). Therefore, this optimized insulator can be used for the design of safer gene therapy vectors which would provide uniform and therefore higher expression and be scalable to large-scale production.

The full-length cHS4 insulator has been previously shown by us and by others to protect viral vectors against chromosomal position effects. The profound deleterious effects on viral titers however, have precluded its utility. Attempts to use only the 5' 250 bp of cHS4, characterized to be the core of the insulator, have failed in viral vectors despite significant activity of the core in plasmid based systems, and loss of insulator activity with mutations in these regions.

Regions surrounding the cHS4 insulator and β-globin promoter have been shown to constitutively higher marks of active chromatin in the native location. The cHS4 prevents the spread of heterochromatin to the β-globin domain, even when adjacent heterochromatin domains have high repressive histone marks, H3K9me3 and H3K27me3. Clones carrying the sBG-I vector integrants showed an enrichment of the active chromatin marks and a striking decrease in repressive chromatin marks over the cHS4 core compared to sBGC, sBG400 and sBG800 vectors, where no significant differences in these epigenetic marks were observed.

Mechanistically, the USF-1/2 element in the insulator has been shown to recruit histone modifying enzymes to the core, and interact with histone lysine methyl transferase SET7/9 and p300/CREB-binding protein-associated factor (PCAF), thus increasing active chromatin marks. However, No such increase was observed in acH3, acH4 and H3K4me2 over the core or the 3' 400 bp when they flanked the transgene in the sBGC, sBG400, sBG800 and sBG3'400 vectors. This effect required the vector carrying the full length cHS4 (sBG-I, FIGS. 10A-10F and 14A-14J) or both the core and 3'400 bp combined sBG650 vector (FIGS. 13A-13G and 14A-14J). ChIP analysis over the hβ-globin promoter showed that compared to an uninsulated vector, the core alone reduced repressive chromatin marks over the promoter to some extent (FIG. 10F), which may account for the reduction in CV from vectors carrying the core. However, the core was dependent on the 3' 400 bp region and conversely, the 3' 400 bp region dependent on the core for the high degree of histone acetylation and absent to minimal repressive marks over both these regions.

Models proposed to explain the effect of the cHS4 on surrounding chromatin include protection against transgene silencing by exclusion of methyl-CpG-binding proteins; indeed, cHS4 has been shown to block silencing by retroviral vectors. No extinction of β-globin expression over time was observed, even with the uninsulated vector in mice, or MEL clones maintained up to 6 months in culture (data not shown) This may be due to several USF-1 elements in the β-globin LCR hypersensitive sites, that have been shown to interact with the E-box elements located in HS2 and in the β-globin gene promoter. It is conceivable that this resistance to silencing conferred by the LCR may override any activity seen with the cHS4 core. These results contrast those by Panell et al that retroviruses including those derived from HIV-1, dominantly silence a linked locus control region (LCR) beta-globin reporter gene in transgenic mice. Methylation was analyzed and it was subsequently reported that there was a lack of CpG methylation and extinction in expression with erythroid-specific SIN-lentivirus vectors in vivo, in primary and secondary recipients. This data suggests that in erythroid vectors, which otherwise resist silencing via promoter methylation, the full-length cHS4 was able to modify the histone patterns over the transgene promoter, and over itself to reduce position effects.

Intriguingly, the in silico analysis of the 3' 400 bp region revealed no CTCF or USF1 binding sites, but sites for multiple known transcription factors. Any of these transcription factors, or perhaps a novel protein may be the interacting partner with the CTCF and/or USF-1. CTCF directly regulates the balance between active and repressive chromatin marks via binding to the cohesin complex. This data reveals that the 3' 400 bp region can also interact with CTCF: although co-immunoprecipitate the 3'400 bp and CTCF from the sBG3'400 provirus (FIGS. 14C-14F) was unsuccessful.

Interestingly, the 3'400 bp co-immunoprecipated with USF-1 antibody only when the 5' core sequences were additionally present, suggesting that USF-1 likely forms a bridge between the 5' and 3' end of cHS4 to reduce position effects. Whether elements within the 3' 400 bp recruit histone acetylases that bind USF-1 or cohesin and/or nucleophosphmin complexes to affect position effects would be important to determine.

Ultimately, a systematic genetic and epigenetic analysis of insulator activity of the cHS4 in vitro and in vivo was performed and novel "core-like" activity in the 3' 400 bp was identified. The 3' 400 bp of cHS4, which contains no consensus sites for USF or CTCF, nevertheless binds CTCF, while USF-1 appears to bind and bridge the 5' core and the 3' 400 bp of cHS4. New vector systems flanked by the optimized '650 bp' cHS4 sequence, can provide excellent insulation of the transgene without significant loss in viral titers and have important safety and efficacy implications for gene therapy.

Example 28

Materials and Methods-Lentivirus Vectors

All vectors were obtained by cloning the different insulator fragments into NheI/EcoRV sites in the U3 3'LTR region of the lentivirus plasmid, as described. This plasmid carried the human (h) β-globin gene and its regulatory elements (BG). All insulator fragments were amplified by PCR using the insulator plasmid pJCI3-1 (kindly provided by Dr. Gary Felsenfeld, NIH, MD) and verified by sequencing, as described. Cloning of the hβ-globin vector with and without the 1.2 kb cHS4 insulator has been described previously. The sBG1C vector was cloned by inserting EcoRI/XbaI 250 bp core insulator PCR product into sBG into BamHI/EcoRI restriction sites of the pBS plasmid. A second copy of the 250 bp core was then added into the pBS 1-core plasmid into EcoRI/KpnI sites, thus obtaining the pBS 2-core plasmid. The two tandem copies of the 250 bp core were then isolated digesting the pBS-2core plasmid with KpnI/XbaI, and then cloned into the sBG vector, obtaining sBG2C. The sBG400 and sBG800 vectors were obtained by cloning the 2 PCR products into the sBG NheI/EcoRV sites. The vectors containing DNA spacers were obtained amplifying different sizes of λ-phage DNA using the following primer combinations: spacerF1 and spacerR1, spacerF1 and spacerR2, amplifying 150 bp, 550 bp λ-DNA, respectively. ClaI/EcoRI digested PCR fragments were ligated into EcoRI/ClaI sites in the pBS-1 core plasmid, and 400 bp and 800 bp fragments from the pBS-1 core plasmid were restricted with HincII/XbaI and XbaI/XhoI, respectively, and cloned into NheI/EcoRV sites of sBG. Virus was produced by transient co-transfection of 293T cells and titrated on MEL cells.

Example 29

Materials and Methods—Cell Lines

MEL cells and 293T cells were maintained in DMEM (Mediatech, Inc) supplemented with 10% heat-inactivated fetal bovine serum (FBS; U.S. Bio-technologies, Inc.) and differentiated as described. MEL cells were transduced to achieve less than 5% transduction efficiency for each of the vectors tested and cloned. Approximately 400 clones, derived from three independent transductions from each vector were screened by PCR for hβ-globin gene; positive clones were screened for an intact insulator region. Clones thus identified were then subjected to qPCR for single integrants, expanded and cryopreserved. An entire set of clones was thawed, differentiated and analyzed concurrently by FACS.

Example 30

Materials and Methods-Murine Hematopoietic Stem Cell Transduction and Transplants Hbbth3/+ thalassemia mice were used for transplants. All animal studies were done using protocols approved by the Institutional Animal Use and Care Committee. Enrichment of lineage—Sca-1+c-kit+ (LSK) hematopoietic stem/progenitor cells was performed on single cell suspension of bone marrow by immunomagnetic separation and FACS sorting (details in supplementary Materials and Methods S1) LSK cells were transduced in Stem Span (Stem Cell Technologies Inc, Vancouver, BC) with concentrated vector supernatants at an MOI of 10, twice at 12 h intervals as previously described. 10,000 transduced LSK cells were co-transplanted with 2×105 LK cells into 10.75 Gy irradiated thalassemia recipients. CFU-S assay: Discrete spleen colony forming units (CFU-S) were dissected at day 12 after transplant of bone marrow cells from primary mice 24 wk after transplant, as described earlier.

Example 31

Materials and Methods-Analysis for hβ-Globin Expression

Complete blood counts were performed on a Hemavet (Drew Scientific, Inc, Oxford, Conn., USA). Reticulocyte count was analyzed by staining 1 μl of whole blood with 200 al of Retic-COUNT reagent (BD Biosciences, CA) and enumerated on the FACSCalibur (BD). Quantitative analysis of hβ-globin protein in RBC was performed on hemolysates of blood by high performance liquid chromatography (HPLC), as previously described and mRNA analysis quantified by real-time RT-PCR using validated primers and probes specific to hβ-globin (ABI Biosystems) using murine α-globin for normalization. FACS analysis following intracellular staining for hβ-globin was done as described before.

Example 32

Materials and Methods—Chromatin Immunoprecipitation (ChIP)

ChIP analysis was performed on MEL clones as described with minor modifications. Briefly, DNA samples from input and antibody-bound chromatin fraction were analyzed by qPCR using SYBR green (Applied Biosystems) using primer sets in triplicate, and data analyzed as previously described. The enrichment ratio was determined by calculating the ratio of DNA-ChIP to DNA-input and histone modification data normalized to the "no antibody" (IgG) control and primers corresponding to the necdin 5' region and promoter region, as controls for repressed chromatin, to normalize the efficiency of immunoprecipitation. All the DNA-ChIP to DNA-input ratios were calculated as: 2[Ct (Input)−Ct (ChIP)] divided with [dilution rate (ChIP)/dilution rate (Input)]. Ct values of all PCR products were determined by the SDS 1.2 software (Applied Biosystems). Mean and SEM values were determined for the fold difference, and two-tailed paired t tests to determine statistical significance ($p<0.05$).

Example 33

Materials and Methods-Integration Site Analysis

Ligation-mediated (LM) polymerase chain reaction was performed as described by Modlich et al to map integration sites using primers and conditions described (Arumugam, Mol Ther 2009, in press citation).

Example 34

Materials and Methods-Statistical Analysis

Vectors were compared to the sBG vector Student's 't" test (unpaired and two tailed). ANOVA (Dunnett multiple comparison test) was also performed between groups for multiple comparisons. Data was expressed as mean±SEM. $P<0.05$ was considered significant.

Example 35

Self-Inactivating Lentiviruses Flanked by the 1.2 Kb Chicken Hypersensitive Site-4 Insulator Element (cHS4) Provide Consistent, Improved Expression of Transgenes, but have Significantly Lower Titers Self-inactivating lentiviruses flanked by the 1.2 Kb chicken hypersensitive site-4 insulator element (cHS4) provide consistent, improved expression of transgenes, but have significantly lower titers. Lengthening the lentivirus transgene cassette by an additional 1.2 Kb by an internal cassette caused no further reduction in titers. However, when cHS4 sequences or inert DNA spacers of increasing size were placed in the 3'LTR, infectious titers decreased proportional to the length of the insert. The stage of vector life-cycle affected by vectors carrying the large cHS4 3'LTR insert was compared to a control vector: There was no increase in read-through transcription with insertion of the 1.2 Kb cHS4 in the 3'LTR. Equal amount of full-length viral mRNA was produced in packaging cells and viral assembly/packaging was unaffected, resulting in comparable amounts of intact virus particles produced by either vectors. However, lentiviruses carrying cHS4 in the 3'LTR were inefficiently processed following target-cell entry, with reduced reverse transcription and integration efficiency, and hence lower transduction titers. Therefore, vectors with large insertions in the 3'LTR are transcribed and packaged efficiently, but the LTR insert hinders viral-RNA processing and transduction of target cells. These studies have important implications in design of integrating vectors.

Example 36

Increased Length of the Vector Genome by 1.2 Kb does not Affect Viral Titers

One objective of the study was to determine if reduction in titers by cHS4 was secondary to additional lengthening of the viral genomes in the otherwise large hp-LCR (BG) lentivirus vector. Large viral RNA genomes are known to be packaged less efficiently in integrating vectors. Replication competent gamma-retroviruses delete added sequences and recombine to revert back to their original viral size. In gamma-retrovirus vectors that exceed the natural size of the virus, reduction in titers occurs at multiple steps of the viral life cycle—generation of full length genome, viral encapsidation/release and post-entry recombination events. Notably, BG lentiviruses contain transgene inserts of ~7 Kb, and therefore do not produce viral-RNA genomes larger than the natural size/packaging capacity of the wild type HIV-1 virus. In lentivirus vectors, however, lowering of viral titers from transgene inserts 6 Kb or larger has been shown to occur from reduced packaging efficiency.

Uninsulated vectors BG and BGM were recently compared with analogous insulated vectors BG-I and BGM-I for position effects. The BG lentivirus vector carries the hβ and LCR, while a similar vector BGM additionally carries a PGK promoter driven methylguanine methyl transferase (P140K) cDNA (PGK-MGMT) insert downstream of the hp-LCR. The PGK-MGMT cassette is 1.2 Kb in size. The BG-I and BGM-I vectors carry the 1.2 Kb cHS4 insulator in the 3'LTR in addition. Virus was produced and processed identically from all four vectors and infectious titers were determined, as previously described. The titers of the concentrated BG vector were $2\pm0.5\times10^8$ IU/mL, while that of BGM, carrying an additional 1.2 Kb internal cassette were slightly higher at $5\pm0.8\times10^8$ IU/mL (n=4). In contrast, addition of the 1.2 Kb cHS4 in the 3'LTR to the BG vector, termed BG-I resulted in reduction in titers by nearly 6-fold to $3.8\pm0.8\times10^7$ IU/mL. A further addition of a 1.2 Kb PGK-MGMT internal cassette to the BG-I vector, termed BGM-I, did not reduce the titers any further (FIG. 20B). These data indicate that cHS4 insertion into the LTR, and not overall viral genome size reduced viral titers. Ramezani et al observed a 3-fold reduction in lentivirus titers when the 1.2 Kb cHS4 was inserted in lentivirus vectors encoding relatively small transgene expression cassettes (2 Kb in size or less). The present data is consistent with their results, although indicating a 6-10 fold reduction in titers with the addition of cHS4. It was additionally observed in the present study that reduction in titers by insertion of insulator elements in the LTR occurred by a distinct mechanism that was not dependent on the increased size of the viral genome.

Example 37

The Size of the Insert in the 3'LTR is Responsible for Reduction in Titers

Although the LV vectors used did not exceed the natural size of the HIV-1 virus, the size of the cHS4 insert (1.2 Kb) exceeded the natural size of the wild type LTR (note that the wt LTR carries an additional 400 bp U3 enhancer, which is deleted from the self-inactivating 3'LTR). Experimentation was conducted to determine whether lowering of viral titers was due to lengthening of the SIN LTR beyond its natural capacity (400 bp), or whether titers were lower due to specific sequences in the insulator, which may potentially affect viral-RNA folding/binding to cellular proteins and thus limit packaging. A series of p-globin vectors were constructed in a self-inactivating lentivirus backbone, sSIN, carrying different length fragments of cHS4 in the 3'LTR (FIG. 15A): the first 250 bp of the insulator, also called the core, a 400 bp cHS4 fragment, matching the size of the U3 promoter/enhancer deletion in the 3' SIN LTR, and a 800 bp cHS4 fragment, to generate $sBG^{C}$, $sBG^{400}$, $sBG^{800}$ vectors, respectively. These vectors were compared to an analogous 'uninsulated' vector, sBG, and a vector carrying the full-length 1.2 Kb insulator, sBG-I. In addition, a vector was cloned with two copies of the core as tandem repeats (250 bp×2), $sBG^{2C}$. The cHS4 core has been shown to have 50% of enhancer blocking activity of the full length (1.2 Kb) insulator; the effect of the core has been shown to be copy number-dependent, with tandem repeats of cHS4 core reported to have the same insulating capacity as the full length 1.2 Kb cHS4.

Virus was generated from sBG, $sBG^{C}$, $sBG^{400}$, $sBG^{2C}$, $sBG^{800}$, sBG-I plasmids by concurrent transient transfections and concentration, and titered by flow cytometry of mouse erythroleukemia (MEL) cells infected with serial dilutions of the viruses, as described. MEL cells support adult type globin production. Each experiment was replicated four times.

It was determined that as the size of the cHS4 insert in the 3'LTR increased, viral titers dropped (FIG. 15B). There was a slight, but statistically significant reduction in titers with inserts of 250 bp and 400 bp. However, titers fell sharply thereafter, proportional to the length of the insulator fragment (FIG. 15B). The titers of the vector with a 1.2 Kb full-length cHS4 insulator, sBG-I were an order of magnitude lower than the uninsulated control vector, sBG. Of note, $sBG^{2C}$ vector, with a tandem repeat of two cHS4 core sequences (500 bp insert) had titers similar to $sBG^{800}$.

To ensure that reduction in titers was not from specific cHS4 sequences but an effect of the size of the LTR insert, three additional vectors were constructed, $sBG^{400\text{-}S}$, $sBG^{800\text{-}S}$ and $sBG^{1200\text{-}S}$. These vectors were analogous to $sBG^{400}$, $sBG^{800}$ and sBG-I, except that they contained spacer elements from the λ phage DNA downstream of the cHS4 core to generate 3' LTR inserts of 400 bp, 800 bp and 1.2 Kb, respectively (FIG. 15A). The core cHS4 sequences were retained as the reduction in titers was minimal (and not observed in initial experiments) with the core; and it was important to determine if additional sequences downstream of the core are necessary for optimal insulator activity. The titers of the vectors containing DNA spacers were identical to those containing similar sized cHS4 fragments, and decreased with increasing size of the fragment in the 3'LTR (FIG. 15D). These data show that lengthening of the 3' LTR lowered titers and this effect was not from specific sequences in cHS4. It has been reported that HIV-1 RT is not a strongly processive polymerase; it dissociates from its template frequently and the viral DNA is synthesized in relatively short segments. Therefore, it is likely that as the size of insert in the U3 LTR increased, there was reduced processivity through the 3' LTR.

Example 38

Recombination Occur with Repeat Elements in the 3'LTR

In order to detect if recombination events occurred in the LTRs from insertion of 2 copies of the core or different size fragments in the LTR, ~12-20 MEL cell clones transduced with the entire series of insulated vectors ($sBG^{C}$, $sBG^{400}$, $sBG^{2C}$, $sBG^{800}$ and sBG-I) were generated. All clones that had a single copy of integrated provirus were identified using qPCR, as previously described. The 250 bp core from the genomic DNA of each clone was then amplified, by a standard PCR. The insulator core sequences could be amplified from clones derived from all vectors except those derived from $sBG^{2C}$ transduced cells. In $sBG^{2C}$ MEL clones, the insulator core was undetectable in 6 of 24 (25%) single copy clones by PCR, suggesting deletion of both tandem repeats of cHS4 core sequences in the 5' and 3' LTR of the provirus (FIG. 20D). To further analyze the frequency of recombined proviruses, a genomic Southern blot analysis on $sBG^{2C}$ transduced MEL cell pools was performed. Genomic DNA from $sBG^{2C}$ and sBG-I MEL cell populations was restricted with an enzyme that cut within the LTRs. FIG. 15E shows the expected lengths of the provirus with the $sBG^{2C}$ vector and the sBG-I vector, used as a control. While a single proviral band was seen in sBG-I transduced MEL cells, the $sBG^{2C}$ provirus in MEL cells showed loss of one or both copies of the cHS4 core sequences. Indeed, proviral bands containing two intact copies of the core were not detected at the level of sensitivity of Southern blot analysis. These data show that tandem repeats in $sBG^{2C}$ recombined at a high frequency. The $sBG^{2C}$ vector, therefore, had lower viral titers from recombination events during reverse transcription, rather than the size of the LTR insert. These results were not unexpected, since repeat elements within gamma-retrovirus and lentivirus vectors have been shown to recombine frequently.

Example 39

Steps in Vector Life-Cycle Affected by Large Inserts into the 3'LTR

Large viral genomes in RNA vectors have been shown to be limited at the level of RNA packaging. In the present study, there was no effect on titers with increasing the virus payload by 1.2 Kb, but titers decreased with increasing length of the insert in the LTR. Next, the mechanism by which this affected viral titers was explored. The following steps in the viral life cycle were studied: 1) characteristics of viral-RNA produced in packaging cells, 2) virus particle production, 3) post-entry steps: reverse transcription, nuclear translocation, integration and proviral integrity. For all of these studies, the vector with the largest insert, sBG-I was compared to the vector without the insulator, sBG.

Example 40

Insertion of cHS4 in the 3'LTR does not Alter the Quantity or Quality of Viral-RNA in Packaging Cells Northern blot analysis was performed on RNA derived from the 293T packaging cells after transient transfection with sBG, sBG-I vector plasmids, along with packaging plasmids (D8.9 and VSV-G). The blot was probed with hp fragment. FIG. 16 shows similar intensity viral-RNA transcripts of the expected lengths of sBG and sBG-I vectors. The probe non-specifically probed the 28S and 18S RNA. Nevertheless, there were no additional bands other than the full length-viral RNA of expected length, suggesting that no recombination or aberrant splicing occurred with insertion of the insulator. Thus, viral-RNA was produced efficiently in packaging cells, independent of the presence of an insert in the LTR.

Example 41

Insertion of cHS4 in the 3'LTR does not Increase Read-Through Transcription

Experimentation was conducted to determine if the cHS4 insert upstream of the viral polyadenylation signal in the LTR could impair transcript termination of the viral RNA. Read-through transcripts have been shown to be excluded from encapsidation, and can lower viral titers. Although the northern blot in FIG. 16 showed the expected size viral-RNA band and no extraneous transcripts, it has been shown that transcriptional read-through is much less in lentivirus vectors, as compared to gamma-retrovirus vectors, that may not be readily detectable via a northern blot. Therefore a sensitive enzyme based assay was used to study read-through transcription.

Plasmid constructs were cloned, in which the wild type HIV-1 LTR, the SIN HIV-1 3'LTR with or without the insulator (from sBG-I or sBG vectors, respectively) were placed downstream of EF1-α promoter. A promoter-less IRES-cre cassette was placed downstream of the LTRs, so that cre expression would occur only from transcriptional read-through from the LTR. An EF1α-IRES-cre plasmid served as a positive control. Equal amounts of these plasmids were transfected into the reporter cell line, TE26, which expresses β-galactosidase proportional to cre expression. A GFP plasmid was co-transfected with the read-through plasmid constructs to normalize β-galactosidase activity for transfection efficiency. A plasmid carrying the truncated rat nerve growth factor receptor served as a negative control. A standard curve was generated that showed a linear correlation of the amount of the positive control IRES-cre plasmid transfected into cells and the β-galactosidase activity measured by spectrophotometer. No significant increase was observed in β-galactosidase activity from transfected constructs containing the insulated SIN lentivirus LTR, as compared to those carrying the SIN LTR without the cHS4 insulator. The results from the β-galactosidase assay were identical when confirmed by Lac-Z staining of TE26 cells plated on cover slips. These results showed that the insertion of cHS4 element upstream of the viral polyadenylation signal did not increase read-through transcription from the LTR.

Example 42

Production of Viral Particles Containing Viral Genomes is not Affected by cHS4

To determine whether viral-RNA was encapsidated effectively into virions, p24 levels, virus associated reverse transcriptase (RT) activity and viral-RNA levels (FIGS. 17A-17C) were measured. Virus was generated in an identical manner concurrently with the two vectors, and concentrated similarly in three separate experiments. To ensure purity of the viral preparation and lack of protein or plasmid contamination, virus was pelleted on a sucrose cushion and subjected to DNAse digestion for these experiments. Lack of plasmid contamination was confirmed by a qPCR for the ampicillin resistance gene, present in the plasmid backbone. The same volumes of virus preparation were then subjected to p24 ELISA and virus-associated RT assays; and viral-RNA was extracted for a dot-blot analysis. FIG. 17A shows that there was no difference in the amount virus-associated RT between the two vectors. The p24 levels in the sBG and sBG-I virus preparations were also similar (FIG. 17B). In order to ensure sBG-I virions contained viral genomes, and were not empty viral like particles; virus was subjected to RNA dot-blot analysis. FIGS. 17C-17D show one of two representative experiments. Viral RNA from sBG and sBG-I was loaded in duplicate in 4 different dilutions of p24 (FIG. 17C); and the intensity of the dots quantified by phosphoimager (FIG. 17D). There were similar amount of viral mRNA encapsidated from either vector. These data suggest that insertion of a 1.2 Kb fragment in the LTR did not affect packaging efficiency of viral mRNA or production of viral particles.

The present results with large inserts into the LTR are in contrast to those by Sutton and colleagues where lentivirus vectors with lengthened internal transgene cassettes are inefficiently packaged into virions. Equal amounts of virus particles produced from the sBG and sBG-I vectors, but significantly lower infectious/transduction titers suggests a post-entry block of large LTR insert bearing viruses, resulting in less integrated units.

Example 43

Large LTR Inserts Affect Reverse Transcription and Integration of Viral cDNA

Post-entry steps were investigated; including reverse transcription, nuclear translocation, integration and proviral integrity. Reverse Transcription: the steps of reverse transcription, location of qPCR primers and probes and the viral DNA products are summarized in FIG. 18A. Reverse transcription initiates from the primer binding site near the 5' end of the genomic RNA, and minus strand synthesis proceeds to the 5' end of the genome (minus strand strong stop DNA (−sssDNA)). The newly formed −sssDNA anneals to the 3'R region of the genome (first strand transfer), minus-strand DNA synthesis resumes, accompanied by RNase H digestion of the viral RNA template. It has been shown that the secondary structure of viral RNA at the 3' end is a critical determinant for the −sssDNA transfer, for the reverse transcription process to be efficient. Therefore, it is likely that presence of the insulator/an insert in the U3 region of the 3' LTR would alter the secondary structure of the region involved in this complex process, resulting in overall decreased reverse transcription efficiency.

To assess reverse transcription efficiency, MEL cells were infected with equal amounts of sBG and sBG-I viral particles, based upon p24 levels, and cells collected at different time points post infection. Absence of plasmid contamination was confirmed by a qPCR for the ampicillin resistance gene present in the plasmid backbone (data not shown). Kinetics of early reverse transcription (production of −sssDNA) were studied using primers and probe spanning the R/U5 region (FIG. 18B). As expected, there was no difference detected in the kinetics between the two viruses, since the 5' ends of sBG or sBG-I viral RNA were identical. Nevertheless, the data validated that qPCR accurately determined viral reverse transcription.

It is conceivable, however, that when RT switches templates (minus strand jump) to reverse transcribe the 3' LTR, alteration of secondary structure from the presence of an insert in the U3 region would reduce reverse transcription products. Quantitative PCRs amplifying the U3/R and ψ regions were performed to quantify the amount of intermediate and late reverse transcribed viral cDNA in cells infected with sBG and sBG-I vectors, respectively (FIGS. 18C-18D). It was discovered that RT efficiency soon after the first strand transfer was impaired. Notably, the U3/R primers amplified viral DNA that was reverse transcribed before the insulator sequences, suggesting that insert in the 3'LTR affected reverse transcription by altering or "poisoning" the 3'LTR. Indeed, the inefficiency in intermediate RT product formation was similar to that seen with late RT products. In both analysis, the peak of viral cDNA synthesis occurred at 12 h for the uninsulated vector sBG and then gradually decreased, consistent with integration of viral cDNA, and previously reported kinetics of reverse transcription. The amount of viral DNA from the insulated vector sBG-I was lower post-entry compared to sBG by about 2-fold at all time points, as early as 6 hours post-target cell entry. These data strongly suggest that reverse transcription after the minus strand jump was rate-limiting in the sBG-I vector.

Nuclear translocation: After the viral DNA is synthesized in the cytoplasm, it is translocated into the nucleus of infected cells, where it can be found as linear DNA or circular DNA (1-LTR and 2-LTR circles) (FIG. 18A). The linear form is circularized at the LTRs and is the direct precursor of the integration process; 1-LTR and 2-LTR circles, instead, are abortive products of homologous recombination and non-homologous DNA end joining, respectively. However, 1LTR and 2LTR circles are specifically localized in the nucleus, and are used as a marker for nuclear translocation. Presence of an insert in the LTR of lentiviruses can possibly interfere with the pre-integration complex (PIC) formation and the nuclear translocation of the viral DNA can lower transduction titers. It has been shown indeed that PIC complexes bind HIV LTR in the cytoplasm, and they are responsible for the transport to the nucleus and the integration of the cDNA into the genome of infected cells.

In order to detect the nuclear translocation, the amount of 2-LTR circles in both vectors were analyzed using a qPCR on DNA from infected MEL cells at different time points in sBG versus sBG-I infected cells. As shown in FIG. 19A, the amounts of 2-LTR circles were not significantly different between the two vectors at early time points. However, at 48 h after infection, the peak at which 2-LTR circles are normally detected, 2-LTR circles were 6.7 times higher in sBG infected cells, but were barely at the detection limit in sBG-I infected cells. Later time points (72 and 96 hours) were also analyzed, but no delay was determined in the kinetics of 2LTR circle formation in the insulated vectors. Indeed, the 2-LTR circles were barely detectable by qPCR in the sBG-I infected cells after 24 hours. These data suggested that nuclear translocation was likely reduced due to presence of the large U3 insert.

Integration: It is also conceivable, however, that two copies of large U3 inserts provide a template for homologous recombination, and the rate of homologous recombination between the two LTRs prior to integration increases, resulting in more 1-LTR circles and reduced 2-LTR circles (as proposed in the cartoon in FIGS. 20A-20E). This would decrease the amount of template available for integration. Due to the nature of reverse transcribed viral cDNA with an insulated and uninsulated vector, 1LTR circles cannot be quantified by a PCR-based technique. Therefore, a Southern blot analysis was performed to detect linear viral cDNA, 1-LTR and 2-LTR circles at 72 hours post infection with equal amounts of sBG and sBG-I (quantified using p24 levels) (FIG. 19B). The Southern blot analysis showed that (i) the linear form of reverse transcribed viral cDNA, the form that integrates, was undetectable in the sBG-I lane at the sensitivity of Southern blot analysis, while it was readily detectable in the sBG lane. (ii) The 2-LTR circles were also undetectable in the Southern analysis in the sBG-I lane, but detectable in the sBG lane, corroborating the qPCR data on 2-LTR circles. (iii) However, large amount of 1-LTR circles were present in sBG-I lane, similar in amount to those seen in the sBG lane. The relative ratios of linear, 1- and 2-LTR circles in sBG versus sBG-I lanes suggested that there was increased homologous recombination of the sBG-I viral DNA. Indeed, these data indicated that nuclear translocation was not affected to any major extent by the U3 insert. But after the reverse transcribed cDNA entered the nucleus, increased 1-LTR circles, representing abortive recombinant integration products were formed due to the large LTR insert and therefore, integration was reduced.

It is conceivable that the integration machinery is also directly affected by the presence of foreign sequences in the LTR. Therefore, sBG and sBG-I viruses were packaged using an integrase defective packaging plasmid, so that effect of the insulator on reverse transcription, nuclear localization, and 1LTR circle formation could be studied independent of integration. The same analysis was performed as with active integrase containing viruses: a q-PCR to study the late reverse transcription product (using psi primers), 2LTR circles and a genomic Southern blot analysis to determine 1LTR circles and other forms of viral cDNA. The results were identical to those seen with sBG and sBG-I packaged with active integrase (shown in FIG. 19B): the same reduction was observed in late RT products and 2LTR circles by qPCR, but increased 1LTR circles by genomic Southern analysis (data not shown). Therefore, sequences inserted into the lentivirus LTR interfered mainly with the reverse transcription process, and increased the frequency of homologous recombination by a mechanism independent of the integrase machinery.

Finally, the integrated sBG and sBG-I provirus were analyzed for stability of transmission and efficiency of integration. The Southern blot analysis in FIG. 19B shows the integrated DNA as a smear, that is of higher intensity in the sBG than the sBG-I lane. In order to confirm and quantify integration, MEL cells were transduced with same amount of p24 levels of sBG or sBG-I virus, cultured for 21 days and a qPCR and Southern blot analysis were performed to compare proviral integration efficiency and stability (FIG. 19C). There were 6.2 proviral copies per cell in sBG MEL cell population by qPCR, while only 0.8 proviral copies were detected in sBG-I MEL cells, a 7.8-fold difference which is consistent with differences seen in transduction titers between the two vectors. Next, DNA was restricted with Afl-II, an enzyme that cuts within the LTRs (FIG. 19C, left panel). Consistent with transduction titers and qPCR, the amount of integrated sBG-I provirus was 8-fold less than sBG, as indicated by phosphoimager quantification of the Southern blot bands (FIG. 19C). The sBG-I vector did not recombine, as shown by the single proviral band of the expected size. Next, the full length insulator was detected by PCR in all single copy clones of sBG-I transduced MEL cells (FIG. 20D). Therefore, the linear sBG-I cDNA, albeit inefficiently formed, integrated as an intact provirus.

The overall reduced viral integration was primarily from a combination of inefficient reverse transcription and increased homologous recombination that hinder the availability of proviral DNA for integration. Since insulators are important for generating viral vectors that would be safe and provide consistent predictable expression, it is important to find a solution to the problem of low viral titers with insulated viruses. One way to overcome the problem would be to flank the internal expression cassette with cHS4 on either end, since further lengthening of the internal cassette did not decrease titers. However, this approach was not tried because repeat elements within retroviruses are known to result in recombination. Since HIV RT is known to have low processivity and frequently dissociate from its template, an attempt was made to increase the amount of RT delivered per vector particle, to assess if that would improve reverse transcription from large LTR inserts. RT was co-packaged in the virions as vpr-RT fusion protein. No significant increase in titers was observed when providing more RT in the virion. The next step was an attempt to increase the integrase (IN) per virion using the same strategy, and copackaged RT-IN-vpr fusion protein in the virion. There was a slight increase in titers providing RT-IN in the viral particle, but the difference was not significant.

Next, a detailed structure-function analysis of the 1.2 Kb cHS4 insulator was performed and a defined 650 bp sequences were determined as the minimum necessary sequences for full insulation effect. The titers of $sBG^{650}$ were $3.6\times10^8$ IU/mL, compared to a titer of $8.2\times10^8$ IU/mL and $9.8\times10^7$ IU/mL of the sBG and sBG-I vectors (FIG. 20C). Vectors with the 650 bp insert had very reasonable viral titers (2.2-fold lower titers than the uninsulated vector sBG, as compared to 9-10-fold lower titers of sBG-I) with no loss of insulator activity.

Ultimately it was determined that low transduction titers were not from an increase in size of the provirus, but increased length of the 3'LTR. The quantity and quality of viral RNA genomes produced were unaffected and viral-RNA encapsidation/packaging was comparable in vectors with and without a 1.2 Kb LTR insert. Reduced viral titers occurred from post-entry steps, from inefficient reverse transcription, increased homologous recombination in the LTRs of viral DNA, making less viral DNA available for integration. Improvements in vector design were made by including smaller insulator inserts that contained essential elements necessary for optimal insulator activity.

The present studies have important implications for future design of vectors with inserts within the 3'LTR, given the usefulness of chromatin insulator elements, customized lineage specific LTR vectors or double copy vectors.

Example 44

Vector Constructs

The cloning of the BG, BGM, BG-I and BGM-I vectors has been previously described. All other vectors were cloned into the sSIN backbone (details provided in Urbinati F, Xia P and Malik P, manuscript in review). All the vectors were obtained cloning the different insulator fragments into a unique Nhe I/EcoR V site was inserted in the U3 3'LTR region of the sSIN LV vector plasmid, which carried the human beta-globin gene and the hypersensitive site 2, 3 and 4 fragments, as previously described. Insulator fragments were amplified by PCR using the insulator plasmid pJCI3-1 as a template. All amplicons were sequenced following the PCR, and after insertion into the 3'LTR. The cloning of the uninsulated beta-globin vector and one that carrying the full length 1.2 Kb cHS4 insulator has been described previously. Briefly, the 1.2 Kb insulator fragment was obtained by digesting pJCI3-1 plasmid with Xba I and cloned into the Nhe I/EcoR V restriction site of sBG. $sBG^{C}$ was cloned inserting into sBG vector the fragment EcoR I/Xba I containing the 250 bp core from the pBS 1core plasmid. The latter was obtained cloning the 250 bp core Insulator PCR product (using Core 1F and Core 1R primers, as described herein) into BamH I/EcoR I restriction sites of a pBS plasmid. A second copy of the 250 bp core was then added into the pBS 1 core plasmid, cloning into EcoR I/Kpn I sites the PCR product (Core 2F and Core 2R), obtaining the pBS 2 core plasmid. 2 tandem copies of the 250 bp core were then isolated digesting the latter plasmid with Kpn I/Xba I, and then cloned into the sBG vector, obtaining $sBG^{2C}$. The $sBG^{400}$ and $sBG^{800}$ vectors were obtained cloning the 2 PCR products (using InsF and Ins400R primers and InsF and Ins800R primers, respectively) into the sBG Nhe I/EcoR V sites. $sBG^{650}$ vector was obtained cloning the 3' 400 fragment of the insulator in EcoRV/BspEI sites of $sBG^{1c}$ vector. The 3' 400 fragment was PCR amplified from the plasmid pJCI3-1 using the following primers: 3' 400 R (BspEI) and 3' 400 F (EcoRV).

The vectors containing the λ DNA spacers were obtained amplifying different size λ phage DNA using the following primer combinations: spacerF1 and spacerR1, spacerF1 and spacerR2 and spacerF1 and spacerR3 amplifying a 150 bp, 550 bp and 950 bp λ DNA fragments, respectively. The three PCR fragments were digested with Cla I and EcoR I restriction enzymes and ligated into EcoR I/Cla I sites in the pBS-1 core plasmid, The 400 bp, 800 bp and 1200 bp fragments were digested from the pBS-1 core plasmid with HincII and XbaI for the 400 bp fragment, and with Xba I and Xho I for the remaining two fragments, and cloned into the EcoR V/Nhe I restriction sites in the sBG vector. All the vectors cloned were confirmed by sequencing. The list of all the primers is available in (FIG. 20E).

Example 45

Cell Lines

Murine erythroleukemia cell (MEL) line and 293T cells were maintained in Dulbecco modified Eagle Medium (DMEM, Mediatech, Inc) supplemented with 10% heat inactivated fetal bovine serum (FBS) (U.S. Bio-technologies, Inc.). MEL cells were induced to differentiate in DMEM containing 20% FBS and 5 mM N, N'-hexamethylene bisacetamide (Sigma), as previously described. To derive single integrant clones, transduced MEL cells were cloned and clones were screened for β-globin sequences by PCR to identify transduced clones. Single copy clones were identified by qPCR for lentivirus y-sequences, and a PCR for the cHS4 core sequences was performed on the single integrant clones to confirm presence of insulator sequences in the provirus.

Example 46

HbA Staining and FACS Analysis

The staining using the anti-human HbA antibody was as previously described. Briefly, cells were fixed in 4% paraformaldehyde for 60 minutes at room temperature, washed once with phosphate-buffered saline (PBS), and the pellet resuspended in 100% methanol for 5 minutes. The fixed cells were then washed with PBS, and nonspecific antibody (Ab) binding was blocked using 5% nonfat dry milk for 10 minutes at room temperature. Subsequently, cells were washed in PBS, pelleted, and permeabilized. The cells were divided into 2 tubes and stained with either anti-Zeta globin-fluorescein isothiocyanate (FITC) (1 μg/$10^6$ cells) as a negative control or anti-HbA-FITC (0.1 μg/$10^6$ cells) (Perkin Elmer) for 30 minutes at room temperature in the dark. Unbound Ab was removed by a final wash with PBS before they were analyzed on FACS Calibur (Becton Dickinson).

Example 47

Virus Production

Virus was produced by transient cotransfection of 293T cells, as previously described, using the vector plasmids, the packaging (Δ8.9 or Δ8.2 for active or inactive integrase respectively) and the VSV-G envelope plasmids; virus-containing supernatant was collected at 60 hours after transfection and concentrated by ultracentrifugation. All vectors in an experiment were packaged simultaneously. Virus was treated with DNase and/or DpnI to remove plasmid DNA contamination and layered on a 20% sucrose cushion to obtain purified viral particles for specific experiments on vector life cycle indicated in the results. Virus was concentrated 1400-fold from all viral supernatants after ultracentrifugation at 25,000 rpm for 90 minutes. Viral titers were determined by infecting mouse erythroleukemia (MEL) cells with serial dilutions of concentrated virus, differentiating them, and analyzing them for HbA expression by fluorescence-activated cell-sorter scanner (FACS).

Example 48

Northern Blot

Total RNA was extracted from 293T cells using RNA-STAT (Tel-Test, INC, Texas), 72 hours after transfection. Northern Blot was then performed according to standard protocol. The blot was hybridized with a $^{32}$-P labeled β-globin probe.

Example 49

RNA Dot Blot

Viral-RNA was extracted from same volumes of concentrated viruses using the QIAamp Viral RNA Mini Kit (Qiagen, Valencia, Calif.) following the manufacturer's instructions. Briefly the virus was lysed under a highly denaturing condition and then bound to a silica-gel-based membrane. Two washing steps efficiently washed away contaminants and v-RNA was eluted in 30 μl of DEPC-H2O. After elution viral-RNA was treated for 20 min. at room temperature with amplification grade DNAse I (Invitrogen). DNase was inactivated incubating the sample at 650. Viral RNA was then denatured in 3 volumes of denaturation buffer (65% formamide, 8% formaldehyde, MOPS IX) for 15 min at 65°. After denaturation 2 volumes of ice-cold 20×SSC were added and the RNA was bound to a nylon membrane by aspiration through a dot-blot apparatus. The blot was hybridized with a $^{32}$-P labeled β-globin specific probe and a film was exposed overnight. Quantification of the dots was performed with a phosphoimager (Biorad, Hercules, Calif.).

Example 50

Reverse Transcriptase Assay

Concentrated virus (1 μL), and serial dilutions (1:10, 1;100, 1:1000) were lysed and processed following the "Reverse transcriptase (RT) assay, colorimetric" Kit (Roche) protocol. Briefly concentrated viral particles were lysed with lysis buffer and viral-RNA reverse transcribed using digoxigenin and biotin-labeled nucleotides. The detection and quantification of synthesized DNA as a parameter of RT activity followed a sandwich ELISA protocol: biotin-labeled DNA was bound to the surface of microplate modules that were pre-coated with streptavidin. In the next step, an antibody to digoxigenin, conjugated to peroxidase (anti-DIG-POD), was bound to the digoxigenin-labeled DNA. In the final step, the peroxidase substrate ABTS was added, that resulted in a colored reaction product that was quantified using an ELISA reader at a wavelength of 405 nm. The amount of colored product directly correlated to the level of RT activity in the sample.

Example 51

P24 Assay

P24 antigen concentration was determined by HIV-1 p24 Antigen EIA Kit (Beckman Coulter). Briefly, serially diluted virus was lysed and incubated onto p24 antigen coated microwells, and washed following manufacturer's protocol. Color absorbance was measured using a spectrophotometer at a wavelength of 450 nm. p24 assay was performed in duplicate.

Example 52

Southern Blot

To analyze the integrity of the provirus we infected MEL cells, expanded them for 21 days and extracted DNA using Qiagen Blood and Cell culture DNA Mini Kit (Qiagen). 10 g of DNA was digested with Afl II, an enzyme that cuts in the LTRs. To determine presence of viral linear DNA, genomic DNA was extracted 72 h after infection of MEL cells and restricted with Stu I, an enzyme that cuts twice within the provirus. The DNA was separated on a 0.8% agarose gel, transfer to a nylon membrane, and probed overnight with a β-globin fragment.

Example 53

Real Time PCR for RT Products and 2LTR Circle

The same amount of p24 was used to transduce MEL cells with sBG and sBG-I vectors, in DMEM media, in the presence of 8 μg/mL polybrene. Cells were harvested at different time point (0.5 h, 3 h, 6 h, 8 h, 12 h, 24 h, 48 h, 72 h) and DNA extracted using Qiagen Blood and Cell culture DNA Mini Kit (Qiagen). Genomic DNA (50 ng) from a single copy MEL clone (confirmed by Southern for a single integrant) was diluted with untransduced DNA to generate copy number standards (1-0.016 copies/cell). The primers and the probe for RT product were designed using the Primer Express Software from Applied Biosystems, Foster City, Calif. Primers and probe sequence for early RT products (R/U5) qPCR assay are: forward primer 5'-GAACCCACTGCTTAAGCCTCAA-3', reverse primer: 5'-ACAGACGGGCACACACTACTTG-3' The reaction was carried out with TaqMan MGB Probe: 5'-AAAGCTTGCCTTGAGTGC-3'. Primers and probe sequence for intermediate RT products (U3/R) qPCR assay are: forward primer 5'-CCCAGGCTCAGATCTGGTCTAA-3', reverse primer: 5'-TGTGAAATTTGTGATGCTATTGCTT-3' The reaction was carried out with TaqMan MGB Probe: 5'-AGACCCAGTACAAGCAAAAAGCAGACCGG-3'. For the late RT product assay (psi) the primers were designed to recognize the ψ region of the provirus: forward primer: 5'-ACCTGAAAGCGAAAGGCAAAC-3', reverse primer: 5'-AGAAGGAGAGAGATGGGTGCG-3'. The reaction was carried out with TaqMan Probe: 5'-AGCTCTCTCGACGCAGGACTCGGC-3' with TAMRA dye as quencher. Normalization for loading was carried out using mouse apoB gene controls. The cycling conditions were 2 min at 50° C. and 10 min at 95° C., then 40 cycles of 95° C. for 15 s and 60° C. for 1 min. The primers and probe for 2LTR circle were as previously described. The PCR mixture was thermo cycled according to the thermal cycler protocol for 96 well plates in Applied Biosystems 7900HT Fast Real-Time PCR System Base Unit.

Example 54

Generally

Sickle cell anemia (SCA) results from a point mutation in the-globin gene ($\beta^S$), resulting in sickle hemoglobin (HbS). HbS polymerizes upon deoxygenation resulting in sickle-shaped RBCs that occlude microvasculature. Patients with SCA have intermittent acute vascular occlusions and cumulative organ damage, reducing the life span to 42 to 58.5 years. Besides sickling, excessive hemolysis and a state of chronic inflammation exist. SCA patients account for approximately 75,000 hospitalizations per year, resulting in an estimated annual expenditure of $1.2 billion dollars in the United States alone. Worldwide, SCA is second only to thalassemia in incidence of monogenic disorders, with more than 200,000 children born annually in Africa.

Current therapies include supportive care for episodic sickling, chronic transfusions with iron chelation, and hydroxyurea to induce fetal hemoglobin (HbF). These therapies impact disease morbidity, but their effectiveness is variable and dependent on compliance to an indefinite treatment regimen. A matched allogeneic hematopoietic stem cell (HSC) transplantation is curative, but restricted by the availability of matched related donors5 and has potential serious complications. A meta-analysis of 187 SCA transplantations shows 6% to 7% conditioning-related peritransplantation mortality, 7% to 10% acute rejection, and 13% to 20% chronic graft-versus host disease (GVHD) in recipients.

Gene therapy of autologous HSCs followed by transplantation could result in a one-time cure, avoid adverse immunologic consequences, and not be limited by availability of donors; it may also not require myeloablative-conditioning regimens, and thereby have lower toxicity. The amount of HbF/anti-sickling globin required to correct SCA via a transgene is unknown.

Expression of HbF postnatally can be therapeutic, as is evident by the protective effect of HbF in neonatal sickle RBCs and in patients with hereditary persistence of HbF and SCA. The proportion of genetically corrected HSCs, the amount of exogenously expressed HbF, and the proportion of F cells that will correct the pathophysiology are unknown. Complete correction of human thalassemia major in vitro, and in xenografted mice in vivo, with a lentivirus vector carrying the β-globin gene and locus control region (LCR) elements has been demonstrated. In this report, this β-globin lentivirus vector was modified to encode γ-globin exons and murine sickle HSCs were transduced. Functional correction was characterized first, with a careful and detailed quantification of RBC sickling, half-life, and deformability, with sickle to normal transplantations and high HbF production to define parameters of correction. Next, using reduced-intensity conditioning and varying the percentage of transduced HSCs, transplantations were performed on sickle mice with significant organ damage and demonstrate the proportions of (1) genetically corrected HSCs, (2) HbF, and (3) F cells, and (4) percentage of HbF/F cell required for correction of the sickle RBC and amelioration of organ damage in SCA.

Example 55

Vector

It has been demonstrated that a 3-γ-globin hybrid gene carrying lentivirus vector, 18H β/γW, 11 expresses high γ-globin mRNA in erythroid cells expressing "adultlike" globins. All β-globin coding sequences were changed to γ-globin using site-directed mutagenesis and the γ-β-globin hybrid gene, and LCR elements were cloned in reverse orientation to the viral transcriptional unit to generate $sG^bG$ lentivirus vector. Virus was made with cotransfection of 293T cells.

Example 56

Murine HSC Enrichment

Bone marrow from 6- to 20-week-old BERK sickle mice was harvested and lineage depleted with biotinylated CD5, CD8, B220, Mac-1, CD11b, Gr-1, and TER-119 antibodies and magnetic beads. The bead-free cells were stained with antibodies to Sca-1, c-kit. Cells that were $7\text{-AAD}^-$, $\text{Lineage}^-$, $\text{c-kit}^+$ then $\text{Sca-1}^+$ (LSK cells) were sorted on FACS-Vantage (BDBiosciences). All experiments using Berkeley transgenic sickle mice and C57/BL6 mice were performed according to protocols approved by the Cincinnati Children's Hospital Medical Center.

Example 57

Gene Transfer and Bone Marrow Transplantation

Myeloablative transplantations were performed from BERK3C57Bl/6 mice because of ease of transplantation and ready availability of normal recipients ($9.5^{+/-}0.6$ weeks old) after 11.75 Gy radiation. Radiation control experiments showed that BERK mice receiving 8 to 9 Gy radiation survived without receiving LSK cells; and the lethal dose was lower than in C57Bl/6 mice. BERK mice receiving more than 10.5 Gy died when no LSK cells were given; those given LSK rescue survived long term. BERK mice are difficult to breed in large numbers at a given time, therefore 2 mice/radiation dose level were to determine the sublethal dose. All BERK recipients ($12.9^{+/-}0.4$ weeks old) received 3 peritransplantation RBC transfusions (days 1-7). Organ pathology in BERK recipients 1 year after transplantation was compared with 12-week-old BERK mice that did not undergo transplantation. The radiation was higher than classical reduced intensity radiation dose of 4 Gy to allow a large degree of donor HSC chimerism. A range of MOI was used to vary the proportion of transduced donor HSCs in the graft. LSK cells were prestimulated overnight and transduced twice at an MOI of 30 for BERK3C57BL/6 transplants and MOI of 30 to 100 for BERK→BERK transplants for 22 to 24 hours; 10,000 to 24,000 LSK cells and untransduced LK cells were cotransplanted into recipient C57BL/6 or BERK mice.

Example 58

Copy Number Analysis

Copy number analysis was done on genomic DNA by real-time polymerase chain reaction using primers and probes described previously.

Example 59

Hematologic Analysis

Hematologic analysis was obtained on Hemavet 950FS (Drew Scientific) under mouse settings. Reticulocyte analysis was performed as follows: 0.1 μL blood and 200 μL BD Retic-COUNT Reagent were mixed (Becton Dickinson), incubated at room temperature for 30 minutes, and analyzed by fluorescence-activated cell sorting (FACS).

Example 60

Hemoglobin Analysis

Hemoglobin electrophoresis was performed on cellulose acetate plates, as described previously. Ion exchange high-performance liquid chromatography (HPLC) was performed with an Alliance 2690 HPLC machine (Waters) using a PolyCATAcolumn (item no. 3.54CT0510; Poly LC Inc).

Example 61

Red Blood Cell Functional Analysis

Irreversibly sickled cells (ISCs) were enumerated by scoring 500 RBCs in consecutive fields. Graded deoxygenation was performed using tonometry. RBC deformability was determined using a laser-assisted optical rotational cell analyzer (LORCA; RR Mechatronics).

Example 62

RBC Half-Life

Mice were injected with 3 mg Sulfo-NHS biotin (Sigma) in 300 μL PBS as 2 separate injections 1 hour apart; 2 to 5 μL blood was drawn at serial times, and stained with APC-Cy7-conjugated streptavidin.

Example 63

Histology

Spleen, liver, bones, brain, and kidney were harvested and placed in 5 mL of 10% formalin. Paraffin blocks were sectioned and stained with hematoxylin and eosin.

Example 64

High HbF after Gene Therapy and Myeloablative Transplantation Corrects SCA

The $sG^bG$ vector carries γ-globin exons and β-globin noncoding and regulatory regions. Based upon a previously studied sBG vector, which expresses high levels of human β-globin, 13 $sG^bG$-transduced LSK cells from Berkeley sickle (BERK) mice were transplanted into lethally irradiated (myeloablated) normal C57Bl/6J mice (termed $sG^bG$ mice). Mock transductions on BERK LSK cells from the same bone marrow pool followed by transplantation resulted in mice with SCA. The majority of RBCs in $sG^bG$ mice expressed HbF. Only $sG^bG$ mice with 100% donor ($HbS^+$) RBCs, with no evidence of residual recipient murine hemoglobin by electrophoresis and HPLC, were analyzed for hematologic, functional, and pathologic analysis. $sG^bG$ mice with a small proportion of recipient murine RBCs, were used only to assess HbF/vector copy and frequency of transduced HSCs. The percentage of HbF (HbF/HbS+HbF) in blood, quantified by FACS, was approximately 40% in primary mice followed for 6 months and in secondary recipients followed for 7.5 months (FIG. 21A). Two-thirds of RBCs were F cells; their proportion was also stable in primary and secondary recipients (FIG. 21B). The proportion of F cells and vector copies correlated with HbF (FIGS. 21C-21D). Taken together, these data show significant HbF expression from the $sG^bG$ vector in the majority of RBC with stable long-term expression.

Example 65

High Levels of HbF Result in Sustained Hematologic Correction

FIG. 21E shows improvement of hematologic parameters in $sG^bG$ mice. The proportion of reticulocytes decreased from approximately 50% in mock mice to approximately 15% in $sG^bG$ mice (P<0.005; FIG. 22A). There was correction of anemia by 12 weeks, which persisted throughout the posttransplantation period (FIGS. 22B-22C)}.

High white blood cell (WBC) counts in humans with SCA and BERK mice reflect the baseline inflammation in this disease. WBC returned to normal levels in $sG^bG$ mice (FIG. 22D; FIG. 21E).

Notably, WBC counts were lower in the mock mice compared with BERK mice that did not undergo transplantation, likely because in the former, sickle HSCs were transplanted into a normal "noninflamed" C57/BL6 background. Indeed, 6 weeks after transplantation, WBC counts in mock group of mice were nearly normal, then gradually rose to high levels seen in SCA (FIG. 22D) Overall, hematologic parameters showed marked improvement to near normal levels, and improvement was stable over a prolonged period in primary and secondary $sG^bG$ mice. The degree of correction correlated with the proportion of F cells (FIGS. 22E-22H) and HbF (data not shown). High levels of HbF improve the functional parameters of RBCs in sickle mice. (1) Sickling: The irreversibly sickled cells (ISCs) were significantly reduced to 2.3% plus or minus 0.7% in $sG^bG$ mice, compared with 12% plus or minus 0.8% in BERK controls and 10.2% plus or minus 0.3% in mock mice (FIGS. 23A-23B). Deoxygenation of blood from a representative $sG^bG$ mouse shows a dramatic reduction in sickling (FIG. 23C). A systematic quantification showed a marked decrease in the proportion of sickle RBCs in $sG^bG$ mice with increasing hypoxia (FIG. 23D). (2) RBC membrane deformability: Normal RBCs deform readily at low shear stress (3 Pascals [Pa]), representative of shear stress in small vessels. Sickle RBCs have relatively rigid membranes with remarkably reduced deformability even at high shear stress (28 Pa; representative of shear stress in large vessels). There was markedly improved deformability of RBCs of $sG^bG$ mice, although it did not achieve normal levels (FIG. 23E). This may reflect the proportion of circulating sickle RBCs that did not contain HbF. (3) RBC survival: Survival of human sickle RBCs is an order of magnitude less than normal RBCs. The time to 50% reduction (half-life) in $sG^bG$ and mock/BERK sickle mice was measured. The overall survival of the $sG^bG$ RBCs was markedly improved, with the time to 50% reduction approximately 4 times longer in RBCs from $sG^bG$ mice compared with BERK or mock mice (FIG. 23F). (4) RBC hemolysis: RBC hemolysis detected by measuring lactate dehydrogenase (LDH) in blood was reduced from 2706 plus or minus 148 mg/dL in mock mice to 1286 plus or minus 345 mg/mL in $sG^bG$ mice (n=5; P<0.004).

Example 66

High Levels of HbF Prevent Chronic Organ Damage Associated with SCA

Bone marrow, spleen, liver, and kidneys at 24 weeks showed complete prevention of organ pathology. There was reduced erythroid hyperplasia in bone marrow and spleen, decreased spleen size, and preservation of the splenic follicular architecture, compared with obliterated follicular architecture from the severe erythroid hyperplasia in mock mice. The focal tubular atrophy and segmental glomerular infarction seen in mock mice were absent in the $sG^bG$ mouse kidneys. Infarctions and extramedullary hematopoiesis seen in livers of mock mice were absent in livers of $sG^bG$ mice (FIG. 23G summarizes the data in all groups of mice). Overall, except for a mild erythroid hyperplasia no organ pathology was observed in the $sG^bG$ mice.

Example 67

High HbF Expression Improves Survival of Sickle Mice

The life span of BERK sickle mice is significantly reduced, as in humans with SCA before modern treatment. Kaplan-Meier survival curves showed a 100% survival of the $sG^bG$ mice at 24 weeks, in contrast to 20% survival in mock mice (n=14, P<0.001).

Example 68

Minimal Parameters Required Correction of SCA

Myeloablative conditioning allows noncompetitive repopulation of gene-corrected donor HSCs, resulting in high transgene-modified HSC engraftment and transgene expression. It was hypothesized that high levels γ-globin expression achieved by myeloablative conditioning may not be necessary for correction, and if so, would reduce transplantation-related morbidity.

Reduced-intensity transplantation was accomplished by transplanting gene-modified BERK LSK cells into sublethally irradiated, but with significantly high radiation dose, BERK mice. The proportion of transduced HSCs and vector copy/cell in the graft was varied by transducing LSK cells with at a range of MOI (30-100). Since the half-life of BERK RBCs was 1.5 to 2 days (FIGS. 24G-24H), mice were transfused in the peritransplantation period and analyzed after 12 weeks. Three serial experiments were carried out with mice followed for 1 year. $sG^bG$ mice were analyzed by separating them into 3 groups based upon percentage of HbF at 18 weeks: HbF=0% (mock, n=4), HbF less than 10% (termed $sG^bG$<10; n=17), and HbF of 10% or more (termed $sG^bG$>10; n=9); (FIG. 24A). The cutoff at 10% HbF was selected as this appeared to be a threshold level of HbF that reflected correction of disease: $sG^bG$<10 mice showed a higher mortality and inconsistent hematologic correction, compared with $sG^bG$>10 described in the following paragraph. The mouse numbers in the groups changed with time primarily due to the increased mortality related to SCA in mice with no/low HbF. The $sG^bG$>10 group of mice had 16% (±1.2%), 17% (±1.8%), and 21% (±2.3%) HbF, whereas the $sG^bG<10$ group of mice had 5% (±1.4%), 4% (±0.6%), and 4% (±0.5%) HbF at 12, 18, and 24 weeks, respectively, that was stable up to 1 year (FIG. 24B). F-cell repopulation was significantly higher in $sG^bG>10$ mice (65%±14%) compared with $sG^bG<10$ mice (30%±9.4%; (FIG. 24C). $sG^bG>10$ mice had 2 to 2.5 vector copies/cell, whereas the $sG^bG<10$ mice had 1.4 copies/cell (FIG. 24D).

Example 69

Hematologic Improvement Occurred with Reduced-Intensity Transplantations

Hematologic parameters stabilized at 18 weeks, due to persistent transfused RBCs in the early posttransplantation period. There was a significant improvement in hematologic parameters in the $sG^bG\geq10$ group of mice (FIG. 23G), in contrast to a small and inconsistent improvement in $sG^bG<10$ mice.

Example 70

Improvement in RBC Function Occurs with Reduced-Intensity Transplantations

Sickling: There was a very significant reduction in ISCs in $sG^bG\geq10$ mice (P<0.005) and a small, but significant reduction in ISCs in $sG^bG<10$ mice compared with mock/BERK controls (P<0.05, FIG. 24E). RBCs from $sG^bG\geq10$ mice showed reduced sickling when exposed to graded hypoxia, compared with RBCs from $sG^bG<10$ or mock/BERK mice (n=20, P<0.01; FIG. 24F). In contrast, there was no significant difference in sickling between $sG^bG<10$ and mock/BERK mice. (2) RBC membrane deformability: Surprisingly, despite similar degree of sickling with hypoxia in RBCs from $sG^bG<10$ mice and mock/BERK mice, there was slight improvement in RBC deformability in the $sG^bG<10$ mice. However, these differences were not statistically significant from the mock/BERK mice due to the high variance (FIG. 24G). In contrast, there was a consistent significant improvement in RBC deformability in $sG^bG\geq10$ mice (P<0.001, FIG. 24H). The deformability pattern suggested improved RBC flow through large vessels and microvessels. (3) RBC survival: RBC half-life of BERK mice was 1.5 days. RBCs of $sG^bG$ mice with 1%, 3%, and 7% HbF had a slightly higher half-life (2 days). Two $sG^bG$ mice with 18% HbF showed an RBC half-life of 6 days, a 4-fold increase, similar to that seen in mice carrying 40% HbF in the myeloablative transplantation model.

Taken together, the $sG^bG$ vector resulted in significant and consistent hematologic and functional correction of SCA, when the HbF production exceeded 10% of the total hemoglobin. Notably, the improvement in phenotype was comparable with that achieved with myeloablative conditioning.

Example 71

Remarkable Improvement in Organ Pathology when HbF Concentrations Exceed 10%

One unique feature of this BERK→BERK transplantation model was presence of significant sickle pathology in recipients at the time of transplantation (determined using BERK controls of comparable age as recipient mice when they underwent transplantation). Therefore, the potential for reversal of organ pathology after gene therapy could be assessed. Organ pathology in the surviving mice at approximately 50 weeks after transplantation was compared with 3-month-old BERK mice that did not undergo transplantation (FIG. 25A; FIG. 25C). The $sG^bG<10$ group of mice showed slight improvement in organ pathology: There was a slight reduction in spleen weight (717±162 mg in $sG^bG<10$ vs 870±71 mg in BERK/mock mice; P value, NS). Bone marrow and spleens showed moderate to severe erythroid hyperplasia; livers had infarctions and extramedullary hematopoiesis; and the kidneys showed occasional focal segmental lesions, focal tubular atrophy, and vascular congestion (FIG. 25D). In contrast, a dramatic reversal of organ pathology was seen in $sG^bG>10$ mice: there was a 50% reduction in spleen weight to 363 plus or minus 85 mg, preservation of splenic follicles, and mild erythroid hyperplasia in bone marrow and spleen. Remarkably, no liver infarctions and no kidney pathology were detected, except in one mouse with a single focus of focal tubular atrophy. Overall, $sG^bG\geq10$ mice showed correction of organ pathology. The lack of organ pathology in $sG^bG$ mice at 15 months of age compared with 3-month-old BERK controls demonstrates that gene therapy with the $sG^bG$ vector in a reduced-intensity transplantation setting prevents any further organ damage, and the existent organ damage at the time of transplantation probably reverses from regeneration.

Example 72

Survival

There was a significant improvement in overall survival in the $sG^bG>10$ mice compared with $sG^bG<10$ or mock mice (FIG. 25B; P<0.05). Indeed, at 24 weeks, survival of the $sG^bG\geq10$ mice was comparable with survival in mice with approximately 40% HbF in the myeloablative transplantation model that were followed for 24 weeks. There was some improvement in early survival in $sG^bG<10$ mice compared with mock mice (P<0.05). However, by 1 year, there was no difference in survival of $sG^bG<10$ mice over mock mice.

Example 73

F Cells and HbF/F Cell Critical for Improved RBC Survival and Correction of SCA

Using biotin surface labeling and intracellular HbF staining, the survival of F cells and non-F cells was studied in the same animal, which allowed quantification of the HbF/F cell necessary for improved sickle RBC survival and deformability. F cells showed a selective prolonged survival, as anticipated (FIG. 26A). The average HbF/F cell20 in $sG^bG$ mice in the BERK3C57Bl/6 model was 64% (in these mice, HbF was 41%±5%, F cells were 64%±6%). In the reduced-intensity transplantation model, $sG^bG$ 10 mice had 32% HbF/F cell (in these mice HbF was 21%±2%, F cells were 65%±14%), and $sG^bG<10$ mice had 13% HbF/F cell (HbF, 4%±0.1%; F cells, 30%±9.4%). Note that $sG^bG$ mice in the myeloablative model and $sG^bG\geq10$ mice had similar F-cell repopulation (64%-65%), suggesting that 32% HbF/F cell was sufficient to correct the sickle phenotype. However $sG^bG<10$ mice with 13% HbF/F cell and 30% F cells had inconsistent and insignificant amelioration of the disease phenotype.

Therefore, the half-life of F cells in mice was determined, grouped by the percentage of HbF/F cell. $sG^bG$ mice with low (16%; n=2), intermediate (33%; n=4), and very high (89%; n=2) HbF/F cell was injected with biotin and followed by periodic blood sampling. It was determined that mice with low HbF/F cell had no improvement in RBC half-life over BERK controls (FIG. 26B), those with 33% HbF/F cell had a 3- to 4-fold improvement in half-life, and mice with very high amounts of HbF/F cell showed RBC survival similar to normal mice. These data demonstrate that if one-third of the hemoglobin within a sickle RBC is HbF, there is significant improvement in RBC survival. Mice with these levels of HbF/F cell showed approximately 65% F cells, more than 10% HbF.

To confirm the impact of percentage of circulating F cells on overall RBC deformability, mice from both the myeloablative and reduced-intensity experiments (n=34) were grouped into 3 groups: mice with less than 33% circulating F cells, 33% to 65% F cells, and 66% or more F cells and measured RBC deformability. Only data from the low (3 Pa) and high (28 Pa) shear rates are plotted in FIG. 26C. Mice with more than 66% F cells had a highly significant improvement in RBC deformability at both high and low shear stress ($P<0.01$). Mice with 33% to 66% F cells had significantly improved RBC deformability only at high shear stress ($P<0.05$). Mice with less than 33% F cells showed inconsistent improvement in RBC deformability at low or high shear stress, which was not significantly different from mock controls. These data quantify the critical amount of HbF/F cell, the proportion of F cells, and overall HbF that are necessary for correction of sickle cell disease.

Example 74

Proportion of Transduced HSCs Required for Phenotypic Correction

The proportion of HSCs transduced with $sG^bG$ in $sG^bG$ mice was analyzed by the secondary spleen colony-forming unit (CFU-S) assay performed at 6 months in both models (FIGS. 27A-27B). Bone marrow aspirates were performed at 6 months in the BERK→BERK mice that were followed for 1 year. The proportion of transduced CFU-S's was determined by HbF expression. It has been previously shown that all vector-positive CFUs express the transgene in an identical vector that encodes β-globin. $sG^bG$ mice in the myeloablative conditioning group had 16% to 87% $sG^bG$-transduced CFU-S's (average HSC transduction was ~50%), and those in the reduced-intensity group had 5% to 60% transduced HSCs (average HSC transduction was ~30%). It is to be noted that in the reduced-intensity model, HSC transduction is overestimated, secondary to the higher mortality of $sG^bG$<10% mice in the first 6 months.

Importantly, 3 mice with 16%, 20%, and 22% transduced CFU-S's had more than 10% HbF (HbF was 20%, 11%, and 18%, respectively) and showed complete phenotypic correction. A vector copy number analysis was performed concurrently at 24 weeks on bone marrow cells and showed 1 to 3 copies/cell and 1 to 2.5 copies/cell in $sG^bG$ mice that underwent transplantation using the myeloablative conditioning and reduced-intensity conditioning models, respectively. When corrected for HSC transduction, there were 1.5 to 5 vector copies/cell.

Example 75

Transduction of Human $CD34^+$ Cells

The percentage of gene-modified HSCs necessary for effective gene therapy is critical in this disease. In vitro studies on SCA marrow can be done only on a small scale, and would read out correction in progenitors, not HSCs. HSC correction was shown in humanized models of SCA with long-term analysis. The extremely limited numbers of RBCs produced from injecting human thalassemia bone marrow $CD34^+$ cells are prohibitive for studies on sickling. Therefore, lentivirus transduction into normal human $CD34^+$ cells was optimized for a preclinical scale-up, using a GFP lentivirus vector and the severe combined immunodeficient (SCID)-repopulating assay. Granulocyte colony-stimulating factor-mobilized peripheral blood $CD34^+$ cells transduced with a GFP lentivirus vector were transplanted into nonobese diabetic (NOD)/LtSz-scid IL2Rynull (NSG) mice. Here, mock mice were those that received a transplant of untransduced CD34+ cells immediately after selection, as controls for the effect of transduction on engraftment and clonogenicity. At 6 weeks, CFUs were plated from bone marrow derived from NSG mice, and 36 individual CFUs/mouse were analyzed for the percentage of gene-marked colonies. The 18-hour transduction did not affect engraftment or clonogenicity (data not shown). A 77% gene transfer on average was observed in the SCID-repopulating cell assay, similar to previous data in human thalassemia $CD34^+$ cells.

The data from this study indicates that lentiviral delivery human γ-globin under β-globin regulatory control elements in HSCs results in sufficient postnatal HbF expression to correct SCA in mice. The amount of HbF and transduced HSCs was then de-scaled, using reduced-intensity conditioning and varying MOI, to assess critical parameters needed for correction. A systematic quantification of functional and hematologic RBC indices, organ pathology, and life span were critical to determine the minimal amount of HbF, F cells, HbF/F cell, and gene-modified HSCs required for reversing the sickle phenotype.

Results indicate the following: (1) Amelioration of disease occurred when HbF exceeded 10%, F cells constituted two-thirds of the circulating RBCs, and HbF/F cell was one-third of the total hemoglobin in RBCs; and when approximately 20% $sG^bG$ modified HSCs repopulated the marrow. (2) Genetic correction was sustained in primary or secondary transplant recipients followed long-term. (3) There is a method of determining minimum HSC chimerism for correction of a hematopoietic disease in an in vivo model, which would contribute to design of cell dose and conditioning regimens to achieve equivalent genetically corrected HSCs in human clinical trials.

One novel aspect of this study is that it addresses, for the first time, the gene dosage and the gene-modified hematopoietic stem cell dosage required for correction of a genetic defect. Expressing a tremendous amount of fetal/antisickling hemoglobin will undoubtedly correct disease, as has been shown by others, but is not practically possible in a clinical setting. As an example, an initial gene therapy for adenosine deaminase (ADA) deficiency was performed using no conditioning, and was not therapeutic, even though few gene-marked stem cells engrafted, and a selective advantage to gene-corrected lymphocytes was evident upon withdrawal of ADA. In a subsequent trial, 4 mg/kg busulfan was used before transplantation, as conditioning, resulting in adequate gene-corrected stem cell dose and gene-modified T cells. Although these pioneering studies provided us with invaluable information, they underscore the critical importance of determining thresholds for genetic correction before embarking on clinical studies.

Although disease has been corrected at 1 to 3 copies/cell, the present study indicates that the percentage of transduced stem cells in this setting of lethal irradiation/transplantation is very high (average HSCs transduced are 50%, as analyzed by a stringent secondary CFU-S assay). This level of HSC transduction would likely not be achieved in the clinical setting unless myeloablation is performed.

Therefore a novel model (BERK to BERK transplantation) was developed to address the minimal gene transfer needed, and answer questions of correction of SCA in a mouse with significant sickle pathology at 12 weeks of life (FIGS. 25A-25D). Notably, a sickle to normal myeloablative transplantation, used by other groups showing correction of SCD, is a disease prevention model, where there was no underlying pathology at time of transplantation. The present studies show that repair of preexisting pathology can occur, if genetic correction results in more than 10% HbF.

BERK mice have some degree of thalassemia. Therefore one concern in using this model for genetic therapy studies for sickle cell anemia is that correction of thalassemia would obscure improvements made by the antisickling effects of HbF. Surprisingly no significant change in MCH in $sG^bG$<10 or $sG^bG$>10 mice, including mice with HbF/F cell as high as 89% were seen (as disclosed herein). These results were surprising, but showed that the correction of sickling in RBCs was not secondary to correction of thalassemia, as seen in murine thalassemia model, where increasing MCH was seen with increases in HbF of 4% or higher. Conceivably, HbF is produced at the expense of HbS.

Although BERK mice exclusively carry human hemoglobin, the total hemoglobin in the mouse RBCs is one-third of a human RBC. Therefore, HbF and HbF/F cell were expressed as a percentage, rather than in absolute amounts, to best compare murine data to human. An increase of HbF from 3.6% to 13.6% has been shown to reduce acute sickle events in patients on decitabine. Similar improvement in sickle events occurs with 25% or more HbF/F cell in patients responsive to hydroxyurea. Data presented here, indicating improvement with 33% HbF/F cell, is concordant with these reports, but more closely resemble RBCs in infants with SCA, where less than one-third HbF/F cell at 10 to 12 months is considered a threshold for intracellular sickle polymerization. The most remarkable effect of γ-globin production with the $sG^bG$ vector was a dramatic absence of chronic organ damage and an improved survival of the sickle mice when HbF exceeded 10%. Patients with high HbF have an improved survival, confirmed by the multicenter study on hydroxyurea. HbF expressed from the $sG^bG$ vector was comparable with, or even better than, effective hydroxyurea treatment. The potential of a one-time correction, where responsiveness to hydroxyurea and compliance to daily life-long administration would not be limiting factors, would be a tremendous advantage of gene therapy. Indeed, we did not anticipate we would get the same conclusion with gene therapy, as derived from collective knowledge on (1) transgenic mice, in which every RBC has the same amount of HbF although we were imposing HbF on SS RBCs; (2) chimeric transplantations, in which normal amounts of HbA-producing RBCs (AA RBC) are present mixed with SS RBCs17,37,38; or (3) SCD patients on hydroxyurea, in whom macrocytosis induced by hydroxyurea would dilute HbS and reduce the threshold for sickling. A much higher threshold of genetically corrected sickle HSCs necessary for F-cell repopulation and correction of SCA phenotype was expected, as HbF was exogenously imposed into a sickle cell with normal amounts of HbS. Notably, despite these distinct differences in transgenics/chimeras, conclusions were similar with exogenous γ-globin expression: Indeed expressing exogenous HbF in RBCs at concentrations from 33% to as high as 89% resulted in no significant increase in MCV or MCH, yet corrected sickling. This data suggests that genetic delivery of HbF decreases endogenous HbS.

The percentage of transduced HSCs in the setting of lethal irradiation/transplantation is very high (50% on average, as analyzed by a stringent secondary CFU-S assay at 24 weeks), a number that would be difficult to achieve in a clinical setting. The BERK→BERK transplantation model, however, shows that 20% autologous HSC correction may suffice for a significant amelioration of sickling, organ damage, and survival. However, whether this percentage of gene-modified HSCs necessary for effective gene therapy is achievable is critical to determine, since there is no survival advantage to the gene-modified HSCs in this disease. High human HSC transduction has been a limitation of gene therapy with the traditional gamma retrovirus vectors. Lentivirus vectors can overcome this barrier: a 20% long-term transduction has been shown in adrenoleukodystrophy with a lentivirus vector. Lentivirus transduction into human CD34+ cells was optimized, using the SCID-repopulating cell assay and achieved approximately 75% gene transfer in SCID-repopulating cell, on average, similar to previous data in human thalassemia CD34+ cells, where 70% transduction was seen 3 to 4 months after transplantation into immune-deficient mice. Notably, this level of gene transfer in the SCID mice is encouraging, and indeed higher than the gene transfer observed in NOD-SCID mice with the adrenoleukodystrophy lentivirus vector in preclinical studies.

Gene therapy using this approach could also overcome the toxicity and immunologic consequences of the traditional allogeneic bone marrow transplantation/reduced-intensity transplantation. Mismatched mixed chimerism of normal and sickle marrow in murine transplantations shows that a near complete chimerism is typically necessary for correction of organ damage. It is encouraging that, in a clinical series, reduced-intensity conditioning (RIC) transplantation with 8 mg/kg busulfan along with fludarabine, antithymocyte globulin, and total lymphoid irradiation in SCA patients has shown an average allogeneic engraftment of 78% at 2 to 8.5 years after transplantation, with correction of SCA phenotype. This high level of donor chimerism even in an allogeneic RIC setting, where immune rejection can occur, suggests that high gene transfer efficiency into autologous CD34+ cells followed by RIC may be a potentially safer alternative to myeloablative conditioning. 77% gene transfer efficiency in human stem/progenitors was demonstrated using a NOD-SCID repopulating cell assay, as well a correction of phenotype in mice with 1.3 to 1.5 copies per cell and approximately 20% gene-marked CFU-Ss (FIGS. 27A-27B).

Significantly, correction occurred at 1 to 3 vector copies per cell, a clinically achievable goal. Flanking the $sG^bG$ virus with a chromatin insulator is expected to increase HbF/vector copy by 2- to 4-fold. In experimental models, the insulator appears to reduce clonal dominance, although whether the insulator element lowers the risk of insertional oncogenesis is unknown. The risk of insertional oncogenesis observed with randomly integrating vectors has been shown to be lower with a lentivirus vector than a gammaretrovirus vector. It would be further lowered when the enhancer element is active only in a restricted erythroid lineage Example 76

Gene Therapy for Sickle Cell Disease

Since HbF is the hemoglobin with the highest anti-sickling effect, a lentivirus vector, $sG^bG$, that carries a normal human γ-globin gene (encoding a normal human gamma-globin protein set forth in SEQ ID NO: 49) was used to produce HbF in Berkeley sickle mice. As disclosed herein, a lentivirus vector incorporating γ-globin exons and β-globin non-coding regions and regulatory elements, sG$^b$G, was designed. This vector showed complete correction of the sickle phenotype in Berkeley sickle mice following transfer of the sG$^b$G vector into HSCs and myeloablative transplants (Example 65, FIGS. 23A-23D, FIG. 28, and Table 1). FIGS. 23A and 23B show the reduction in irreversibly sickled cells in blood of the mice, FIGS. 23C and 23D show experimentally induced sickling of RBC from the mice and the proportion of sickled cells, and FIG. 28 shows the improvement in survival of mice following successful gene therapy.

TABLE 1

Hematological correction is obtained in the sG$^b$G group of Berkeley sickle mice; correction is sustained long-term in primary and secondary transplants.

| Mice | N | WBC | RBC | Hb | MCV | MCH | RDW | Plt | Retic (%) |
|---|---|---|---|---|---|---|---|---|---|
| BERK | 5 | 56.8 ± 5.4 | 5.3 ± 0.4 | 5.8 ± 0.5 | 48.2 ± 1 | 10.7 ± 0.5 | 35.3 ± 1.6 | 733 ± 80 | 60.8 ± 5.0 |
| sGbG Prim. | 5 | 10.6 ± 3.1 | 9.4 ± 0.8 | 10.0 ± 0.8 | 40.7 ± 1 | 10.4 ± 0.6 | 27.6 ± 1.1 | 733 ± 82 | 15.8 ± 3.2 |
| Mock Prim. | 10 | 29.7 ± 1.4 | 5.8 ± 0.4 | 7.6 ± 0.7 | 48.5 ± 1 | 10.7 ± 0.2 | 32.0 ± 0.9 | 921 ± 50 | 40.0 ± 3.0 |
| P value* | | 0.001 | 0.007 | 0.03 | 0.001 | 0.9 | 0.009 | 0.06 | 0.006 |
| sG$^b$G Sec. | 6 | 6.8 ± 1.4 | 8.9 ± 0.4 | 10.1 ± 0.5 | 40.5 ± 2 | 11.4 ± 0.5 | 28.3 ± 1.4 | 658 ± 33 | 13.8 ± 2.9 |
| Mock Sec. | 1 | 31.7 | 5.2 | 6.4 | 47.6 | 12.2 | 32.1 | 923 | 49 |

Analysis of blood parameters of mice is shown 18 weeks following primary (Prim.) and secondary (Sec.) transplants of sG$^b$G or Mock transduced lineage (−), Sca (+) and Kit (+) cells.

The critical parameters necessary to correct SCA pathophysiology using a reduced intensity transplant were then determined. Complete correction of the hematological and functional RBC parameters, inflammation, and organ pathology was observed in SCD mice following myeloablative-conditioning and transplant. Correction was sustained long-term in primary and secondary transplant recipients. The critical parameters necessary to correct SCA pathophysiology using a reduced intensity transplant were also determined. There was 100% 6-month survival of genetically-corrected Berkeley sickle mice, compared to 20% survival of mock-transplanted Berkeley sickle mice.

Using reduced-intensity conditioning and simulating conditions of autologous transplant, different proportions of gene-modified Berkeley sickle HSC were transplanted into sub-lethally irradiated Berkeley sickle mice. The minimal proportions of genetically-corrected HSC, HbF, HbF-containing RBC (F-cells) and HbF/F-cell required for correction of sickle cell anemia were then defined. With 15-20% gene modified HSC repopulating the Berkeley sickle mouse bone marrow, approximately 2 vector copies per cell, ≥10% HbF, and >66% F cells, there was complete correction of the sickle phenotype, including organ pathology and survival. With 15-20% gene-modified HSCs repopulating the Berkeley sickle mouse bone marrow, approximately 2 vector copies per cell, ≥10% HbF, and >66% F cells, there was complete correction of the sickle phenotype, including organ pathology and survival.

Example 77

Gene Therapy for Beta Thalassemia

Expression of HbF via lentivirus vectors carrying the human γ-globin gene has been previously shown (Persons et al. Blood 10:2175-83 (2003); Pestina et al. Mol. Ther. 17:245-52 (2009)). In order to confirm the ability of the sG$^b$G vector to correct β-thalassemia, thalassemia mice (Hbbth3/+) were treated using the same approach as used in sickle transgenic mice. Thalassemia mice were transplanted with thalassemia stem/progenitor cells (Lin− Sca+ Kit+ [LSK] cells) transduced twice about 8 hours apart with sG$^b$G (MOI of 2×20). Control (Mock) animals were concurrently treated with media only. Approximately 10,000 transduced LSK+ cells were injected/co-transplanted with 200,000 irradiated Lin−Sca−Kit− cells into lethally irradiated thalassemia recipient mice (split dose of 700+375 rads). The primary animals were monitored over a period of 7-8 months, and secondary transplants were performed thereafter for a total follow up of 18 months.

Figure 29D:
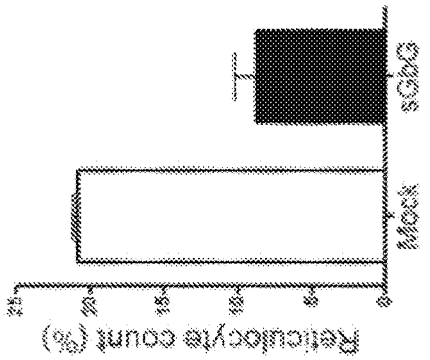

The vector resulted in increased HbF to 22±3% (mean+ SEM); which corrected the thalassemia phenotype (FIGS. 29A-29D). There was a rise in hemoglobin from a mean of 8.8±0.2 μg/dL in mock transplanted mice to 12.5±0.5 μg/dL in sG$^b$G transplanted mice (FIG. 29A); hematocrit rose from 31.8±0.3 to 42.1±1.07 (FIG. 29B). This was accompanied by a fall in reticulocytosis from 20.8±0.3% to 8.7±1.4% (FIG. 29D). The microcytosis seen in thalassemia was also corrected, with an increase in MCV from 38.1±0.3 to 45.3±1.7 fl. This correction was stable over time and was sustained in primary and secondary mice.

Example 78

Improved HbF Expressing Vector with Superior Anti-Sickling Properties

As described above, production of >10% HbF was shown to correct the SCD phenotype in the mouse model. While the sG$^b$G vector efficiently corrected the phenotype in the Berkeley sickle mouse model (Example 65, FIGS. 23A-23D, FIG. 28; Perumbeti et al., Blood 114:1174-85 (2009)), it was far less efficacious in the knock-in sickle mouse model (UAB mice), unless very high vector copies were present per cell.

The Berkeley sickle mice are transgenic for the human α- and β$^S$-globin transgenes, and knock-out of mouse globins and the human transgenes leads to imbalanced globin chain production. Berkeley sickle mice have a relative excess of human α globin chains, as compared to β$^S$ globin chains, allowing the γ-globin (SEQ ID NO: 49) produced by the sG$^b$G vector to form HbF ($α_2γ_2$) readily, in the presence of β$^S$ globin that also binds α-globin to form HbS ($α_2β^S_2$). The UAB mice, on the other hand, are knock-ins for human α in place of the mouse α globin and human β$^S$ in place of the mouse β$^{major}$ globin gene, producing human globins in place of mouse globins. These mice therefore have completely balanced human α and β$^S$ chains and resemble patients with homozygous sickle cell anemia (Hb SS disease). Patients with homozygous SCD (and the UAB knock-in sickle mouse model) have balanced (equal amounts of) α and $\beta^S$ molecules, and the genetically introduced γ-globin has to compete with $\beta^S$ for α-globin. Hence, a far excess of γ-globin is required to outcompete $\beta^S$ globin to form HbF.

Accordingly, in Berkeley sickle mice, γ-globin produced by this vector effectively binds the excess a globin to form HbF, without much competition from $\beta^S$ globin, which binds with a globin to form HbS. Hence, in Berkeley sickle mice, at clinically achievable vector copies, correction of disease is observed. However, in UAB mice, the a globin chains become rate limiting due to equal amounts of competing $\beta^S$ globin chains. Therefore, a high level/excess of vector-derived γ globin is required to be able to out compete $\beta^S$ globin to form HbF.

To address this, several changes were made to the gene transfer protocol and strategy. The γ-globin gene was modified with a G→A point mutation at bp 50 in exon 1. This modification changes the amino acid glycine (GGC) to aspartic acid (GAC) in order to improve its affinity for α-globin without altering its functional properties, so that HbF is formed at higher efficiency than HbS in RBCs. The ability of the original γ globin vector ($sG^bG$) was then compared to that with a point mutation in the γ globin coding sequence ($sG^bG^M$) in sickle mice. The annotated vector map for the $sG^bG^M$ is depicted in FIG. 30, with the various regions of the sequence identified in FIGS. 30 and 31A-31M. The $sG^bG^M$ sequence is shown in FIGS. 31A-31M.

Comparative studies between the $sG^bG$ and $sG^bG^M$ vectors were done in Berkeley sickle mice and in UAB sickle mice, where lineage depleted, Sca+ Kit+ (LSK) cells, that are highly enriched in hematopoietic stem cells, were sorted, transduced with medium alone (mock), the $sG^bG$ vector, or the $sG^bG^M$ vector, and transplanted into sub-lethally irradiated Berkeley or UAB sickle recipient mice, as previously described for the $sG^bG$ efficacy studies (Perumbeti et al., Blood 114:1174-85 (2009)). Mice were bled at 6, 12, and 24 weeks post-transplant to assess hematological parameters and HbF expression, and six to eight mice per arm were then followed for 6-12 months. The 12-week data in Berkeley sickle mice are shown in FIGS. 32A-32B, which demonstrates the superior HbF production per vector copy and improved reticulocytosis from the $sG^bG^M$ vector.

Figure 33A:
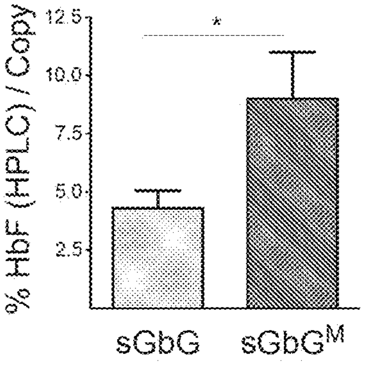
Figure 33B:
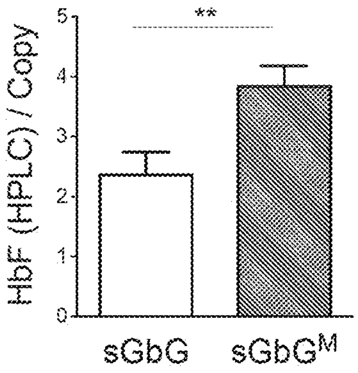
Figure 33C:
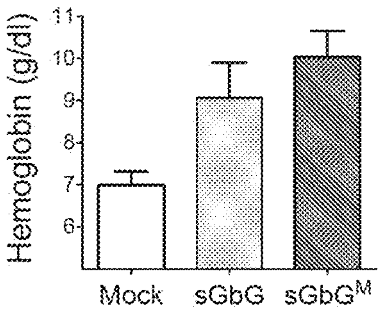
Figure 33D:
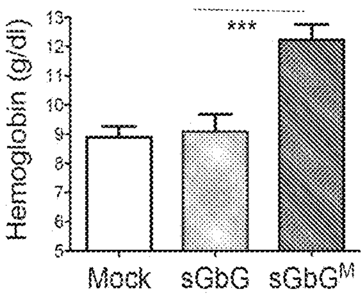
Figure 33E:
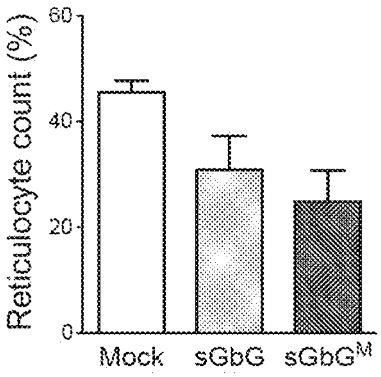
Figure 33F:
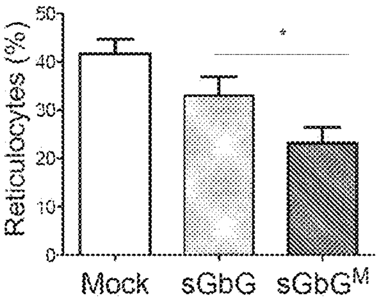

Comparative results between Berkeley and knock-in UAB sickle mice are shown in FIGS. 33A-33F. The data shown are results from a 6-month analysis. The amount of HbF produced per vector copy from the $sG^bG$ and $sG^bG^M$ vectors is shown in Berkeley sickle mice (FIG. 33A) and UAB knock-in sickle mice (FIG. 33B). The $sG^bG^M$ mice showed nearly 1.5-2 times superior ability to form HbF as compared with the $sG^bG$ vector in both types of sickle mice. It is notable that the amount of HbF produced per copy of the $sG^bG^M$ vector is nearly twice in the Berkeley mice when compared to UAB mice with the $sG^bG^M$ vector, showing the ease with which HbF tetramers form if excess α-globin chains are present and the difficulty forming these tetramers if α-globin chains are rate limiting.

The HbF generated from the $sG^bG^M$ vector was functional, showing correction of sickling, a superior reduction in reticulocytosis, and a rise in hemoglobin in both types of sickle mice. Correction of anemia was observed in UAB mice transplanted with the $sG^bG^M$ vector but not the $sG^bG$ vector. Some of these mice have now been followed for nearly one year, and the expression is stable. Much better correction of RBC half-life and RBC membrane deformability was also observed with the $sG^bG^M$ vector as compared to the $sG^bG$ vector when HbF levels are the same. FIGS. 32A-32B shows that despite HbF levels of 30-35% with the $sG^bG$ vector (filled diamonds, FIG. 32B), mice had an average reticulocyte count of approximately 15%, while the reticulocyte count was 5% in $sG^bG^M$ mice with similar HbF levels (open diamonds). This demonstrates that the mutation also improved the lifespan of the RBCs by reducing sickling, despite the similar levels of HbF. Thus, the engineered mutated gamma globin vector also produces a superior anti-sickling HbF, improving RBC quality and lifespan. Studies relating to the effect on organ damage, RBC membrane deformability, RBC half-life, and the oxygen affinity of the mutant HbF compared to normal HbF to determine the mechanism behind this unexpected favorable property of HbF are ongoing.

These results demonstrate that the point-mutated γ-globin gene in the $sG^bG^M$ vector prevents sickling and therefore prolongs sickle RBC half-life, leading to lower reticulocyte counts (FIGS. 33A-33F). This higher production of HbF and reduction in reticulocytosis results in a proportional rise in hemoglobin and hematological correction of the sickle phenotype. The $sG^bG^M$ vector has no change in the vector backbone or any of the transcriptional regulatory elements.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the specific number of genes or targeted by a therapeutic product, the type of gene, the type of genetic disease or deficiency, and the gene(s) specified. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A mutated human gamma-globin gene, wherein the mutated human gamma-globin gene encodes a human gamma-globin protein, in which the glycine residue at a position corresponding to position 17 of a native human gamma-globin (SEQ ID NO: 49) is substituted.

2. The mutated human gamma-globin gene of claim 1, wherein the glycine residue is substituted with an aspartic acid residue.

3. The mutated human gamma-globin gene of claim 1, wherein the mutated human globin gene encodes a protein represented by SEQ ID NO: 1 and wherein the mutated human globin gene comprises a nucleotide sequence having a sequence identity of 70% or greater to SEQ ID NO: 2.

4. A viral expression vector comprising the mutated human gamma-globin gene of claim 1.

5. The viral expression vector of claim 4, further comprising a lentiviral vector backbone, which comprises:

(a) lentiviral cis elements comprising (i) a packaging signal (ψ), (ii) a gag fragment, (iii) an env fragment comprising a rev response element (RRE) and a splice acceptor sequence, and (iv) a central flap/polypurine tract (cPPT), wherein the gag fragment comprises a 5' fragment of gag that is about 300 bp;

(b) a 3'-long terminal repeat (LTR), which comprises one or more upstream polyadenylation (polyA) enhancer sequences; and (c) a heterologous polyA signal sequence downstream from the 3'-LTR.

6. The viral expression vector of claim 5, wherein the one or more upstream polyA enhancer sequences are present in a U3 deletion region of the 3'-LTR.

7. The viral expression vector of claim 6, wherein the one or more upstream polyA enhancer sequences are derived from an SV40 late polyA signal sequence.

8. The viral expression vector of claim 5, wherein the lentiviral vector backbone further comprises one or more chromatin insulator elements in the 3'-LTR.

9. The viral expression vector of claim 8, wherein the chromatin insulator elements include one or more reduced-length chicken hypersensitive site-4 (cHS4) elements.

10. The viral expression vector of claim 5, wherein the mutated human gamma-globin gene is placed in a reverse orientation to a transcriptional unit in the lentiviral vector backbone.

11. The viral expression vector of claim 4, further comprising one or more elements of a beta-globin locus control region.

12. The viral expression vector of claim 11, wherein the one or more elements of a beta-globin locus control region are in the reverse orientation to the transcriptional unit in the lentiviral vector backbone.

13. The viral expression vector of claim 11, wherein the one or more elements of the beta-globin locus control region include HS2, HS3, and HS4 elements of the beta-globin locus control region.

14. The viral expression vector of claim 4, wherein the mutated human gamma-globin gene is operably linked to a lineage-specific promoter.

15. The viral expression vector of claim 14, wherein the lineage-specific promoter is an erythroid lineage specific promoter.

16. The viral expression vector of claim 4, wherein the mutated human gamma-globin gene is operably linked to a beta-globin promoter.

17. The viral expression vector of claim 4, further comprising one or more non-coding sequences of a beta-globin gene.

18. A cell comprising the mutated human gamma-globin gene of claim 1.

19. The cell of claim 18, wherein the cell is a hematopoietic stem cell.

20. A method for preparing a transgenic cell, comprising transducing a cell with the viral expression vector of claim 4.

21. The method of claim 20, wherein the cell is a hematopoietic stem cell.

22. A method of treating sickle cell anemia or β-thalassemia or reducing symptoms thereof in a human subject, the method comprising:

administering the viral expression vector of claim 4 to, or transplanting a hematopoietic stem cell comprising the viral expression vector of claim 4 into, a human subject in need of treatment for sickle cell anemia or β-thalassemia or reduction of symptoms thereof.

23. The method of claim 22, wherein the hematopoietic stem cell is autologous.

24. The method of claim 22, further comprising treating the subject with reduced intensity conditioning prior to the transplantation.

* * * * *

SEQUENCE LISTING

```
<160> NUMBER OF SEQ ID NOS: 49

<210> SEQ ID NO 1
<211> LENGTH: 147
<212> TYPE: PRT
<213> ORGANISM: Artificial Sequence
<220> FEATURE:
<223> OTHER INFORMATION: Mutated human gamma globin

<400> SEQUENCE: 1

Met Gly His Phe Thr Glu Glu Asp Lys Ala Thr Ile Thr Ser Leu Trp
1               5                   10                  15

Asp Lys Val Asn Val Glu Asp Ala Gly Gly Glu Thr Leu Gly Arg Leu
            20                  25                  30

Leu Val Val Tyr Pro Trp Thr Gln Arg Phe Phe Asp Ser Phe Gly Asn
        35                  40                  45

Leu Ser Ser Ala Ser Ala Ile Met Gly Asn Pro Lys Val Lys Ala His
    50                  55                  60
```

-continued

```
Gly Lys Lys Val Leu Thr Ser Leu Gly Asp Ala Ile Lys His Leu Asp
65                  70                  75                  80

Asp Leu Lys Gly Thr Phe Ala Gln Leu Ser Glu Leu His Cys Asp Lys
                85                  90                  95

Leu His Val Asp Pro Glu Asn Phe Lys Leu Leu Gly Asn Val Leu Val
            100                 105                 110

Thr Val Leu Ala Ile His Phe Gly Lys Glu Phe Thr Pro Glu Val Gln
        115                 120                 125

Ala Ser Trp Gln Lys Met Val Thr Ala Val Ala Ser Ala Leu Ser Ser
    130                 135                 140

Arg Tyr His
145


<210> SEQ ID NO 2
<211> LENGTH: 444
<212> TYPE: DNA
<213> ORGANISM: Artificial Sequence
<220> FEATURE:
<223> OTHER INFORMATION: Mutated human gamma globin gene coding region
      (CDS), sense orientation

<400> SEQUENCE: 2

atgggtcatt tcacagagga ggacaaggct actatcacaa gcctgtggga caaggtgaat     60

gtggaagatg ctggaggaga aaccctggga aggctcctgg ttgtctaccc atggacccag    120

aggttctttg acagctttgg caacctgtcc tctgcctctg ccatcatggg caaccccaaa    180

gtcaaggcac atggcaagaa ggtgctgact tccttgggag atgccataaa gcacctggat    240

gatctcaagg gcacctttgc ccagctgagt gaactgcact gtgacaagct gcatgtggat    300

cctgagaact tcaagctcct gggcaacgtg ctggtcaccg tgctggccat tcactttggc    360

aaagaattca cccctgaggt gcaggcttcc tggcagaaga tggtgactgc agtggccagt    420

gccctgtcct ccagatacca ctga                                           444


<210> SEQ ID NO 3
<211> LENGTH: 2141
<212> TYPE: DNA
<213> ORGANISM: Artificial Sequence
<220> FEATURE:
<223> OTHER INFORMATION: Mutated human gamma globin gene, sense
      orientation

<400> SEQUENCE: 3

gtaaatacac ttgcaaagga ggatgttttt agtagcaatt tgtactgatg gtatggggcc     60

aagagatata tcttagaggg agggctgagg gtttgaagtc caactcctaa gccagtgcca    120

gaagagccaa ggacaggtac ggctgtcatc acttagacct caccctgtgg agccacaccc    180

tagggttggc caatctactc ccaggagcag ggagggcagg agccagggct gggcataaaa    240

gtcagggcag agccatctat tgcttacatt tgcttctgac acaactgtgt tcactagcaa    300

cctcaaacag acaccatggg tcatttcaca gaggaggaca aggctactat cacaagcctg    360

tgggacaagg tgaatgtgga agatgctgga ggagaaaccc tgggaaggta ggctctggtg    420

accaggacaa gggagggaag gaaggaccct gtgcctggca aaagtccagg ttgcttctca    480

ggatttgtgg caccttctga ctgtcaaact gttcttgtca atctcacagg ctcctggttg    540

tctacccatg gacccagagg ttctttgaca gctttggcaa cctgtcctct gcctctgcca    600

tcatgggcaa ccccaaagtc aaggcacatg gcaagaaggt gctgacttcc ttgggagatg    660

ccataaagca cctggatgat ctcaagggca cctttgccca gctgagtgaa ctgcactgtg    720
```

acaagctgca tgtggatcct gagaacttca aggtgagtct atgggaccct tgatgttttc 780
tttccccttc ttttctatgg ttaagttcat gtcataggaa ggggagaagt aacagggtac 840
acatattgac caaatcaggg taattttgca tttgtaattt taaaaaatgc tttcttcttt 900
taatatactt ttttgtttat cttatttcta atactttccc taatctcttt ctttcagggc 960
aataatgata caatgtatca tgcctctttg caccattcta aagaataaca gtgataattt 1020
ctgggttaag gcaatagcaa tatttctgca tataaatatt tctgcatata aattgtaact 1080
gatgtaagag gtttcatatt gctaatagca gctacaatcc agctaccatt ctgcttttat 1140
tttatggttg ggataaggct ggattattct gagtccaagc taggcccttt tgctaatcat 1200
gttcatacct cttatcttcc tcccacagct cctgggcaac gtgctggtca ccgtgctggc 1260
cattcacttt ggcaaagaat tcacccctga ggtgcaggct tcctggcaga agatggtgac 1320
tgcagtggcc agtgccctgt cctccagata ccactgagcc tcttgcccat gattcagagc 1380
tttcaaggat aggctttatt ctgcaagcaa tacaaataat aaatctattc tgctgagaga 1440
tcacacatga ttttcttcag ctcttttttt tacatctttt taaatatatg agccacaaag 1500
ggtttatatt gagggaagtg tgtatgtgta tttctgcatg cctgtttgtg tttgtggtgt 1560
gtgcatgctc ctcatttatt tttatatgag atgtgcattt tgttgagcaa ataaaagcag 1620
taaagacact tgtacacggg agttctgcaa gtgggagtaa atggtgtagg agaaatccgg 1680
tgggaagaaa gacctctata ggacaggact tctcagaaac agatgttttg gaagagatgg 1740
gaaaaggttc agtgaagacc tgggggctgg attgattgca gctgagtagc aaggatggtt 1800
cttaatgaag ggaaagtgtt ccaagctcgg ctagccggtg ctagtctccc ggaactatca 1860
ctctttcaca gtctgctttg gaaggactgg gcttagtatg aaaagttagg actgagaaga 1920
atttgaaagg gggctttttg tagcttgata ttcactactg tcttattacc ctatcatagg 1980
cccaccccaa atggaagtcc cattcttcct caggatgttt aagattagca ttcaggaaga 2040
gatcagaggt ctgctggctc ccttatcatg tcccttatgg tgcttctggc tccggctagc 2100
accggtgatg atcctcgcga gctcgactct agaggatccc c 2141

<210> SEQ ID NO 4
<211> LENGTH: 11868
<212> TYPE: DNA
<213> ORGANISM: Artificial Sequence
<220> FEATURE:
<223> OTHER INFORMATION: sSIN Mutated human gamma globin gene
<220> FEATURE:
<221> NAME/KEY: misc_feature
<222> LOCATION: (10813)..(10816)
<223> OTHER INFORMATION: n is a, c, g, or t

<400> SEQUENCE: 4
caggtggcac ttttcgggga aatgtgcgcg gaacccctat ttgtttattt ttctaaatac 60
attcaaatat gtatccgctc atgagacaat aaccctgata aatgcttcaa taatattgaa 120
aaaggaagag tatgagtatt caacatttcc gtgtcgccct tattcccttt tttgcggcat 180
tttgccttcc tgtttttgct cacccagaaa cgctggtgaa agtaaaagat gctgaagatc 240
agttgggtgc acgagtgggt tacatcgaac tggatctcaa cagcggtaag atccttgaga 300
gttttcgccc cgaagaacgt tttccaatga tgagcacttt taaagttctg ctatgtggcg 360
cggtattatc ccgtattgac gccgggcaag agcaactcgg tcgccgcata cactattctc 420
agaatgactt ggttgagtac tcaccagtca cagaaaagca tcttacggat ggcatgacag 480

-continued

```
taagagaatt atgcagtgct gccataacca tgagtgataa cactgcggcc aacttacttc    540
tgacaacgat cggaggaccg aaggagctaa ccgctttttt gcacaacatg ggggatcatg    600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt catttttaat ttaaaaggat ctaggtgaag atcctttttg   1080
ataatctcat gaccaaaatc ccttaacgtg agttttcgtt ccactgagcg tcagaccccg   1140
tagaaaagat caaaggatct tcttgagatc ctttttttct gcgcgtaatc tgctgcttgc   1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttggc   2220
cattgcatac gttgtatcca tatcataata tgtacattta tattggctca tgtccaacat   2280
taccgccatg ttgacattga ttattgacta gttattaata gtaatcaatt acggggtcat   2340
tagttcatag cccatatatg gagttccgcg ttacataact tacggtaaat ggcccgcctg   2400
gctgaccgcc caacgacccc cgcccattga cgtcaataat gacgtatgtt cccatagtaa   2460
cgccaatagg gactttccat tgacgtcaat gggtggagta tttacggtaa actgcccact   2520
tggcagtaca tcaagtgtat catatgccaa gtacgccccc tattgacgtc aatgacggta   2580
aatggcccgc ctggcattat gcccagtaca tgaccttatg ggactttcct acttggcagt   2640
acatctacgt attagtcatc gctattacca tggtgatgcg gttttggcag tacatcaatg   2700
ggcgtggata gcggtttgac tcacggggat ttccaagtct ccaccccatt gacgtcaatg   2760
ggagtttgtt ttggcaccaa aatcaacggg actttccaaa atgtcgtaac aactccgccc   2820
cattgacgca aatgggcggt aggcgtgtac ggtgggaggt ctatataagc agagctcgtt   2880
```

-continued

```
tagtgaaccg gggtctctct ggttagacca gatctgagcc tgggagctct ctggctaact   2940
agggaaccca ctgcttaagc ctcaataaag cttgccttga gtgcttcaag tagtgtgtgc   3000
ccgtctgttg tgtgactctg gtaactagag atccctcaga cccttttagt cagtgtggaa   3060
aatctctagc agtggcgccc gaacagggac ttgaaagcga aagggaaacc agaggagctc   3120
tctcgacgca ggactcggct tgctgaagcg cgcacggcaa gaggcgaggg gcggcgactg   3180
gtgagtacgc caaaaatttt gactagcgga ggctagaagg agagagatgg gtgcgagagc   3240
gtcagtatta agcgggggag aattagatcg cgatgggaaa aaattcggtt aaggccaggg   3300
ggaaagaaaa aatataaatt aaaacatata gtatgggcaa gcagggagct agaacgattc   3360
gcagttaatc ctggcctgtt agaaacatca gaaggctgta gacaaatact gggacagcta   3420
caaccatccc ttcagacagg atcagaagaa cttagatcat tatataatac agtagcaacc   3480
ctctattgtg tgcatcaaag gatagagata aaagacacca aggaagcttt agacaagata   3540
gaggaagagc aaaacaaaag taagaccacc gcacagcaag cggccgctga tcttcagacc   3600
tggaggagga gatatgaggg acaattggag aagtgaatta tataaatata aagtagtaaa   3660
aattgaacca ttaggagtag cacccaccaa ggcaaagaga agagtggtgc agagagaaaa   3720
aagagcagtg ggaataggag ctttgttcct tgggttcttg ggagcagcag gaagcactat   3780
gggcgcagcg tcaatgacgc tgacggtaca ggccagacaa ttattgtctg gtatagtgca   3840
gcagcagaac aatttgctga gggctattga ggcgcaacag catctgttgc aactcacagt   3900
ctggggcatc aagcagctcc aggcaagaat cctggctgtg gaaagatacc taaaggatca   3960
acagctcctg gggatttggg gttgctctgg aaaactcatt tgcaccactg ctgtgccttg   4020
gaatgctagt tggagtaata aatctctgga acagatttgg aatcacacga cctggatgga   4080
gtgggacaga gaaattaaca attacacaag cttaatacac tccttaattg aagaatcgca   4140
aaaccagcaa gaaaagaatg aacaagaatt attggaatta gataaatggg caagtttgtg   4200
gaattggttt aacataacaa attggctgtg gtatataaaa ttattcataa tgatagtagg   4260
aggcttggta ggtttaagaa tagtttttgc tgtactttct atagtgaata gagttaggca   4320
gggatattca ccattatcgt ttcagaccca cctcccaacc ccgaggggac ccgacaggcc   4380
cgaaggaata gaagaagaag gtggagagag agacagagac agatccattc gattagtgaa   4440
cggatctcga cggtatcgat agcgggacaa atggcagtat tcatccacaa ttttaaaaga   4500
aaagggggga ttggggggta cagtgcaggg gaaagaatag tagacataat agcaacagac   4560
atacaaacta aagaattaca aaaacaaatt acaaaaattc aaaattttcg ggtttattac   4620
agggacagca gagatccagt ttggatcgtc gacatcgccg gtgaattcac tagtggatcg   4680
ctctcgaggg gatcctctag agtcgagctc gcgaggatca tcaccggtgc tagccggagc   4740
cagaagcacc ataagggaca tgataaggga gccagcagac ctctgatctc ttcctgaatg   4800
ctaatcttaa acatcctgag gaagaatggg acttccattt ggggtgggcc tatgataggg   4860
taataagaca gtagtgaata tcaagctaca aaaagccccc tttcaaattc ttctcagtcc   4920
taacttttca tactaagccc agtccttcca aagcagactg tgaaagagtg atagttccgg   4980
gagactagca ccggctagcc gagcttggaa cactttccct tcattaagaa ccatccttgc   5040
tactcagctg caatcaatcc agcccccagg tcttcactga accttttccc atctcttcca   5100
aaacatctgt ttctgagaag tcctgtccta tagaggtctt tcttcccacc ggatttctcc   5160
tacaccattt actcccactt gcagaactcc cgtgtacaag tgtctttact gcttttattt   5220
```

```
gctcaacaaa atgcacatct catataaaaa taaatgagga gcatgcacac accacaaaca   5280
caaacaggca tgcagaaata cacatacaca cttccctcaa tataaaccct ttgtggctca   5340
tatatttaaa aagatgtaaa aaaaagagct gaagaaaatc atgtgtgatc tctcagcaga   5400
atagatttat tatttgtatt gcttgcagaa taaagcctat ccttgaaagc tctgaatcat   5460
gggcaagagg ctcagtggta tctggaggac agggcactgg ccactgcagt caccatcttc   5520
tgccaggaag cctgcacctc aggggtgaat tctttgccaa agtgaatggc cagcacggtg   5580
accagcacgt tgcccaggag ctgtgggagg aagataagag gtatgaacat gattagcaaa   5640
agggcctagc ttggactcag aataatccag ccttatccca accataaaat aaaagcagaa   5700
tggtagctgg attgtagctg ctattagcaa tatgaaacct cttacatcag ttacaattta   5760
tatgcagaaa tatttatatg cagaaatatt gctattgcct taacccagaa attatcactg   5820
ttattcttta gaatggtgca aagaggcatg atacattgta tcattattgc cctgaaagaa   5880
agagattagg gaaagtatta gaaataagat aaacaaaaaa gtatattaaa agaagaaagc   5940
attttttaaa attacaaatg caaaattacc ctgatttggt caatatgtgt accctgttac   6000
ttctcccctt cctatgacat gaacttaacc atagaaaaga aggggaaaga aaacatcaag   6060
ggtcccatag actcaccttg aagttctcag gatccacatg cagcttgtca cagtgcagtt   6120
cactcagctg ggcaaaggtg cccttgagat catccaggtg ctttatggca tctcccaagg   6180
aagtcagcac cttcttgcca tgtgccttga ctttggggtt gcccatgatg gcagaggcag   6240
aggacaggtt gccaaagctg tcaaagaacc tctgggtcca tgggtagaca accaggagcc   6300
tgtgagattg acaagaacag tttgacagtc agaaggtgcc acaaatcctg agaagcaacc   6360
tggacttttg ccaggcacag ggtccttcct tccctccctt gtcctggtca ccagagccta   6420
ccttcccagg gtttctcctc cagcatcttc cacattcacc ttgtcccaca ggcttgtgat   6480
agtagccttg tcctcctctg tgaaatgacc catggtgtct gtttgaggtt gctagtgaac   6540
acagttgtgt cagaagcaaa tgtaagcaat agatggctct gccctgactt ttatgcccag   6600
ccctggctcc tgccctccct gctcctggga gtagattggc caaccctagg gtgtggctcc   6660
acagggtgag gtctaagtga tgacagccgt acctgtcctt ggctcttctg gcactggctt   6720
aggagttgga cttcaaaccc tcagccctcc ctctaagata tatctcttgg ccccatacca   6780
tcagtacaaa ttgctactaa aaacatcctc ctttgcaagt gtatttacga cggtatcgat   6840
gtatgtgagc atgtgtcctc taacagcaca ggccttttgc cacctagctg tccaggggtg   6900
ccttaaaatg gcaaacaagg tttgttttct tttcctgttt tcatgccttc ctcttccata   6960
tccttgtttc atattaatac atgtgtatag atcctaaaaa tctatacaca tgtattaata   7020
aagcctgatt ctgccgcttc taggtataga ggccacctgc aagataaata tttgattcac   7080
aataactaat cattctatgg caattgataa caacaaatat atatatatat atatatatac   7140
gtatatgtgt atatatatat atatatatat atattcagga aataatatat tctagaatat   7200
gtcacattct gtctcaggca tccattttct ttatgatgcc gtttgaggtg gagttttagt   7260
caggtggtca gcttctcctt ttttttgcca tctgccctgt aagcatcctg ctggggaccc   7320
agataggagt catcactcta ggctgagaac atctgggcac acaccctaag cctcagcatg   7380
actcatcatg actcagcatt gctgtgcttg agccagaagg tttgcttaga aggttacaca   7440
gaaccagaag gcgggggtgg ggcactgacc ccgacagggg cctggccaga actgctcatg   7500
cttggactat gggaggtcac taatggagac acacagaaat gtaacaggaa ctaagggaat   7560
tccggtgccc tgcttaggag cttaatcttt aatgaaagct aagctttcat taaaaaaagt   7620
```

```
ctaaccagct gcattcgact ttgactgcag cagctggtta gaaggttcta ctggaggagg   7680
gtcccagccc attgctaaat taacatcagg ctctgagact ggcagtatat ctctaacagt   7740
ggttgatgct atcttctgga acttgcctgc tacattgaga ccactgaccc atacatagga   7800
agcccatagc tctgtcctga actgttaggc cactggtcca gagagtgtgc atctcctttg   7860
atcctcataa taaccctatg agatagacac aattattact cttactttat agatgatgat   7920
cctgaaaaca taggagtcaa ggcacttgcc cctagctggg ggtatagggg agcagtccca   7980
tgtagtagta gaatgaaaaa tgctgctatg ctgtgcctcc cccacctttc ccatgtctgc   8040
cctctactca tggtctatct ctcctggctc ctgggagtca tggactccac ccagcaccac   8100
caacctgacc taaccaccta tctgagcctg ccagcctata acccatctgg gccctgatag   8160
ctggtggcca gccctgaccc caccccaccc tccctggaac ctctgataga cacatctggc   8220
acaccagctc gcaaagtcac cgtgagggtc ttgtgtttgc tgagtcaaaa ttccttgaaa   8280
tccaagtcct tagagactcc tgctcccaaa tttacagtca tagacttctt catggctgtc   8340
tcctttatcc acagaatgat tcctttgctt cattgcccca tccatctgat cctcctcatc   8400
agtgcagcac agggcccatg agcagtagct gcagagtctc acataggtct ggcactgcct   8460
ctgacatgtc cgaccttagg caaatgcttg actcttctga gctcggatcc cttgagctca   8520
ggaggtcaag gctgcagtga gacatgatct tgccactgca ctccagcctg gacagcagag   8580
tgaaaccttg cctcacgaaa cagaatacaa aaacaaacaa acaaaaaact gctccgcaat   8640
gcgcttcctt gatgctctac cacataggtc tgggtacttt gtacacatta tctcattgct   8700
gttcataatt gttagattaa ttttgtaata ttgatattat tcctagaaag ctgaggcctc   8760
aagatgataa cttttatttt ctggacttgt aatagctttc tcttgtattc accatgttgt   8820
aactttctta gagtagtaac aatataaagt tattgtgagt ttttgcaaac acagcaaaca   8880
caacgaccca tatagacatt gatgtgaaat tgtctattgt caatttatgg gaaaacaagt   8940
atgtactttt tctactaagc cattgaaaca ggaataacag aacaagattg aaagaataca   9000
ttttccgaaa ttacttgagt attatacaaa gacaagcacg tggacctggg aggagggtta   9060
ttgtccatga ctggtgtgtg gagacaaatg caggtttata atagatggga tggcatctag   9120
cgcaatgact ttgccatcac ttttagagag ctcttggggg ccccagtaca caagagggga   9180
cgcagggtat atgtagacat ctcattcttt ttcttagtgt gagaataaga atagccatga   9240
cctgagttta tagacaatga gcccttttct ctctcccact cagcagctat gagatggctt   9300
gccctgcctc tctactaggc tgactcactc caaggcccag caatgggcag ggctctgtca   9360
gggctttgat agcactatct gcagagccag ggccgagaag gggtggactc cagagactct   9420
ccctcccatt cccgagcagg gtttgcttat ttatgcattt aaatgatata tttattttaa   9480
aagaaataac aggagactgc ccagccctgg ctgtgacatg gaaactatgt agaatatttt   9540
gggttccatt tttttttcct tctttcagtt agaggaaaag gggctcactg cacatacact   9600
agacagaaag tcaggagctt tgaatccaag cctgatcatt tccatgtcat actgagaaag   9660
tccccaccct tctctgagcc tcagtttctc tttttataag taggagtctg gagtaaatga   9720
tttccaatgg ctctcatttc aatacaaaat ttccgtttat taaatgcatg agcttctgtt   9780
actccaagac tgagaaggaa attgaacctg agactcattg actggcaaga tgtccccaga   9840
ggctctcatt cagcaataaa attctcacct tcacccaggc ccactgagtg tcagatttgc   9900
atgcggatcc actagttcta gagcggccgg ggtcgacgaa ttcgagctcg gtacctttaa   9960
```

-continued

```
gaccaatgac ttacaaggca gctgtagatc ttagccactt tttaaaagaa aaggggggac  10020

tggaagggct aattcactcc caacgaagac aagatcgcta gcgatatctc cggatttatt  10080

tgtgaaattt gtgatgctat tgctttattt gaccggtctg ctttttgctt gtactgggtc  10140

tctctggtta gaccagatct gagcctggga gctctctggc taactaggga acccactgct  10200

taagcctcaa taaagcttgc cttgagtgct tcaagtagtg tgtgcccgtc tgttgtgtga  10260

ctctggtaac tagagatccc tcagaccctt ttagtcagtg tggaaaatct ctagcaacgc  10320

gtccatctgt tgtttgcccc tcccccgtgc cttccttgac cctggaaggt gccactccca  10380

ctgtcctttc ctaataaaat gaggaaattg catcgcattg tctgagtagg tgtcattcta  10440

ttctgggggg tggggtgggg cagcacagca agggggagga ttgggaagac aatagcaggc  10500

atgctgggga tgcggtgggc tctatgggta cccaggtgct gaagaattga cccggttcct  10560

cctgggccag aaagaagcag gcacatcccc ttctctgtga cacaccctgt ccacgcccct  10620

ggttcttagt tccagcccca ctcataggac actcatagct caggagggct ccgccttcaa  10680

tcccacccgc taaagtactt ggagcggtct ctccctccct catcagccca ccaaaccaaa  10740

cctagcctcc aagagtggga agaaattaaa gcaagatagg ctattaagtg cagagggaga  10800

gaaaatgcct ccnnnnccgc gggtagtagt tcatgtcatc ttattattca gtatttataa  10860

cttgcaaaga aatgaatatc agagagtgag aggaacttgt ttattgcagc ttataatggt  10920

tacaaataaa gcaatagcat cacaaatttc acaaataaag catttttttc actgcattct  10980

agttgtggtt tgtccaaact catcaatgta tcttatcatg tctggctcta gctatcccgc  11040

ccctaactcc gcccatcccg cccctaactc cgcccagttc cgcccattct ccgccccatg  11100

gctgactaat tttttttatt tatgcagagg ccgaggccgc ctcggcctct gagctattcc  11160

agaagtagtg aggaggcttt tttggaggcc taggcttttg cgtcgagacg tacccaattc  11220

gccctatagt gagtcgtatt acgcgcgctc actggccgtc gttttacaac gtcgtgactg  11280

ggaaaaccct ggcgttaccc aacttaatcg ccttgcagca catccccctt tcgccagctg  11340

gcgtaatagc gaagaggccc gcaccgatcg cccttcccaa cagttgcgca gcctgaatgg  11400

cgaatggcgc gacgcgccct gtagcggcgc attaagcgcg gcgggtgtgg tggttacgcg  11460

cagcgtgacc gctacacttg ccagcgccct agcgcccgct cctttcgctt tcttcccttc  11520

ctttctcgcc acgttcgccg gctttccccg tcaagctcta aatcgggggc tccctttagg  11580

gttccgattt agtgctttac ggcacctcga ccccaaaaaa cttgattagg gtgatggttc  11640

acgtagtggg ccatcgccct gatagacggt ttttcgccct ttgacgttgg agtccacgtt  11700

ctttaatagt ggactcttgt tccaaactgg aacaacactc aaccctatct cggtctattc  11760

ttttgattta taagggattt tgccgatttc ggcctattgg ttaaaaaatg agctgattta  11820

acaaaaattt aacgcgaatt ttaacaaaat attaacgttt acaatttc              11868
```

<210> SEQ ID NO 5
<211> LENGTH: 6651
<212> TYPE: DNA
<213> ORGANISM: Artificial Sequence
<220> FEATURE:
<223> OTHER INFORMATION: sSIN only
<220> FEATURE:
<221> NAME/KEY: misc_feature
<222> LOCATION: (5596)..(5599)
<223> OTHER INFORMATION: n is a, c, g, or t

<400> SEQUENCE: 5

```
caggtggcac ttttcgggga aatgtgcgcg gaacccctat ttgtttattt ttctaaatac     60
```

-continued

```
attcaaatat gtatccgctc atgagacaat aaccctgata aatgcttcaa taatattgaa    120
aaaggaagag tatgagtatt caacatttcc gtgtcgccct tattcccttt tttgcggcat    180
tttgccttcc tgtttttgct cacccagaaa cgctggtgaa agtaaaagat gctgaagatc    240
agttgggtgc acgagtgggt tacatcgaac tggatctcaa cagcggtaag atccttgaga    300
gttttcgccc cgaagaacgt tttccaatga tgagcacttt taaagttctg ctatgtggcg    360
cggtattatc ccgtattgac gccgggcaag agcaactcgg tcgccgcata cactattctc    420
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgctttttt gcacaacatg ggggatcatg    600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt catttttaat ttaaaaggat ctaggtgaag atcctttttg   1080
ataatctcat gaccaaaatc ccttaacgtg agttttcgtt ccactgagcg tcagaccccg   1140
tagaaaagat caaaggatct tcttgagatc ctttttttct gcgcgtaatc tgctgcttgc   1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttggc   2220
cattgcatac gttgtatcca tatcataata tgtacattta tattggctca tgtccaacat   2280
taccgccatg ttgacattga ttattgacta gttattaata gtaatcaatt acggggtcat   2340
tagttcatag cccatatatg gagttccgcg ttacataact tacggtaaat ggcccgcctg   2400
```

-continued

```
gctgaccgcc caacgacccc cgcccattga cgtcaataat gacgtatgtt cccatagtaa   2460
cgccaatagg gactttccat tgacgtcaat gggtggagta tttacggtaa actgcccact   2520
tggcagtaca tcaagtgtat catatgccaa gtacgccccc tattgacgtc aatgacggta   2580
aatggcccgc ctggcattat gcccagtaca tgaccttatg ggactttcct acttggcagt   2640
acatctacgt attagtcatc gctattacca tggtgatgcg gttttggcag tacatcaatg   2700
ggcgtggata gcggtttgac tcacggggat ttccaagtct ccaccccatt gacgtcaatg   2760
ggagtttgtt ttggcaccaa aatcaacggg actttccaaa atgtcgtaac aactccgccc   2820
cattgacgca aatgggcggt aggcgtgtac ggtgggaggt ctatataagc agagctcgtt   2880
tagtgaaccg gggtctctct ggttagacca gatctgagcc tgggagctct ctggctaact   2940
agggaaccca ctgcttaagc ctcaataaag cttgccttga gtgcttcaag tagtgtgtgc   3000
ccgtctgttg tgtgactctg gtaactagag atccctcaga cccttttagt cagtgtggaa   3060
aatctctagc agtggcgccc gaacagggac ttgaaagcga aagggaaacc agaggagctc   3120
tctcgacgca ggactcggct tgctgaagcg cgcacggcaa gaggcgaggg gcggcgactg   3180
gtgagtacgc caaaaatttt gactagcgga ggctagaagg agagagatgg gtgcgagagc   3240
gtcagtatta agcgggggag aattagatcg cgatgggaaa aaattcggtt aaggccaggg   3300
ggaaagaaaa aatataaatt aaaacatata gtatgggcaa gcagggagct agaacgattc   3360
gcagttaatc ctggcctgtt agaaacatca gaaggctgta gacaaatact gggacagcta   3420
caaccatccc ttcagacagg atcagaagaa cttagatcat tatataatac agtagcaacc   3480
ctctattgtg tgcatcaaag gatagagata aaagacacca aggaagcttt agacaagata   3540
gaggaagagc aaaacaaaag taagaccacc gcacagcaag cggccgctga tcttcagacc   3600
tggaggagga gatatgaggg acaattggag aagtgaatta tataaatata aagtagtaaa   3660
aattgaacca ttaggagtag cacccaccaa ggcaaagaga agagtggtgc agagagaaaa   3720
aagagcagtg ggaataggag ctttgttcct tgggttcttg ggagcagcag gaagcactat   3780
gggcgcagcg tcaatgacgc tgacggtaca ggccagacaa ttattgtctg gtatagtgca   3840
gcagcagaac aatttgctga gggctattga ggcgcaacag catctgttgc aactcacagt   3900
ctggggcatc aagcagctcc aggcaagaat cctggctgtg gaaagatacc taaaggatca   3960
acagctcctg gggatttggg gttgctctgg aaaactcatt tgcaccactg ctgtgccttg   4020
gaatgctagt tggagtaata aatctctgga acagatttgg aatcacacga cctggatgga   4080
gtgggacaga gaaattaaca attacacaag cttaatacac tccttaattg aagaatcgca   4140
aaaccagcaa gaaaagaatg aacaagaatt attggaatta gataaatggg caagtttgtg   4200
gaattggttt aacataacaa attggctgtg gtatataaaa ttattcataa tgatagtagg   4260
aggcttggta ggtttaagaa tagtttttgc tgtactttct atagtgaata gagttaggca   4320
gggatattca ccattatcgt ttcagaccca cctcccaacc ccgaggggac ccgacaggcc   4380
cgaaggaata gaagaagaag gtggagagag agacagagac agatccattc gattagtgaa   4440
cggatctcga cggtatcgat agcgggacaa atggcagtat tcatccacaa ttttaaaaga   4500
aaagggggga ttggggggta cagtgcaggg gaaagaatag tagacataat agcaacagac   4560
atacaaacta aagaattaca aaaacaaatt acaaaaattc aaaattttcg ggtttattac   4620
agggacagca gagatccagt ttggatcgtc gacatcgccg gtgaattcac tagtggatcg   4680
ctctcgagga tccactagtt ctagagcggc cggggtcgac gaattcgagc tcggtacctt   4740
taagaccaat gacttacaag gcagctgtag atcttagcca ctttttaaaa gaaaaggggg   4800
```

```
gactggaagg gctaattcac tcccaacgaa gacaagatcg ctagcgatat ctccggattt   4860

atttgtgaaa tttgtgatgc tattgcttta tttgaccggt ctgctttttg cttgtactgg   4920

gtctctctgg ttagaccaga tctgagcctg ggagctctct ggctaactag ggaacccact   4980

gcttaagcct caataaagct tgccttgagt gcttcaagta gtgtgtgccc gtctgttgtg   5040

tgactctggt aactagagat ccctcagacc cttttagtca gtgtggaaaa tctctagcaa   5100

cgcgtccatc tgttgtttgc cctcccccg tgccttcctt gaccctggaa ggtgccactc   5160

ccactgtcct ttcctaataa aatgaggaaa ttgcatcgca ttgtctgagt aggtgtcatt   5220

ctattctggg gggtggggtg gggcagcaca gcaaggggga ggattgggaa gacaatagca   5280

ggcatgctgg ggatgcggtg ggctctatgg gtacccaggt gctgaagaat tgacccggtt   5340

cctcctgggc cagaaagaag caggcacatc cccttctctg tgacacaccc tgtccacgcc   5400

cctggttctt agttccagcc ccactcatag gacactcata gctcaggagg gctccgcctt   5460

caatcccacc cgctaaagta cttggagcgg tctctccctc cctcatcagc ccaccaaacc   5520

aaacctagcc tccaagagtg ggaagaaatt aaagcaagat aggctattaa gtgcagaggg   5580

agagaaaatg cctccnnnnc cgcgggtagt agttcatgtc atcttattat tcagtattta   5640

taacttgcaa agaaatgaat atcagagagt gagaggaact tgtttattgc agcttataat   5700

ggttacaaat aaagcaatag catcacaaat ttcacaaata aagcattttt ttcactgcat   5760

tctagttgtg gtttgtccaa actcatcaat gtatcttatc atgtctggct ctagctatcc   5820

cgcccctaac tccgcccatc ccgcccctaa ctccgcccag ttccgcccat tctccgcccc   5880

atggctgact aattttttt atttatgcag aggccgaggc cgcctcggcc tctgagctat   5940

tccagaagta gtgaggaggc ttttttggag gcctaggctt ttgcgtcgag acgtacccaa   6000

ttcgccctat agtgagtcgt attacgcgcg ctcactggcc gtcgttttac aacgtcgtga   6060

ctgggaaaac cctggcgtta cccaacttaa tcgccttgca gcacatcccc ctttcgccag   6120

ctggcgtaat agcgaagagg cccgcaccga tcgcccttcc caacagttgc gcagcctgaa   6180

tggcgaatgg cgcgacgcgc cctgtagcgg cgcattaagc gcggcgggtg tggtggttac   6240

gcgcagcgtg accgctacac ttgccagcgc cctagcgccc gctcctttcg ctttcttccc   6300

ttcctttctc gccacgttcg ccggctttcc ccgtcaagct ctaaatcggg ggctcccttt   6360

agggttccga tttagtgctt tacggcacct cgaccccaaa aaacttgatt agggtgatgg   6420

ttcacgtagt gggccatcgc cctgatagac ggtttttcgc cctttgacgt tggagtccac   6480

gttctttaat agtggactct tgttccaaac tggaacaaca ctcaacccta tctcggtcta   6540

ttcttttgat ttataaggga ttttgccgat ttcggcctat tggttaaaaa atgagctgat   6600

ttaacaaaaa tttaacgcga attttaacaa aatattaacg tttacaattt c            6651
```

```
<210> SEQ ID NO 6
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 6

ccatcgatag cgctctcgag cccggggtcg acgaattcc                             39


<210> SEQ ID NO 7
<211> LENGTH: 24
<212> TYPE: DNA
```

<213> ORGANISM: Artificial Sequence
<220> FEATURE:
<223> OTHER INFORMATION: Synthetic Polynucleotide

<400> SEQUENCE: 7
ataaacccgg gagcagtggg aata 24

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 8
acatgatatc gcaaatgagt tttcc 25

<210> SEQ ID NO 9
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 9
acatgatatc ataccgtcga gatcc 25

<210> SEQ ID NO 10
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 10
actgctctcg agcaatggga aaaaattcgg t 31

<210> SEQ ID NO 11
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 11
actgctctcg aggcagcttc ctcattgatg 30

<210> SEQ ID NO 12
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 12
actgctctcg agatcagcgg ccgcttgctg t 31

<210> SEQ ID NO 13
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 13
tatcgtttcg aacccacctc c 21

```
<210> SEQ ID NO 14
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 14

ggaggtgggt tcgaaacgat a                                              21


<210> SEQ ID NO 15
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 15

gaacccactg cttaagcctc aa                                             22


<210> SEQ ID NO 16
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 16

acagacgggc acacactact tg                                             22


<210> SEQ ID NO 17
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 17

aaagcttgcc ttgagtgc                                                  18


<210> SEQ ID NO 18
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 18

cccaggctca gatctggtct aa                                             22


<210> SEQ ID NO 19
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 19

tgtgaaattt gtgatgctat tgctt                                          25


<210> SEQ ID NO 20
<211> LENGTH: 29
<212> TYPE: DNA
<213> ORGANISM: Artificial Sequence
<220> FEATURE:
```

-continued

<223> OTHER INFORMATION: Synthetic Polynucleotide

<400> SEQUENCE: 20
agacccagta caagcaaaaa gcagaccgg 29

<210> SEQ ID NO 21
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 21
acctgaaagc gaaaggcaaa c 21

<210> SEQ ID NO 22
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 22
agaaggagag agatgggtgc g 21

<210> SEQ ID NO 23
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 23
agctctctcg acgcaggact cggc 24

<210> SEQ ID NO 24
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 24
aagcccccag ggatgtaat 19

<210> SEQ ID NO 25
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 25
aaagcttttt ccccgtatcc 20

<210> SEQ ID NO 26
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 26
tgaacacagt tgtgtcagaa gc 22

<210> SEQ ID NO 27
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 27
cacttgcaaa ggaggatgtt t 21

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 28
tcaaatcatg aaggctggaa 20

<210> SEQ ID NO 29
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 29
ctgactccgt cctggagttg 20

<210> SEQ ID NO 30
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 30
gtctgagcct gcatgtttga 20

<210> SEQ ID NO 31
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 31
gtccctggag gtgatgaaga 20

<210> SEQ ID NO 32
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 32
ggtcctgctc tgatccgaag 20

<210> SEQ ID NO 33
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 33
gggtcgctca ggtccttact t 21

<210> SEQ ID NO 34
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 34
ttcagtagct gatgcccagg t 21

<210> SEQ ID NO 35
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 35
gggaggatac cagagatggg a 21

<210> SEQ ID NO 36
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 36
aatgatatct ctagagggac agccccccc 29

<210> SEQ ID NO 37
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 37
aatgatatcc ctgcaggcat tcaaggccag 30

<210> SEQ ID NO 38
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 38
aatgatatca ccatcaaaca tgcaggctca 30

<210> SEQ ID NO 39
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 39
cgggatcccg agctcacggg gacagccccc c 31

<210> SEQ ID NO 40
<211> LENGTH: 34

<212> TYPE: DNA
<213> ORGANISM: Artificial Sequence
<220> FEATURE:
<223> OTHER INFORMATION: Synthetic Polynucleotide

<400> SEQUENCE: 40
ggaattccga tatcaagctt tttccccgta tccc 34

<210> SEQ ID NO 41
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 41
ggaattccga tatcgagctc acggggacag cccccc 36

<210> SEQ ID NO 42
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 42
cggggtaccc cgaagctttt tccccgtatc cccc 34

<210> SEQ ID NO 43
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 43
actggatatc atgtgtctga gcctgcatgt tt 32

<210> SEQ ID NO 44
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 44
tgactccgga agccccatcc tcactgactc cgtcc 35

<210> SEQ ID NO 45
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 45
ggaattccgc ttgccaacga cat 23

<210> SEQ ID NO 46
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 46

-continued

```
ccatcgatca caccctgttt ctcc                                              24


<210> SEQ ID NO 47
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 47

ccatcgatcg ctggcgttct cgc                                               23


<210> SEQ ID NO 48
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 48

ccatcgattt cgcactcaat ccgcc                                             25


<210> SEQ ID NO 49
<211> LENGTH: 147
<212> TYPE: PRT
<213> ORGANISM: Homo sapiens

<400> SEQUENCE: 49

Met Gly His Phe Thr Glu Glu Asp Lys Ala Thr Ile Thr Ser Leu Trp
1               5                   10                  15

Gly Lys Val Asn Val Glu Asp Ala Gly Gly Glu Thr Leu Gly Arg Leu
            20                  25                  30

Leu Val Val Tyr Pro Trp Thr Gln Arg Phe Phe Asp Ser Phe Gly Asn
        35                  40                  45

Leu Ser Ser Ala Ser Ala Ile Met Gly Asn Pro Lys Val Lys Ala His
    50                  55                  60

Gly Lys Lys Val Leu Thr Ser Leu Gly Asp Ala Ile Lys His Leu Asp
65                  70                  75                  80

Asp Leu Lys Gly Thr Phe Ala Gln Leu Ser Glu Leu His Cys Asp Lys
                85                  90                  95

Leu His Val Asp Pro Glu Asn Phe Lys Leu Leu Gly Asn Val Leu Val
            100                 105                 110

Thr Val Leu Ala Ile His Phe Gly Lys Glu Phe Thr Pro Glu Val Gln
        115                 120                 125

Ala Ser Trp Gln Lys Met Val Thr Ala Val Ala Ser Ala Leu Ser Ser
    130                 135                 140

Arg Tyr His
145
```